United States Patent
Nardi et al.

(10) Patent No.: US 9,725,459 B2
(45) Date of Patent: *Aug. 8, 2017

(54) 3-OXO-TETRAHYDRO-FURO[3,2-B]PYRROL-4(5H)-YL) DERIVATIVES I

(71) Applicant: GRÜNENTHAL GMBH, Aachen (DE)

(72) Inventors: Antonio Nardi, Herzogenrath (DE); Paul Ratcliffe, Aachen (DE); Tobias Craan, Aachen (DE); Torsten Hertrampf, Köln (DE); Bernhard Lesch, Aachen (DE); Robert Kime, Stolberg (DE); Henning Steinhagen, Schwalbach (DE)

(73) Assignee: GRUNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,987

(22) Filed: Apr. 23, 2015

(65) Prior Publication Data

US 2015/0307507 A1 Oct. 29, 2015

(30) Foreign Application Priority Data

Apr. 23, 2014 (EP) .................... 14001459

(51) Int. Cl.
C07D 491/048 (2006.01)

(52) U.S. Cl.
CPC ................ C07D 491/048 (2013.01)

(58) Field of Classification Search
CPC .................................................. C07D 400/02
See application file for complete search history.

(56) References Cited

U.S. PATENT DOCUMENTS

2007/0117785 A1 5/2007 Butler et al.
2010/0010009 A1 1/2010 Quibell et al.
2011/0009385 A1 1/2011 Quibell et al.

FOREIGN PATENT DOCUMENTS

WO WO 2008/007127 A1 1/2008
WO 2009/112839 A1 9/2009

OTHER PUBLICATIONS

Vippagunta et al (2001).*
U.S. Appl. No. 14/693,975, filed Apr. 23, 2015.*

Artursson et al, "Caco-2 and Emerging Alternatives for Prediction of Intestinal Drug Transport: A general Overview"; Drug Bioavailability 2003, 72-88.
Barclay et al., "Role of the cysteine protease cathepsin S in neuropathic hyperalgesia"; Pain, 2007, 130, 225-234.
Bossard et al., "Proteolytic Activity of Human Osteoclast Cathepsin K"; J. Biol. Chem. 1996, 271, 12517-12524.
Cheng et al., "Increased Expression of Elastolytic Cysteine Proteases, Cathepsins S and K, in the Neointima of Balloon-Injured Rat Carotid Arteries"; Am. J. Pathol., 2004, 164, 243-251.
Gupta et al.; "Cysteine cathepsin S as an immunomodulator target: present and future trends"; Expert Opin. Ther. Targets, 2008, 12, 291-299.
Hidalgo et al; "Characterization of the Human Colon Carcinoma Cell Line (Caco-2) as a Model System for Intestinal Epithelial Permeability"; Gastroenterology 1989, 96, 736-749.
Lee-Dutra et al.,; "Cathepsin S inhibitors: 2004-2010"; Expert Opin. Ther. Patents, 2011, 21, 311-337.
Petermann et al.; "Lysosomal, cytoskeletal, and metabolic alterations in cardiomyopathy of cathepsin L knockout mice"; FASEB J. 2006, 20, 1266-1268, E587-E598.
Potts et al,; "Cathespin L-deficient mice exhibit abnormal skin and bone development and show increased resistance to osteoporosis following ovariectomy"; Int. J. Exp. Path. 2004, 85, 85-96.
Stypmann et al.; Dilated cardiomyopathy in mice deficient for the lysosomal cysteine peptidase cathepsin L; PNAS, 2002, 99, 6234-6239.
Sukhova et al.; "Expression of the elastolytic cathepsins S and K in human atheroma and regulation of their production in smooth muscle cells"; J. Clin. Invest., 1998, 102, 576-583.
Turk et al.; "Cysteine cathepsins: from structure, function and regulation to new frontiers" Biochim. Biophys. Acta, 2012. 1824, 68-88.
Wiener et al.; "Recent advances in the design of cathepsin S inhibitors"; Curr. Top. Med. Chem. 2010, 10, 717-732.
Yasuda et al.; "The role of cathepsins in osteoporosis and arthritis: Rationale for the design of new therapeutics"; Adv. Drug Deliv. Rev., 2005, 57, 973-993.
Zerbini et al.; "Odanacatib in postmenopausal women with low bone mineral density: a review of current clinical evidence"; Ther. Adv. Musculoskel. Dis. 2013, 5(4), 199-209.

* cited by examiner

*Primary Examiner* — Paul V Ward
(74) *Attorney, Agent, or Firm* — Norris McLaughlin & Marcus, P.A.

(57) ABSTRACT

The invention relates to amidic oxotetrahydro-2H-furo[3.2-b]pyrrol-4(5H)-yl) derivatives as dual CatS/K inhibitors. to pharmaceutical compositions containing these compounds and also to these compounds for use in the treatment and/or prophylaxis of pain and further diseases and/or disorders.

15 Claims, No Drawings

3-OXO-TETRAHYDRO-FURO[3,2-B]PYRROL-4(5H)-YL) DERIVATIVES I

This application claims priority of European Patent Application No. 14001459.8, filed Apr. 23, 2014, the entire contents of which is incorporated herein by reference.

FIELD OF THE INVENTION

The present invention relates to compounds that are dual inhibitors of the cysteine proteinases cathepsin S (CatS) and cathepsin K (CatK), pharmaceutical compositions containing said compounds, and their use in medical therapy. Such compounds are particularly useful for the therapeutic treatment of diseases which are at least partially modulated by CatS and CatK.

BACKGROUND OF THE INVENTION

Cysteine proteases represent a specific class of peptidases which bear a cysteine residue in the catalytic site of the enzyme. Many pathological disorders or diseases are the results of abnormal activity of cysteine proteases such as over expression or enhanced activation.

The cysteine cathepsins, e.g. cathepsins B, K, O, L, S, V and F, are a class of lysosomal protease enzymes which are implicated in a multitude of house-keeping roles, but also in various disease processes and disorders including inflammation, autoimmune diseases, e.g. rheumatoid arthritis, psoriasis, asthma, osteoarthritis, osteoporosis, tumors, coronary disease, atherosclerosis, and infectious diseases.

In contrast to the ubiquitously expressed housekeeping enzymes cathepsins B, O and L, cathepsin S (CatS) is highly expressed in antigen presenting cells of lymphatic tissues, primarily in dendritic cells, B cells and macrophages (Wiener et al., Curr. Top. Med. Chem., 2010, 10, 717). In the antigen presenting cells, CatS plays a major role in antigen presentation by degradation of invariant chain that is associated with the major histocompatibility class II complex.

There currently exists a major unmet need for safe orally administered medications for the treatment of inflammatory diseases such as rheumatoid arthritis, osteoarthritis, chronic obstructive pulmonary disease (COPD) and cardiovascular disease, which exhibit significant damage and remodeling of extracellular matrix (ECM).

Destruction of the ECM takes place through proteolysis of its elastin, collagen and proteoglycan constituents, which provide structure, elasticity and tensile strength to materials such as cartilage, bone, lung and vascular tissue.

US 2007/0117785 discloses inhibitors of CatS, supporting the use of CatS inhibitors for the treatment of certain allergic conditions, such as rheumatoid arthritis or psoriasis.

CatS has also been demonstrated to mediate a pronociceptive effect, thereby indicating that endogenous CatS released by peripheral macrophages may contribute to the maintenance of neuropathic hyperalgesia following nerve injury (Barclay et al., Pain, 2007, 130, 225).

CatK is predominantly expressed in osteoclasts (Yasuda et al., Adv. Drug Deliv. Rev., 2005, 57, 973). By cleavage of bone matrix proteins, CatK is involved in extracellular matrix metabolism necessary for normal bone growth and remodelling (Bossard et al., J. Biol. Chem. 1996, 271, 12517). Hence, inhibition of CatK should result in a reduction of osteoclast mediated bone resorption. The CatK inhibitor Odanacatib has been validated in humans for the treatment of osteoporosis (Zerbini and McClung, Ther. Adv. Musculoskel. Dis. 2013, 5(4), 199-209).

The proteolytic enzymes cathepsin S and cathepsin K are up-regulated under inflammatory conditions and have been implicated in the degradation of ECM components. For instance, CatK and CatS are found over-expressed in rheumatoid and osteoarthritic synovium. They have been shown to degrade collagen type-I and type-II, as well as aggrecan (a multidomain proteoglycan component of articular cartilage) respectively (Yasuda et al., Adv. Drug Deliv. Rev., 2005, 57, 973).

Besides destruction of articular cartilage, CatS and CatK demonstrate potent elastinolytic activity and are involved in a broad spectrum of pathological conditions associated with elastin degradation, such as COPD and cardiovascular disease. Both enzymes are readily secreted by macrophages and smooth muscle cells and have been shown to degrade elastins from bovine aorta and lung tissue. CatS and CatK are also responsible for the vascular tissue damage associated with chronic cardiovascular disease and vascular injury.

Further, CatS and CatK have been found to play a crucial role in atherosclerotic lesion destabilization and eventually induction of atherosclerotic plaque rupture (Sukhova et al., J. Clin. Invest., 1998, 102, 576). CatS and CatK have also been associated with vascular remodeling and causing ECM damage during the development of atherosclerosis and vascular injury-induced neointimal formation (Cheng et al., Am. J. Pathol., 2004, 164, 243).

Thus, inhibition of CatS and CatK offer an attractive approach to prevent the tissue destruction underlying chronic inflammatory diseases such as rheumatoid arthritis, osteoarthritis, COPD and cardiovascular disease.

Since CatS and CatK appear to work in tandem and both are present in many chronic inflammatory diseases, a single compound possessing dual inhibitory activity would be a distinct advantage. There are presently no human therapeutic dual inhibitors. The use of dual CatS/K inhibitors for the treatment of conditions with inflammatory and joint-destructive components, such as rheumatoid arthritis has been suggested (Gupta et al. Expert Opin. Ther. Targets, 2008, 12, 291) and demonstrated in a collagen-induced murine arthritis model (Lee-Dutra et al., Expert Opin. Ther. Patents, 2011, 21, 311).

WO 2009/112839 A1 describes particular 6-(1S)-chloro-tetrahydrofuro[3,2-b]pyrrol-3-ones according to general formula (I*), exhibiting potent dual inhibition versus both human CatS and CatK:

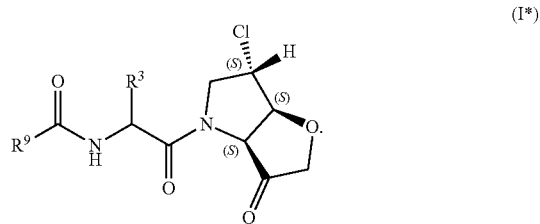

(I*)

A major challenge in the development of such dual CatS/K inhibitors arises from selectivity issues towards other cathepsins. In particular, lysosomal, cytoskeletal and metabolic alterations in cardiomyopathy have been attributed to inhibition of cathepsin L (CatL) in CatL knock-out mice (Petermann et al., FASEB J. 2006, 20, 1266; Stypmann et al., PNAS, 2002, 99, 6234). Furthermore, it was shown that disruption of the cathepsin L gene leads to major abnormalities in skin and hair development and differentiation and alterations in trabecular bone deposition (Potts et al, Int. J. Exp. Path. 2004, 85, 85).

Structurally, the cathepsins K, L and S possess a high sequence homology (Lee-Dutra et al., Expert Opin. Ther. Patents 2011, 21, 311; Turk et al., Biochim. Biophys. Acta, 2012. 1824, 68). Therefore, a sufficient selectivity over ubiquitously expressed CatL to avoid the undesired effects associated with inhibition of CatL is regarded to be one of the prerequisites for therapeutic suitability of CatS inhibitors (Wiener et al., Curr. Top. Med. Chem. 2010, 10, 717), but will equally refer to dual CatS/CatK inhibitors.

SUMMARY OF THE INVENTION

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by both human CatS and human CatK.

Surprisingly, it has now been found that specific 6-(1S)-chlorotetrahydrofuro[3,2-b]pyrrol-3-ones not only exhibit potent dual inhibition of both human CatS and human CatK, but possess an significantly increased selectivity over CatL compared to the compounds known from WO 2009/112839 A1.

Additionally, the compounds according to the invention have surprisingly been found to exhibit superior physico-chemical properties resulting in an advantageous pharmacokinetic and pharmacodynamic profile of the compounds according to the invention over compounds disclosed in WO 2009/112839 A1.

The present invention therefore relates to a compound of general formula (I),

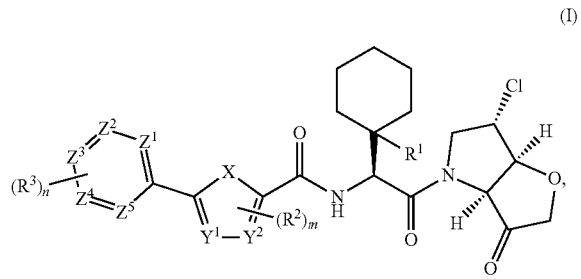

(I)

wherein
$R^1$ represents H or F,
X represents S or O;
$Y^1$ and $Y^2$ independently represents CH or N;
$Z^1, Z^2, Z^3, Z^4$ and $Z^5$ independently represents CH or N, with the proviso that 1, 2 or 3 of $Z^1, Z^2, Z^3, Z^4$ and $Z^5$ represent N;
m denotes 0, 1 or 2;
n denotes 0, 1, 2 or 3;
each $R^2$ and each $R^3$ is independently selected from the group consisting of F; Cl; Br; CN; $CF_3$; $CF_2H$; $CFH_2$; $CF_2Cl$; $CFCl_2$; $C_{1-4}$-alkyl; C(=O)—($C_{1-4}$-alkyl); C(=O)—$NH_2$; C(=O)—N(H)($C_{1-4}$-alkyl); C(=O)—N($C_{1-4}$-alkyl)$_2$; OH; O—$C_{1-4}$-alkyl; $OCF_3$; $OCF_2H$; $OCFH_2$; $OCF_2Cl$; $OCFCl_2$; $NH_2$; N(H)($C_{1-4}$-alkyl); N($C_{1-4}$-alkyl)$_2$; N(H)—C(=O)—($C_{1-4}$-alkyl); N($C_{1-4}$-alkyl)-C(=O)—($C_{1-4}$-alkyl); N(H)—S(=O)$_2$—($C_{1-4}$-alkyl); N(H)—C(=O)—$NH_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl);
wherein the above-mentioned substituents $C_{1-4}$-alkyl and cyclopropyl, may in each case be unsubstituted or substituted one or more times by identical or different substituents, and the above-mentioned substituent $C_{1-4}$-alkyl may in each case be branched or unbranched;
in the form of an individual stereoisomer or a mixture thereof; in the form of a tautomer; of a free compound; of an N-oxide; or in the form of a solvate and/or of a physiologically acceptable salt.

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The term "$C_{1-4}$-alkyl" comprise in the sense of this invention acyclic saturated aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3 or 4 carbon atoms. Preferred $C_{1-4}$-alkyl groups are selected from the group consisting of methyl, ethyl, n-propyl, 2-propyl, n-butyl, isobutyl, sec-butyl and tert-butyl.

In relation to the term "$C_{1-4}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of CH(OH)CHCl$_2$. The multiple substitution can be carried out using the same or using different substituents.

In relation to the terms "$C_{1-4}$-alkyl" and "cyclopropyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; $NO_2$; CN; =O; =NH; =N(OH); =N(O—$C_{1-4}$-alkyl); $CF_3$; $CF_2H$; $CFH_2$; $CF_2Cl$; $CFCl_2$; $C_{1-4}$-alkyl; C(=O)—H; C(=O)—$C_{1-4}$-alkyl; C(=O)—OH; C(=O)—O—$C_{1-4}$-alkyl; C(=O)—N(H)(OH); C(=O)—$NH_2$; C(=O)—N(H)($C_{1-4}$-alkyl); C(=O)—N($C_{1-4}$-alkyl)$_2$; C(=N—OH)—H; C(=N—OH)—$C_{1-4}$-alkyl; C(=N—O—$C_{1-4}$-alkyl)-H; C(=N—O—$C_{1-4}$-alkyl)-$C_{1-4}$-alkyl; OH; $OCF_3$; $OCF_2H$; $OCFH_2$; $OCF_2Cl$; $OCFCl_2$; O—$C_{1-4}$-alkyl; O—C(=O)—$C_{1-4}$-alkyl; O—C(=O)—O—$C_{1-4}$-alkyl; O—(C=O)—N(H)($C_{1-4}$-alkyl); O—C(=O)—N($C_{1-4}$-alkyl)$_2$; O—S(=O)$_2$—$C_{1-4}$-alkyl; O—S(=O)$_2$—OH; O—S(=O)$_2$—O—$C_{1-4}$-alkyl;

O—S(=O)$_2$—NH$_2$; O—S(=O)$_2$—N(H)(C$_{1-4}$-alkyl); O—S(=O)$_2$—N(C$_{1-4}$-alkyl)$_2$; NH$_2$; N(H)(C$_{1-4}$-alkyl); N(C$_{1-4}$-alkyl)$_2$; N(H)—C(=O)—C$_{1-4}$-alkyl; N(H)—C(=O)—O—C$_{1-4}$-alkyl; N(H)—C(=O)—NH$_2$; N(H)—C(=O)—N(H)(C$_{1-4}$-alkyl); N(H)—C(=O)—N(C$_{1-4}$-alkyl)$_2$; N(C$_{1-4}$-alkyl)-C(=O)—C$_{1-4}$-alkyl; N(C$_{1-4}$-alkyl)-C(=O)—O—C$_{1-4}$-alkyl; N(C$_{1-4}$-alkyl)-C(=O)—NH$_2$; N(C$_{1-4}$-alkyl)-C(=O)—N(H)(C$_{1-4}$-alkyl); N(C$_{1-4}$-alkyl)-C(=O)—N(C$_{1-4}$-alkyl)$_2$; N(H)—S(=O)$_2$—OH; N(H)—S(=O)$_2$—C$_{1-4}$-alkyl; N(H)—S(=O)$_2$—O—C$_{1-4}$-alkyl; N(H)—S(=O)$_2$—NH$_2$; N(H)—S(=O)$_2$—N(H)(C$_{1-4}$-alkyl); N(H)—S(=O)$_2$—N(C$_{1-4}$-alkyl)$_2$; N(C$_{1-4}$-alkyl)-S(=O)$_2$—OH; N(C$_{1-4}$-alkyl)-S(=O)$_2$—C$_{1-4}$-alkyl; N(C$_{1-4}$-alkyl)-S(=O)$_2$—O—C$_{1-4}$-alkyl; N(C$_{1-4}$-alkyl)-S(=O)$_2$—NH$_2$; N(C$_{1-4}$-alkyl)—S(=O)$_2$—N(H)(C$_{1-4}$-alkyl); N(C$_{1-4}$-alkyl)-S(=O)$_2$—N(C$_{1-4}$-alkyl)$_2$; SH; SCF$_3$; SCF$_2$H; SCFH$_2$; SCF$_2$Cl; SCFCl$_2$; S—C$_{1-4}$-alkyl; S(=O)—C$_{1-4}$-alkyl; S(=O)$_2$—C$_{1-4}$-alkyl; S(=O)$_2$—OH; S(=O)$_2$—O—C$_{1-4}$-alkyl; S(=O)$_2$—NH$_2$; S(=O)$_2$—N(H)(C$_{1-4}$-alkyl); S(=O)$_2$—N(C$_{1-4}$-alkyl)$_2$; C$_{3-10}$-cycloalkyl; 3 to 7 membered heterocyclyl; aryl or heteroaryl.

Preferred substituents of "C$_{1-4}$-alkyl" are selected from the group consisting of F; Cl; Br; CF$_3$; C(=O)—NH$_2$; C(=O)—N(H)(C$_{1-4}$-alkyl); C(=O)—N(C$_{1-6}$-alkyl)$_2$; C$_{3-6}$-cycloalkyl or 3 to 7 membered heterocyclyl; OH; O—C$_{1-4}$-alkyl; NH$_2$; N(H)(C$_{1-4}$-alkyl); N(C$_{1-4}$-alkyl)$_2$; N(H)—C(=O)—C$_{1-4}$-alkyl; N(H)—S(=O)$_2$—C$_{1-4}$-alkyl; N(C$_{1-4}$-alkyl)-S(=O)$_2$—C$_{1-4}$-alkyl; N(H)—S(=O)$_2$—NH$_2$; SH; S—C$_{1-4}$-alkyl; S(=O)$_2$—C$_{1-4}$-alkyl and S(=O)$_2$—N(H)(C$_{1-4}$-alkyl).

Preferred substituents of "cycloalkyl" are selected from the group consisting of F; Cl; Br; CF$_3$; CN; =O; C$_{1-4}$-alkyl; C$_{3-6}$-cycloalkyl or 3 to 7 membered heterocyclyl; CHO; C(=O)—C$_{1-4}$-alkyl; CO$_2$H; C(=O)O—C$_{1-4}$-alkyl; CONH$_2$; C(=O)NH—C$_{1-4}$-alkyl; C(=O)N(C$_{1-4}$-alkyl)$_2$; OH; O—C$_{1-4}$-alkyl; OCF$_3$; O—C(=O)—C$_{1-4}$-alkyl; NH$_2$; NH—C$_{1-4}$-alkyl; N(C$_{1-4}$-alkyl)$_2$; NH—C(=O)—C$_{1-4}$-alkyl; SH; S—C$_{1-4}$-alkyl; SCF$_3$; S(=O)$_2$—C$_{1-4}$-alkyl; S(=O)$_2$OH; S(=O)$_2$O—C$_{1-4}$-alkyl and S(=O)$_2$—NH—C$_{1-4}$-alkyl.

The term "C$_{3-10}$-cycloalkyl" mean for the purposes of this invention cyclic aliphatic hydrocarbons containing 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloalkyl group can be bound to the respective superordinate general structure via any desired and possible ring member of the cycloalkyl group. The cycloalkyl group can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. C$_{3-10}$-cycloalkyls can furthermore be singly or multiply bridged such as, for example, in the case of adamantyl, bicyclo[2.2.1]heptyl or bicyclo[2.2.2]octyl. Preferred C$_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

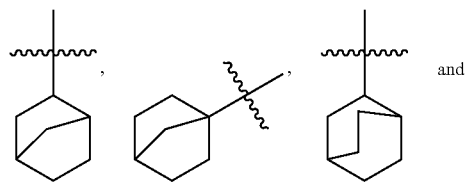

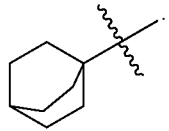

Particularly preferred C$_{3-10}$-cycloalkyl groups are C$_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic saturated or unsaturated (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N(C$_{1-4}$-alkyl) such as N(CH$_3$), wherein the ring members can be unsubstituted or mono- or polysubstituted. The cycloalkyl groups can also be condensed with further saturated or (partially) unsaturated cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further saturated or (partially) unsaturated cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

Within the scope of the present invention, the symbols

or - - - used in the formulae denotes a link of a corresponding residue to the respective superordinate general structure.

In one embodiment of the first aspect of the invention, the compound according to general formula (I) is characterized in that $R^1$ is H.

In another embodiment of the first aspect of the invention, the compound according to general formula (I) is characterized in that $Y^1$ represents CH or N and $Y^2$ represents CH; or $Y^1$ represents CH and $Y^2$ represents CH or N.

In yet another embodiment of the first aspect of the invention, the compound according to general formula (I) is characterized in that X represents S.

Preferably, $R^1$ is H and X represents S, as given in formula (I-1):

(I-1)

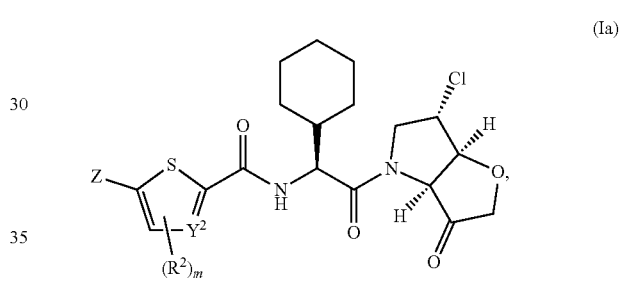

In yet another embodiment of the first aspect of the invention, the compound according to general formula (I) is characterized in that X represents S, $Y^1$ represents CH and $Y^2$ represents CH.

Preferably, $R^1$ is H, X represents S, $Y^1$ represents CH and $Y^2$ represents CH, as given in formula (I-2):

(I-2)

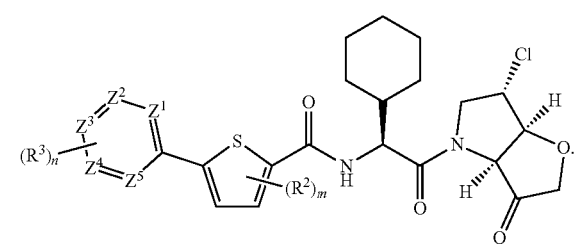

In yet another embodiment of the first aspect of the invention, the compound according to general formula (I) is characterized in that X represents S, $Y^1$ represents CH and $Y^2$ represents N.

Preferably, $R^1$ is H, X represents S, $Y^1$ represents CH and $Y^2$ represents N, as given in formula (I-3):

(I-3)

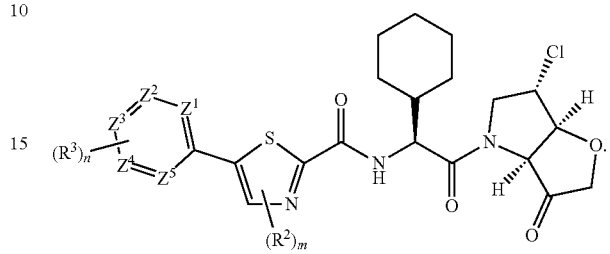

Yet another embodiment of the first aspect of the invention is characterized in that the compound according to general formula (I) is a compound according to general formula (Ia), (Ia)

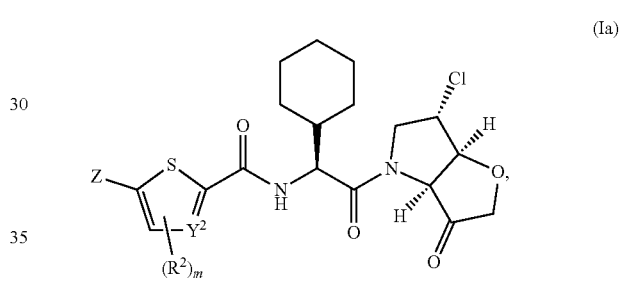

wherein Z represents

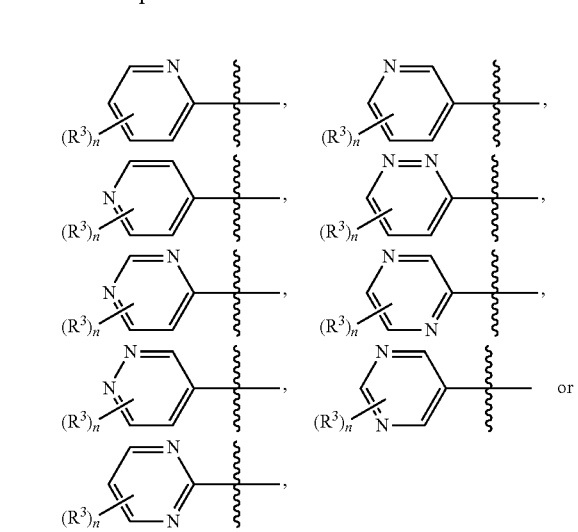

m denotes 0 or 1;
$Y^2$ represents N or CH;
$R^2$ is selected from the group consisting of F; Cl; Br; CN; $CF_3$; $CF_2H$; $CFH_2$; $CF_2Cl$; $CFCl_2$; $C_{1-4}$-alkyl; C(=O)—($C_{1-4}$-alkyl); C(=O)—$NH_2$; C(=O)—N(H)($C_{1-4}$-alkyl); C(=O)—N($C_{1-4}$-alkyl)$_2$; OH; O—$C_{1-4}$-alkyl; $OCF_3$; $OCF_2H$; $OCFH_2$; $OCF_2Cl$; $OCFCl_2$; $NH_2$; N(H)($C_{1-4}$- alkyl); N(C$_{1-4}$-alkyl)$_2$; N(H)—C(=O)—(C$_{1-4}$-alkyl); N(C$_{1-4}$-alkyl)-C(=O)—(C$_{1-4}$-alkyl); N(H)—S(=O)$_2$—(C$_{1-4}$-alkyl); N(H)—C(=O)—NH$_2$; N(H)—C(=O)—N(H)(C$_{1-4}$-alkyl); N(H)—C(=O)—N(C$_{1-4}$-alkyl)(C$_{1-4}$-alkyl); S—(C$_{1-4}$-alkyl); S(=O)—(C$_{1-4}$-alkyl); S(=O)$_2$—(C$_{1-4}$-alkyl); S(=O)$_2$—N(H)(C$_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl);

n denotes 0, 1 or 2 and

R$^3$ is independently selected from the group consisting of F; Cl; Br; CN; CF$_3$; CF$_2$H; CFH$_2$; CF$_2$Cl; CFCl$_2$; C$_{1-4}$-alkyl; C(=O)—(C$_{1-4}$-alkyl); C(=O)—NH$_2$; C(=O)—N(H)(C$_{1-4}$-alkyl); C(=O)—N(C$_{1-4}$-alkyl)$_2$; OH; O—C$_{1-4}$-alkyl; OCF$_3$; OCF$_2$H; OCFH$_2$; OCF$_2$Cl; OCFCl$_2$; NH$_2$; N(H)(C$_{1-4}$-alkyl); N(C$_{1-4}$-alkyl)$_2$; N(H)—C(=O)—(C$_{1-4}$-alkyl); N(C$_{1-4}$-alkyl)-C(=O)—(C$_{1-4}$-alkyl); N(H)—S(=O)$_2$—(C$_{1-4}$-alkyl); N(H)—C(=O)—NH$_2$; N(H)—C(=O)—N(H)(C$_{1-4}$-alkyl); N(H)—C(=O)—N(C$_{1-4}$-alkyl)(C$_{1-4}$-alkyl); S—(C$_{1-4}$-alkyl); S(=O)—(C$_{1-4}$-alkyl); S(=O)$_2$—(C$_{1-4}$-alkyl); S(=O)$_2$—N(H)(C$_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl).

Preferably, m denotes 0; Y$^2$ represents N or CH; n denotes 0, 1 or 2 and

R$^3$ is independently selected from the group consisting of F; Cl; Br; CN; CF$_3$; CF$_2$H; CFH$_2$; CF$_2$Cl; CFCl$_2$; C$_{1-4}$-alkyl; C(=O)—(C$_{1-4}$-alkyl); C(=O)—NH$_2$; C(=O)—N(H)(C$_{1-4}$-alkyl); C(=O)—N(C$_{1-4}$-alkyl)$_2$; OH; O—C$_{1-4}$-alkyl; OCF$_3$; OCF$_2$H; OCFH$_2$; OCF$_2$Cl; OCFCl$_2$; NH$_2$; N(H)(C$_{1-4}$-alkyl); N(C$_{1-4}$-alkyl)$_2$; N(H)—C(=O)—(C$_{1-4}$-alkyl); N(C$_{1-4}$-alkyl)-C(=O)—(C$_{1-4}$-alkyl); N(H)—S(=O)$_2$—(C$_{1-4}$-alkyl); N(H)—C(=O)—NH$_2$; N(H)—C(=O)—N(H)(C$_{1-4}$-alkyl); N(H)—C(=O)—N(C$_{1-4}$-alkyl)(C$_{1-4}$-alkyl); S—(C$_{1-4}$-alkyl); S(=O)—(C$_{1-4}$-alkyl); S(=O)$_2$—(C$_{1-4}$-alkyl); S(=O)$_2$—N(H)(C$_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl).

In another embodiment of the first aspect of the invention, the compound according to general formula (Ia) is characterized in that m denotes 0; Y$^2$ represents N or CH; n denotes 0, 1 or 2 and R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

In another embodiment of the first aspect of the invention, the compound according to general formula (Ia) is characterized in that m denotes 1; R$^3$ is F; Y$^2$ represents N or CH; n denotes 0, 1 or 2 and R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Preferably, m denotes 0; Y$^2$ represents CH; n denotes 0, 1 or 2 and

R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Yet preferably, m denotes 1; R$^3$ is F; Y$^2$ represents CH; n denotes 0, 1 or 2 and R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

Yet preferably, m denotes 0; Y$^2$ represents N; n denotes 0, 1 or 2 and

R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

In another embodiment of the first aspect of the invention, the compound according to general formula (Ia) is characterized in that m denotes 0 or 1; R$^3$ is F; Y$^2$ represents N or CH;

Z represents

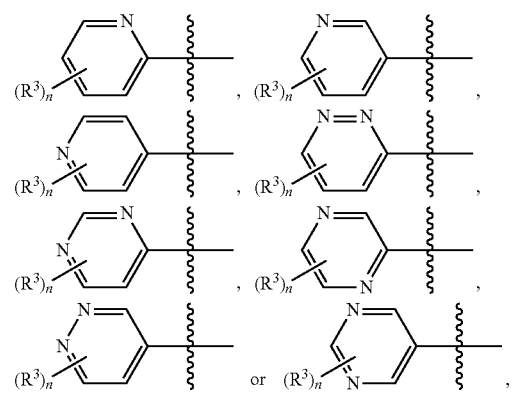

n denotes 0 or 1 or 2 and

R$^3$ is independently selected from the group consisting of F; Cl; CN; CF$_3$; CF$_2$H; CFH$_2$CH$_3$; CH$_2$CH$_3$; CH(CH$_3$)$_2$; C(=O)CH$_3$; C(=O)NH$_2$; C(=O)N(H)(CH$_3$); C(=O)N(CH$_3$)$_2$; OH; OCH$_3$; OCF$_3$; OCF$_2$H; OCFH$_2$; NH$_2$; N(H)(CH$_3$); N(CH$_3$)$_2$; N(H)—C(=O)CH$_3$; N(H)—S(=O)$_2$CH$_3$; S(=O)CH$_3$; S(=O)$_2$CH$_3$; S(=O)$_2$—N(H)(CH$_3$); cyclopropyl and O-cyclopropyl.

In another embodiment of the first aspect of the invention, the compound according to general formula (Ia) is characterized in that m denotes 0; Y$^2$ represents N or CH;

Z represents

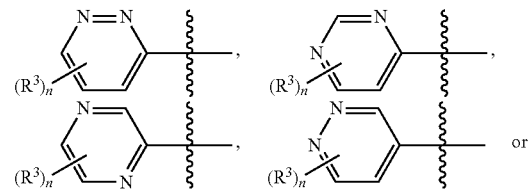

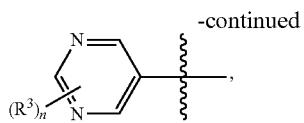

n denotes 0 or 1 and
R³ is independently selected from the group consisting of F; Cl; CN; CF₃; CF₂H; CFH₂CH₃; CH₂CH₃; CH(CH₃)₂; C(=O)CH₃; C(=O)NH₂; C(=O)N(H)(CH₃); C(=O)N(CH₃)₂; OH; OCH₃; OCF₃; OCF₂H; OCFH₂; NH₂; N(H)(CH₃); N(CH₃)₂; N(H)—C(=O)CH₃; N(H)—S(=O)₂CH₃; S(=O)CH₃; S(=O)₂CH₃; S(=O)₂—N(H)(CH₃); cyclopropyl and O-cyclopropyl.

Yet another embodiment of the first aspect of the invention is characterized in that the compound according to general formula (I) is a compound according to general formula (Ib),

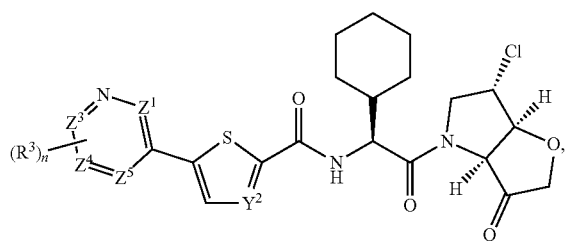

(Ib)

wherein Y² represents CH or N;
Z³, Z⁴ and Z⁵ each represent CH and Z¹ represents N or
Z¹, Z⁴ and Z⁵ each represent CH and Z³ represents N or
Z¹, Z³ and Z⁵ each represent CH and Z⁴ represents N or
Z¹, Z³ and Z⁴ each represent CH and Z⁵ represents N;
n denotes 0 or 1 or 2 and
R³ is selected from the group consisting of F; Cl; CN; CF₃; CF₂H; CFH₂; CH₃; CH₂CH₃; S(=O)CH₃; S(=O)₂CH₃; OCH₃; OCF₃ and cyclopropyl.

Preferably, the compound according to general formula (Ib) is characterized in that Y² represents CH.

Yet preferably, the compound according to general formula (Ib) is characterized in that Y² represents N.

In another embodiment of the first aspect of the invention, the compound according to general formula (Ib) is characterized in that Y² represents CH;
Z³, Z⁴ and Z⁵ each represent CH and Z¹ represents N or
Z¹, Z⁴ and Z⁵ each represent CH and Z³ represents N and m denotes 0.

Yet another embodiment of the first aspect of the invention is characterized in that the compound according to general formula (I) is a compound according to general formula (Ic),

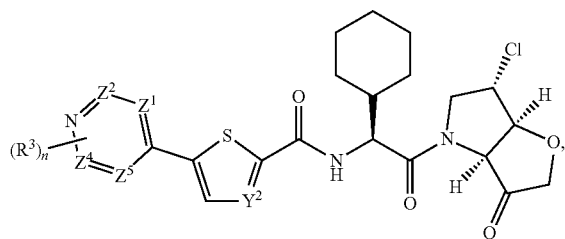

(Ic)

wherein Y² represents CH or N;
Z², Z⁴ and Z⁵ each represent CH and Z¹ represents N or
Z¹, Z⁴ and Z⁵ each represent CH and Z² represents N;
n denotes 0 or 1 or 2 and R³ is selected from the group consisting of F; Cl; CN; CF₃; CF₂H; CFH₂; CH₃; CH₂CH₃; S(=O)CH₃; S(=O)₂CH₃; OCH₃; OCF₃ and cyclopropyl.

In another embodiment of the first aspect of the invention, the compound according to general formula (Ib) or (Ic) is characterized in that Y² represents CH.

Particularly preferred compounds according to the invention are selected from the group consisting of 1 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiophene-2-carboxamide
2 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)thiophene-2-carboxamide
3 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)thiophene-2-carboxamide
4 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)thiophene-2-carboxamide
5 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)thiophene-2-carboxamide
6 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)thiophene-2-carboxamide
7 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)thiophene-2-carboxamide
8 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)thiophene-2-carboxamide
9 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-2-yl)thiophene-2-carboxamide
10 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)furan-2-carboxamide
11 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)furan-2-carboxamide
12 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)furan-2-carboxamide
13 N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridin-3-yl)thiazole-5-carboxamide
14 N-((S)-2-((3aS,6S,6aS)-6-chloro-3-oxotetrahydro-2H-furo[3,2-b]pyrrol-4(5H)-yl)-1-cyclohexyl-2-oxoethyl)-4-methyl-2-(pyridin-3-yl)thiazole-5-carboxamide
15 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)thiazole-2-carboxamide
16 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyridin-3-yl)thiophene-2-carboxamide
17 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-chloropyridin-3-yl)thiophene-2-carboxamide
18 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)thiazole-2-carboxamide
19 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)furan-2-carboxamide 20 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)furan-2-carboxamide
21 N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridazin-4-yl)oxazole-5-carboxamide
22 N-((S)-2-((3aS,6S,6aS)-6-chloro-3-oxotetrahydro-2H-furo[3,2-b]pyrrol-4(5H)-yl)-1-cyclohexyl-2-oxoethyl)-4-methyl-2-(pyrazin-2-yl)thiazole-5-carboxamide
23 N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridin-3-yl)-4-(trifluoromethyl)thiazole-5-carboxamide
24 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)thiazole-2-carboxamide
25 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)furan-2-carboxamide
26 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)thiazole-2-carboxamide
27 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)furan-2-carboxamide
28 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)-1,3,4-thiadiazole-2-carboxamide
29 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiophene-2-carboxamide
30 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiophene-2-carboxamide
31 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiophene-2-carboxamide
32 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiazole-2-carboxamide
33 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-4-yl)thiophene-2-carboxamide
34 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-3-yl)thiophene-2-carboxamide
35 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-3-yl)thiophene-2-carboxamide
36 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyrimidin-4-yl)thiophene-2-carboxamide
37 N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyrimidin-5-yl)thiophene-2-carboxamide
38 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-fluoropyridazin-3-yl)thiophene-2-carboxamide
39 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiophene-2-carboxamide
40 N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-4-yl)thiophene-2-carboxamide
41 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide
42 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridin-3-yl)thiazole-2-carboxamide
43 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiazole-2-carboxamide
44 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-3-yl)thiophene-2-carboxamide
45 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)thiazole-2-carboxamide
46 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiazole-2-carboxamide
47 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyridin-3-yl)thiazole-2-carboxamide
48 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)thiazole-2-carboxamide
49 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)thiazole-2-carboxamide
50 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiazole-2-carboxamide
51 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiazole-2-carboxamide
52 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-chloropyridin-3-yl)thiazole-2-carboxamide
53 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyrimidin-5-yl)thiophene-2-carboxamide
54 N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-3-yl)thiophene-2-carboxamide
55 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiophene-2-carboxamide
56 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methoxypyridin-4-yl)thiophene-2-carboxamide
57 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiazole-2-carboxamide
58 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-methylpyridazin-4-yl)thiophene-2-carboxamide
59 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-3-yl)thiophene-2-carboxamide
60 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-4-yl)thiophene-2-carboxamide
61 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiophene-2-carboxamide
62 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiophene-2-carboxamide 63  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiophene-2-carboxamide 64  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiazole-2-carboxamide 65  N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridin-3-yl)thiophene-2-carboxamide 66  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiophene-2-carboxamide 67  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiazole-2-carboxamide 68  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiazole-2-carboxamide 69  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiophene-2-carboxamide 70  3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridine 1-oxide 71  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-4-yl)thiophene-2-carboxamide 72  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methoxypyridazin-3-yl)thiophene-2-carboxamide 73  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-ethylpyridazin-3-yl)thiophene-2-carboxamide 74  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyclopropylpyridazin-3-yl)thiophene-2-carboxamide 75  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiazole-2-carboxamide 76  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfinyl)pyridazin-3-yl)thiophene-2-carboxamide 77  4-(2-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiazol-5-yl)-6-methylpyridazine 1-oxide 78  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfonyl)pyridazin-3-yl)thiophene-2-carboxamide 79  3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridazine 1-oxide 80  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-hydroxypyridazin-4-yl)thiophene-2-carboxamide 81  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,4-dimethylpyrimidin-5-yl)thiophene-2-carboxamide 82  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiazole-2-carboxamide 83  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-3-yl)thiophene-2-carboxamide 84  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(4-methylpyridazin-3-yl)thiophene-2-carboxamide 85  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-ethylpyridazin-4-yl)thiophene-2-carboxamide 86  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiophene-2-carboxamide 87  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiazole-2-carboxamide 88  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,5-dimethylpyridin-4-yl)thiophene-2-carboxamide 89  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3,6-dimethylpyridazin-4-yl)thiophene-2-carboxamide 90  N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-4-yl)thiophene-2-carboxamide optionally in the form of a single stereoisomer or a mixture of stereoisomers, in the form of the free compound and/or a physiologically acceptable salt or solvate thereof.

Compounds of general formula (I) are useful for the in vivo treatment or prevention of diseases in which participation of a cysteine protease is implicated.

Preferably, the compound of general formula (I) is a dual inhibitor of CatS and CatK (CatS/K inhibitors).

The term "dual for CatS and CatK" is to be understood that the inhibitor is a potent inhibitor of both CatS and CatK. Furthermore, preference may be given to compounds according to the invention that cause at least a 50% inhibition at a concentration of 3 µM in a functional enzyme assay for both CatS as well as CatK, preferably less than 1000 nM for both CatS and CatK, particularly preferably less than 300 nM for both CatS and CatK, most particularly preferably less than 100 nM for both CatS and CatK, even more preferably less than 75 nM for both CatS and CatK, additionally preferably less than 50 nM for both CatS and CatK, most preferably less than 10 nM for both CatS and CatK.

For these purposes functional enzyme assays using co-incubations of commercially available recombinant human cathepsines and respective fluorogenic substrates were conducted, as described hereinafter.

Preferably, the compounds according to present invention possess a balanced activity in both CatS enzyme assay and CatK enzyme assay. Preferably, the Ki values of CatK and CatS are in similar range. This is to be understood that the Ki(CatS)/Ki(CatK) is preferably close to 1. Preferably the difference in activity between CatS and CatK (or CatK and CatS respectively) is less than 50 fold (relating to Ki(CatS)/Ki(CatK)=0.02 to 50), preferably less than 20 fold (relating to Ki(CatS)/Ki(CatK)=0.05 to 20), more preferably less than 10 fold (relating to Ki(CatS)/Ki(CatK)=0.1 to 10), even more preferably less than 5 fold (relating to Ki(CatS)/Ki(CatK)=0.2 to 5) and most preferably less than 2 fold (relating to Ki(CatS)/Ki(CatK)=0.5 to 2).

Furthermore, preference may be given to compounds according to the invention that do not inhibit CatL significantly. This means that the compounds cause preferably less than 50% inhibition at a concentration of 31.6 µM in a functional CatL enzyme assay.

Additionally, the compounds according to present invention exhibit a significant selectivity for both CatS as well as CatK over CatL. Preferably, the compounds possess a selectivity to CatS and to CatK over CatL of at least 100

(Ki(CatL)/Ki(CatK)>100 and Ki(CatL)/Ki(CatS)>100), preferably of at least 250 (Ki(CatL)/Ki(CatK)>250 and Ki(CatL)/Ki(CatS)>250), more preferably of at least 500 (Ki(CatL)/Ki(CatK)>500 and Ki(CatL)/Ki(CatS)>500) and most preferably of at least 1000 (Ki(CatL)/Ki(CatK)>1000 and Ki(CatL)/Ki(CatS)>1000).

Furthermore, preference may be given to compounds according to the invention that do not inhibit CatB significantly. This means that the compounds cause preferably less than 50% inhibition at a concentration of 31.6 µM in a functional CatB enzyme assay. Additionally, the compounds according to present invention exhibit a significant selectivity for both CatS as well as CatK over CatB.

Preferably, the compounds possess a selectivity to CatS and to CatK over CatB of at least 100 (Ki(CatB)/Ki(CatK)>100 and Ki(CatB)/Ki(CatS)>100), preferably of at least 250 (Ki(CatB)/Ki(CatK)>250 and Ki(CatB)/Ki(CatS)>250), more preferably of at least 500 (Ki(CatB)/Ki(CatK)>500 and Ki(CatB)/Ki(CatS)>500) and most preferably of at least 1000 (Ki(CatB)/Ki(CatK)>1000 and Ki(CatB)/Ki(CatS)>1000).

The present invention further relates to a compound according to the present invention for modulation of both CatS and CatK, preferably for use in inhibition of CatS and CatK activity. The present invention therefore further relates to a compound according to the present invention for the prophylaxis and/or treatment of disorders and/or diseases which are mediated, at least in part, at least in part, by both CatS and CatK without the inhibition of CatL and/or CatB.

According to a further aspect of the invention, there is provided the use of a compound according to the present invention in the preparation of a medicament for preventing or treating diseases in which the disease pathology may be modified by inhibiting a CatS and/or CatK.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

In the normal physiological process certain cysteine proteases function in the protein degradation in animals, including humans, e.g. in the degradation of connective tissue. Elevated levels of these cysteine proteases in the body may result in pathological conditions leading to disease. CatS and CatK are believed to be involved in a variety of diseases or disorders in mammals such as humans. These include pain (in particular chronic pain, inflammatory pain, mixed pain), inflammatory diseases and bone/cartilage preservation disorders.

Particularly useful are dual CatS and CatK (CatS/K) inhibitors for the treatment of rheumatoid arthritis (RA), osteoarthritis (OA), chronic obstructive pulmonary disease (COPD), atherosclerosis and cardiovascular diseases which exhibit significant damage and remodeling of extracellular matrix (ECM) and chronic pain.

Another embodiment of the present invention is at least one compound according the present invention for the treatment and/or prophylaxis of one or more disorders selected from the group consisting of nociceptive pain, neuropathic pain; erosive osteoarthritis (EO), in particular erosive osteoarthritis of the hand; Sjögren's Syndrome; rheumatoid arthritis (RA); psoriatic arthritis (PsA), Psoriasis, Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopulation with osteoporosis; and asthma, in particular severe asthma subpopulation with osteoporosis.

Another embodiment of the present invention therefore relates to use of at least one compound according to the present invention for the preparation of a pharmaceutical composition for the treatment and/or prophylaxis of one or more disorders or diseases, particularly selected from the group consisting of nociceptive pain, neuropathic pain; erosive osteoarthritis (EO), in particular erosive osteoarthritis of the hand; Sjögren's Syndrome; rheumatoid arthritis (RA); psoriatic arthritis (PsA), Psoriasis, Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopulation with osteoporosis; and asthma, in particular severe asthma subpopulation with osteoporosis.

Another aspect of the present invention is a method of treatment and/or prophylaxis of disorders and/or diseases in a mammal, preferably of disorders and/or diseases selected from the group consisting of nociceptive pain; neuropathic pain; erosive osteoarthritis (EO), in particular erosive osteoarthritis of the hand; Sjögren's Syndrome; rheumatoid arthritis (RA); psoriatic arthritis (PsA); Psoriasis; Spondylarthritis, in particular ankylosing spondylitis; osteoporosis; Complex Regional Pain Syndrome (in particular CRPS I); Lupus erythematodes (SLE); Lupus nephritis; asthma; multiple sclerosis (MS); diabetes; chronic obstructive pulmonary disease (COPD), in particular COPD subpopulation with osteoporosis; and asthma, in particular severe asthma subpopulation with osteoporosis.

All preferred embodiments of the first aspect of the invention are preferred vice versa for the other aspects and embodiments.

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

All reactions were conducted under nitrogen unless stated otherwise and monitored by TLC on silica gel coated glass plates or aluminium sheets. Flash column chromatography was performed on pre-packed silica gel columns (GraceResolve™) using the indicated solvents mixtures. All solvents were used without prior drying. Dry solvents were dried on molecular sieves (4 A).

The NMR spectra were determined in DMSO-$d_6$ solutions, using a Bruker 400-UltraShield. Spectra are reported in □ units (ppm) and J values (Hz) with Me$_4$Si as the internal standard.

Acid HPLC analyses were conducted using an Agilent system, column: Waters XSelect (C18, 50×2.1 mm, 3.5μ), flow: 0.8 ml/min, column temp: 35° C., Eluent A: 0.1% Formic acid in acetonitrile, Eluent B: 0.1% Formic acid in water, lin. gradient: t=0 min 2% A, t=3.5 min 98% A, t=6 min 98% A, detection: DAD (220-320 nm), detection: MSD (ESI pos/neg) mass range: 100-800.

Basic HPLC analyses were conducted using an Agilent system, column: Waters XSelect (C18, 50×2.1 mm, 3.5μ), flow: 0.8 ml/min, column temp: 35° C., Eluent A: 95% acetonitrile+5% 10 mM NH$_4$HCO$_3$ in water, Eluent B: 10 mM NH$_4$HCO$_3$ in water (pH=9.0), lin. gradient: t=0 min 2% A, t=3.5 min 98% A, t=6 min 98% A, detection: DAD (220-320 nm), detection: MSD (ESI pos/neg) mass range: 100-800.

The indication "equivalents" ("eq." or "eq" or "equiv.") means molar equivalents, "RT" or "rt" means RTT (23±7° C.), "M" are indications of concentration in mol/l, "aq." means aqueous, "sat." means saturated, "sol." means solution, "conc." means concentrated. The mixing ratios of solvents are usually stated in the volume/volume ratio.

Further Abbreviations:

CC=column chromatography; d=day(s); DME=1,2-dimethoxyethane; DCM=dichloromethane; DMF=N,N-Dimethylformamide; DMP=Dess-Martin periodinane; EDCl: N-(3-dimethylaminopropyl)-N'-ethylcarbodiimide hydrochloride; Et$_2$O=diethyl ether; EtOAc=ethyl acetate; FC=flash chromatography; h=hour(s); HOAt=1-hydroxy-7-azabenzotriazole; LDA=Lithium diisopropylamide; MeCN=acetonitrile; MeOH=methanol; PdCl$_2$(dppf)=1,1'-bis(diphenylphosphino)ferrocene]palladium(II) dichloride; RM=reaction mixture; RT=room temperature; NEt$_3$=triethylamine; T3P=propylphosphonic anhydride; TFA=trifluoroacetic acid; THF=tetrahydrofuran.

INT-1 was prepared analogously to synthetic methods known from WO2009112839.

Example 1

N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiophene-2-carboxamide

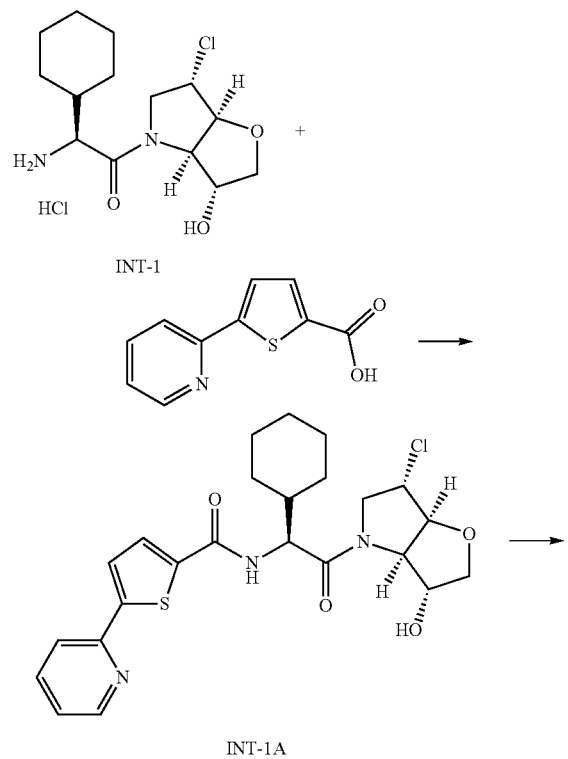

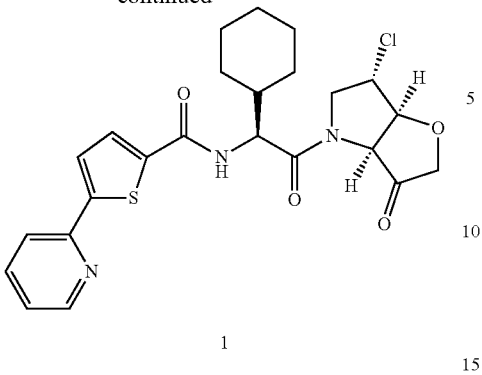

1 i) A suspension of INT-1 (0.25 g, 0.73 mmol), 5-(pyridin-2-yl)thiophene-2-carboxylic acid (0.18 g, 0.88 mmol), propylphosphonic anhydride (50% (w/w) in DMF, 0.68 mL, 1.10 mmol) and NEt$_3$ (0.37 g, 3.68 mmol, 0.51 mL) in DMF (5 mL) was stirred at RT for 18 h. The RM was diluted with aqueous saturated NaHCO$_3$ (10 mL) and extracted with EtOAc (3×10 mL). The combined organic layer was washed with brine (20 mL), dried over Na$_2$SO$_4$ and concentrated in vacuo. FC (EtOAc/heptane 0:1→1:0) afforded INT-1A (0.22 g, 0.45 mmol, 61%). LCMS: calc. for [M+H]$^+$=490.15, found 490.0.

ii) DMP (0.38 g, 0.90 mmol) was added to a solution of INT-1A (0.22 g, 0.45 mmol) in DCM (20 mL). The RM was stirred at RT for 4 h. An aqueous solution of Na$_2$S$_2$O$_3$ (10%, 50 mL) was added and the RM was stirred vigorously for 30 min. The layers were separated and the aqueous layer was extracted with DCM (3×20 mL). The combined organic layer was washed with brine (20 mL), dried over Na$_2$SO$_4$ and concentrated in vacuo. FC (EtOAc/heptane 0:1→1:0) and lyophilisation (MeCN/H$_2$O) afforded compound 1 (0.20 g, 0.41 mmol, 91%). LCMS: calc. for [M+H]$^+$=488.13, found 488.0. $^1$H NMR (400 MHz, DMSO-d$_6$) as a RM of hydrates and rotamers δ 8.89 (d, J=8.2 Hz, 0.38H), 8.77-8.72 (m, 0.53H), 8.56-8.55 (m, 1H), 8.10-8.09 (m, 0.47H), 8.00-7.95 (m, 1.62H), 7.90-7.79 (m, 2H), 7.36-7.32 (m, 1H), 6.76 (s, 0.36H), 6.46 (s, 0.19H), 6.39 (s, 0.36H), 5.83 (s, 0.19H), 5.08-3.49 (m, 8H), 1.99-1.53 (m, 6H), 1.23-0.91 (m, 5H) ppm.

Example 2

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridin-3-yl)thiophene-2-carboxamide

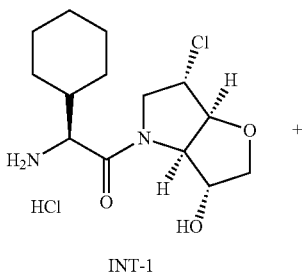

INT-1

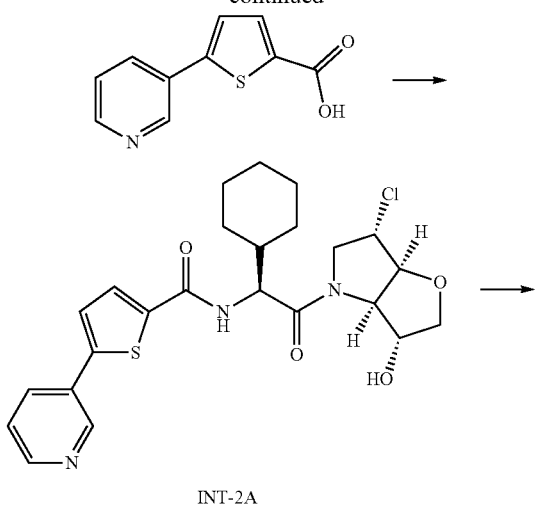

INT-2A

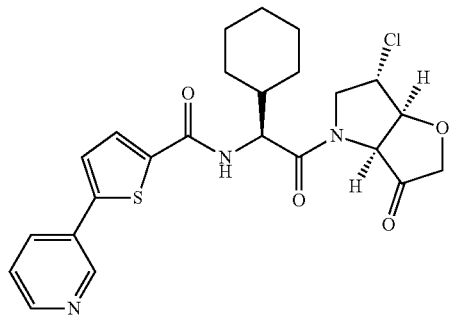

2 i) A suspension of INT-1 (0.30 g, 0.99 mmol), 5-(pyridin-3-yl)thiophene-2-carboxylic acid (0.24 g, 1.19 mmol), propylphosphonic anhydride (50% (w/w) in DMF, 0.85 mL, 1.38 mmol) and NEt$_3$ (0.50 g, 4.95 mmol, 0.68 mL) in DMF (5 mL) was stirred at RT for 48 h. The RM was diluted with aqueous saturated NaHCO$_3$ (10 mL) and extracted with EtOAc (3×10 mL). The combined organic layer was washed with brine (20 mL), dried over Na$_2$SO$_4$ and concentrated in vacuo. FC (MeOH/DCM 0:1→7:93) afforded INT-2A (0.33 g, 0.67 mmol, 68%). LCMS: calc. for [M+H]$^+$=490.15, found 490.2.

ii) DMP (0.66 g, 1.57 mmol) was added to a solution of INT-2A (0.35 g, 0.71 mmol) in DCM (20 mL). The RM was stirred at RT for 5 h. An aqueous solution of Na$_2$S$_2$O$_3$ (10%, 50 mL) was added and the RM was stirred vigorously for 30 min. The layers were separated and the aqueous layer was extracted with DCM (3×20 mL). The combined organic layer was washed with brine (20 mL), dried over Na$_2$SO$_4$ and concentrated in vacuo. FC (EtOAc/heptane 0:1→1:0) and lyophilisation (MeCN/H$_2$O) afforded compound 2 (0.14 g, 0.28 mmol, 40%). LCMS: calc. for [M+H]$^+$=488.13, found 488.2. $^1$H NMR (400 MHz, DMSO-d$_6$) as a RM of hydrates and rotamers δ 8.96-8.94 (m, 1.30H), 8.83-8.78 (m, 0.60H), 8.57-8.54 (m, 1H), 8.19-8.01 (m, 2.10H), 7.70-7.65 (m, 1H), 7.50-7.45 (m, 1H), 6.73 (s, 0.30H), 6.46 (s, 0.16H), 6.34 (s, 0.30H), 5.83 (s, 0.16H), 5.06-3.49 (m, 8H), 1.95-1.51 (m, 6H), 1.23-0.90 (m, 5H) ppm.

Example 3

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridin-4-yl)thiophene-2-carboxamide (3)

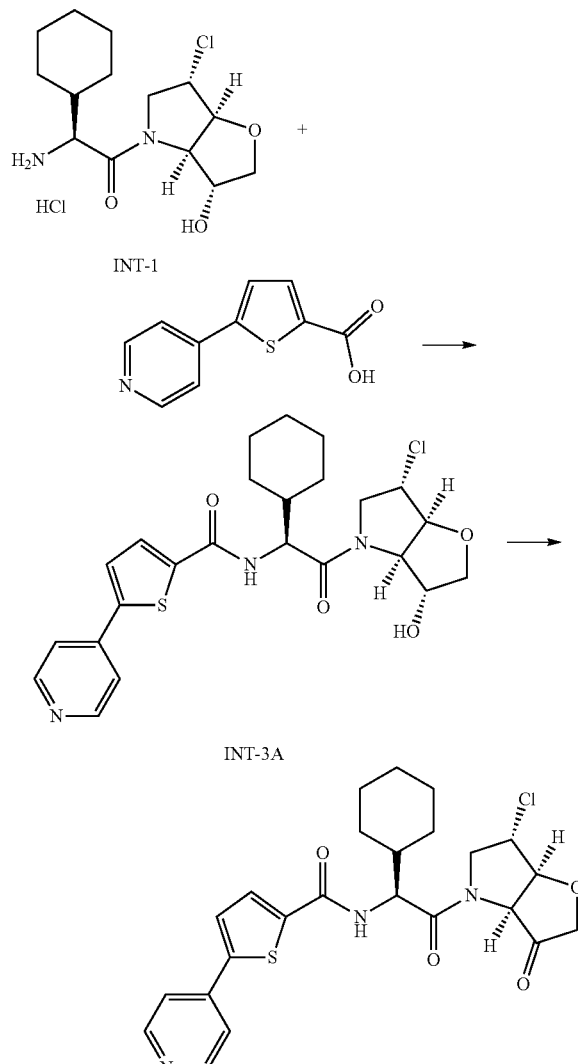

i) A suspension of INT-1 (0.30 g, 0.99 mmol), 5-(pyridin-4-yl)thiophene-2-carboxylic acid (0.24 g, 1.18 mmol), propylphosphonic anhydride (50% (w/w) in DMF, 0.85 mL, 1.38 mmol) and NEt$_3$ (0.50 g, 4.95 mmol, 0.68 mL) in DMF (5 mL) was stirred at RT for 48 h. The RM was diluted with aqueous saturated NaHCO$_3$ (10 mL) and extracted with EtOAc (3×10 mL). The combined organic layer was washed with brine (20 mL), dried over Na$_2$SO$_4$ and concentrated in vacuo. FC (MeOH/DCM 0:1→1:10) afforded INT-3A (0.35 g, 0.71 mmol, 72%). LCMS: calc. for [M+H]$^+$=490.15, found 490.2.

ii) DMP (0.66 g, 1.57 mmol) was added to a solution of INT-3A (0.35 g, 0.71 mmol) in DCM (20 mL). The RM was stirred at RT for 5 h. An aqueous solution of Na$_2$S$_2$O$_3$ (10%, 50 mL) was added and the RM was stirred vigorously for 30 min. The layers were separated and the aqueous layer was extracted with DCM (3×20 mL). The combined organic layer was washed with brine (20 mL), dried over Na$_2$SO$_4$ and concentrated in vacuo. FC (MeCN/DCM 1:4) and lyophilisation (MeCN/H$_2$O) afforded compound 3 (0.25 g, 0.51 mmol, 72%). LCMS: calc. for [M+H]$^+$=488.13, found 488.2. $^1$H NMR (400 MHz, DMSO-d$_6$) as a RM of hydrates and rotamers δ 8.90-8.88 (d, 0.4H), 8.77-8.72 (m, 0.5H), 8.56-8.55 (m, 1.0H), 8.10-8.09 (m, 0.5H), 8.00-7.95 (m, 1.6H), 7.90-7.79 (m, 2H), 7.36-7.32 (m, 1H), 6.76 (s, 0.37H), 6.46 (s, 0.22H), 6.39 (s, 0.37H), 5.83 (s, 0.22H), 5.08-3.49 (m, 8H), 1.99-1.53 (m, 6H), 1.23-0.91 (m, 5H) ppm.

Example 4

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrazin-2-yl)thiophene-2-carboxamide

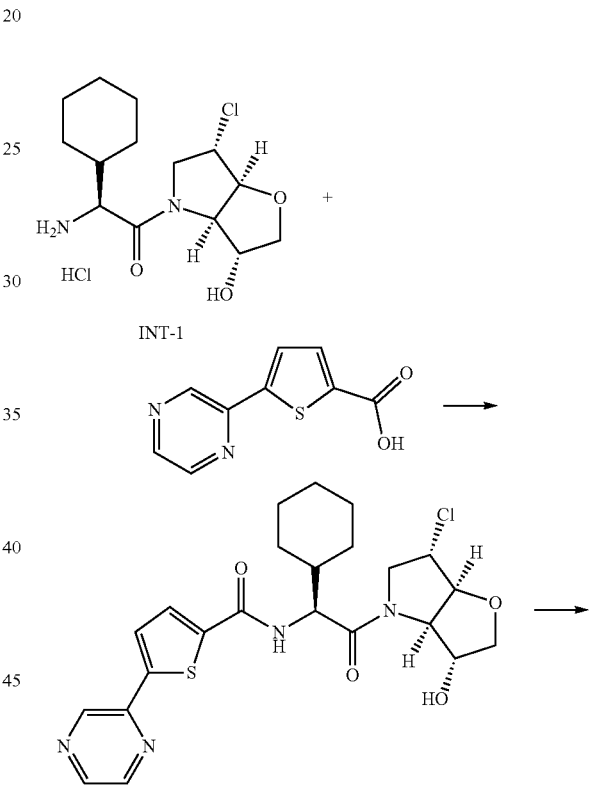

i) A suspension of INT-1 (0.30 g, 0.99 mmol), 5-(pyrazin-2-yl)thiophene-2-carboxylic acid hydrochloride (0.22 g, 0.89 mmol), propylphosphonic anhydride (50% (w/w) in DMF, 0.73 mL, 1.19 mmol) and NEt₃ (0.50 g, 4.95 mmol, 0.68 mL) in DMF (5 mL) was stirred at RT for 48 h. The RM was diluted with aqueous saturated NaHCO₃ (10 mL) and extracted with EtOAc (3×10 mL). The combined organic layer was washed with brine (20 mL), dried over Na₂SO₄ and concentrated in vacuo. FC (EtOAc/heptane 0:1→1:0) afforded INT-4A (0.33 g, 0.67 mmol, 68%). LCMS: calc. for [M+H]$^+$=491.14, found 491.1.

ii) DMP (0.66 g, 1.57 mmol) was added to a solution of INT-4A (0.35 g, 0.71 mmol) in DCM (20 mL). The RM was stirred at RT for 5 h. An aqueous solution of Na₂S₂O₃ (10%, 50 mL) was added and the RM was stirred vigorously for 30 min. The layers were separated and the aqueous layer was extracted with DCM (3×20 mL). The combined organic layer was washed with brine (20 mL), dried over Na₂SO₄ and concentrated in vacuo. FC (EtOAc/heptane 0:1→1:0) and lyophilisation (MeCN/H₂O) afforded compound 4 (200 g, 0.41 mmol, 57%). LCMS: calc. for [M+H]$^+$=489.13, found 489.2. ¹H NMR (400 MHz, DMSO-d₆) as a RM of hydrates and rotamers δ 9.29 (d, J=10.8 Hz, 1H), 8.98 (d, J=8.2 Hz, 0.44H), 8.86-8.82 (m, 0.51H), 8.64-8.57 (m, 2H), 8.21 (d, J=8.2, 0.05H), 8.16 (d, J=4.0 Hz, 0.43H), 8.03-7.97 (m, 1.57H), 6.75 (s, 0.42H), 6.46 (s, 0.23H), 6.35 (s, 0.42 Hz), 5.83 (s, 0.23H), 5.08-3.49 (m, 8H), 1.99-1.51 (m, 6H), 1.23-0.90 (m, 5H) ppm.

Example 5

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-5-yl)thiophene-2-carboxamide (5)

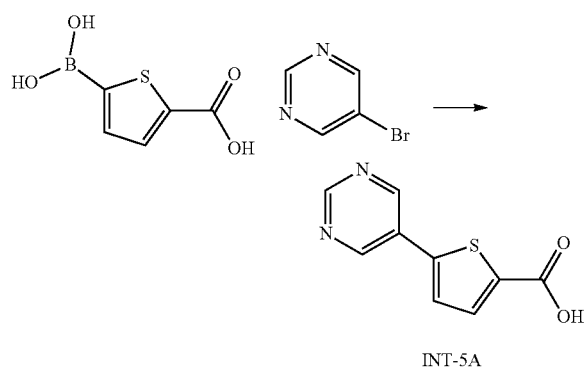

A suspension of 5-boronothiophene-2-carboxylic acid (2.00 g, 11.63 mmol), potassium carbonate (1.46 g, 10.6 mmol) and 5-bromopyrimidine (1.68 g, 10.57 mmol) in DME (80 mL) and water (20 mL) was degassed with Ar and tetrakis(triphenylphosphine)palladium(0) (0.611 g, 0.529 mmol) and stirred for 16 h at 100° C. The reaction RM was poured into H₂O (150 mL) and washed with EtOAc (150 mL). The aqueous phase was acidified with aqueous 1M HCl until pH 3-4 and extracted with EtOAc (3×200 mL). The three last organic layers were combined, washed with brine, dried with Na₂SO₄ and concentrated in vacuo. Trituration with Et₂O and filtration afforded INT-5A (1.69 g, 7.79 mmol, 74%) as an off white solid. LCMS: calc. for [M+H]$^+$= 207.01, found 207.2.

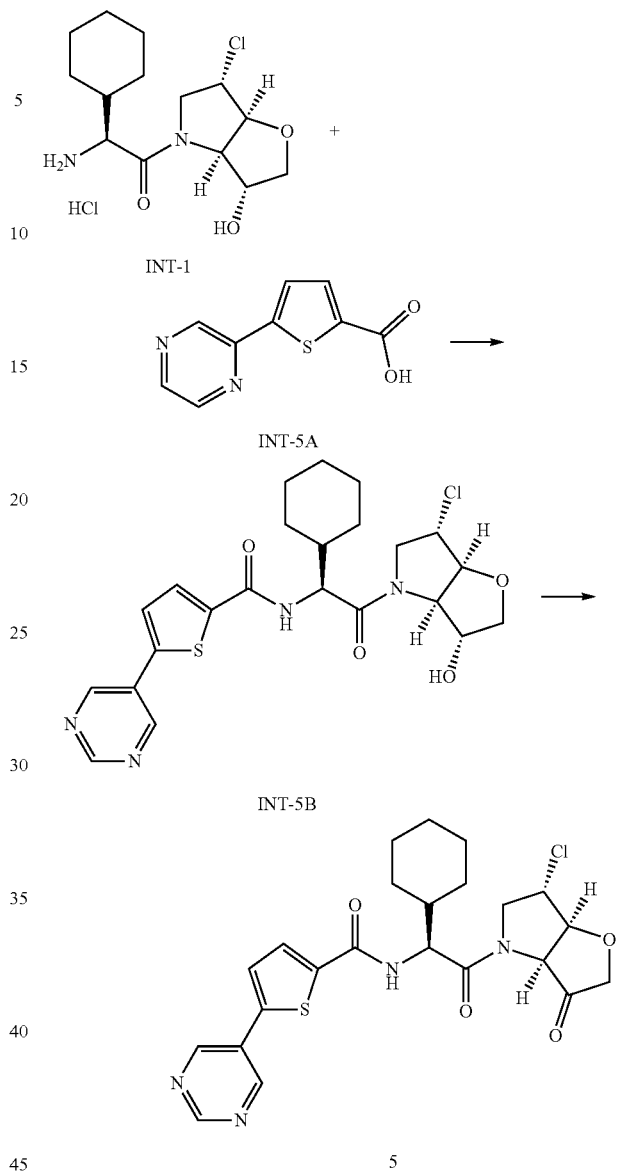

i) A suspension of INT-1 (0.300 g, 0.884 mmol), INT-5A (0.182 g, 0.884 mmol), propylphosphonic anhydride (50% (w/w) solution in DMF) 0.844 g, 1.33 mmol, 0.744 mL), NEt₃ (0.447 g, 4.42 mmol, 0.616 mL) in dry DMF (5 mL) was stirred at RT for 16 h. The reaction RM was diluted with EtOAc (5 mL) and poured in an aqueous saturated solution of NaHCO₃ (15 mL). The aqueous layer was extracted with EtOAc (10 mL). The organic layer was washed with brine (5×10 mL), dried over Na₂SO₄ and concentrated in vacuo. The crude product was purified by FC (EtOAc) to afford INT-5B (0.430 g, 0.832 mmol, 94%) as a colorless oil. LCMS: calc. for [M+H]$^+$=491.14, found 491.2.

ii) DMP (0.411 g, 0.969 mmol) was added to a solution of INT-5B (0.238 g, 0.485 mmol) in DCM (5 mL). The RM was stirred at RT overnight. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. FC (EtOAc/heptane 0:1→1:0) and lyophilisation (MeCN/H₂O) afforded 5 (0.131 g, 0.225 mmol, 53%). LCMS: calc. for [M+H]⁺=430.15, found 430.2. ¹H NMR (400 MHz, DMSO-d₆) as a RM of hydrates and rotamers δ 9.23-9.13 (m, 3H), 9.00 (d, J=8.3 Hz, 0.5H), 8.92-8.82 (m, 0.5H), 8.25 (d, J=8.2 Hz, 0.04H), 8.18 (d, J=4.0 Hz, 0.42H), 8.09-8.02 (m, 0.64H), 7.81 (d, J=4.0 Hz, 0.5H), 7.79-7.74 (m, 0.5H), 6.72 (s, 0.42H), 6.46 (s, 0.24H), 6.32 (s, 0.42H), 5.83 (s, 0.24H), 5.11-3.45 (m, 8H), 2.01-1.47 (m, 6H), 1.38-0.89 (m, 5H) ppm.

Example 6

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-3-yl)thiophene-2-carboxamide

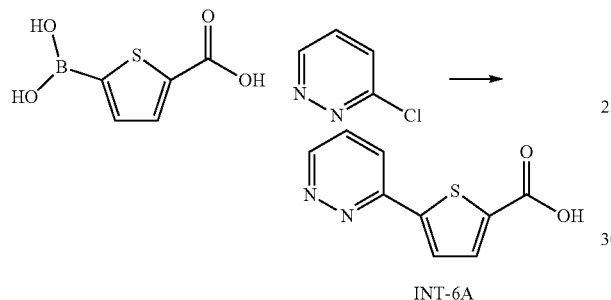

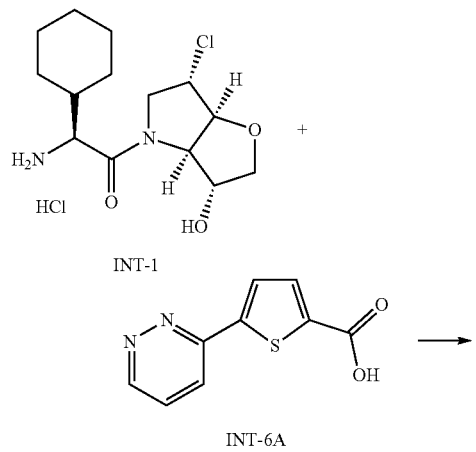

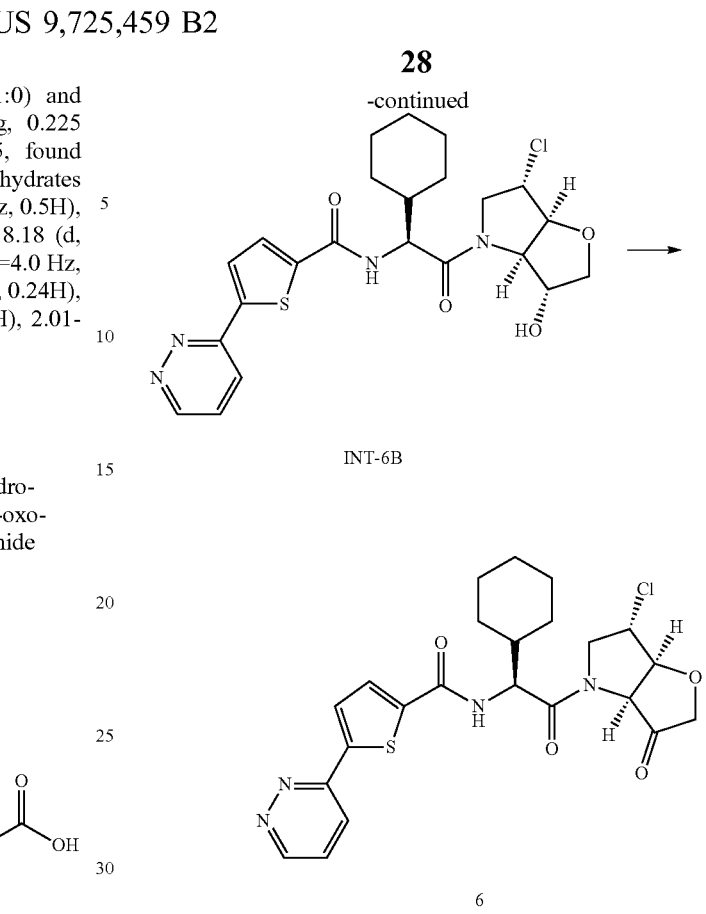

5-Boronothiophene-2-carboxylic acid (1.51 g, 8.79 mmol), 3-chloropyridazine (0.915 g, 7.99 mmol) and K₂CO₃ (1.10 g, 7.99 mmol) were mixed in DME (40 mL) and water (10 mL) and degassed with Ar. Tetrakis(triphenylphosphine)palladium(0) (0.462 g, 0.399 mmol) was added and the RM was stirred at 100° C. for 16 h. The reaction RM was poured into water (300 mL) and washed with EtOAc (300 mL). The aqueous phase was acidified with aqueous 1 M HCl to pH 3-4. The aquous layer was concentrated in vacuo and redissolved in 2 mL H₂O. The solid was filtered off and washed with Et₂O yielding INT-6A (0.390 g, 1.80 mmol, 22%). LCMS: calc. for [M+H]⁺=207.01, found 207.0.

i) A suspension of INT-1 (0.300 g, 0.884 mmol), INT-6A (0.182 g, 0.884 mmol), EDCl (0.203 g, 1.06 mmol), NEt₃ (0.179 g, 1.77 mmol, 0.247 mL) and HOAt (0.024 g, 0.18 mmol) in DMF (5 mL) was stirred at RT for 16 h. The RM was diluted with EtOAc (30 mL) and washed with aqueous 0.5 M KHSO₄ (30 mL). The layers were separated and the organic layer was washed with aqueous saturated NaHCO₃ (30 mL). The aqueous layer was extracted with EtOAc (2×30 mL). The combined organic layer was washed with brine (30 mL), dried over Na₂SO₄ and concentrated in vacuo. FC (EtOAc/heptane 0:1→1:0, 12 g silica) afforded INT-6B (0.400 g, 0.770 mmol, 88%). LCMS: calc. for [M+H]⁺=491.14, found 491.2.

ii) DMP (0.691 g, 1.63 mmol) was added to a solution of INT-6B (0.400 g, 0.815 mmol) in CH₂Cl₂ (5 mL). The RM was stirred at RT for 16 h. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with CH₂Cl₂ (2×10 mL). The combined organic layer was dried over Na₂SO₄, filtered and concentrated in vacuo. FC (EtOAc/heptane 0:1→1:0, 12 g silica) and lyophilisation (MeCN/H₂O) afforded 6 (0.148 g, 0.288 mmol, 35%). LCMS: calc. for [M+H]⁺=489.13, found 489.2. ¹H NMR (400 MHz, DMSO-d₆) as a RM of hydrates and rotamers δ 9.23-9.11 (m, 1H), 9.04-8.81 (m, 1H), 8.36-8.20 (m, 1H), 8.19-7.91 (m, 2H), 7.85-7.74 (m, 1H), 6.76 (s, 0.18H), 6.47 (s, 0.09H), 6.37 (s, 0.18H), 5.83 (s, 0.09H), 5.13-3.46 (m, 8H), 2.03-1.48 (m, 6H), 1.29-0.86 (m, 5H) ppm.

Example 7

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-4-yl)thiophene-2-carboxamide

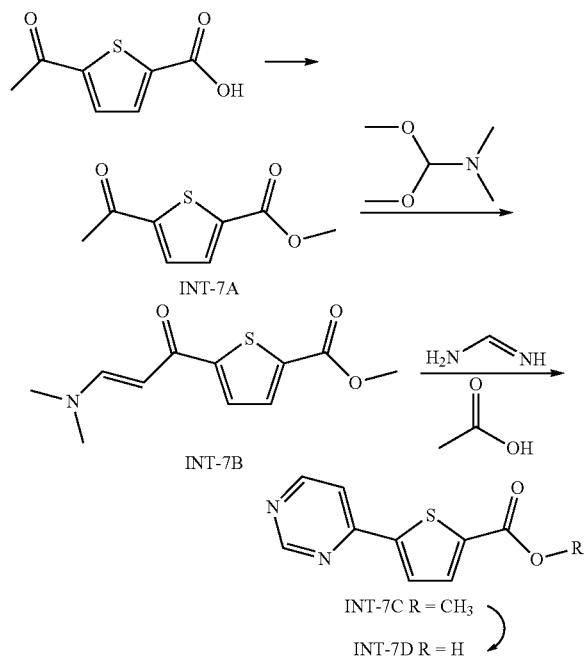

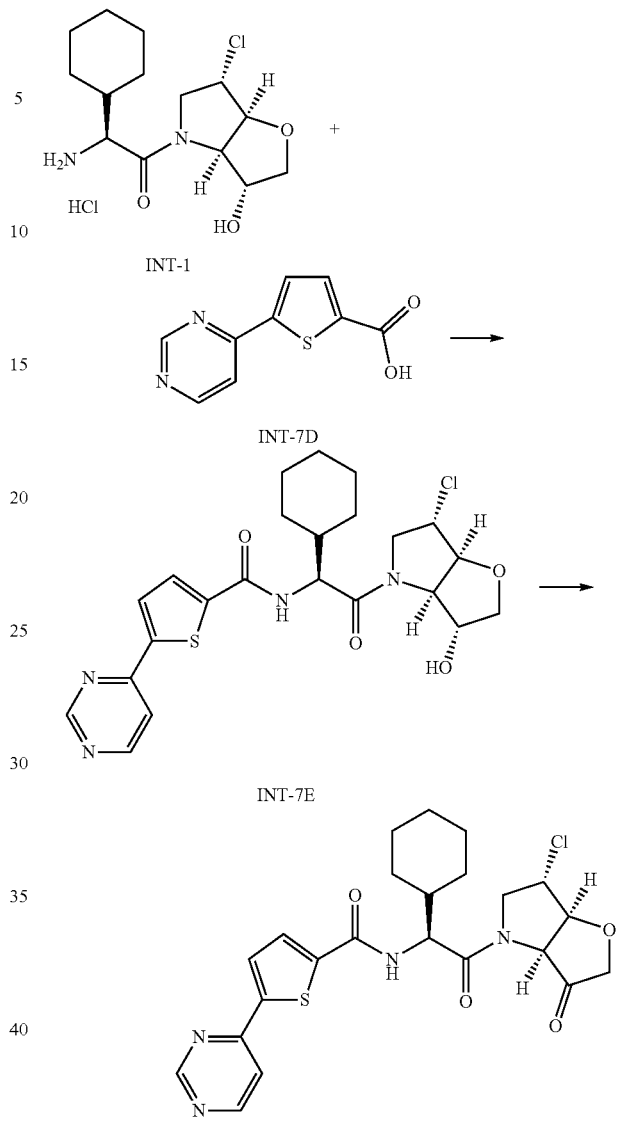

i) To a solution of 5-acetylthiophene-2-carboxylic acid (5.00 g, 29.4 mmol) in dry DMF (24 mL) were added $K_2CO_3$ (12.2 g, 88.0 mmol) and iodomethane (5.00 g, 35.3 mmol, 2.20 ml) and the RM was stirred at RT for 72 h. Upon completion the RM was acidified with 1M HCl (50 mL) and extracted with EtOAc (3×20 mL). The combined organic layers were washed with aqueous saturated solution of $NaHCO_3$ (20 mL), dried with $Na_2SO_4$, filtered and concentrated in vacuo. Trituration with diethyl ether and filtration afforded INT-7A (4.11 g, 21.2 mmol, 72%) as a brown solid. LCMS: calc. for $[M+H]^+$=185.02, found 185.2.

ii) A RM of INT-7A (3.03 g, 16.5 mmol) and DMF-dimethyl acetal (7.85 g, 65.8 mmol, 8.75 mL) was stirred at 75° C. for 16 h. Upon completion the RM was concentrated in vacuo. Trituration with $Et_2O$ and filtering afforded INT-7B (3.58 g, 14.2 mmol, 86%) as a light brown solid. LCMS: calc. for $[M+H]^+$=240.06, found 240.2.

iii) A RM of INT-7B (3.58 g, 15.0 mmol) and formamidine acetate (9.35 g, 90.0 mmol) was heated to 200° C. for 4 hour. The RM was cooled to RT and EtOAc (50 mL) and brine (50 mL) were added. The organic phase was separated, dried with $Na_2SO_4$ and concentrated in vacuo. Crystallization from EtOH and filtration afforded INT-7C (1.01 g, 3.53 mmol, 24%) as a cream brown solid. LCMS: calc. for $[M+H]^+$=221.03, found 221.0.

iv) To a RM of INT-7C (1.01 g, 4.59 mmol) in THF (20 mL) and water (20 mL) was added $LiOH \cdot H_2O$ (0.580 g, 13.8 mmol). The RM was stirred at RT for 16 h. The RM was diluted with aqueous 1 M HCl until acidic. The water layer was extracted with EtOAc (3×40 mL). The aqueous layer was concentrated in vacuo and the solids redissolved in 2 mL $H_2O$ and filtered off to give INT-7D (0.875 g, 3.82 mmol, 83%) as an off-white solid. LCMS: calc. for $[M+H]^+$=207.01, found 207.0.

i) A suspension of INT-1 (0.300 g, 0.884 mmol), INT-7D (0.182 g, 0.884 mmol), EDCl (0.203 g, 1.06 mmol), $NEt_3$ (0.179 g, 1.77 mmol, 0.247 mL) and HOAt (0.025 g, 0.18 mmol) in DMF (5 mL) was stirred at RT for 16 h. The RM was diluted with EtOAc (30 mL) and washed with aqueous 0.5 N $KHSO_4$ (30 mL), aqueous saturated solution of $NaHCO_3$ (30 mL) and brine (30 mL). The combined organic layer was dried over $Na_2SO_4$ and concentrated in vacuo. Reversed phase chromatography ($MeCN/H_2O$ (+0.1% HCOOH) 1:19→1:0) afforded INT-7E (0.285 g, 0.551 mmol, 62%). LCMS: calc. for $[M+H]^+$=491.14, found 491.2.

ii) DMP (0.492 g, 1.16 mmol) was added to a solution of INT-7E (0.285 g, 0.580 mmol) in DCM (5 mL). The RM was stirred at RT for 16 h. An aqueous solution of $Na_2S_2O_3$ (10%, 5 mL) was added and the RM was stirred vigorously for 30 min. An aqueous saturated solution of $NaHCO_3$ (10 mL) was added and the layers were separated. The aqueous layer was extracted with DCM (2×10 mL). The combined organic layer was dried over $Na_2SO_4$ and concentrated in vacuo. Reversed phase chromatography (MeCN/H₂O (+0.1% HCOOH) 1:19→1:0) followed by basic preparative HPLC (C18, MeCN (1% 10 mM NH₄HCO₃), 10 mM NH₄HCO₃ in H₂O) and lyophilization afforded 7 (0.108 g, 0.210 mmol, 36%). LCMS: calc. for [M+H]⁺=489.13, found 489.2. ¹H NMR (400 MHz, DMSO-d₆) as a RM of hydrates and rotamers δ 9.25-9.11 (m, 1H), 9.02 (d, J=8.2 Hz, 0.2H), 8.99-8.77 (m, 1.8H), 8.28 (d, J=7.8 Hz, 0.1H), 8.23-7.98 (m, 2.9H), 6.77 (s, 0.18H), 6.50 (s, 0.1H), 6.34 (s, 0.18H), 5.86 (s, 0.1H), 5.17-3.45 (m, 8H), 2.04-1.48 (m, 6H), 1.35-0.90 (m, 5H) ppm.

Example 8

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-4-yl)thiophene-2-carboxamide (8)

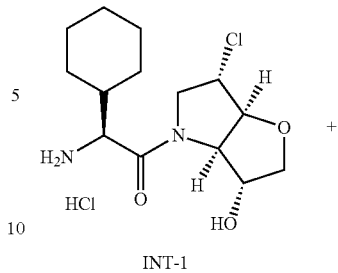

INT-1

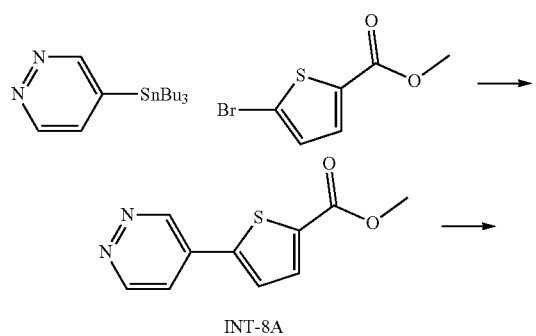

INT-8A

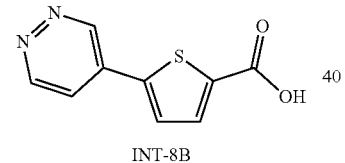

INT-8B

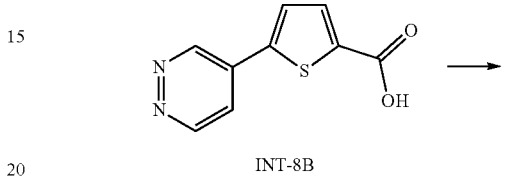

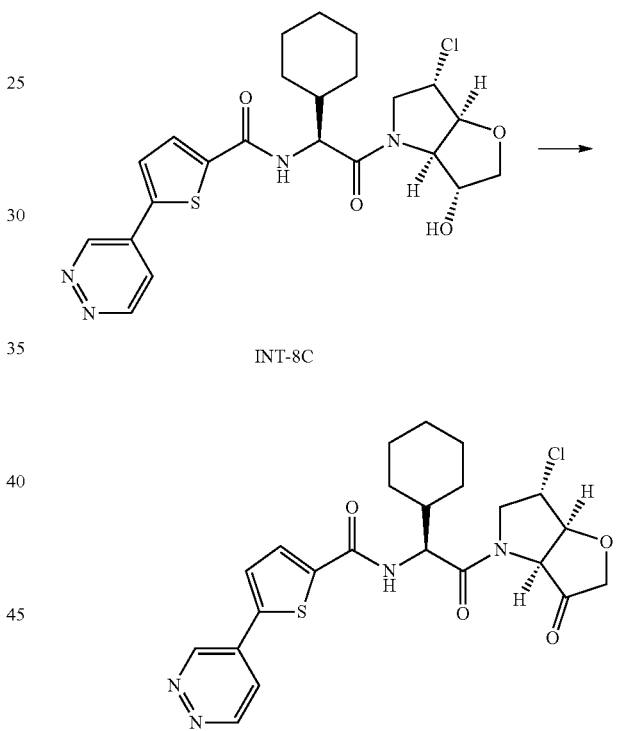

8 i) A RM of the methyl 5-bromothiophene-2-carboxylate (0.350 g, 1.58 mmol), CsF (0.480 g, 3.16 mmol) and the 4-(tributylstannyl)pyridazine (0.642 g, 1.74 mmol) was dissolved in DMF (4 mL). Tetrakis(triphenylphosphine)palladium(0) (0.183 g, 0.158 mmol) and CuI (0.060 g, 0.32 mmol) were added and the RM was degassed with Ar. The RM was stirred at 80° C. for 2 h and diluted with DCM (50 mL) and H₂O (20 mL). The organic layer was dried with Na₂SO₄ and filtered through celite. The filtercake was washed with DCM/EtOAc (100 mL, 1:1). The RM was concentrated in vacuo and the residue triturated with Et₂O. The solvent was filtered off affording INT-8A (0.396 g, 1.71 mmol, quantitative yield) as a white solid. LCMS: calc. for [M+H]⁺=221.03, found 221.0.

ii) To a RM of INT-8A (0.396 g, 1.80 mmol) in THF (20 mL) and water (20 mL) was added LiOH.H₂O (0.226 g, 5.39 mmol). The reaction RM was stirred at RT for 16 h. The RM was concentrated in vacuo. Reversed phase chromatography (MeCN/H₂O (+0.1% HCOOH) 1:19→1:0) afforded INT-8B (0.465 g, 2.08 mmol, quantitative yield) as an off white solid. LCMS: calc. for [M+H]⁺=207.01, found 207.0.

i) A suspension of INT-1 (0.320 g, 0.943 mmol), INT-8B (0.200 g, 0.943 mmol), EDCl (0.217 g, 1.13 mmol), NEt₃ (0.191 g, 1.89 mmol, 0.263 mL) and HOAt (0.026 g, 0.19 mmol) in DMF (5 mL) was stirred at RT for 16 h. The RM was diluted with EtOAc (30 mL) and washed with aqueous 0.5 N KHSO₄ (30 mL), aqueous saturated solution of NaHCO₃ (30 mL) and brine (30 mL). The combined organic layer was dried over Na₂SO₄ and concentrated in vacuo. Reversed phase chromatography (MeCN/H₂O (+0.1% HCOOH) 1:19→1:0) afforded INT-8C (0.110 g, 0.213 mmol, 23%). LCMS: calc. for [M+H]⁺=491.14, found 491.2.

ii) DMP (0.190 g, 0.449 mmol) was added to a solution of INT-8C (0.110 g, 0.224 mmol) in DCM (5 mL). The RM was stirred at RT for 16 h. An aqueous solution Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. Reversed phase chromatography (MeCN/H₂O (+0.1% HCOOH) 1:19→1:0) and lyophilisation afforded 8 (0.052 g, 0.10 mmol, 45%). LCMS: calc. for [M+H]⁺=489.13, found 489.2. ¹H NMR (400 MHz, DMSO-d₆) as a RM of hydrates and rotamers δ 9.76-9.54 (m, 1H), 9.30-9.21 (m, 1H), 9.11-9.02 (m, 0.5H), 8.99-8.89 (m, 0.46H), 8.38-8.30 (m, 0.04H), 8.23-8.17 (m, 0.5H), 8.13-8.06 (m, 0.5H), 8.05-7.92 (m, 2H), 6.73 (s, 0.51H), 6.48 (s, 0.32H), 6.30 (s, 0.51H), 5.84 (s, 0.32H), 5.15-3.20 (m, 8H), 2.10-1.46 (m, 6H), 1.35-0.84 (m, 5H) ppm.

Example 9

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-2-yl)thiophene-2-carboxamide

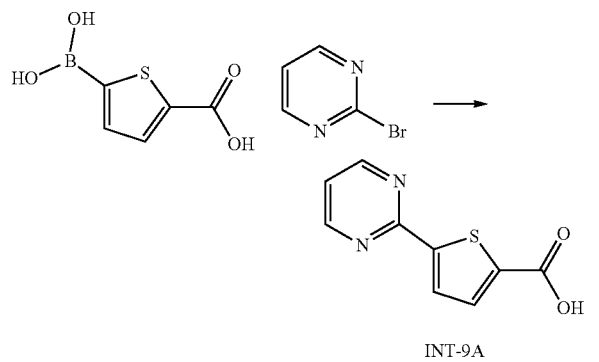

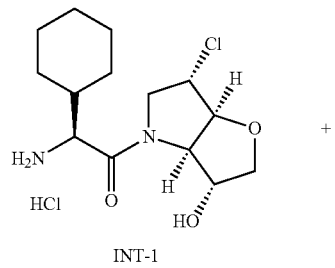

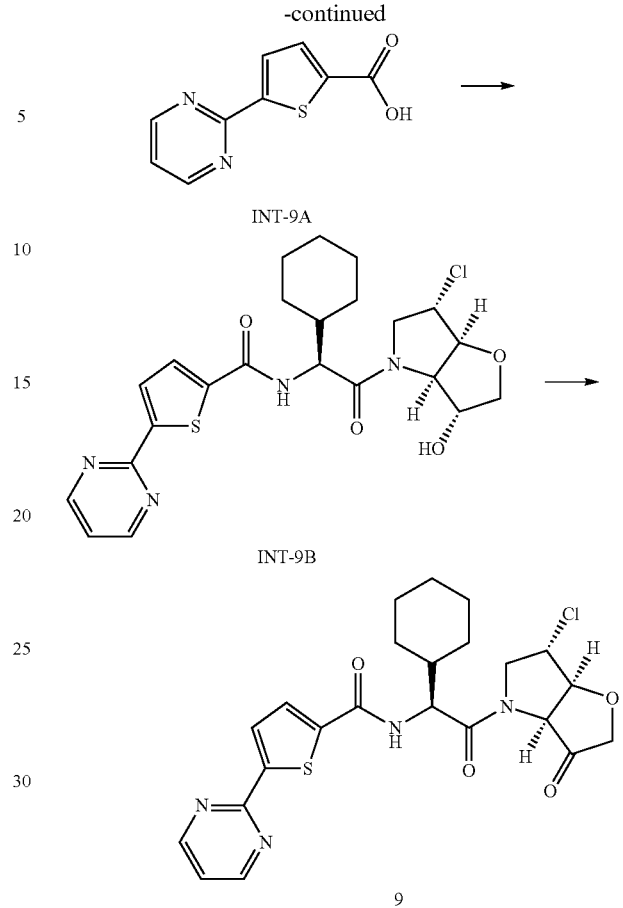

2-Bromopyrimidine (1.05 g, 6.60 mmol), 5-boronothiophene-2-carboxylic acid (1.25 g, 7.26 mmol) and K₂CO₃ (0.913 g, 6.60 mmol) were mixed in DME (40 mL) and water (10 mL) and degassed with Ar. Then tetrakis(triphenylphosphine)palladium(0) (0.382 g, 0.330 mmol) was added and the RM was stirred at 100° C. for 16 h. Upon completion the reaction RM was poured into H₂O (150 mL) and washed with EtOAc (150 mL). The aqueous phase was acidified with aqueous 1M HCl until pH 2-3 and extracted with EtOAc (3×200 mL). The three last organic layers were combined, washed with brine, dried with Na₂SO₄ and concentrated in vacuo. Trituration with Et₂O and filtering afforded INT-9A (0.109 g, 0.502 mmol, 7%) as a white solid. LCMS: calc. for [M+H]⁺=207.01, found 207.2.

i) A suspension of INT-1 (0.179 g, 0.529 mmol), INT-9A (0.109 g, 0.529 mmol), EDCl (0.122 g, 0.634 mmol), NEt₃ (0.107 g, 1.06 mmol, 0.147 mL) and HOAt (0.014 g, 0.106 mmol) in DMF (5 mL) was stirred at RT for 16 h. The RM was diluted with EtOAc (30 mL) and washed with aqueous 0.5 N KHSO₄ (30 mL), aqueous saturated solution of NaHCO₃ (30 mL) and brine (30 mL). The combined organic layer was dried over Na₂SO₄ and concentrated in vacuo. FC (EtOAc/heptane 0:1→1:0) afforded INT-9B (0.170 g, 0.329 mmol, 62%). LCMS: calc. for [M+H]⁺=491.14, found 491.2.

ii) DMP (0.294 g, 0.692 mmol) was added to a solution of INT-9B (0.170 g, 0.346 mmol) in DCM (5 mL). The RM was stirred at RT for 16 h. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. FC (EtOAc/heptane 0:1→1:0) and lyophilisation (MeCN/H₂O) afforded 9 (0.101 g, 0.196 mmol, 57%). LCMS: calc. for [M+H]⁺=489.13, found 489.2. ¹H NMR (400 MHz, DMSO-d₆) as a RM of hydrates and rotamers δ 9.11-8.96 (m, 0.5H), 8.95-8.76 (m, 2.5H), 8.28-8.19 (m, 0.05H), 8.18-8.08 (m, 0.45H), 8.05-7.99 (m, 0.5H), 7.98-7.89 (m, 1H), 7.49-7.35 (m, 1H), 6.75 (s, 0.41H), 6.46 (s, 0.24H), 6.36 (s, 0.41H), 5.83 (s, 0.24H), 5.14-3.44 (m, 8H), 2.04-1.47 (m, 6H), 1.32-0.83 (m, 5H) ppm.

Example 10

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridin-3-yl)furan-2-carboxamide

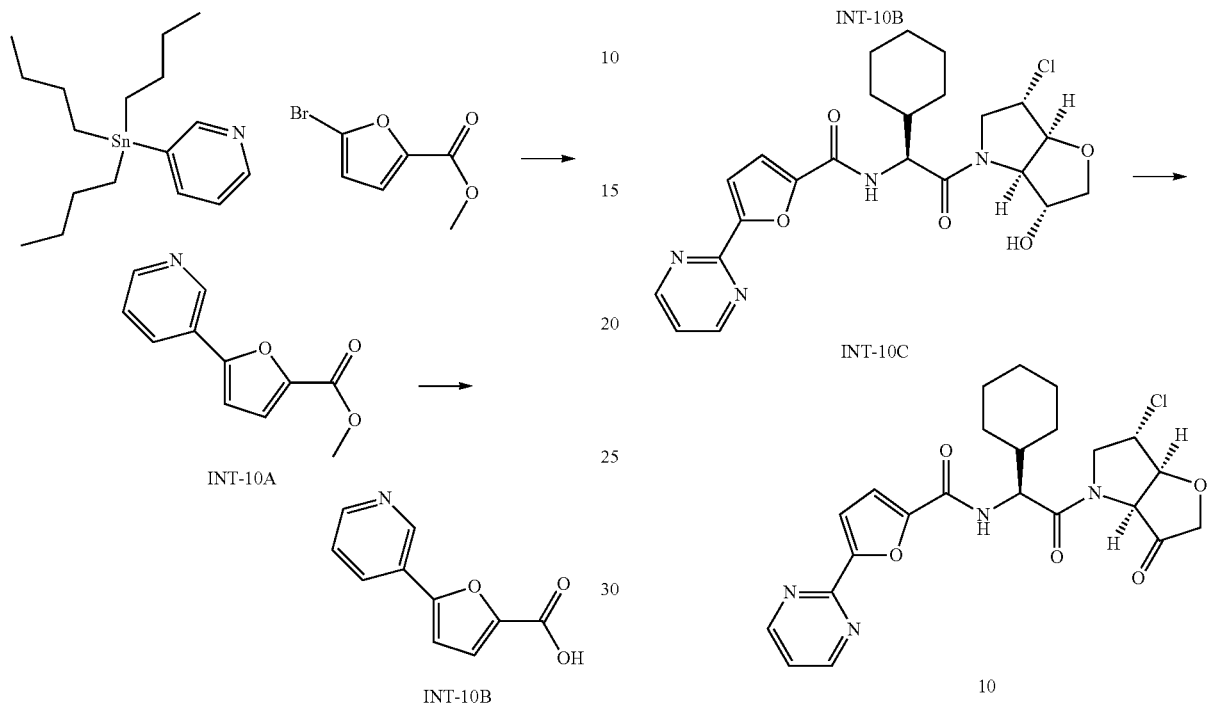

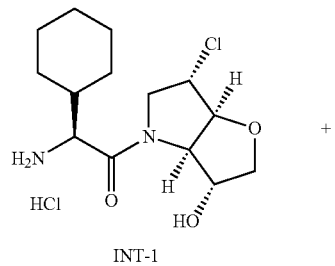

i) A solution of 3-(tributylstannyl)pyridine (0.449 g, 1.22 mmol) and methyl 5-bromofuran-2-carboxylate (0.250 g, 1.22 mmol) in DMF (13 mL) was degassed with Ar. CsF (0.556 g, 3.66 mmol), CuCl (0.016 g, 0.159 mmol) and tetrakis(triphenylphosphine)palladium (0.071 g, 0.061 mmol) were added and the RM was heated at 110° C. by microwave irradiation for 1 h. The RM was diluted with water (50 mL) and extracted with EtOAc (2×50 mL). The combined organic layer was washed with brine (2×50 mL), dried over $Na_2SO_4$ and concentrated in vacuo. FC (EtOAc/heptane 1:19→4:6) afforded INT-10A (0.215 g, 1.06 mmol, 87%) as a pale yellow solid. LCMS: calc. for [M+H]⁺= 204.06, found 204.2.

ii) LiOH.H₂O (0.102 g, 2.44 mmol) was added to a RM of INT-10A (0.165 g, 0.812 mmol) in tetrahydrofuran (3 mL) and water (2 mL). The reaction was stirred at RT until completion. The residue was acidified to pH 2-3 using aqueous 1 M HCl. The solids were filtered off and washed with water and diisopropyl ether to obtain INT-10B (0.150 g, 0.812 mmol, 98%) as a white solid.

i) A suspension of INT-1 (0.269 g, 0.793 mmol), INT-10B (0.150 g, 0.793 mmol), EDCl (0.167 g, 0.872 mmol), NEt₃ (0.221 mL, 1.59 mmol) and HOAt (0.011 g, 0.079 mmol) in DMF (8 mL) was stirred at RT until completion. Aqueous saturated NaHCO₃ (20 mL) was added and the RM was extracted with EtOAc (2×15 mL). The combined organic layer was washed with water (10 mL) and brine (2×10 mL), dried on $Na_2SO_4$ and concentrated in vacuo to obtain INT-10C (0.300 g, 0.570 mmol, 72%). LCMS: calc. for [M+H]⁺=474.17, found 474.2.

ii) DMP (0.483 g, 1.14 mmol) was added to a solution of INT-10C (0.300 g, 0.570 mmol) in DCM (10 mL). The RM was stirred at RT for 16 h. An aqueous solution of $Na_2S_2O_3$ (10%, 15 mL) was added and the RM was stirred vigorously for 30 min. An aqueous saturated solution of NaHCO₃ (30 mL) was added. The aqueous layer was extracted with DCM (2×30 mL). The combined organic layer was dried over $Na_2SO_4$ and concentrated in vacuo. The residue was dissolved in DCM (10 mL). DMP (0.242 g, 0.570 mmol) was added and the RM was stirred at RT until completion. An aqueous solution of $Na_2S_2O_3$ (10%, 15 mL) was added and the RM was stirred vigorously for 30 min. An aqueous saturated solution of NaHCO₃ (30 mL) was added. The aqueous layer was extracted with DCM (2×30 mL). The combined organic layer was dried over $Na_2SO_4$ and concentrated in vacuo. The product was purified by FC (EtOAc/heptane 2:8→1:0). Purification by basic preparative HPLC (C18, MeCN (1% 10 mM NH₄HCO₃), 10 mM NH₄HCO₃ in H₂O) and lyophilisation afforded 10 (0.108 g, 0.284 mmol, 50%) as a white solid. LCMS: calc. for [M+H]⁺=472.16, found 472.1. ¹H NMR (400 MHz, DMSO-d₆) as a RM of hydrates and rotamers δ 9.27-9.13 (m, 1H), 8.95-8.70 (m, 1H), 8.64-8.53 (m, 1H), 8.39-8.25 (m, 1H), 7.63-7.45 (m, 1H), 7.43-7.19 (m, 2H), 6.74 (s, 0.4H), 6.48 (s, 0.2H), 6.36 (s, 0.4H), 5.86 (s, 0.2H), 5.11-3.40 (m, 8H), 2.09-1.50 (m, 6H), 1.40-0.73 (m, 5H) ppm.

Example 11

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-5-yl)furan-2-carboxamide

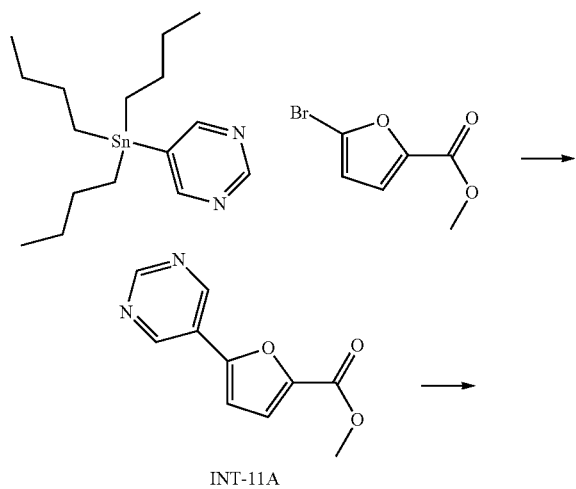

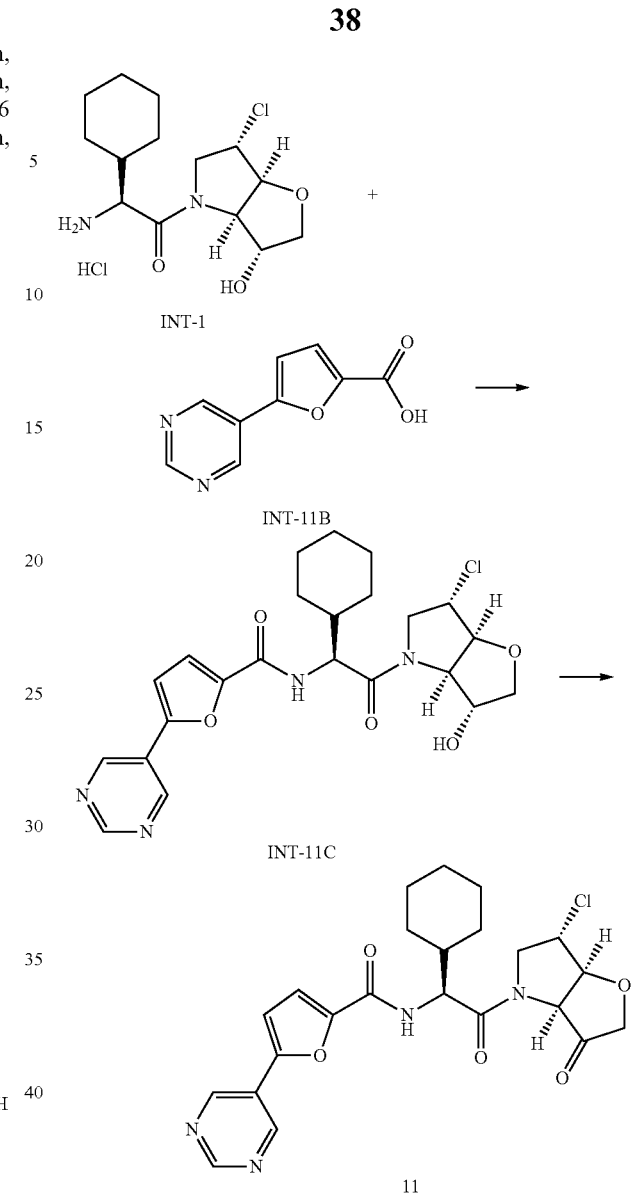

i) A solution of 5-(tributylstannyl)pyrimidine (0.500 g, 1.36 mmol) and methyl 5-bromofuran-2-carboxylate (0.278 g, 1.36 mmol) in DMF (13 mL) was degassed with Ar. CsF (0.617 g, 4.06 mmol), CuCl (0.017 g, 0.18 mmol) and tetrakis(triphenylphosphine)palladium (0.078 g, 0.068 mmol) were added and the RM was heated at 110° C. for 1 h. The RM was diluted with water (75 mL) and extracted with EtOAc (2×75 mL). The combined organic layer was washed with brine (2×50 mL), dried over Na$_2$SO$_4$ and concentrated in vacuo. FC (EtOAc/heptane 1:19→4:6) afforded INT-11A (0.180 g, 0.882 mmol, 65%) as a pale yellow solid. LCMS: calc. for [M+H]$^+$=205.05, found 205.2.

ii) At RT LiOH.H$_2$O (0.111 g, 2.64 mmol) was added to a RM of INT-11A (0.180 g, 0.882 mmol) in THF (3 mL) and water (2 mL). The reaction was stirred at RT for 1 hour. The residue was acidified to pH 2-3 using aqueous 1 M HCl. The solids were filtered off and washed with water and diisopropyl ether to obtain INT-11B (0.103 g, 0.0540 mmol, 61%) as a white solid. The filtrate was extracted with EtOAc (2×10 mL). The combined organic layer was dried on Na$_2$SO$_4$ and concentrated in vacuo to afford INT-11B (0.058 g, 0.31 mmol, 35%) as a white solid.

i) A suspension of INT-1 (0.285 g, 0.841 mmol), INT-11B (0.160 g, 0.841 mmol), EDCI (0.177 g, 0.926 mmol), NEt$_3$ (0.235 mL, 1.68 mmol) and HOAt (0.011 g, 0.084 mmol) in DMF (8 mL) was stirred at RT for 16 h. Aqueous saturated NaHCO$_3$ (20 mL) was added and the RM was extracted with EtOAc (2×15 mL). The combined organic layer was washed with water (10 mL) and brine (2×10 mL), dried on Na$_2$SO$_4$ and concentrated in vacuo to obtain INT-11C (0.400 g, 0.716 mmol, 85%). LCMS: calc. for [M+H]$^+$=475.17, found 475.2.

ii) DMP (0.607 g, 1.43 mmol) was added to a solution of INT-11C (0.400 g, 0.716 mmol) in DCM (10 mL). The RM was stirred at RT for 2 h. An aqueous solution of Na$_2$S$_2$O$_3$ (10%, 15 mL) was added and the RM was stirred vigorously for 30 min. An aqueous saturated solution of NaHCO$_3$ (30 mL) was added. The aqueous layer was extracted with DCM (2×30 mL). The combined organic layer was dried over Na$_2$SO$_4$ and concentrated in vacuo. The product was purified by FC (EtOAc/heptane 1:9→1:0). Purification by basic preparative HPLC (C18, MeCN (1% 10 mM NH$_4$HCO$_3$), 10 mM NH$_4$HCO$_3$ in H$_2$O) and lyophilisation afforded 11 (0.170 g, 0.359 mmol, 50%). LCMS: calc. for [M+

H]⁺=473.15, found 473.1. ¹H NMR (400 MHz, DMSO-d₆) as a RM of hydrates and rotamers δ 9.50-9.29 (m, 2H), 9.18 (d, J=6.9 Hz, 1H), 9.05-8.73 (m, 1H), 7.51-7.24 (m, 2H), 6.73 (s, 0.33H), 6.48 (s, 0.17H), 6.32 (s, 0.33H), 5.85 (s, 0.17H), (m, 8H), 2.06-1.44 (m, 6H), 1.29-0.84 (m, 5H) ppm.

Example 12

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridin-4-yl)furan-2-carboxamide

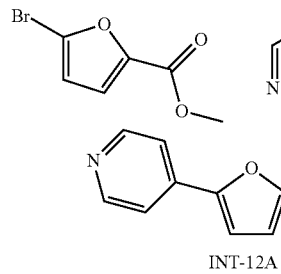

INT-12A

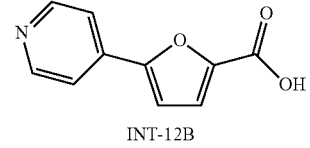

INT-12B i) In a microwave vessel methyl 5-bromofuran-2-carboxylate (286 mg, 1.39 mmol) and 4-(tributylstannyl)pyridine (513 mg, 1.39 mmol) were dissolved in DMF (10 mL). CsF (0.635 g, 4.18 mmol), CuCl (0.018 g, 0.18 mmol) and [1,1'-bis(diphenylphosphino)ferrocene]dichloropalladium (II) (0.127 g, 0.139 mmol) were added after degassing the RM with Ar. The vessel was capped and heated at 100° C. for 30 min in the microwave. The reaction RM was diluted with water (100 mL) and EtOAc (100 mL). The water layer was twice extracted with EtOAc (100 mL). Organic layer was dried over Na₂SO₄ and then filtered over celite. The filter cake was washed with EtOAc (100 mL) and the filtrate was concentrated in vacuo. FC (EtOAc/heptane 0:1→1:0) afforded INT-12A (0.268 g, 1.253 mmol, 90%) as a white solid. LCMS: calc. for [M+H]⁺=204.06, found 204.2.

ii) At RT LiOH.H₂O (0.166 g, 3.96 mmol) was added to a RM of INT-12A (0.268 g, 1.32 mmol) in tetrahydrofuran (3 mL) and water (3 mL). The reaction was stirred at RT for 1 h. The RM was acidified with aqueous 1 M HCl (10 mL) to pH 3-4. The RM was extracted with EtOAc (3×20 mL). The collected organic layer was washed with brine (20 mL), dried over Na₂SO₄ and concentrated in vacuo to give INT-12B (0.140 g, 0.703 mmol, 53%) as a white solid. LCMS: calc. for [M+H]⁺=190.04, found 190.2.

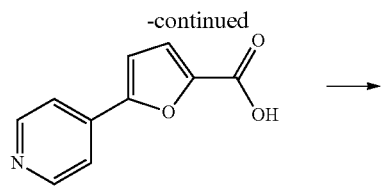

INT-12B

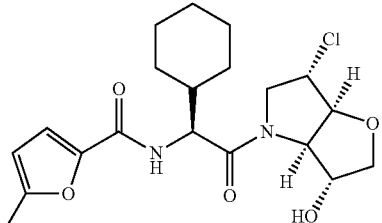

INT-12C

12 i) A suspension of INT-1 (0.251 g, 0.740 mmol), INT-12B (0.140 g, 0.740 mmol), EDCl (0.170 g, 0.888 mmol), NEt₃ (0.300 g, 2.960 mmol, 0.413 mL) and HOAt (0.020 g, 0.15 mmol) in DMF (5 mL) was stirred at RT for 16 h. The RM was diluted with EtOAc (30 mL) and washed with aqueous 0.5 N KHSO₄ (30 mL), aqueous saturated solution of NaHCO₃ (30 mL) and brine (30 mL). The combined organic layer was dried over Na₂SO₄ and concentrated in vacuo. FC (EtOAc/heptane 0:1→1:0) and lyophilisation (MeCN/H₂O) afforded INT-12C (0.255 g, 0.511 mmol, 69%). LCMS: calc. for [M+H]⁺=474.17, found 474.2.

ii) DMP (0.456 g, 1.08 mmol) was added to a solution of INT-12C (0.255 g, 0.538 mmol) in DCM (5 mL). The RM was stirred at RT for 16 h. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. FC (EtOAc/heptane 0:1→1:0) and lyophilisation (MeCN/H₂O) afforded 12 (0.113 g, 0.227 mmol, 42%). LCMS: calc. for [M+H]⁺=472.16, found 472.2. ¹H NMR (400 MHz, DMSO-d₆) as a RM of hydrates and rotamers δ 8.98-8.77 (m, 1H), 8.74-8.56 (m, 2H), 8.18-8.03 (m, 0.05H), 8.00-7.75 (m, 1.95H), 7.48-7.26 (m, 2H), 6.73 (s, 0.28H), 6.49 (s, 0.16H), 6.35 (s, 0.28H), 5.87 (s, 0.16H), 5.18-3.44 (m, 8H), 2.11-1.48 (m, 6H), 1.33-0.85 (m, 5H) ppm.

Example 13

N-((S)-2-((3aS,6S,6aS)-6-chloro-3-oxotetrahydro-2H-furo[3,2-b]pyrrol-4(5H)-yl)-1-cyclohexyl-2-oxo-ethyl)-2-(pyridin-3-yl)thiazole-5-carboxamide

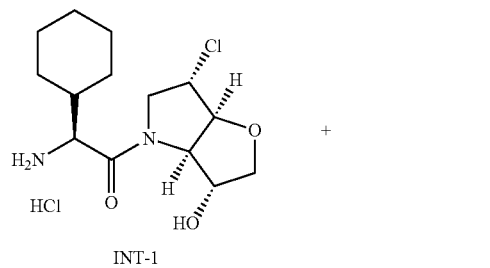

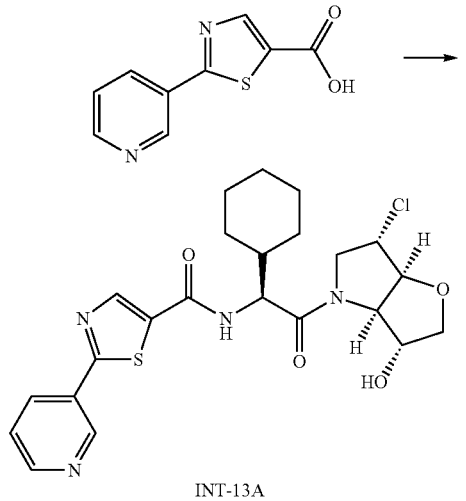

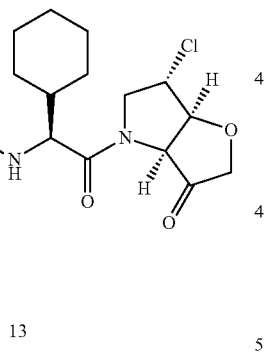

i) A suspension of INT-1 (0.823 g, 2.43 mmol), 2-(pyridin-3-yl)thiazole-5-carboxylic acid (500 mg, 2.43 mmol), EDCl (0.558 g, 2.91 mmol), NEt₃ (0.981 g, 9.70 mmol, 1.35 mL) and HOAt (0.066 g, 0.49 mmol) in DMF (8 mL) was stirred at RT for 16 h. The RM was diluted with EtOAc (30 mL) and washed with aqueous 0.5 N KHSO₄ (30 mL), aqueous saturated solution of NaHCO₃ (30 mL) and brine (30 mL). The combined organic layer was dried over Na₂SO₄ and concentrated in vacuo. FC (EtOAc/heptane 0:1→1:0) afforded INT-13A (0.390 g, 0.755 mmol, 31%). LCMS: calc. for [M+H]$^+$=491.14, found 491.2.

ii) DMP (0.674 g, 1.59 mmol) was added to a solution of INT-13A (0.390 g, 0.794 mmol) in DCM (8 mL). The RM was stirred at RT for 16 h. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. Purification by basic preparative HPLC (C18, MeCN (1% 10 mM NH₄HCO₃), 10 mM NH₄HCO₃ in H₂O) and lyophilization afforded 13 (0.088 g, 0.17 mmol mismatch of significant digits, 22%). LCMS: calc. for [M+H]$^+$=489.13, found 489.2. $^1$H NMR (400 MHz, DMSO-d₆) as a RM of hydrates and rotamers δ 9.28-8.98 (m, 2H), 8.84-8.78 (m, 0.05H), 8.76-8.64 (m, 1.8H), 8.64-8.50 (m, 0.15H), 8.47-8.24 (m, 1H), 7.66-7.48 (m, 1H), 5.26-3.49 (m, 8H), 2.07-1.47 (m, 6H), 1.33-0.84 (m, 5H) ppm.

Example 14

N-((S)-2-((3aS,6S,6aS)-6-chloro-3-oxotetrahydro-2H-furo[3,2-b]pyrrol-4(5H)-yl)-1-cyclohexyl-2-oxo-ethyl)-4-methyl-2-(pyridin-3-yl)thiazole-5-carboxamide

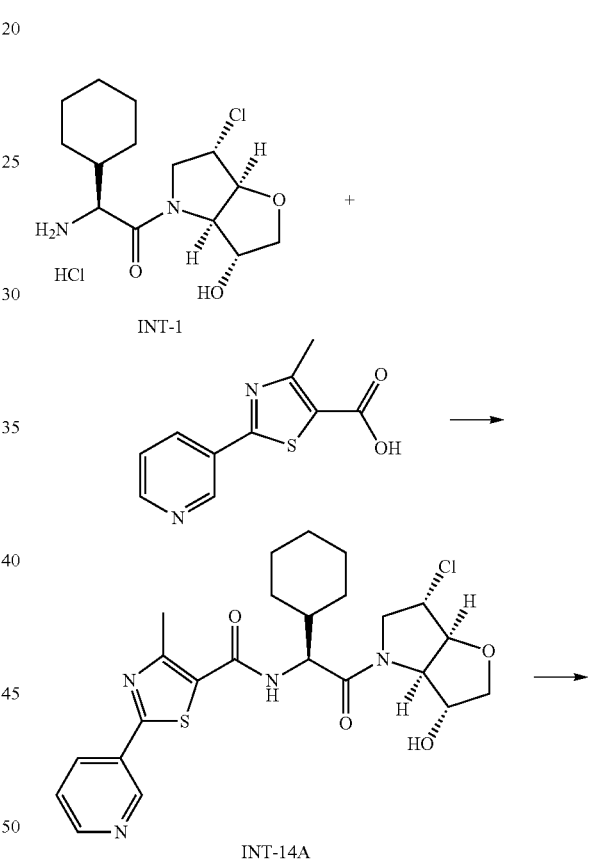

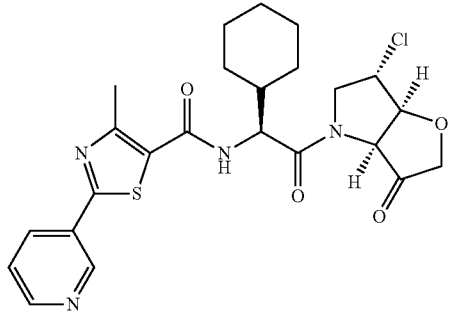

i) A suspension of INT-1 (0.770 g, 2.27 mmol), 4-methyl-2-(3-pyridinyl)-1,3-thiazole-5-carboxylic acid (500 mg, 2.27 mmol), EDCl (0.522 g, 2.72 mmol), NEt₃ (0.919 g, 9.08 mmol, 1.27 mL) and HOAt (0.062 g, 0.45 mmol) in DMF (8 mL) was stirred at RT for 16 h. The RM was diluted with EtOAc (30 mL) and washed with aqueous 0.5 N KHSO₄ (30 mL), aqueous saturated solution of NaHCO₃ (30 mL) and brine (30 mL). The combined organic layer was dried over Na₂SO₄ and concentrated in vacuo. FC (EtOAc/heptane 0:1→1:0) afforded INT-14A (0.755 g, 1.42 mmol, 63%). LCMS: calc. for [M+H]⁺=505.16, found 505.2.

ii) DMP (1.268 g, 1.495 mmol) was added to a solution of INT-14A (0.755 g, 1.50 mmol) in DCM (8 mL). The RM was stirred at RT for 16 h. An aqueous solution of Na₂S₂O₃ (10%, 5 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. Purification by basic preparative HPLC (C18, MeCN (1% 10 mM NH₄HCO₃), 10 mM NH₄HCO₃ in H₂O) and lyophilized afforded 14 (0.108 g, 0.204 mmol, 14%). LCMS: calc. for [M+H]⁺=503.14, found 503.2. ¹H NMR (400 MHz, DMSO-d₆) as a RM of hydrates and rotamers δ 9.24-9.04 (m, 1H), 8.82-8.48 (m, 2H), 8.40-8.23 (m, 1H), 7.99-7.87 (m, 0.05H), 7.67-7.44 (m, 0.95H), 6.68 (s, 0H), 6.46 (s, 0H), 6.37 (s, 0H), 5.84 (s, 0H), 5.19-3.42 (m, 8H), 2.75-2.55 (m, 3H), 2.09-1.45 (m, 6H), 1.33-0.88 (m, 5H) ppm.

Example 15

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-3-yl)thiazole-2-carboxamide

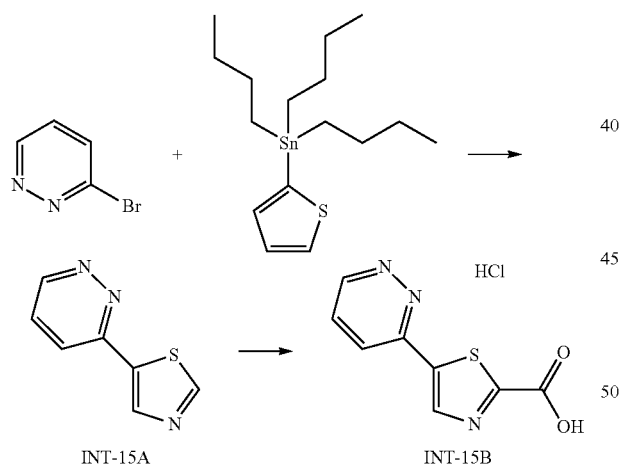

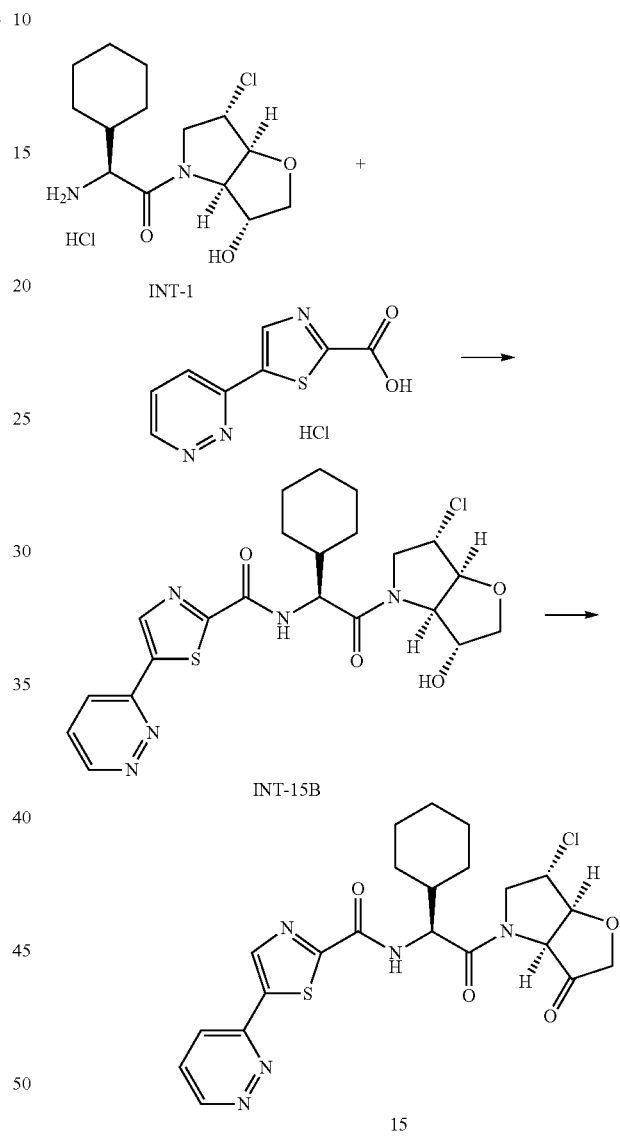

i) 3-Bromopyridazine (1.02 g, 6.41 mmol), 5-(tributyl-stannyl)thiazole (2.00 g, 5.35 mmol), tri(furan-2-yl)phosphine (0.250 g, 1.07 mmol) and bis(dibenzylideneacetone) palladium (0.49 g, 0.53 mmol) were dissolved in dry dioxane (5 mL) and the resulting solution was heated at 90° C. and stirred for 16 h. The RM was cooled to RT and filtered using a phase separator and the solvent was evaporated. FC (EtOAc) afforded INT-15A (0.550 g, 3.37 mmol, 63%). LCMS: calc. for [M+H]⁺=164.02, found 164.0.

ii) Thiazole INT-15A (0.550 g, 3.37 mmol) was added to a solution of lithium diisopropylamine (1 M in tetrahydrofuran/heptane/ethylbenzene, 26 mmol, 26 mL) in dry THF (10 mL) at −78° C. and the RM was stirred for 30 min. CO₂ (solid) (14.8 g, 336 mmol) was added and the reaction was stirred for 2 h. The reaction was allowed to reach RT and the solvent was evaporated in vacuo. The crude was dissolved in water (10 mL) and washed with EtOAc (10 mL). The aqueous layer was acidified using a 1N HCl solution to pH 5-6 and INT-15B (0.35 g) precipitated out as a yellow solid and was collected. LCMS: calc. for [M+H]⁺=208.01, found 208.0.

i) At RT NEt₃ (0.620 g, 6.16 mmol, 0.850 mL) and propylphosphonic anhydride (50% w/w in DMF, 0.55 g, 0.86 mmol, 0.51 mL) were added to a solution of INT-1 (0.23 g, 0.67 mmol) and INT-15B (0.20 g) in DMF (5 mL). The RM was stirred at RT for 16 h. The RM was diluted with aqueous saturated NaHCO₃ (10 mL) and extracted with EtOAc (3×20 mL). The combined organic layer was dried over Na₂SO₄ and concentrated in vacuo. FC (EtOAc then MeOH/DCM 95:5) afforded INT-15C (0.20 g, 0.40 mmol, 20% over 2 steps). LCMS: calc. for [M+H]⁺=492.14, found 492.1.

ii) DMP (0.34 g, 0.81 mmol) was added to a solution of INT-15C (0.20 g, 0.40 mmol) in DCM (20 mL). The RM was stirred at RT for 16 h. An aqueous solution of Na₂S₂O₃

(10%, 20 mL) was added and the RM was stirred vigorously for 30 min. The RM was diluted with a saturated aqueous solution of NaHCO₃ (20 mL). The aqueous layer was extracted with DCM (20 mL×3). The combined organic layer was dried over Na₂SO₄ and concentrated in vacuo. Recrystallization (DCM/heptane) and lyophilisation (MeCN/H₂O) afforded compound 15 (0.15 g, 0.30 mmol, 75%) as a white solid. LCMS: calc. for [M+H]⁺=490.12, found 490.2. ¹H NMR (400 MHz, DMSO-d₆) as a RM of hydrates and rotamers δ 9.29-9.17 (m, 1H), 8.90-8.77 (m, 1H), 8.68-7.93 (m, 2H), 7.90-7.77 (m, 1H), 6.64 (s, 0.47H), 6.47 (s, 0.47H), 6.42 (s, 0.18H), 5.81 (s, 0.18H), 5.27-3.39 (m, 8H), 2.12-1.47 (m, 6H), 1.26-0.91 (m, 5H) ppm.

Example 16

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(5-fluoropyridin-3-yl)thiophene-2-carbox-amide

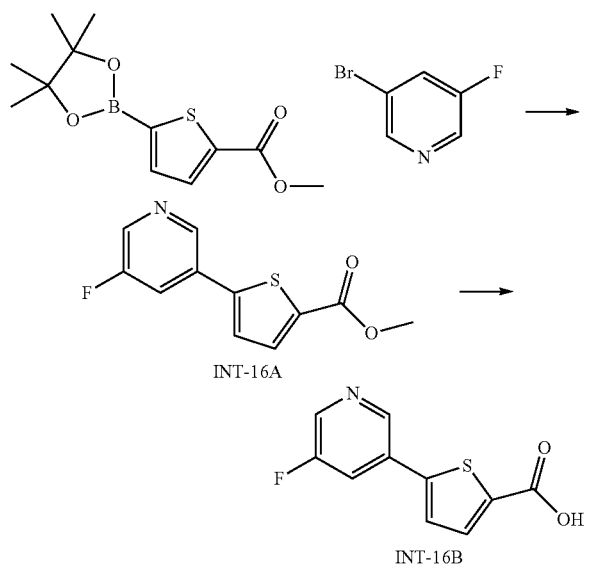

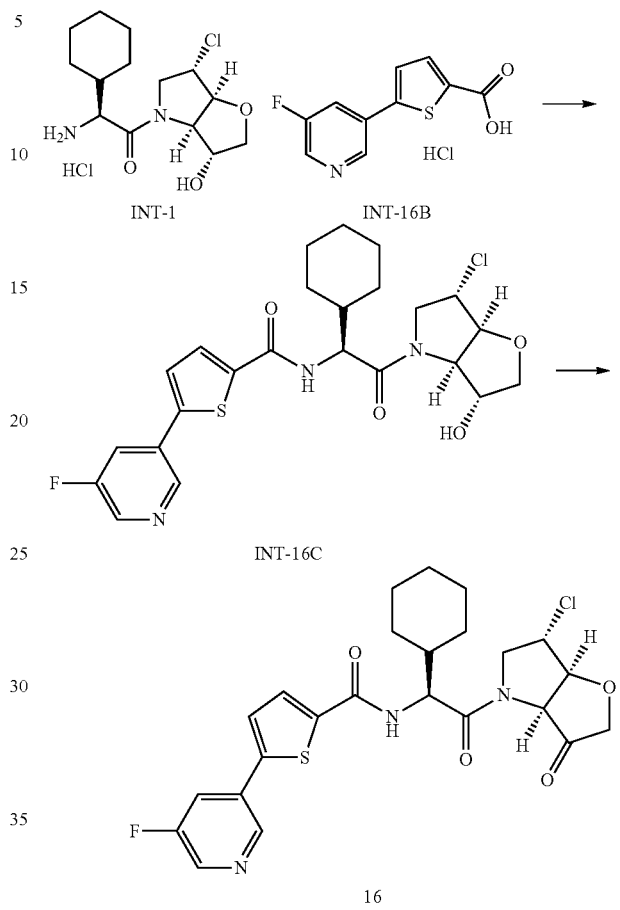

i) A suspension of methyl 5-(4,4,5,5-tetramethyl-1,3,2-dioxaborolan-2-yl)thiophene-2-carboxylate (0.500 g, 1.87 mmol), Cs₂CO₃ (1.66 g, 5.09 mmol) and 5-bromo-3-fluoropyridine (0.298 g, 1.70 mmol) was degassed with Ar and [1,1'-bis(diphenylphosphino)ferrocene]dichloropalladium (II) (0.077 g, 0.085 mmol) and stirred for 16 h at 100° C. An aqueous saturated solution of NaHCO₃ (20 mL) was added and the RM was extracted with EtOAc (3×30 mL). The combined organic layer was washed with brine (10 mL), dried over Na₂SO₄ and concentrated in vacuo. FC (EtOAc/heptane 0:1→1:0) afforded INT-16A (0.331 g, 1.33 mmol, 78%) as a white solid. LCMS: calc. for [M+H]⁺=238.03, found 238.2.

ii) At RT LiOH.H₂O (0.179 g, 4.19 mmol) was added to a RM of INT-16A (0.331 g, 1.33 mmol) in tetrahydrofuran (20 mL) and water (8 mL). The reaction was stirred at RT for 16 h. The reaction was acidified with aqueous 1 M HCl (10 mL) to pH 3-4. The RM was extracted with EtOAc (3×20 mL). The collected organic layer was washed with brine (20 mL), dried over Na₂SO₄ and concentrated in vacuo to give INT-16B (0.263 g, 1.12 mmol, 80%) as a white solid. LCMS: calc. for [M+H]⁺=224.01, found 224.2.

i) A suspension of INT-1 (0.400 g, 1.18 mmol), INT-16B (0.263 g, 1.12 mmol), EDCl (0.271 g, 1.42 mmol), NEt₃ (0.477 g, 4.72 mmol, 0.657 mL) and HOAt (0.032 g, 0.24 mmol mismatch of significant digits) in DMF (8 mL) was stirred at RT for 16 h. The RM was diluted with EtOAc (20 mL) and washed with aqueous saturated solution of NaHCO₃ (20 mL) and brine (10 mL). The combined organic layer was dried over Na₂SO₄ and concentrated in vacuo. FC (EtOAc/heptane 0:1→1:0) afforded INT-16C (0.524 g, 0.980 mmol, 83%). LCMS: calc. for [M+H]⁺=508.14, found 508.1.

ii) DMP (0.875 g, 2.06 mmol) was added to a solution of INT-16C (0.524 g, 0.980 mmol) in DCM (8 mL). The RM was stirred at RT for 16 h. An aqueous solution of Na₂S₂O₃ (10%, 25 mL) was added and the RM was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. The crude was dissolved in a small amount of boiling EtOAc and cooled to RT. Heptane was added until a precipitate formed and the RM was reheated to boiling temperature until a clear solution was formed. The solution was left for 16 h at RT and the solids formed were filtered off. Lyophilisation (MeCN/H₂O) afforded 16 (0.189 g, 0.355 mmol, 34%). LCMS: calc. for [M+H]⁺=506.12, found 506.1. ¹H NMR (400 MHz, DMSO-d₆) as a RM of hydrates and rotamers δ 9.06-8.76 (m, 2H), 8.72-8.50 (m, 1H), 8.26-8.08 (m, 1H), 8.08-7.94 (m, 1H), 7.87-7.66 (m, 1H), 6.71 (s, 0.01H), 6.44 (s, 0.01H), 6.31 (s, 0.01H), 5.80 (s, 0.01H), 5.12-3.35 (m, 8H), 2.01-1.48 (m, 6H), 1.26-0.90 (m, 5H) ppm.

Example 17

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(6-chloropyridin-3-yl)thiophene-2-carboxamide

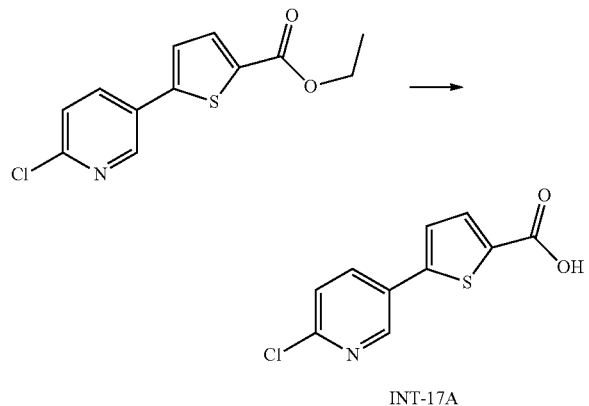

LiOH.H$_2$O (0.166 g, 3.96 mmol) was added to a solution of ethyl 5-(6-chloropyridin-3-yl)thiophene-2-carboxylate (0.353 g, 1.32 mmol) in tetrahydrofuran (15 mL) and water (6 mL). The reaction RM was stirred at RT for 48 h. The RM was acidified with aqueous 1 M HCl to pH 3-4 (10 mL) and extracted with EtOAc (2×10 mL). The combined organic layer was dried over Na$_2$SO$_4$ and concentrated in vacuo to obtain INT-17A (0.276 g, 1.09 mmol, 83%). LCMS: calc. for [M+H]$^+$=239.98, found 240.0.

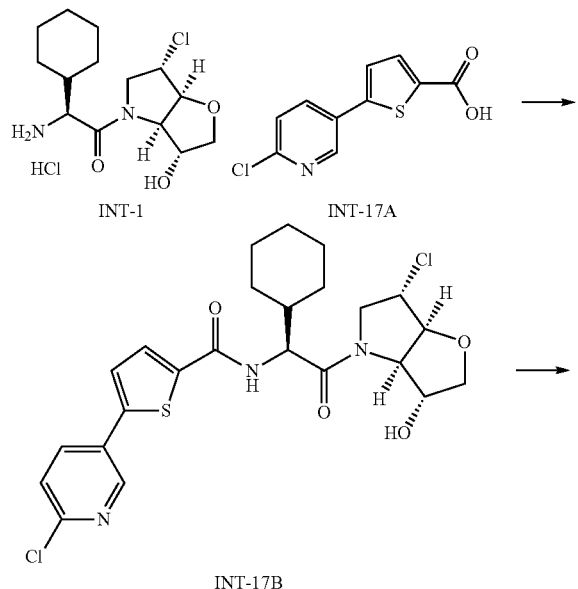

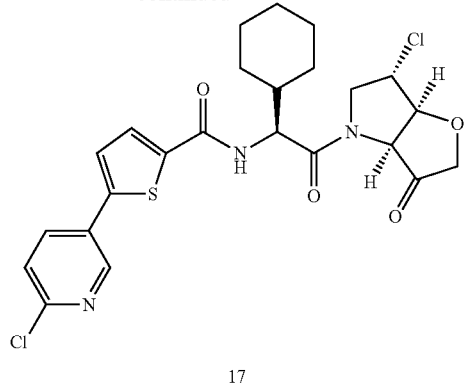

i) NEt$_3$ (0.583 g, 5.76 mmol, 0.803 mL) and propylphosphonic anhydride (50% w/w in DMF, 1.10 g, 1.73 mmol, 1.01 mL) were added consecutively to a solution of INT-1 (0.391 g, 1.15 mmol) and INT-17A (0.276 g, 1.09 mmol) in dry DMF (5 mL). The reaction was stirred at RT for 16 h. The RM was diluted with EtOAc (5 mL) and washed with aqueous saturated NaHCO$_3$ (5 mL). The water layer was extracted with EtOAc (5 mL). The combined organic layer was washed with brine (10 mL), dried over Na$_2$SO$_4$ and concentrated in vacuo. The crude product was purified by flash column chromatography (EtOAc) to afford INT-17B (0.400 g, 0.725 mmol, 67%) as a white solid. LCMS: calc. for [M+H]$^+$=524.11, found 524.0.

ii) DMP (0.647 g, 1.53 mmol) was added to a solution of INT-17B (0.400 g, 0.725 mmol) in DCM (8 mL). The RM was stirred at RT for 16 h. An aqueous solution of Na$_2$S$_2$O$_3$ (10%, 25 mL) was added and the RM was stirred vigorously for 30 min. An aqueous saturated solution of NaHCO$_3$ (10 mL) was added and extracted with DCM (2×10 mL). The combined organic layer was dried over Na$_2$SO$_4$ and concentrated in vacuo. The crude product was purified by trituration from heptane/EtOAc. The precipitate was obtained by filtration, washed with pentane, dried and lyophilized (MeCN/H$_2$O) to afford 17 (0.272 g, 0.495 mmol, 65%). LCMS: calc. for [M+H]$^+$=522.09, found 522.0. $^1$H-NMR (400 MHz, DMSO-d$_6$) as a RM of hydrates and rotamers δ 8.99-8.71 (m, 2H), 8.24-7.95 (m, 2H), 7.76-7.51 (m, 2H), 6.71 (s, 0.30H), 6.44 (s, 0.16H), 6.31 (s, 0.30H), 5.80 (s, 0.16H), 5.09-3.46 (m, 8H), 2.02-1.49 (m, 6H), 1.33-0.78 (m, 5H) ppm.

Example 18

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-4-yl)thiazole-2-carboxamide

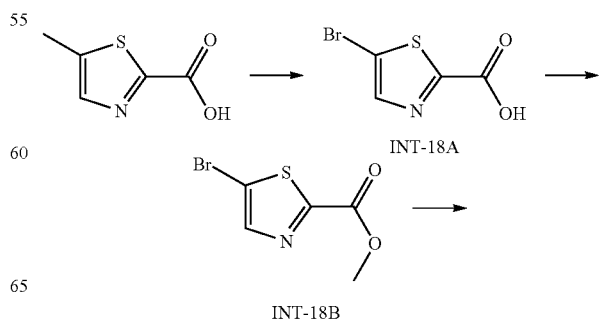

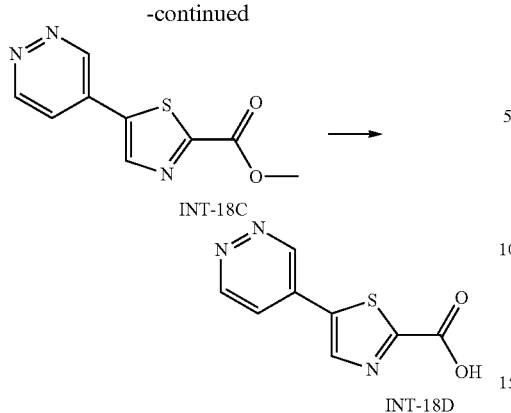

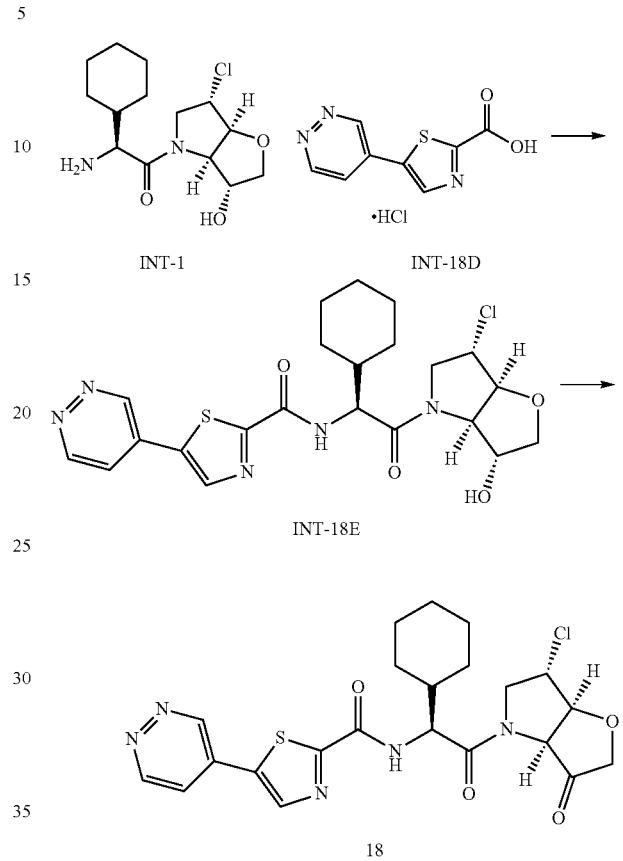

i) Thiazole-2-carboxylic acid (1.60 g, 12.4 mmol) was added to a solution of lithium diisopropylamine (1 M in THF/heptane/ethylbenzene, 26 mmol, 26 mL) in dry THF (100 mL) at −78° C. and the RM was stirred for 30 min. Tetrabromomethane (4.52 g, 13.6 mmol) was added and the RM was stirred for 2 h. The reaction RM was quenched by adding water (30 mL). The RM was allowed to reach RT and diluted by adding an aqueous saturated solution of $NaHCO_3$ (50 mL). The RM was filtered through a pad of celite and extracted with EtOAc (50 mL). The organic layer was discarded and the aqueous layer acidified using a 1 N solution of HCl until pH 3-4. The solution was then extracted with EtOAc (3×30 mL). The combined organic layer was dried over $Na_2SO_4$ and concentrated in vacuo to leave INT-18A (0.420 g, 2.02 mmol, 16%). LCMS: calc. for $[M+H]^+$=207.90, found 208.0.

ii) Oxalyl chloride (0.210 mL, 2.44 mmol) was added to a solution of INT-18A (0.420 g, 2.02 mmol) in dry DCM (10 mL) containing a catalytic amount of dry DMF (0.05 mL) at RT and the resulting RM was stirred for 4 h. MeOH (4.00 mL, 125 mmol) was added to the solution and the RM was stirred for an additional 2 h. The RM was diluted with a saturated aqueous solution of $NaHCO_3$ (20 mL) and extracted with DCM (3×10 mL). The combined organic layer was washed with water (20 mL) and brine (2×20 mL), dried over $Na_2SO_4$ and concentrated in vacuo. FC (EtOAc/heptane 0:1→3:7) afforded INT-18B (0.230 g, 1.03 mmol, mismatch of significant digits 51%). LCMS: calc. for $[M+H]^+$=221.91, found 221.9.

iii) Bromide INT-18B (0.230 g, 1.03 mmol), 4-(tributylstannyl)pyridazine (0.380 g, 1.03 mmol), tri(furan-2-yl)phosphine (0.050 g, 0.20 mmol) and bis(dibenzylideneacetone) palladium (0.090 g, 0.10 mmol) were dissolved in dry 1,4-dioxane (5 mL) and the resulting solution was heated at 90° C. and stirred for 16 h. The reaction was cooled to RT, diluted with a saturated aqueous solution of $NaHCO_3$ (10 mL) and extracted with EtOAc (3×10 mL). The combined organic layer was dried over $Na_2SO_4$ and concentrated in vacuo. FC (EtOAc) afforded INT-18C (0.11 g, 0.49 mmol, 48%). LCMS: calc. for $[M+H]^+$=222.03, found 222.1.

iv) At RT $LiOH \cdot H_2O$ (0.03 g, 0.7 mmol) was added to a mixture of INT-18C (0.10 g, 0.47 mmol) in THF (5 mL) and water (5 mL). The reaction was stirred at RT for 2 h. The RM was acidified with aqueous 1 M HCl (10 mL). INT-18D (0.090 g, 0.43 mmol, 92%) precipitated out of the solution as a white solid and was collected. LCMS: calc. for $[M+H]^+$=208.21, found 208.2.

i) At RT $NEt_3$ (0.22 g, 2.21 mmol, 0.30 mL) and propylphosphonic anhydride (50% w/w in DMF, 0.37 g, 0.60 mmol, 0.38 mL) were added to a solution of INT-1 (0.15 g, 0.43 mmol) and INT-18D for 48 h. The mixture was diluted with a saturated aqueous solution of $NaHCO_3$ (10 mL) and extracted with EtOAc (3×20 mL). The combined organic layer was dried over $Na_2SO_4$ and concentrated in vacuo. FC (EtOAc/heptane 0:1→1:0) afforded INT-18E (0.15 g, 0.30 mmol, 70%). LCMS: calc. for $[M+H]^+$=492.24, found 492.2.

ii) DMP (0.26 g, 0.61 mmol) was added to a solution of INT-18E (0.15 g, 0.30 mmol) in DCM (20 mL). The mixture was stirred at RT for 16 h. An aqueous solution of $Na_2S_2O_3$ (10%, 20 mL) was added and the mixture was stirred vigorously for 30 min. The mixture was diluted with a saturated aqueous solution of $NaHCO_3$ (20 mL). The aqueous layer was extracted with DCM (20 mL). The combined organic layer was dried over $Na_2SO_4$ and concentrated in vacuo. Recrystallization (DCM/heptane) and lyophilisation ($MeCN/H_2O$) afforded compound 18 (0.080 g, 0.16 mmol, 53%) as a white solid. LCMS: calc. for $[M+H]^+$=490.12, found 490.2. $^1H$ NMR (400 MHz, DMSO-$d_6$) as a mixture of hydrates and rotamers δ 9.91-9.61 (m, 1H), 9.94-9.24 (m, 1H), 8.90-7.94 (m, 3H), 6.65 (s, 0.38H), 6.49 (s, 0.38H), 6.44 (s, 0.18H), 5.84 (s, 0.18H), 5.28-3.46 (m, 8H), 2.12-1.43 (m, 6H), 1.36-0.81 (m, 5H) ppm.

Example 19

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-4-yl)furan-2-carboxamide

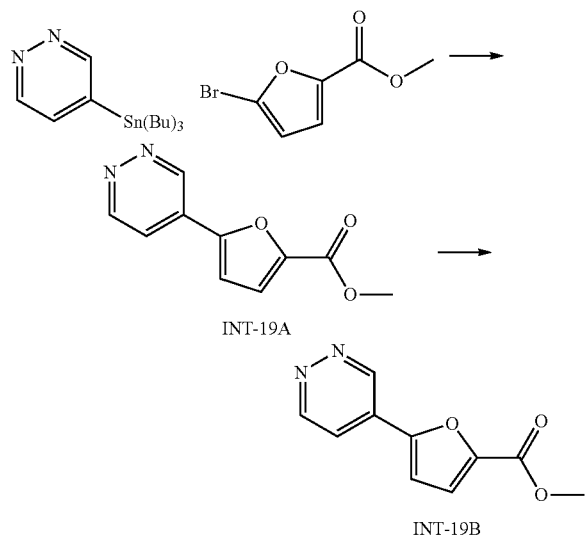

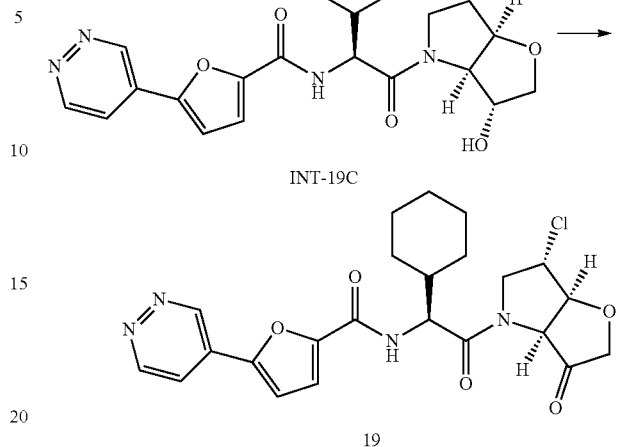

i) A solution of 4-(tributylstannyl)pyridazine (0.800 g, 2.16 mmol) and methyl 5-bromofuran-2-carboxylate (0.454 g, 2.22 mmol) in dry DMF (7 mL) was degassed with $N_2$. CsF (0.988 g, 6.50 mmol), CuCl (0.028 g, 0.28 mmol) and tetrakis(triphenylphosphine)palladium (0.176 g, 0.152 mmol) were added and the mixture was heated at 110° C. under microwave conditions for 30 min. The mixture was diluted with DCM (30 mL) and poured in water (20 mL). The water layer was extracted with DCM (2×30 mL). The combined organic layer was washed with brine (30 mL), dried over $Na_2SO_4$ and filtered over celite. The filter cake was washed with DCM/EtOAc (1:1, 50 mL). The filtrate was concentrated in vacuo. The crude product was purified by FC (EtOAc/heptane 1:9→1:0) to afford INT-19A (0.290 g, 1.42 mmol, 66%) as beige solid. LCMS: calc. for [M+H]$^+$=205.05, found 205.2.

ii) LiOH.$H_2O$ (0.117 g, 2.79 mmol) was added to a solution of INT-19A (0.282 g, 1.38 mmol) in THF (4.5 mL) and water (1.5 mL). The RM was stirred at RT 1.5 h. The RM was concentrated in vacuo. The residue was acidified to pH 3-4 by addition of aqueous 2 M HCl (~1.40 mL) and triturated with 2-propanol (2.5 mL). The resulting solid was obtained by filtration, washed with cold 2-propanol (2.5 mL) and $Et_2O$ (2×2.0 mL) and dried to afford INT-19B (0.191 g, 1.00 mmol, 73%) as a beige solid. LCMS: calc. for [M+H]$^+$=191.04, found 191.1.

i) A suspension of INT-1 (0.334 g, 0.985 mmol), INT-19B (0.187 g, 0.983 mmol), EDCl (0.226 g, 1.18 mmol), $NEt_3$ (0.176 g, 1.74 mmol, 0.242 mL) and HOAt (0.013 g, 0.098 mmol) in dry DMF (5 mL) was stirred at RT until completion. The RM was diluted with EtOAc (20 mL), poured in an aqueous saturated solution of $NaHCO_3$ (50 mL) and extracted with EtOAc (4×20 mL). The combined organic layer was washed with brine (20 mL), dried over $Na_2SO_4$ and concentrated in vacuo. The crude product was purified by FC (MeOH/DCM 0:1→5:95) to afford INT-19C (0.256 g, 0.539 mmol, 55%) as a colorless oil LCMS: calc. for [M+H]$^+$=475.17, found 475.2.

ii) DMP (0.558 g, 1.32 mmol) was added to a solution of INT-19C (0.250 g, 0.526 mmol) in DCM (6 mL). The mixture was stirred at RT for 16 h. An aqueous solution of $Na_2S_2O_3$ (10%, 20 mL) was added and the mixture was stirred vigorously for 1.5 h. An aqueous saturated solution of $NaHCO_3$ (15 mL) was added and extracted with DCM (4×15 mL). The combined organic layer was dried over $Na_2SO_4$ and concentrated in vacuo. The crude product was purified by trituration from heptane/EtOAc (1:1, 8.0 mL). The precipitate was obtained by filtration, washed with pentane (2×3 mL), dried and lyophilized (MeCN/$H_2O$) to afford 19 (0.110 g, 0.233 mmol, 44%) as a green solid. LCMS: calc. for [M+H]$^+$=473.15, found 473.2. $^1$H NMR (400 MHz, DMSO-$d_6$) as a mixture of hydrates and rotamers δ 9.95-9.74 (m, 1H), 9.43-9.24 (m, 1H), 9.10-8.89 (m, 1H), 8.27-8.06 (m, 1H), 7.72-7.55 (m, 1H), 7.51-7.27 (m, 1H), 6.70 (s, 0.44H), 6.47 (s, 0.28H), 6.29 (s, 0.44H), 5.84 (s, 0.28H), 5.11-3.45 (m, 8H), 2.06-1.45 (m, 6H), 1.35-0.82 (m, 5H) ppm.

Example 20

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridazin-3-yl)furan-2-carboxamide

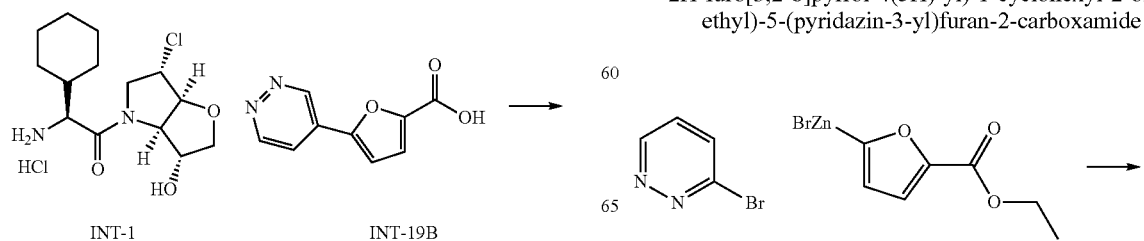

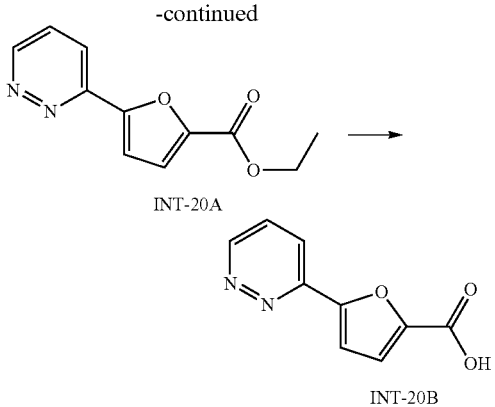

i) A solution of (5-(ethoxycarbonyl)furan-2-yl)zinc(II) bromide (6.29 mL, 0.5 M in tetrahydrofuran, 3.14 mmol and 3-bromopyridazine (0.500 g, 3.14 mmol) in THF (10 mL) was degassed with Ar. 1,1'-Bis(diphenylphosphino)ferrocenepalladium(II) dichloride (0.161 g, 0.220 mmol) was added and the mixture was heated at reflux temperature for 2 h. The mixture was filtered over celite. The filtrate was concentrated under reduced pressure. Purification by reversed phase chromatography (C18, MeCN, H$_2$O, HCOOH) afforded INT-20A. LCMS: calc. for [M+H]$^+$=219.07, found 219.2.

ii) LiOH.H$_2$O (0.088 g, 2.1 mmol) was added to a mixture of INT-20A in THF (5 mL) and water (3 mL). The reaction was heated to 65° C. for 2 h. The RM was concentrated in vacuo. The residue was acidified to pH 2-3 using aqueous 1 M HCl. 2-Propanol (10 mL) was added and the solids were filtered off and washed with diethyl ether to obtain INT-20B (0.063 g, 0.33 mmol, 11% over 2 steps) as a white solid. LCMS: calc. for [M+H]$^+$=191.04, found 191.2.

i) A suspension of INT-1 (0.111 g, 0.326 mmol), INT-20B (0.062 g, 0.33 mmol), EDCl (0.069 g, 0.36 mmol), NEt$_3$ (0.11 mL, 0.82 mmol 0.082 g) and HOAt (0.0040 g, 0.033 mmol) in DMF (10 mL) was stirred at RT for 72 h. Aqueous saturated NaHCO$_3$ (20 mL) was added and the mixture was extracted with EtOAc (2×20 mL). The combined organic layer was washed with water (10 mL) and brine (2×10 mL), dried on Na$_2$SO$_4$ and concentrated in vacuo. FC (EtOAc/heptane 1:1→1:0) afforded INT-20C (0.081 g, 0.17 mmol, 52%). LCMS: calc. for [M+H]$^+$=475.17, found 475.2.

ii) DMP (0.145 g, 0.341 mmol) was added to a solution of INT-20C (0.081 g, 0.17 mmol) in DCM (3 mL). The mixture was stirred at RT for 3 h. An aqueous solution of Na$_2$S$_2$O$_3$ (10%, 10 mL) was added and the mixture was stirred vigorously for 30 min. An aqueous saturated solution of NaHCO$_3$ (20 mL) was added. The aqueous layer was extracted with DCM (2×30 mL). The combined organic layer was dried on Na$_2$SO$_4$ and concentrated in vacuo. Trituration from EtOAc/heptane followed by lyophilisation (MeCN/H$_2$O) afforded 20 (0.053 g, 0.11 mmol, 66%) as a white solid. LCMS: calc. for [M+H]$^+$=473.15, found 473.1. $^1$H NMR (400 MHz, DMSO-d$_6$) as a mixture of hydrates and rotamers δ 9.31-9.19 (m, 1H), 8.99-8.78 (m, 1H), 8.47-8.30 (m, 1H), 7.93-7.78 (m, 1H), 7.55-7.34 (m, 2H), 6.72 (s, 0.43H), 6.47 (s, 0.23H), 6.33 (s, 0.43H), 5.85 (s, 0.23H), 5.11-3.45 (m, 8H), 2.04-1.50 (m, 6H), 1.29-0.85 (m, 5H) ppm.

Example 21

N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridazin-4-yl)oxazole-5-carboxamide

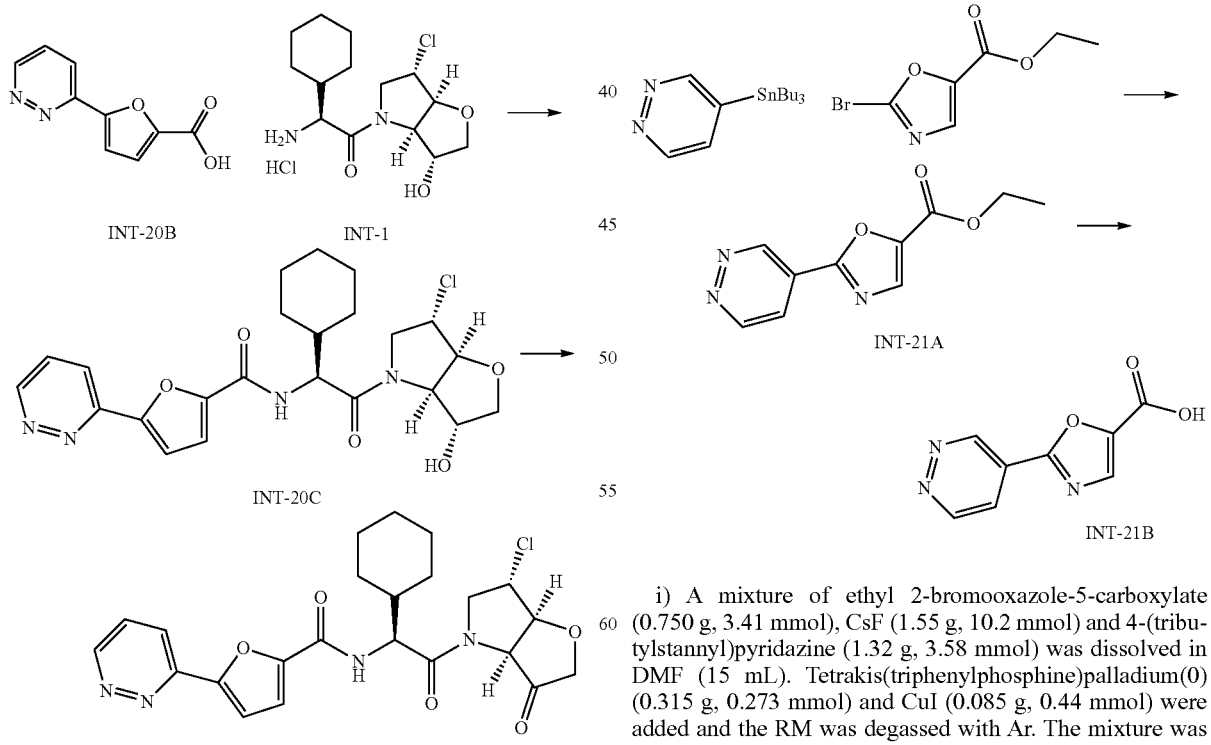

i) A mixture of ethyl 2-bromooxazole-5-carboxylate (0.750 g, 3.41 mmol), CsF (1.55 g, 10.2 mmol) and 4-(tributylstannyl)pyridazine (1.32 g, 3.58 mmol) was dissolved in DMF (15 mL). Tetrakis(triphenylphosphine)palladium(0) (0.315 g, 0.273 mmol) and CuI (0.085 g, 0.44 mmol) were added and the RM was degassed with Ar. The mixture was stirred in the microwave at 80° C. for 30 min. The RM was diluted with EtOAc (50 mL) and an aqueous saturated solution of KF (50 mL) and stirred for 16 h. The mixture was filtered; the aqueous layer was extracted with EtOAc. The combined organic layer was washed with an aqueous saturated solution of NaHCO$_3$ (100 mL), water (2×100 mL) and brine (100 mL). The organic layer was dried over Na$_2$SO$_4$ and concentrated in vacuo. FC (EtOAc/heptane 1:9→1:0) afforded INT-21A (0.349 g, 1.59 mmol, 47%) as a white solid. LCMS: calc. for [M+H]$^+$=220.06, found 220.2.

ii) LiOH.H$_2$O (0.267 g, 6.36 mmol) was added to a suspension of INT-21A (0.349 g, 1.59 mmol) in THF (10 mL) and water (10 mL). The mixture was stirred at RT for 2 h. The RM was concentrated in vacuo and stripped with toluene (2×5 mL) and DCM (2×5 mL). The residue was acidified to pH 3-4) using aqueous 2 M HCl (~1.2 mL). To this i-PrOH (4 mL) was added. The solids were filtered off and washed with i-PrOH and diethyl ether, dried in vacuo to obtain INT-21B (0.304 g, 1.59 mmol, 100%) as a red-brown solid. LCMS: calc. for [M+H]$^+$=192.03, found 192.2.

tane 1:4→1:0) afforded INT-21C (0.192 g, 0.403 mmol, 28%). LCMS: calc. for [M+H]$^+$=476.16, found 476.2.

ii) DMP (0.342 g, 0.807 mmol) was added to a solution of INT-21C (0.192 g, 0.403 mmol) in DCM (10 mL). The RM was stirred at RT for 16 h. An aqueous solution of Na$_2$S$_2$O$_3$ (10%, 10 mL) was added and the RM was stirred vigorously for 2 h. The mixture was diluted with an aqueous saturated solution of NaHCO$_3$ (20 mL) and DCM (10 mL). The aqueous layer was extracted with DCM (20 mL). The combined organic layer was washed with an aqueous saturated solution of NaHCO$_3$ (25 mL) and brine (25 mL), dried over Na$_2$SO$_4$ and concentrated in vacuo. Recrystallization (EtOAc/heptane) and lyophilisation (MeCN/H$_2$O) afforded compound 21 (0.108 g, 0.228 mmol, 57%). LCMS: calc. for [M+H]$^+$=474.15, found 474.2. $^1$H NMR (400 MHz, DMSO-d$_6$) as a mixture of hydrates and rotamers δ 9.96-9.81 (m, 1H), 9.61-9.42 (m, 1H), 9.24-9.05 (m, 1H), 8.39-8.26 (m, 1H), 8.26-8.10 (m, 1H), 6.66 (s, 0.36H), 6.47 (s, 0.26H), 6.23 (s, 0.36H), 5.84 (s, 0.26H), 5.17-3.46 (m, 8H), 2.04-1.51 (m, 6H), 1.29-0.88 (m, 5H) ppm.

Example 22

N-((S)-2-((3aS,6S,6aS)-6-chloro-3-oxotetrahydro-2H-furo[3,2-b]pyrrol-4(5H)-yl)-1-cyclohexyl-2-oxo-ethyl)-4-methyl-2-(pyrazin-2-yl)thiazole-5-carboxamide

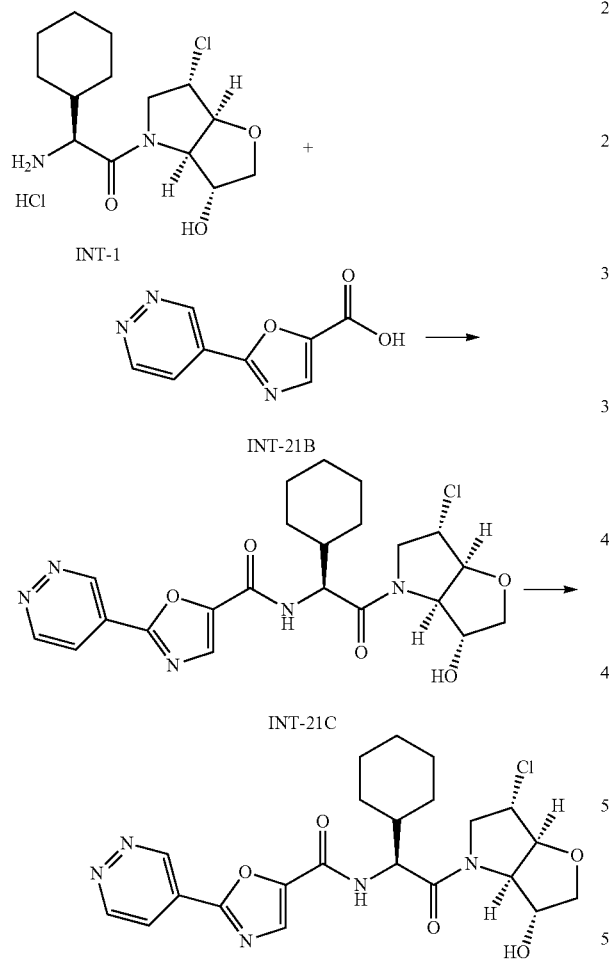

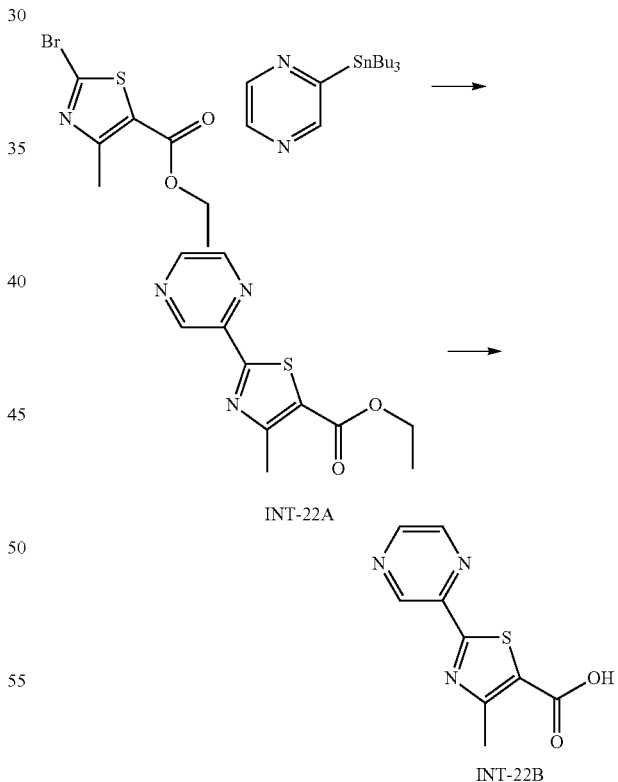

i) A suspension of INT-1 (0.491 g, 1.45 mmol), INT-21B (0.304 g, 1.59 mmol), EDCl (0.365 g, 1.90 mmol), NEt$_3$ (0.513 g, 5.06 mmol, 0.706 mL) and HOAt (0.019 g, 0.15 mmol) in DMF (15 mL) was stirred at RT for 96 h and at 50° C. for 16 h. The mixture was diluted with EtOAc (75 mL) and an aqueous saturated solution of NaHCO$_3$ (75 mL). The water layer was extracted with EtOAc (2×75 mL). The combined organic layer washed with an aqueous saturated solution of NaHCO$_3$ (3×150 mL) and brine (150 mL), dried over Na$_2$SO$_4$ and concentrated in vacuo. FC (EtOAc/hepi) In a microwave vessel ethyl 2-bromo-4-methyl)thiazole-5-carboxylate (0.678 g, 2.71 mmol) and 2-(tributylstannyl)pyrazine (1.00 g, 2.71 mmol) were dissolved in DMF (20 mL). CsF (1.24 g, 8.13 mmol), CuCl (0.035 g, 0.35 mmol) and [1,1'-bis(diphenylphosphino)ferrocene]dichloropalladium(II) (0.246 g, 0.271 mmol) were added after degassing the mixture with Ar. The vessel was capped and heated to 100° C. for 30 min in the microwave. The RM was diluted with water (100 mL) and EtOAc (100 mL). The water layer was extracted with EtOAc (2×100 mL). Organic layer was dried over Na$_2$SO$_4$ and then filtered over celite. The filter cake was washed with EtOAc (100 mL) and the filtrate was concentrated in vacuo. FC (EtOAc/heptane 0:1→1:0) afforded INT-22A (0.502 g, 1.91 mmol, 71%) as a white solid. LCMS: calc. for [M+H]$^+$=250.06, found 250.2.

ii) At RT LiOH.H$_2$O (0.166 g, 3.96 mmol) was added to a mixture of INT-22A (0.502 g, 1.91 mmol) in THF (20 mL) and water (8 mL). The RM was stirred at RT for 16 h. The reaction was acidified with aqueous 1 M HCl (10 mL) to pH 3-4. The mixture was extracted with EtOAc (3×20 mL). The collected organic layer was washed with brine (20 mL), dried over Na$_2$SO$_4$ and concentrated in vacuo to give INT-22B (0.363 g, 1.56 mmol, 77%) as a white solid. LCMS: calc. for [M+H]$^+$=222.03, found 222.2.

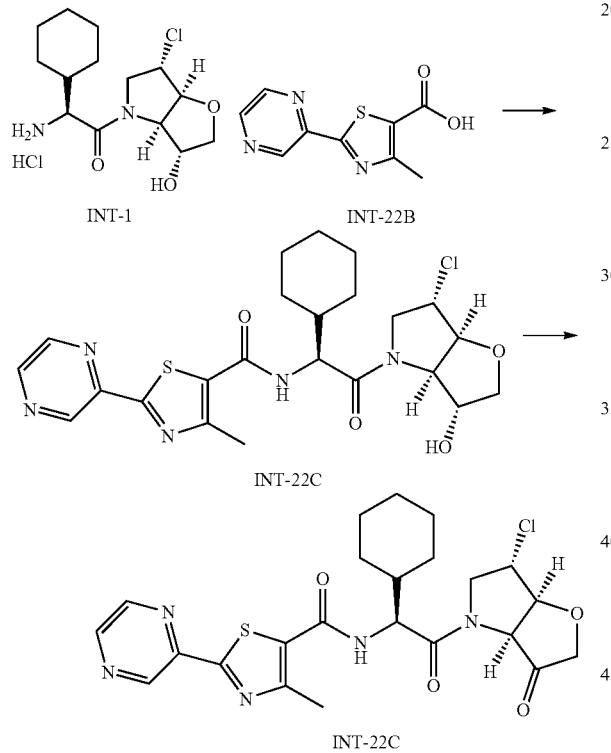

i) A suspension of INT-1 (0.557 g, 1.64 mmol), INT-22B (0.363 g, 1.64 mmol), EDCl (0.377 g, 1.93 mmol), NEt$_3$ (0.664 g, 6.56 mmol, 0.915 mL) and HOAt (0.045 g, 0.33 mmol) in DMF (8 mL) was stirred at RT for 16 h. The mixture was diluted with EtOAc (20 mL) and washed with aqueous saturated solution of NaHCO$_3$ (20 mL) and brine (10 mL). The combined organic layer was dried over Na$_2$SO$_4$ and concentrated in vacuo. FC (EtOAc/heptane 0:1→1:0) afforded INT-22C (0.486 g, 0.912 mmol, 56%). LCMS: calc. for [M+H]$^+$=506.16, found 506.1.

ii) DMP (0.815 g, 1.92 mmol) was added to a solution of INT-22C (0.486 g, 0.960 mmol) in DCM (8 mL). The mixture was stirred at RT for 16 h. An aqueous solution of Na$_2$S$_2$O$_3$ (10%, 25 mL) was added and the mixture was stirred vigorously for 30 min. An aqueous saturated solution of NaHCO$_3$ (10 mL) was added and the layers were separated. The aqueous layer was extracted with DCM (2×10 mL). The combined organic layer was dried over Na$_2$SO$_4$ and concentrated in vacuo. The crude was dissolved in a small amount of boiling EtOAc and cooled to RT. Heptane was added until a precipitate formed and the mixture was reheated at boiling temperature until a clear solution was formed. The solution was left at RT standing for 16 h and the solids formed were filtered off. Lyophilisation (MeCN/H$_2$O) afforded 22 (0.300 g, 0.565 mmol, 59%). LCMS: calc. for [M+H]$^+$=504.14, found 504.2. $^1$H NMR (400 MHz, DMSO-d$_6$) as a mixture of hydrates and rotamers δ 9.43-9.23 (m, 1H), 8.82-8.66 (m, 2.97H), 8.12-8.05 (m, 0.3H), 6.68 (s, 0.42H), 6.46 (s, 0.27H), 6.36 (s, 0.42H), 5.82 (s, 0.27H), 5.13-3.45 (m, 8H), 2.72-2.57 (m, 3H), 2.03-1.49 (m, 6H), 1.33-0.83 (m, 5H) ppm.

Example 23

N-((S)-2-((3aS,6S,6aS)-6-chloro-3-oxotetrahydro-2H-furo[3,2-b]pyrrol-4(5H)-yl)-1-cyclohexyl-2-oxo-ethyl)-2-(pyridin-3-yl)-4-(trifluoromethyl)thiazole-5-carboxamide

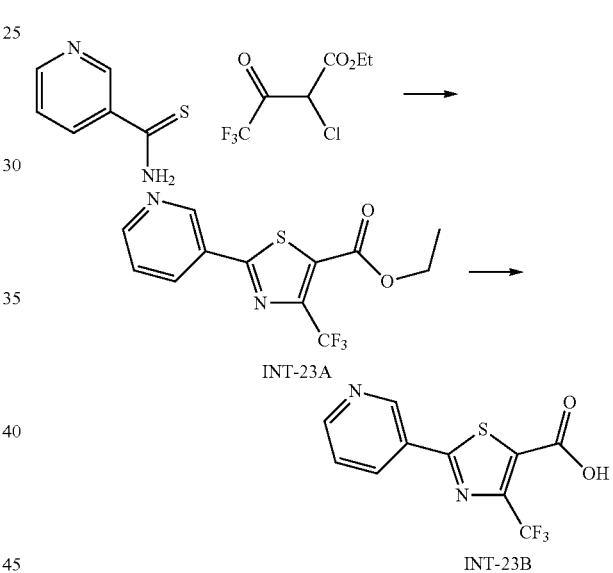

i) To a solution of thionicotinamide (0.500 g, 3.62 mmol) in EtOH (10 mL) was added ethyl 2-chloro-4,4,4-trifluoro-3-oxobutanoate (1.58 g, 7.24 mmol) and the mixture was heated to 150° C. for 10 min. NEt$_3$ (1.10 g, 10.9 mmol, 1.51 mL) was added and the RM was stirred at 130° C. for 1 minute. The RM was concentrated in vacuo and redissolved in EtOAc (150 mL). The organic phase was washed with water (2×50 mL), dried with Na$_2$SO$_4$ and concentrated in vacuo. FC (EtOAc/heptane 0:1→1:0) afforded INT-23A (0.491 g, 1.54 mmol, 43%). LCMS: calc. for [M+H]$^+$=303.03, found 303.2.

ii) At RT LiOH.H$_2$O (0.204 g, 4.87 mmol) was added to a mixture of INT-23A (0.491 g, 1.54 mmol) in THF (20 mL) and water (8 mL). The reaction was stirred at RT for 16 h. The RM was acidified with aqueous 1 M HCl to pH 3-4 (10 mL). The mixture was extracted with EtOAc (3×20 mL). The collected organic layer was washed with brine (20 mL), dried over Na$_2$SO$_4$ and concentrated in vacuo to give INT-23B (0.171 g, 0.592 mmol, 37%) as an off-white solid. LCMS: calc. for [M+H]$^+$=275.00, found 275.2.

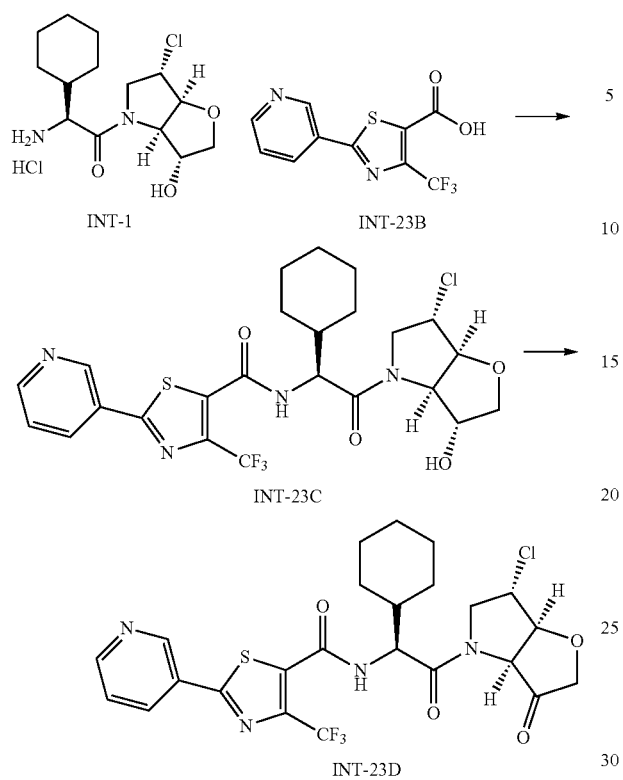

INT-1, INT-23B, INT-23C, INT-23D i) A suspension of INT-1 (0.319 g, 0.941 mmol), INT-23B (0.258 g, 0.941 mmol), EDCl (0.216 g, 1.13 mmol), NEt₃ (0.381 g, 3.76 mmol, 0.525 mL) and HOAt (0.026 g, 0.19 mmol) in DMF (8 mL) was stirred at RT for 16 h. Additional EDCl (0.216 g, 1.13 mmol), and HOAt (0.026 g, 0.19 mmol) were added and the mixture stirred for 16 h. The mixture was diluted with EtOAc (20 mL) and washed with aqueous saturated solution of NaHCO₃ (20 mL) and brine (10 mL). The combined organic layer was dried over Na₂SO₄ and concentrated in vacuo. FC (EtOAc/heptane 0:1→1:0) afforded INT-23C (0.245 g, 0.416 mmol, 44%). LCMS: calc. for [M+H]⁺=559.13, found 559.2.

ii) DMP (0.372 g, 0.877 mmol) was added to a solution of INT-23C (0.245 g, 0.416 mmol) in DCM (8 mL). The mixture was stirred at RT for 16 h. An aqueous solution of Na₂S₂O₃ (10%, 25 mL) was added and the mixture was stirred vigorously for 30 min. An aqueous saturated solution of NaHCO₃ (10 mL) was added and the layers were separated. The aqueous layer was extracted with DCM (2×10 mL). The combined organic layer was dried over Na₂SO₄ and concentrated in vacuo. The crude was dissolved in a small amount of hot EtOAc and cooled to RT. Heptane was added until a precipitate formed and the mixture was reheated until a clear solution was formed. The solution was left overnight and the solids formed were filtered off. Basic preparative HPLC (C18, MeCN (1% 10 mM NH₄HCO₃), 10 mM NH₄HCO₃ in H₂O) and lyophilisation afforded 23 (0.055 g, 0.094 mmol, 21%). LCMS: calc. for [M+H]⁺= 557.12, found 557.2. ¹H NMR (400 MHz, DMSO-d₆) as a mixture of hydrates and rotamers δ 9.55-9.29 (m, 1H), 9.24-8.98 (m, 1H), 8.82-8.70 (m, 1H), 8.58-8.32 (m, 1H), 7.68-7.52 (m, 1H), 7.01-5.34 (m, 0.09H), 5.29-3.44 (m, 8H), 1.91-1.48 (m, 6H), 1.29-0.92 (m, 5H) ppm.

Example 24

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-5-yl)thiazole-2-carboxamide

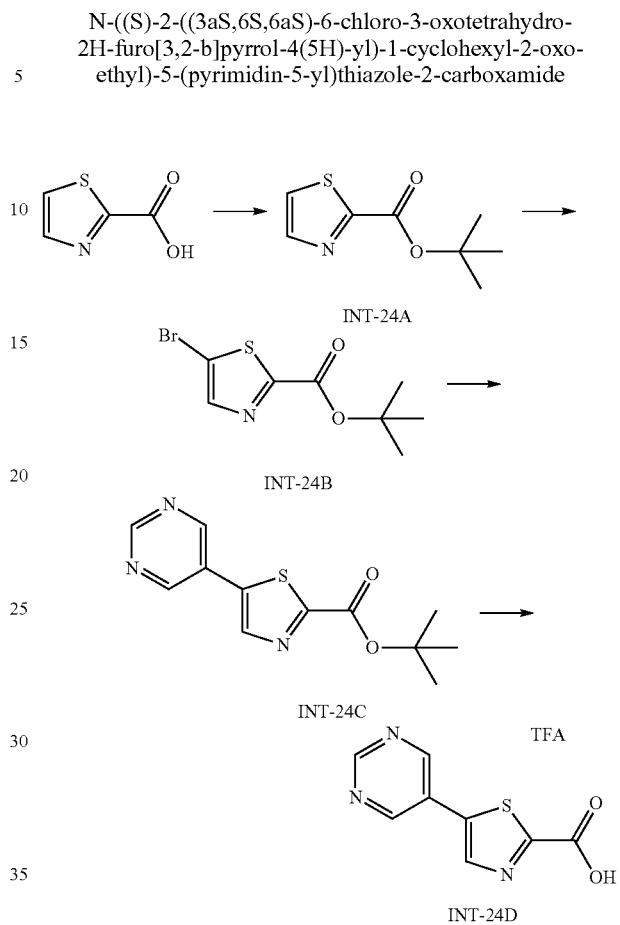

INT-24A, INT-24B, INT-24C, INT-24D i) Thiazole-2-carboxylic acid (2.50 g, 19.4 mmol) was dissolved in DCM (100 mL) and 2 drops of DMF were added, followed by oxalyl chloride (3.19 g, 25.2 mmol, 2.16 mL). The RM was stirred for 3 h at RT. Vacuum was applied to eliminate the excess of HCl formed and potassium 2-methylpropan-2-olate (5.65 g, 50.3 mmol) was added. The RM was stirred until completion. Water (75 mL) was added and the aqueous layer was extracted with DCM (3×10 ml). The combined organic layer was dried over Na₂SO₄ and concentrated in vacuo. FC (EtOAc/heptane 0:1→3:7) afforded INT-24A (2.00 g, 10.8 mmol, 56%). LCMS: calc. for [M+H]⁺=186.05, found 186.1.

ii) Thiazole INT-24A (0.500 g, 2.70 mmol) was added to a solution of lithium diisopropylamide (1 M in THF/heptane/ethylbenzene, 2.97 mmol, 2.97 mL) in dry THF (10 mL) at −78° C. and the RM was stirred for 1 hour. Tetrabromomethane (1.16 g, 3.51 mmol) was added and the RM was stirred for 3 h. The RM was quenched by adding a saturated aqueous solution of NH₄Cl (10 mL). The mixture was allowed to reach RT. The aqueous layer was extracted with EtOAc (2×10 ml). The combined organic layer was dried over Na₂SO₄ and concentrated in vacuo. FC (EtOAc/heptane 0:1→1:4) afforded INT-24B (0.300 g, 1.14 mmol, 42%). LCMS: calc. for [M+H]⁺=263.96, found 264.0.

iii) Bromide INT-24B (0.300 g, 1.14 mmol), 4-(tributylstannyl)pyridazine (0.419 g, 1.14 mmol), tri(furan-2-yl)phosphine (0.53 g, 0.23 mmol) and bis(dibenzylideneacetone) palladium (0.104 g, 0.114 mmol) were dissolved in dry 1,4-dioxane (5 mL) and the resulting solution was heated at 90° C. and stirred for 16 h. The reaction was cooled to RT, diluted with an aqueous solution of saturated NaHCO₃ (10 mL) and extracted with EtOAc (3×10 mL). The combined organic layer was dried over Na₂SO₄ and concentrated in vacuo. FC (EtOAc/heptane 0:1→1:1) afforded INT-24C (0.210 g, 0.798 mmol, 70%). LCMS: calc. for [M+H]⁺= 264.07, found 264.1.

iv) TFA (5 mL) was added to a solution of INT-24C (0.210 g, 0.798 mmol) in DCM at −10° C. The RM was allowed to warm to RT and stirred for 4 h. The solvent was evaporated in vacuo to give INT-24D (0.240 g, 0.747 mmol, 94%) as its TFA salt. LCMS: calc. for [M+H]⁺=208.01, found 208.0.

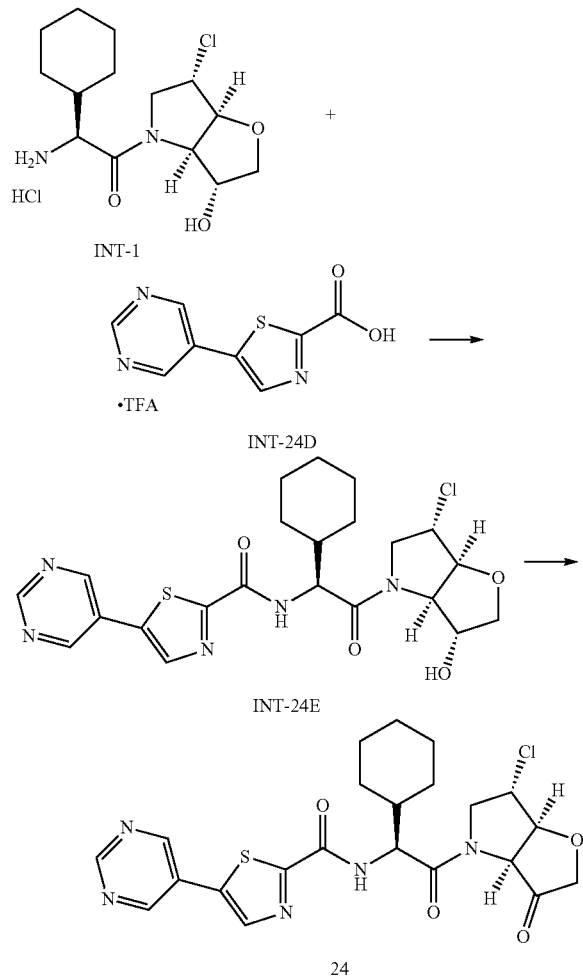

i) At RT NEt₃ (0.377 g, 3.74 mmol, 0.519 mL) and propylphosphonic anhydride (50% w/w in DMF, 0.666 g, 1.05 mmol, 0.641 mL) were added to a solution of INT-1 (0.253 g, 0.747 mmol) and the TFA salt of INT-24D (0.240 g, 0.747 mmol) in dry DMF (50 mL). The RM was stirred at RT for 16 h. The mixture was diluted with aqueous saturated NaHCO₃ (10 mL) and extracted with EtOAc (3×20 mL). The combined organic layer was dried over Na₂SO₄ and concentrated in vacuo. FC (DCM/MeOH 99:1→96:4) afforded INT-24E (0.170 g, 0.346 mmol, 46%). LCMS: calc. for [M+H]⁺=492.14, found 492.1.

ii) DMP (0.352 g, 0.829 mmol) was added to a solution of INT-24E (0.170 g, 0.346 mmol) in DCM (20 mL). The mixture was stirred at RT for 16 h. An aqueous solution of Na₂S₂O₃ (10%, 20 mL) was added and the mixture was stirred vigorously for 30 min. The mixture was diluted with an aqueous solution of saturated NaHCO₃ (20 mL). The aqueous layer was extracted with DCM (20 mL×3). The combined organic layer was dried over Na₂SO₄ and concentrated in vacuo. Recrystallization (DCM/heptane) and lyophilisation (MeCN/H₂O) afforded compound 24 (0.130 g, 0.265 mmol, 77%) as a white solid. LCMS: calc. for [M+H]⁺=490.12, found 490.2. ¹H NMR (400 MHz, DMSO-d₆) as a mixture of hydrates and rotamers δ 9.31-9.18 (m, 3H), 8.76-7.91 (m, 2H), 6.66 (s, 0.41H), 6.49 (s, 0.41H), 6.45 (s, 0.16H), 5.84 (s, 0.16H), 5.23-3.41 (m, 8H), 2.04-1.52 (m, 6H), 1.31-0.89 (m, 5H) ppm.

Example 25

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrazin-2-yl)furan-2-carboxamide

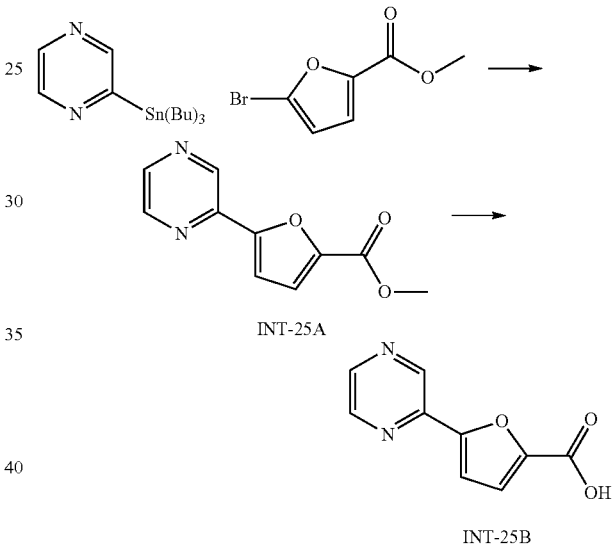

i) A solution of 2-(tributylstannyl)pyrazine (0.470 g, 1.27 mmol) and methyl 5-bromofuran-2-carboxylate (0.266 g, 1.30 mmol) in dry DMF (7 mL) was degassed with N₂. CsF (0.580 g, 3.82 mmol), CuCl (0.016 g, 0.17 mmol) and [1,1'-bis(diphenylphosphino)ferrocene]palladium(II) dichloride (0.104 g, 0.127 mmol) were added and the RM was heated at 110° C. under microwave conditions for 30 min. The RM was diluted with DCM (15 mL) and poured in water (15 mL). The water layer was extracted with DCM (2×30 mL). The combined organic layer was washed with brine (20 mL), dried over Na₂SO₄ and filtered over celite. The filter cake was washed with DCM (45 mL). The filtrate was concentrated in vacuo. The crude product was purified by FC (EtOAc/heptane 5:95→4:6) to afford INT-25A (0.150 g, 0.455 mmol, 36%) as a pink solid. LCMS: calc. for [M+H]⁺=205.05, found 205.2.

ii) LiOH.H₂O (0.147 g, 0.446 mmol) was added to a solution of INT-25A (0.049 g, 1.2 mmol) in THF (3.0 mL) and water (1.0 mL). The RM was stirred at RT for 2 h. The RM was concentrated in vacuo. The residue was acidified to pH 3-4 by addition of aqueous 2 M HCl (~1.20 mL) and triturated with 2-propanol (1.5 mL). The resulting solid was obtained by filtration, washed with cold 2-propanol (2×2.0 mL) and diethyl ether (2×3.0 mL) and dried to afford INT-25B (0.088 g, 0.43 mmol, 95%) as a yellow solid. LCMS: calc. for [M+H]+=191.04, found 191.1.

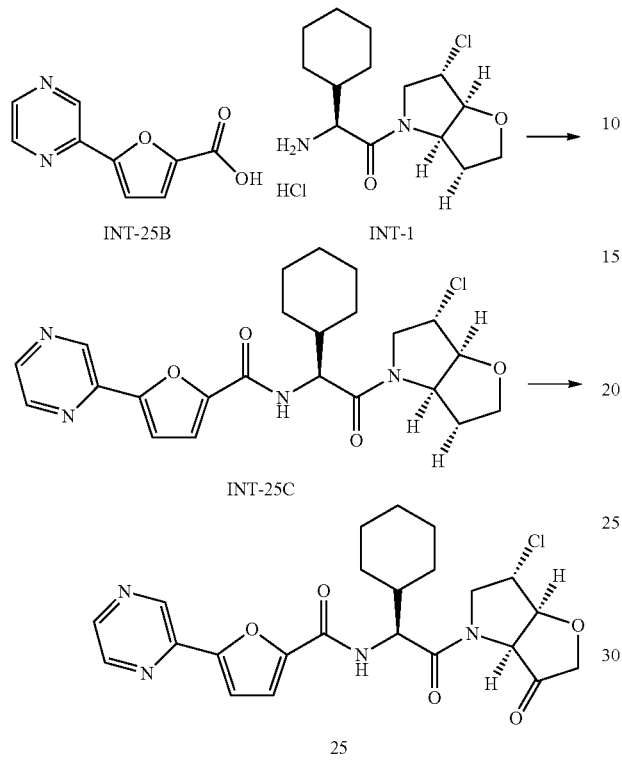

i) A suspension of INT-1 (0.155 g, 0.458 mmol), INT-25B (0.087 g, 0.46 mmol), EDCl (0.105 g, 0.549 mmol), NEt₃ (0.185 g, 1.83 mmol, 0.254 mL) and HOAt (0.006 g, 0.05 mmol) in dry DMF (5 mL) was stirred at RT for 72 h. The RM was diluted with EtOAc (20 mL), poured in an aqueous saturated solution of NaHCO₃ (25 mL) and extracted with EtOAc (4×10 mL). The combined organic layer was washed with brine (25 mL), dried over Na₂SO₄ and concentrated in vacuo. The crude product was purified by FC (MeOH/DCM 0:1→6:94) to afford INT-25C (0.094 g, 0.20 mmol, 43%) as a white solid. LCMS: calc. for [M+H]⁺=475.17, found 475.2.

ii) DMP (0.208 g, 0.490 mmol) was added to a solution of INT-25C (0.093 g, 0.196 mmol) in DCM (3 mL). The mixture was stirred at RT for 16 h. An aqueous solution of Na₂S₂O₃ (10%, 10 mL) was added and the mixture was stirred vigorously for 1.5 h. An aqueous saturated solution of NaHCO₃ (10 mL) was added and extracted with DCM (4×10 mL). The combined organic layer was dried over Na₂SO₄ and concentrated in vacuo. The crude product was purified by trituration from heptane/EtOAc (1:1, 4.0 mL). The precipitate was obtained by filtration, washed with pentane (2×2.0 mL), dried and lyophilized (MeCN/H₂O) to afford 25 (0.049 g, 0.101 mmol, 52%) as a white solid. LCMS: calc. for [M+H]⁺=473.15, found 473.2. ¹H NMR (400 MHz, DMSO-d₆) as a mixture of hydrates and rotamers δ 9.52-9.29 (m, 1H), 8.97-8.79 (m, 1H), 8.79-8.58 (m, 2H), 7.53-7.25 (m, 2H), 6.72 (s, 0.42H), 6.47 (s, 0.24H), 6.33 (s, 0.42H), 5.85 (s, 0.24H), 5.19-3.42 (m, 8H), 2.11-1.43 (m, 6H), 1.36-0.79 (m, 5H) ppm.

Example 26

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-4-yl)thiazole-2-carboxamide (26)

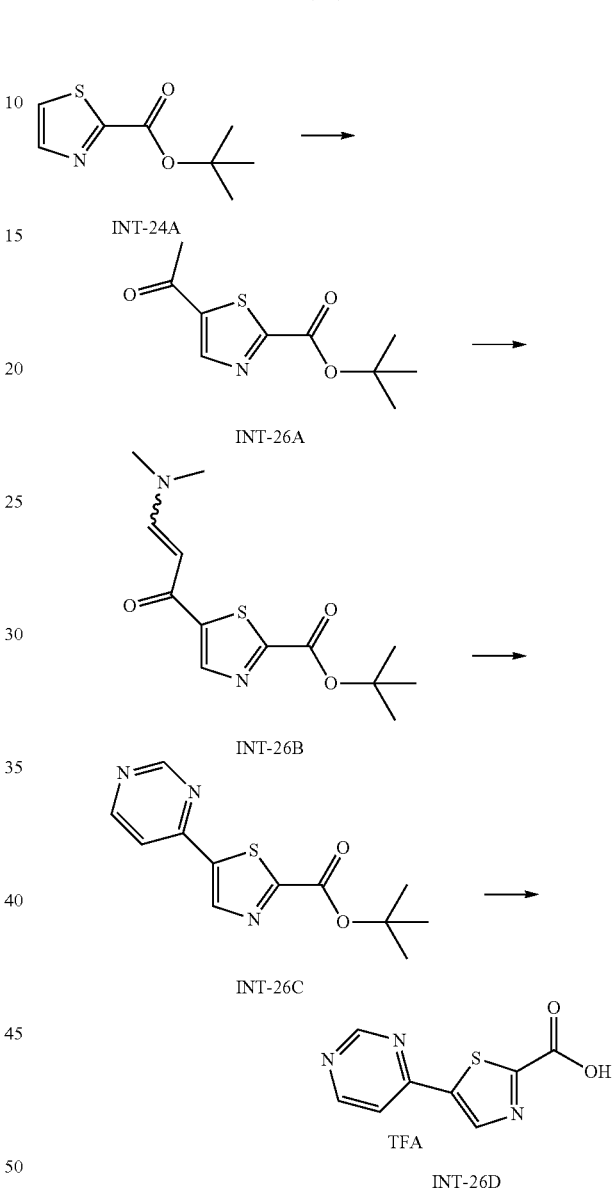

i) Thiazole INT-24A (1.15 g, 6.21 mmol) was added to a solution of lithium diisopropylamine (1 M in THF/heptane/ethylbenzene, 6.83 mmol, 6.83 mL) in dry tetrahydrofuran (15 mL) at −78° C. and the RM was stirred for 30 min. N-Methoxy-N-methylacetamide (0.96 g, 9.3 mmol) was added and the RM was stirred for 3 h. The RM was quenched by adding a saturated aqueous solution of NH₄Cl (10 mL). The mixture was allowed to reach to RT. The aqueous layer was extracted with EtOAc (2×10 ml). The combined organic layer was dried over Na₂SO₄ and concentrated in vacuo. FC (EtOAc/heptane 0:1→1:4) afforded INT-26A (0.40 g, 1.8 mmol, 28%). LCMS: calc. for [M+H]⁺=228.06, found 228.1.

ii) Thiazole INT-26A (0.500 g, 2.20 mmol) was dissolved in 1,1-dimethoxy-N,N-dimethylmethanamine (5.24 g, 44.0 mmol, 6.55 mL) and the mixture was warmed up to 70° C. and stirred for 2 h. The RM was allowed to reach RT and the solvent evaporated to leave INT-26B (0.70 g). LCMS: calc. for [M+H]⁺=283.10, found 283.2.

iii) Thiazole INT-26B (0.70 g) was added to a solution of formimidamide acetate (1.29 g, 12.4 mmol) in dry DMF (10 mL) and the reaction was heated up to 95° C. and stirred for 5 h. The reaction was cooled to RT and diluted with aqueous saturated NaHCO₃ (10 mL) and extracted with EtOAc (3×20 mL). The combined organic layer was dried over Na₂SO₄ and concentrated in vacuo. FC (DCM) afforded INT-26C (0.300 g, 1.13 mmol, 46% over 2 steps). LCMS: calc. for [M+H]⁺=264.07, found 264.1.

iv) TFA (5 mL) was added to a solution of INT-26C (0.30 g, 1.13 mmol) in DCM at −10° C. The RM was allowed to warm to RT and stirred for 3 h. The solvent was evaporated in vacuo to give INT-26D (0.360 g, 1.12 mmol, 98%) as its TFA salt. LCMS: calc. for [M+H]⁺=208.01, found 208.0.

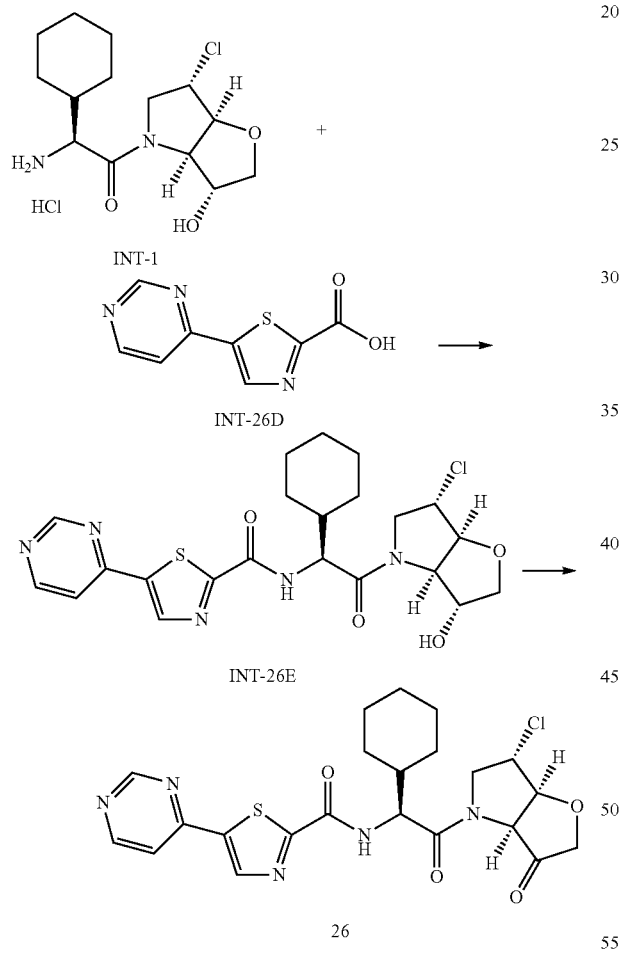

i) At RT NEt₃ (0.570 g, 5.60 mmol, 0.780 mL) and propylphosphonic anhydride (50% w/w in DMF, 1.00 g, 1.57 mmol, 0.96 mL) were added to a solution of INT-1 (0.380 g, 1.12 mmol) and the TFA salt of INT-26D (0.360 g, 1.12 mmol) in 10 mL of dry DMF. The RM was stirred at RT for 16 h. The mixture was diluted with aqueous saturated NaHCO₃ (10 mL) and extracted with EtOAc (3×20 mL). The combined organic layer was dried over Na₂SO₄ and concentrated in vacuo. FC (DCM/MeOH 99:1→96:4) afforded INT-26E (0.17 g, 0.34 mmol, 31%). LCMS: calc. for [M+H]⁺=492.14, found 492.2.

ii) DMP (0.36 g, 0.86 mmol) was added to a solution of INT-26E (0.17 g, 0.34 mmol) in DCM (20 mL). The RM was stirred at RT for 16 h. An aqueous solution of Na₂S₂O₃ (10%, 20 mL) was added and the mixture was stirred vigorously for 30 min. The mixture was diluted with an aqueous solution of saturated sodium bicarbonate (20 mL). The aqueous layer was extracted with DCM (20 mL×3). The combined organic layer was dried over Na₂SO₄ and concentrated in vacuo. The crude was purified by FC (EtOAc (1% Et₃N)/heptane 1:1→1:0) and then by basic preparative HPLC (C18, MeCN (1% 10 mM NH₄HCO₃), 10 mM NH₄HCO₃ in H₂O) and lyophilized (MeCN/H₂O) to afford 26 (0.12 g, 0.24 mmol, 71%) as a white solid. LCMS: calc. for [M+H]⁺=490.12, found 490.1. ¹H NMR (400 MHz, DMSO-d₆) as a mixture of hydrates and rotamers δ 9.26-9.20 (m, 1H), 8.99-8.91 (m, 2H), 8.81-7.73 (m, 2H), 6.66 (s, 0.51H), 6.50 (s, 0.51H), 6.49 (s, 0.17H), 5.84 (s, 0.17H), 5.28-3.42 (m, 8H), 2.07-1.49 (m, 6H), 1.33-0.71 (m, 5H) ppm.

Example 27

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyrimidin-4-yl)furan-2-carboxamide

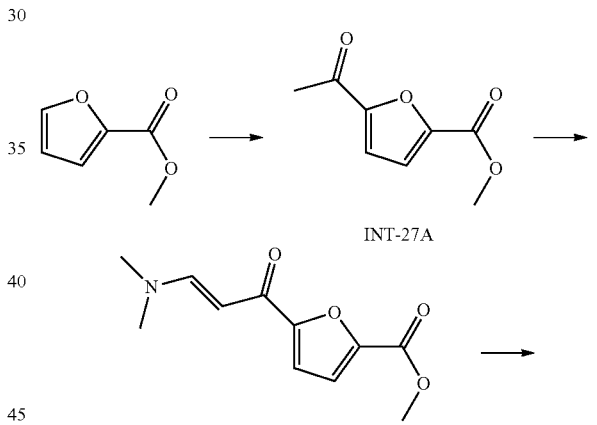

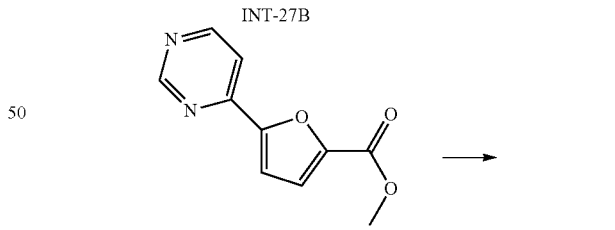

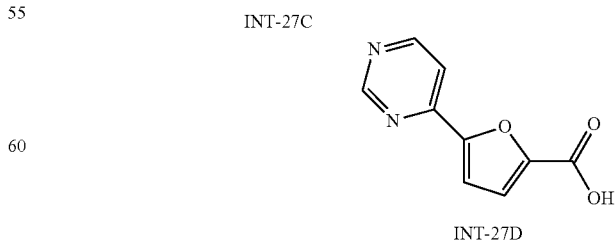

i) Boron trifluoride diethyl etherate (2.61 mL, 20.6 mmol) was added to a mixture of methyl furan-2-carboxylate (1.701 mL, 15.86 mmol) and acetic anhydride (10 mL, 106 mmol). The RM was heated at 70° C. for 2 h. The mixture was diluted with water (100 mL) and extracted with EtOAc (3×50 mL). The combined organic layer was washed with brine (50 mL), dried on Na$_2$SO$_4$ and concentrated under reduced pressure. FC (EtOAc/heptane 1:9→8:2) afforded INT-27A (0.550 g, 3.27 mmol, 21%) as a solid. LCMS: calc. for [M+H]$^+$=169.04, found 169.2.

ii) Ketone INT-27A (0.550 g, 3.27 mmol) in DMF dimethyl acetal (10 mL, 74.7 mmol) was heated at reflux temperature for 2 h. The RM was concentrated under reduced pressure. Trituration from Et$_2$O afforded INT-27B (0.580 g, 2.60 mmol, 79%) as a dark red solid. LCMS: calc. for [M+H]$^+$=224.08, found 224.1.

iii) A suspension of (E)-methyl 5-(3-(dimethylamino)acryloyl)furan-2-carboxylate INT-27B (0.580 g, 2.60 mmol), formamidine acetate (0.406 g, 3.90 mmol) and K$_2$CO$_3$ (0.539 g, 3.90 mmol) in DMF (20 mL) was heated to 120° C. for 20 h. The mixture was diluted with EtOAc (100 mL) and washed with water (50 mL) and brine (2×50 mL), dried on Na$_2$SO$_4$ and concentrated under reduced pressure. FC (EtOAc/heptane 1:9→1:0) afforded INT-27C (0.164 g, 0.803 mmol, 31%) as a yellow solid. LCMS: calc. for [M+H]$^+$=205.05, found 205.1.

iv) LiOH.H$_2$O (0.078 g, 1.9 mmol) was added to a mixture of INT-27C (0.164 g, 0.803 mmol) in THF (8 mL) and water (4 mL). The reaction was stirred at RT for 1 h. The RM was acidified to pH 3-4 using aqueous 1 M HCl. 2-Propanol (10 mL) was added and the solids were filtered off and washed with diethyl ether to obtain INT-27D (0.110 g, 0.578 mmol, 72%) as a pale yellow solid. LCMS: calc. for [M+H]$^+$=191.04, found 191.2.

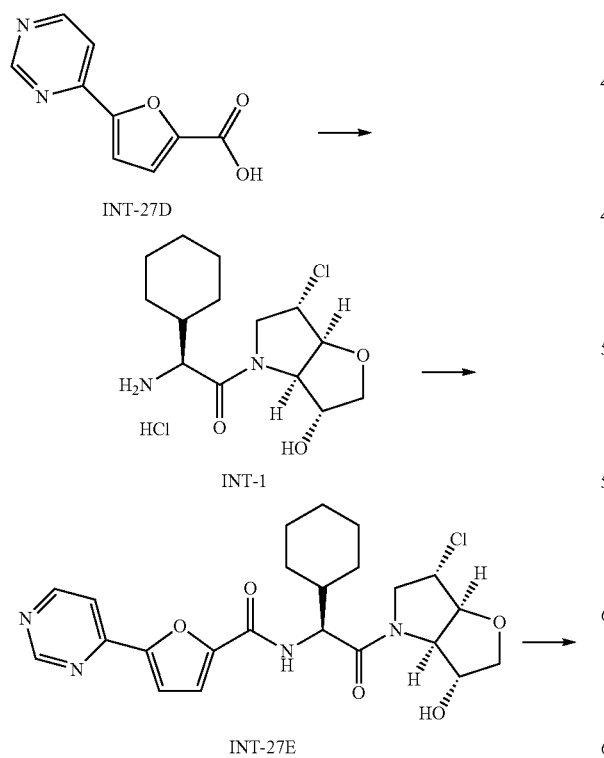

INT-27D

INT-1

INT-27E

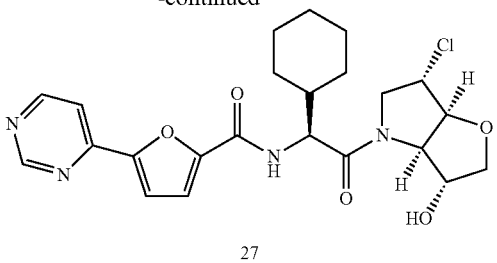

27 i) A suspension of INT-1 (0.200 g, 0.590 mmol), INT-27D (0.110 g, 0.578 mmol), EDCl (0.122 g, 0.636 mmol), NEt$_3$ (0.242 mL, 1.74 mmol) and HOAt (0.008 g, 0.06 mmol) in DMF (10 mL) was stirred at 50° C. for 48 h. Aqueous saturated NaHCO$_3$ (20 mL) was added and the mixture was extracted with EtOAc (2×20 mL). The combined organic layer was washed with water (10 mL) and brine (2×10 mL), dried on Na$_2$SO$_4$ and concentrated in vacuo. FC (EtOAc) afforded INT-27E (0.133 g, 0.280 mmol, 48%). LCMS: calc. for [M+H]$^+$=475.17, found 475.2.

ii) DMP (0.238 g, 0.560 mmol) was added to a solution of INT-27E (0.133 g, 0.280 mmol) in DCM (10 mL). The mixture was stirred at RT for 1.5 h. An aqueous solution of Na$_2$S$_2$O$_3$ (10%, 5 mL) was added and the mixture was stirred vigorously for 30 min. An aqueous saturated solution of NaHCO$_3$ (20 mL) was added. The aqueous layer was extracted with DCM (2×30 mL). The combined organic layer was dried on Na$_2$SO$_4$ and concentrated in vacuo. Purification by basic preparative HPLC (C18, MeCN (1% 10 mM NH$_4$HCO$_3$), 10 mM NH$_4$HCO$_3$ in H$_2$O) and lyophilisation afforded 27 (0.100 g, 0.211 mmol, 76%) as a white solid. LCMS: calc. for [M+H]$^+$=473.15, found 473.2. $^1$H NMR (400 MHz, DMSO-d$_6$) as a mixture of hydrates and rotamers δ 9.11 (m, 1H), 9.00-8.81 (m, 2H), 8.27-7.93 (m, 1H), 7.60-7.29 (m, 2H), 6.71 (s, 0.35H), 6.48 (s, 0.23H), 6.32 (s, 0.35H), 5.86 (s, 0.23H), 5.18-3.43 (m, 8H), 2.07-1.46 (m, 6H), 1.32-0.83 (m, 5H) ppm.

Example 28

N-((S)-2-((3aS,6S,6aS)-6-chloro-3-oxotetrahydro-2H-furo[3,2-b]pyrrol-4(5H)-yl)-1-cyclohexyl-2-oxo-ethyl)-5-(pyridin-4-yl)-1,3,4-thiadiazole-2-carboxamide

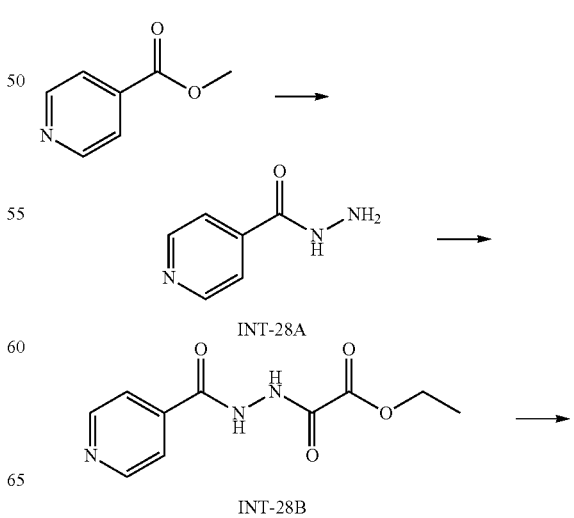

INT-28A

INT-28B

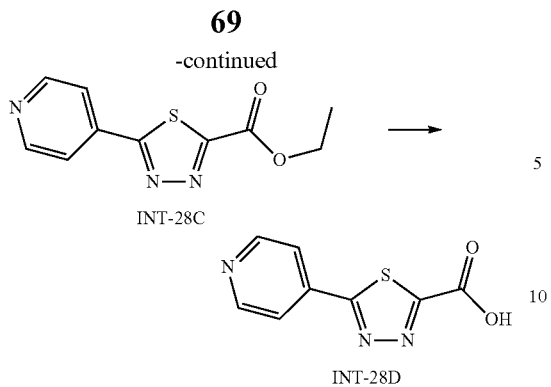

i) A solution of methyl isonicotinate (1.00 mL, 8.47 mmol) and hydrazine hydrate (1.23 mL, 25.4 mmol) in ethanol (10 mL) was stirred at RT for 16 h. Concentration and subsequent coevaporation with toluene and DCM gave INT-28A (1.00 g, 7.31 mmol, 86%). LCMS: calc. for [M+H]$^+$=138.07, found 138.1.

ii) To a solution of INT-28A (1.00 g, 7.29 mmol) in DCM (10 mL) was added ethyl 2-chloro-2-oxoacetate (0.978 mL, 8.75 mmol) drop wise at 0° C. and the RM was stirred for 16 h at RT. Water was added and the mixture was extracted with DCM (3×10 mL). The organic layers were dried over Na$_2$SO$_4$ and concentrated to yield INT-28B as thick orange oil. Used in the next step as such.

iii) To a solution of INT-28B (0.438 g, 1.85 mmol) in dry toluene (5 mL) was added Lawesson's reagent (0.747 g, 1.85 mmol) and the mixture was heated at 110° C. for 1 h. After cooling to RT, water was added and the mixture was washed with DCM (3×10 mL). The combined organic layers were dried over Na$_2$SO$_4$ and concentrated. FC (EtOAc/heptane 0:1→1:0) afforded INT-28C (0.447 g, 1.90 mmol, 31% over 2 steps). LCMS: calc. for [M+H]$^+$=236.05, found 236.1.

iv) LiOH.H$_2$O (0.368 g, 8.77 mmol) was added to a suspension of INT-28C (0.447 g, 1.90 mmol) in THF (5 mL) and water (5 mL). The RM was stirred at RT for 3 h. The mixture was concentrated in vacuo. The residue was acidified to pH 3-4 using aqueous 1M HCl (~8.8 mL). The solids were filtered off and washed with water, dried in vacuo to obtain INT-28D (0.356 g, 1.72 mmol, 90%). LCMS: calc. for [M+H]$^+$=208.02, found 208.0.

i) A suspension of INT-1 (0.300 g, 0.884 mmol), INT-28D (0.183 g, 0.884 mmol), EDCl (0.203 g, 1.06 mmol), NEt$_3$ (0.430 mL, 3.09 mmol) and HOAt (0.012 g, 0.088 mmol) in DMF (4 mL) was stirred at RT for 16 h. The RM was diluted with water and extracted with DCM (2×8 mL). The combined organic layer was washed with brine, dried over Na$_2$SO$_4$ and concentrated in vacuo. FC (EtOAc/heptane 0:1→1:0, 12 g silica) afforded INT-28E (0.250 g, 0.508 mmol, 58%). LCMS: calc. for [M+H]$^+$=492.15, found 492.1.

ii) DMP (0.431 g, 1.02 mmol) was added to a solution of INT-28E (0.250 g, 0.508 mmol) in DCM (6 mL). The mixture was stirred at RT for 16 h. An aqueous solution of Na$_2$S$_2$O$_3$ (10%, 10 mL) was added and the mixture was stirred vigorously for 30 min. The aqueous layer was extracted with DCM (3×10 mL). The combined organic layer was dried over Na$_2$SO$_4$. The filtrate was concentrated in vacuo. Purification by FC (1% Et$_3$N in EtOAc/1% Et$_3$N in heptane 0:1→1:0, 12 g silica) and lyophilisation (H$_2$O/MeCN) afforded 28 (0.234 g, 0.478 mmol, 94%) as a white solid. LCMS: calc. for [M+H]$^+$=490.13, found 490.1. $^1$H NMR (400 MHz, DMSO-d$_6$) as a mixture of rotamers and hydrates δ 9.43-9.04 (m, 0.5H), 8.90-8.73 (m, 2H), 8.54-8.19 (m, 0.5H), 8.08-7.95 (m, 2H), 6.64 (s, 0.25H), 6.48 (s, 0.25H), 6.45 (s, 0.12H), 5.84 (s, 0.12H), 5.26-3.39 (m, 8H), 2.04-1.48 (m, 6H), 1.34-0.76 (m, 5H) ppm.

Example 29

N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiophene-2-carboxamide

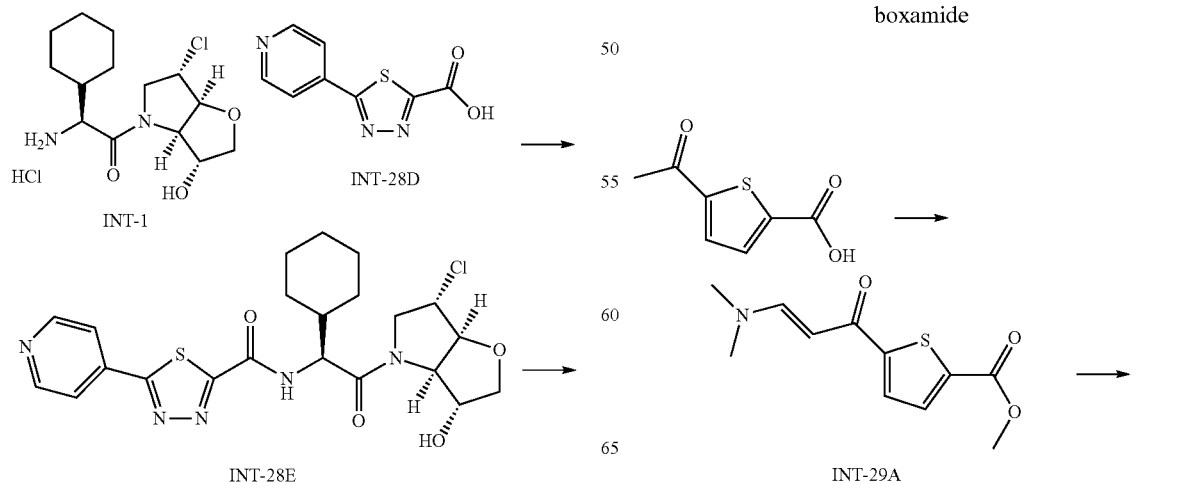

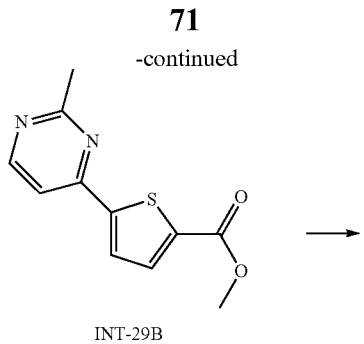

INT-29B

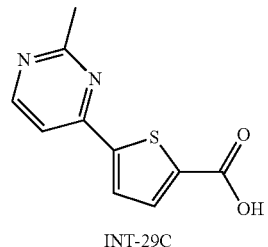

INT-29C i) A solution of 5-acetylthiophene-2-carboxylic acid (1.00 g, 5.88 mmol) in DMF dimethyl acetal (5.00 mL, 37.3 mmol, 4.45 g) was heated to reflux temperature for 16 h. The mixture was concentrated under reduced pressure. Trituration from diethyl ether afforded INT-29A as a yellow solid. LCMS: calc. for [M+H]$^+$=240.06, found 240.2.

ii) A suspension of (E)-methyl 5-(3-(dimethylamino)acryloyl)thiophene-2-carboxylate INT-29A, acetamidine hydrochloride (1.11 g, 11.7 mmol) and K$_2$CO$_3$ (1.94 g, 14.1 mmol) in DMF (40 mL) was heated at 120° C. for 2 h. The mixture was diluted with EtOAc (200 mL) and washed with water (100 mL) and brine (2×75 mL), dried on Na$_2$SO$_4$ and concentrated under reduced pressure. FC (EtOAc/heptane 1:9→1:0) afforded INT-29B (0.838 g, 3.58 mmol, 61% over 2 steps) as a white solid. LCMS: calc. for [M+H]$^+$=235.05, found 235.0.

iii) LiOH.H$_2$O (0.320 g, 7.63 mmol) was added to a solution of INT-29B (0.838 g, 3.58 mmol) in THF (15 mL) and water (10 mL). The RM was stirred at RT for 1.5 h. The RM was acidified to pH 2-3 using aqueous 1 M HCl. 2-Propanol (10 mL) was added and the solids were filtered off and washed with Et$_2$O to obtain INT-29C (0.677 g, 3.07 mmol, 86%) as a solid. LCMS: calc. for [M+H]$^+$=221.03, found 221.0.

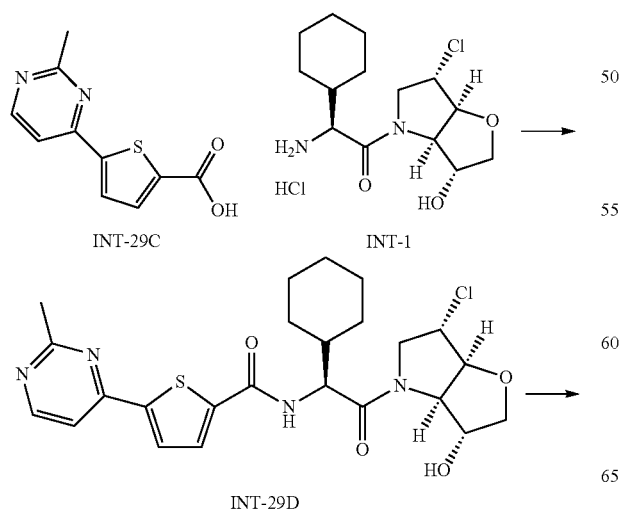

INT-29C      INT-1

INT-29D

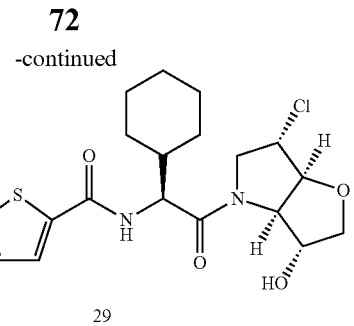

29 i) A suspension of INT-1 (0.300 g, 0.884 mmol), INT-29C (0.214 g, 0.973 mmol), EDCl (0.186 g, 0.973 mmol), NEt$_3$ (0.370 mL, 2.65 mmol) and HOAt (0.012 g, 0.088 mmol) in DMF (10 mL) was stirred at RT for 72 h. Aqueous saturated NaHCO$_3$ (30 mL) was added and the mixture was extracted with EtOAc (2×30 mL). The combined organic layer was washed with water (15 mL) and brine (2×15 mL), dried on Na$_2$SO$_4$ and concentrated in vacuo. FC (EtOAc/heptane 1:9→1:0) afforded INT-29D (0.321 g, 0.636 mmol, 72%). LCMS: calc. for [M+H]$^+$=505.16, found 505.2.

ii) DMP (0.554 g, 1.31 mmol) was added to a solution of INT-29D (0.330 g, 0.653 mmol) in DCM (10 mL). The mixture was stirred at RT for 16 h. An aqueous solution of Na$_2$S$_2$O$_3$ (10%, 15 mL) was added and the mixture was stirred vigorously for 30 min. An aqueous saturated solution of NaHCO$_3$ (20 mL) and DCM (30 mL) were added. The layers were separated over a phase separation filter. The organic layer was concentrated in vacuo. Purification by acid preparative HPLC (C18, MeCN (0.1% HCOOC), H$_2$O (0.1% HCOOC) and lyophilisation afforded 29 (0.171 g, 0.340 mmol, 52%) as a white solid. LCMS: calc. for [M+H]$^+$=503.14, found 503.2. $^1$H NMR (400 MHz, DMSO-d$_6$) as a mixture of hydrates and rotamers δ 9.03-8.82 (m, 1H), 8.78-8.69 (m, 1H), 8.17-8.05 (m, 1H), 8.05-7.99 (m, 1H), 7.89-7.79 (m, 1H), 6.75 (s, 0.46H), 6.47 (s, 0.27H), 6.32 (s, 0.46H), 5.84 (s, 0.27H), 4.94-3.46 (m, 8H), 2.63 (s, 1.5H), 2.62 (s, 1.5H), 2.04-1.49 (m, 6H), 1.29-0.82 (m, 5H) ppm.

The following compound were prepared as comparative examples:

Comparative Example C1

N-((S)-2-((3aS,6S,6aS)-6-chloro-3-oxotetrahydro-2H-furo[3,2-b]pyrrol-4(5H)-yl)-1-cyclohexyl-2-oxo-ethyl)3-(1H-pyrazol-4-yl)benzamide

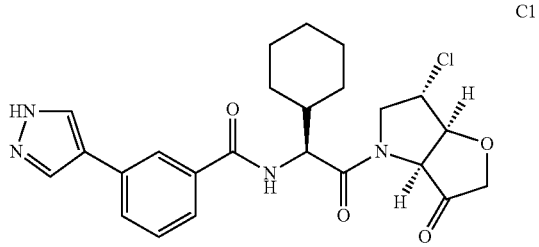 [SMILES: O=C(N[C@H](C(=O)N1C[C@H](Cl)[C@H]2OCC(=O)[C@H]21)C1CCCCC1)c1cccc(-c2cn[nH]c2)c1]

C1

(Example 7 of WO 2009/112839):
Biaryl Acids A

In general, the biaryl acids A can be obtained from cross coupling reactions of boronic acids or stannates with (hetero)aromatic halides (Scheme 1).

Scheme 1: General synthesis of biaryl acids A

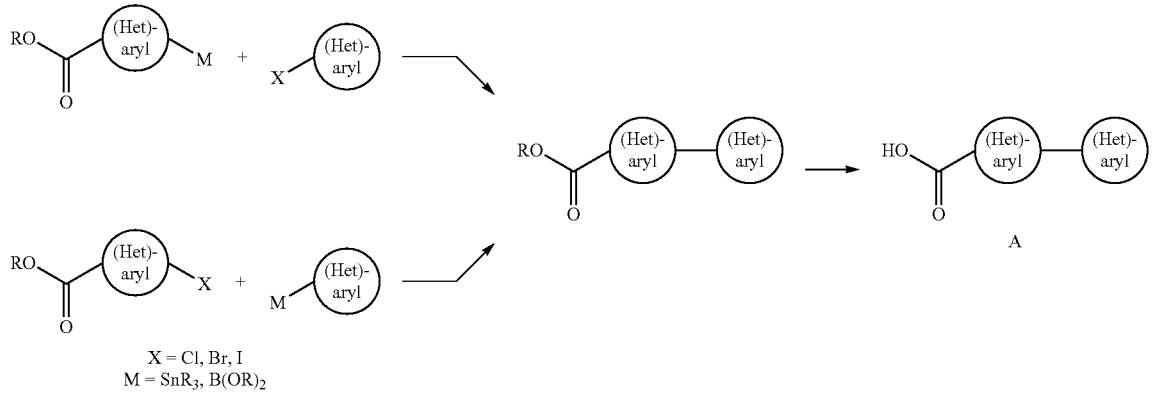

X = Cl, Br, I
M = SnR$_3$, B(OR)$_2$

Synthesis of 5-(2-methylpyrimidin-5-yl)thiazole-2-carboxylic acid trifluoroacetate (A1)

Synthesis of tert-butyl thiazole-2-carboxylate

Thiazole-2-carboxylic acid (5.00 g, 38.7 mmol) was dissolved in 500 ml DCM (500 mL). DMF (0.1 mL) was added, followed by oxalyl chloride (4.98 mL, 58.1 mmol). The mixture was stirred at RT for 5 h. Potassium 2-methylpropan-2-olate (5.65 g, 50.3 mmol) was added. The mixture was stirred at RT for 1 h. Water (200 mL) and saturated aqueous NH$_4$Cl (200 mL) were added and the layers were separated. The aqueous layer was extracted with DCM (3×200 mL). The combined organic layer was dried on Na$_2$SO$_4$ and concentrated under reduced pressure. The residue was dissolved in Et$_2$O and filtered over Celite. The filtrate was concentrated under reduced pressure. FC (EtOAc/heptane 0:1→3:7) afforded tert-butyl thiazole-2-carboxylate (4.80 g, 25.9 mmol, 67%). LCMS: calc. for [M+H]$^+$=186.05, found 186.1.

Synthesis of tert-butyl 5-bromothiazole-2-carboxylate tert-butyl thiazole-2-carboxylate (0.500 g, 2.70 mmol) was added to a solution of lithium bis(trimethylsilyl)amide (2.97 mL, 1 M in THF, 2.97 mmol) in Et$_2$O (20 mL) at −100° C. The mixture was stirred for 15 min. CBr$_4$ (0.985 g, 2.97 mmol) was added at −100° C., the mixture was stirred for at this temperature for 10 min and then allowed to reach RT. The reaction was quenched with saturated aqueous NH$_4$CL (20 mL). The layers were separated. The aqueous layer was extracted with Et$_2$O (3×10 mL). The combined organic layer was dried on Na$_2$SO$_4$ and concentrated under reduced pressure. FC (EtOAc/heptane 0:1→3:17) afforded tert-butyl 5-bromothiazole-2-carboxylate (0.580 g, 2.20 mmol, 81%). LCMS: calc. for [M+H]$^+$=263.69, found 264.1.

Synthesis of tert-butyl 5-(2-methylpyrimidin-5-yl)thiazole-2-carboxylate

A solution of 2-methyl-5-(4,4,5,5-tetramethyl-1,3,2-dioxaborolan-2-yl)pyrimidine (0.156 g, 0.708 mmol), tert-butyl 5-bromothiazole-2-carboxylate (0.170 g, 0.644 mmol) and Na$_2$CO$_3$ (0.205 g, 1.93 mmol) in dioxane (10 mL) and water (3 mL) was degassed with Ar. Tetrakis(triphenylphosphine)palladium (0.037 g, 0.032 mmol) was added and the mixture was heated at 90° C. for 1 h. The mixture was poured into saturated aqueous NH$_4$Cl (30 mL) and extracted with EtOAc (2×20 mL). The combined organic layer was washed with water (20 mL) and brine (10 mL), dried on Na$_2$SO$_4$ and concentrated under reduced pressure. Purification by FC (EtOAc/heptane 1:9→1:0) afforded tert-butyl 5-(2-methylpyrimidin-5-yl)thiazole-2-carboxylate (0.156 g, 0.562 mmol, 87%) as a white solid. LCMS: calc. for [M+H]$^+$=278.09, found 278.2.

5-(2-methylpyrimidin-5-yl)thiazole-2-carboxylic acid trifluoroacetate (A1)

A solution of tert-butyl 5-(2-methylpyrimidin-5-yl)thiazole-2-carboxylate (0.156 g, 0.562 mmol) in DCM (3 mL) was cooled to −15° C. TFA (3 mL) was slowly added. After addition, the mixture was allowed to warm up to RT and stirred for 4 h. The mixture was concentrated under reduced pressure and co-evaporated with DCM to obtain 5-(2-methylpyrimidin-5-yl)thiazole-2-carboxylic acid as its TFA salt. LCMS: calc. for [M+H]$^+$=222.03, found 222.0.

The following biaryls were synthesized as described for A1

| Biaryl acid A | | Starting materials | analytical data |
|---|---|---|---|
| 5-(6-methylpyridin-3-yl)thiazole-2-carboxylic acid trifluoroacetate | A2 | thiazole-2-carboxylic acid, (6-methylpyridin-3-yl)boronic acid | LCMS [M + H$^+$] = 221.2 |
| 5-(5-cyanopyridin-3-yl)thiazole-2-carboxylic acid trifluoroacetate | A3 | thiazole-2-carboxylic acid, 5-(4,4,5,5-tetramethyl-1,3,2-dioxaborolan-2-yl)nicotinonitrile | LCMS [M + H$^+$] = 232.0 |
| 5-(5-fluoropyridin-3-yl)thiazole-2-carboxylic acid trifluoroacetate | A4 | thiazole-2-carboxylic acid, (5-fluoropyridin-3-yl)boronic acid | LCMS [M + H$^+$] = 225.0 |

-continued

| Biaryl acid A | | Starting materials | analytical data |
|---|---|---|---|
| 5-(3-fluoropyridin-4-yl)thiazole-2-carboxylic acid trifluoroacetate | A5 | thiazole-2-carboxylic acid, 3-fluoro-4-(4,4,5,5-tetramethyl-1,3,2-dioxaborolan-2-yl)pyridine | LCMS [M + H$^+$] = 225.2 |
| 5-(6-cyclopropylpyridin-3-yl)thiazole-2-carboxylic acid trifluoroacetate | A6 | thiazole-2-carboxylic acid, 2-cyclopropyl-5-(4,4,5,5-tetramethyl-1,3,2-dioxaborolan-2-yl)pyridine | LCMS [M + H$^+$] = 247.0 |
| 5-(6-(trifluoromethyl)pyridin-3-yl)thiazole-2-carboxylic acid trifluoroacetate | A7 | thiazole-2-carboxylic acid, (6-(trifluoromethyl)pyridin-3-yl)boronic acid | LCMS [M + H$^+$] = 275.0 |

Synthesis of 5-(2-methylpyrimidin-5-yl)thiophene-2-carboxylic acid (A8)

Synthesis of ethyl 5-(2-methylpyrimidin-5-yl)thiophene-2-carboxylate

2-Methylpyrimidine-5-boronic acid pinacol ester (0.920 g, 4.18 mmol), ethyl 5-bromothiophene-2-carboxylate (0.568 mL, 3.80 mmol) and Na$_2$CO$_3$ (1.21 g, 11.4 mmol) were mixed in DME (30 mL) and water (7.5 mL) and degassed with Ar. Then PdCl$_2$(dppf) (0.133 g, 0.190 mmol) was added and the mixture was stirred at 100° C. for 1 h. Water (20 mL) was added and the mixture was extracted with EtOAc (3×20 mL). The combined organic layer was washed with brine (20 mL), dried over Na$_2$SO$_4$ and concentrated in vacuo. FC (EtOAc/heptane 0:1→1:0) afforded ethyl 5-(2-methylpyrimidin-5-yl)thiophene-2-carboxylate (0.740 g, 2.98 mmol, 78%). LCMS: calc. for [M+H]$^+$= 249.07, found 249.1.

Synthesis of 5-(2-methylpyrimidin-5-yl)thiophene-2-carboxylic acid (A8)

At RT, LiOH.H$_2$O (0.500 g, 11.9 mmol) was added to a mixture of ethyl 5-(2-methylpyrimidin-5-yl)thiophene-2-carboxylate (0.740 g, 2.98 mmol) in THF (7.5 mL) and water (7.5 mL). The reaction was stirred at RT for 3 h. The reaction was acidified with aqueous 1 M HCl (11.9 mL). The solids were filtered, washed with i-PrOH (5 mL) and dried in vacuo to give to give 5-(2-methylpyrimidin-5-yl)thiophene-2-carboxylic acid (A8, 0.625 g, 2.84 mmol, 95%) as a white solid. LCMS: calc. for [M+H]$^+$=221.04, found 221.1.

The following biaryls were synthesized as described for A8

| Biaryl acid A | | Starting materials | analytical data |
|---|---|---|---|
| 5-(3-fluoropyridin-4-yl)thiophene-2-carboxylic acid | A9 | ethyl 5-bromothiophene-2-carboxylate, 3-fluoro-4-(4,4,5,5-tetramethyl-1,3,2-dioxaborolan-2-yl)pyridine | LCMS [M + H$^+$] = 224.2 |
| 5-(2-methylpyridin-4-yl)-thiophene-2-carboxylic acid | A10 | ethyl 5-bromothiophene-2-carboxylate, (2-methylpyridin-4-yl)boronic acid | LCMS [M + H$^+$] = 220.1 |
| 5-(2-methoxypyridin-4-yl)thiophene-2-carboxylic acid | A12 | methyl 5-bromothiophene-2-carboxylate, (2-methoxypyridin-4-yl)boronic acid | LCMS [M + H$^+$] = 236.0 |
| 5-(6-(trifluoromethyl)-pyridin-3-yl)thiophene-2-carboxylic acid | A13 | ethyl 5-bromothiophene-2-carboxylate, (6-(trifluoromethyl)pyridin-3-yl)boronic acid | LCMS [M + H$^+$] = 274.0 |
| 5-(6-cyclopropylpyridin-3-yl)thiophene-2-carboxylic acid | A14 | ethyl 5-bromothiophene-2-carboxylate, 2-cyclopropyl-5-(4,4,5,5-tetramethyl-1,3,2-dioxaborolan-2-yl)pyridine | LCMS [M + H$^+$] = 246.1 |
| 5-(2-cyclopropylpyridin-4-yl)thiophene-2-carboxylic acid | A15 | ethyl 5-bromothiophene-2-carboxylate, (2-cyclopropylpyridin-4-yl)boronic acid | LCMS [M + H$^+$] = 246.0 |

Synthesis of 5-(5-cyanopyridin-3-yl)thiophene-2-carboxylic acid (A11)

(5-Cyanopyridin-3-yl)boronic acid pinacol ester (0.720 g, 3.13 mmol), 5-bromothiophene-2-carboxylic acid (0.589 g, 2.84 mmol) and Na$_2$CO$_3$ (0.905 g, 8.53 mmol) were mixed in DME (30 mL) and water (7.5 mL) and degassed with Ar. Then PdCl$_2$(dppf) (0.100 g, 0.142 mmol) was added and the mixture was stirred at 100° C. for 2 h. The reaction was allowed to cool to RT. Water (30 mL) was added to redissolve the product and the mixture was filtered over Celite to remove the undissolved palladium. The mother liquor was acidified with 1N aqueous HCl to pH 1.9-2.0. Solids were filtered off and washed with water (3×10 mL). The solid was suspended in water and lyophilization (MeCN/H$_2$O) afforded 5-(5-cyanopyridin-3-yl)thiophene-2-carboxylic acid (A11, 0.374 g, 1.62 mmol, 57%) as an off-white solid. LCMS: calc. for [M+H]$^+$=252.05, found 252.1.

Synthesis of 5-(pyridin-3-yl)thiazole-2-carboxylic acid (A17)

Synthesis of 5-bromothiazole-2-carboxylic acid

Thiazole-2-carboxylic acid (1.60 g, 12.4 mmol) was added to a solution of LDA (1 M in THF/heptane/ethylbenzene, 26.0 mmol, 26 mL) in dry THF (100 mL) at −78° C. and the mixture was stirred for 30 min. CBr$_4$ (4.52 g, 13.6 mmol) was added and the reaction was stirred for 2 h. The RM was quenched by adding water (30 mL). The mixture was allowed to reach RT and diluted by adding an aqueous saturated solution of NaHCO$_3$ (50 mL). The mixture was filtered through a pad of Celite and extracted with EtOAc (50 mL). The organic layer was discarded and the aqueous layer acidified using a 1 M solution of HCl until pH acidic. The solution was then extracted with EtOAc (3×30 mL). The combined organic layer was dried over Na$_2$SO$_4$ and concentrated in vacuo to leave 5-bromothiazole-2-carboxylic acid (0.42 g, 2.0 mmol, 16%). LCMS: calc. for [M+H]$^+$=207.90, found 208.0.

Synthesis of methyl 5-bromothiazole-2-carboxylate

Oxalyl chloride (0.21 mL, 2.4 mmol) was added to a solution of 5-bromothiazole-2-carboxylic acid (0.42 g, 2.0 mmol) in dry DCM (10 mL) containing a catalytic amount of dry DMF (0.05 mL) at RT and the resulting mixture was stirred for 4 h. MeOH (4.00 mL, 125 mmol) was added to the solution and the reaction was stirred for an additional 2 h. The mixture was diluted with a saturated aqueous solution of NaHCO$_3$ (20 mL) and extracted with DCM (3×10 mL). The combined organic layer was washed with water (20 mL) and brine (2×20 mL), dried over Na$_2$SO$_4$ and concentrated in vacuo. FC (EtOAc/heptane 0:1→3:7) afforded methyl 5-bromothiazole-2-carboxylate (0.23 g, 1.0 mmol, 51%). LCMS: calc. for [M+H]$^+$=221.91, found 221.9.

Synthesis of methyl 5-(pyridin-3-yl)thiazole-2-carboxylate

A solution of methyl 5-bromothiazole-2-carboxylate (0.340 g, 1.53 mmol) and 3-(tributylstannyl)pyridine (0.564 g, 1.53 mmol) in dioxane (7 mL) was degassed with N$_2$. Tri-2-furylphosphine (0.071 g, 0.306 mmol) and Pd$_2$(dba)$_3$ (0.140 g, 0.153 mmol) were added and the mixture was heated at 90° C. for 16 h. The mixture was filtered over Celite. The filtrate was concentrated and purified by FC (EtOAc/heptane 0:1→1:0) to obtain methyl 5-(pyridin-3-yl)thiazole-2-carboxylate (0.143 g, 0.518 mmol, 46%) as a yellow solid. LCMS: calc. for [M+H]+=221.03, found 221.2.

Synthesis of 5-(pyridin-3-yl)thiazole-2-carboxylic acid (A17)

LiOH.H$_2$O (0.102 g, 2.43 mmol) was added to a solution of methyl 5-(pyridin-3-yl)thiazole-2-carboxylate (0.349 g, 1.59 mmol) in THF (6 mL) and water (2 mL). The RM was stirred at RT for 1.5 h. The RM was concentrated in vacuo. The residue was acidified to pH ~4 by addition of aqueous 2 M HCl (~1.3 mL) and triturated with i-PrOH (5 mL). The resulting solid was obtained by filtration, washed with cold i-PrOH (2 mL) and pentane (2×5 mL) and dried to afford 5-(pyridin-3-yl)thiazole-2-carboxylic acid (A17, 0.308 g, 1.49 mmol, 94%) as a yellow solid. LCMS: calc. for [M+H]$^+$=207.01, found 207.2.

Synthesis of 5-(pyridin-2-yl)thiazole-2-carboxylic acid trifluoroacetate (A18)

Synthesis of tert-butyl 5-(pyridin-2-yl)thiazole-2-carboxylate

A solution of tert-butyl 5-bromothiazole-2-carboxylate (0.185 g, 0.700 mmol, synthesis see above) and 2-(tributylstannyl)pyridine (0.258 g, 0.700 mmol) in dioxane (5 mL) was degassed with Ar. Tri-2-furylphosphine (0.033 g, 0.14 mmol) and Pd$_2$(dba)$_3$ (0.064 g, 0.070 mmol) were added and the mixture was heated at 90° C. overnight. The mixture was filtered over Celite. The filtrate was concentrated and purified by FC (EtOAc/heptane 1:9→1:0) to obtain tert-butyl 5-(pyridin-2-yl)thiazole-2-carboxylate (0.140 g, 0.534 mmol, 76%) as a yellow solid. LCMS: calc. for [M+H]$^+$= 263.08, found 263.2.

Synthesis of 5-(pyridin-2-yl)thiazole-2-carboxylic acid trifluoroacetate (A18)

A solution of tert-butyl 5-(pyridin-2-yl)thiazole-2-carboxylate (0.140 g, 0.534 mmol) in DCM (3 mL) was cooled to −15° C. TFA (3 mL) was slowly added. After addition, the mixture was allowed to warm up to RT and stirred for 4 h. The mixture was concentrated under reduced pressure and co-evaporated with DCM to obtain 5-(pyridin-2-yl)thiazole-2-carboxylic acid its TFA salt (A18). LCMS: calc. for [M+H]$^+$=207.01, found 207.2.

The following biaryls were synthesized as described for A18

| Biaryl acid A | | Starting materials | analytical data |
| --- | --- | --- | --- |
| 5-(pyrazin-2-yl)thiazole-2-carboxylic acid trifluoroacetate | A19 | tert-butyl 5-bromothiazole-2-carboxylate, 2-(tributylstannyl)pyrazine | LCMS [M + H$^+$] = 208.0 |
| 5-(pyridin-4-yl)thiazole-2-carboxylic acid trifluoroacetate | A20 | tert-butyl 5-bromothiazole-2-carboxylate, 4-(tributylstannyl)pyridine | LCMS [M + H$^+$] = 207.2 |
| 5-(2-methylpyridin-4-yl)-thiazole-2-carboxylic acid trifluoroacetate | A21 | tert-butyl 5-bromothiazole-2-carboxylate, 2-methyl-4-(tributylstannyl)pyridine | LCMS [M + H$^+$] = 221.2 |
| 5-(6-chloropyridin-3-yl)-thiazole-2-carboxylic acid trifluoroacetate | A22 | tert-butyl 5-bromothiazole-2-carboxylate, 2-chloro-5-(tributylstannyl)pyridine | LCMS [M + H$^+$] = 297.2 |

Synthesis of 4-fluoro-5-(pyrimidin-5-yl)thiophene-2-carboxylic acid (A23)

Synthesis of 5-(methoxycarbonyl)thiophene-3-diazonium hexafluorophosphate

Methyl 4-aminothiophene-2-carboxylate hydrobromide (3.50 g, 14.7 mmol) was dissolved in HCl (6 M solution in water, 80 mL) and stirred at RT for 10 min. The reaction was cooled to 0° C. and NaNO$_2$ (1.21 g, 17.6 mmol) was added. The mixture was stirred for 1 h at 0° C. and hexafluoro phosphoric acid in (60% in water, 10 mL) was added. The solid diazonium salt precipitated out of the solution and stirring was continued for 10 min and the reaction allowed to warm up to 15° C. The solid was filtered off washed with diluted hexafluoro phosphoric acid (5 mL), MeOH (5 mL) and Et$_2$O (5 mL) and dried at the air to give 5-(methoxycarbonyl)thiophene-3-diazonium hexafluorophosphate (4.00 g, 12.7 mmol, 87%).

Synthesis of methyl 4-fluorothiophene-2-carboxylate

A mixture of 5-(methoxycarbonyl)thiophene-3-diazonium hexafluorophosphate (5.50 g, 15.9 mmol) and sand (30 g) was warmed to 250° C. under vacuum (0.01 torr) in a Kugelrohr apparatus equipped with a trap at −78° C. and two traps in liquid N$_2$. A yellow liquid started to distill and condensed in the traps and it was carefully collected using Et$_2$O as solvent. The solvent was evaporated to give methyl 4-fluorothiophene-2-carboxylate (1.5 g, 9.4 mmol, 59%). GCMS: calc. for [M]$^+$=160.00, found 160.0.

Synthesis of methyl 5-bromo-4-fluorothiophene-2-carboxylate

Br$_2$ (2.29 g, 14.4 mmol, 0.740 ml) was added to a mixture of methyl 4-fluorothiophene-2-carboxylate (0.230 g, 1.43 mmol) in CHCl$_3$ (5 mL) and the mixture was warmed up to 60° C. and stirred for 1 h. The solution was cooled to RT and poured in an aqueous solution of Na$_2$S$_2$O$_3$ (10%, 10 mL) and stirred for 30 min. The phases were separated and the aqueous layer extracted with DCM (3×10 mL). The collected organic layer was washed with brine (20 mL), dried over Na$_2$SO$_4$ and evaporated in vacuo to leave a yellow solid (0.800 g). The solid was sublimated in the kugelrohr at 150° C. under vacuum (50 torr) to yield methyl 5-bromo-4-fluorothiophene-2-carboxylate 0.280 g, 1.17 mmol, 82%).

Synthesis of methyl 4-fluoro-5-(pyrimidin-5-yl)thiophene-2-carboxylate

A solution of 5-(tributylstannyl)pyrimidine (0.108 g, 0.293 mmol) and 5-bromo-4-fluorothiophene-2-carboxylate (0.070 g, 0.293 mmol) in DMF (4 mL) was degassed with Ar. CsF (0.133 g, 0.878 mmol), CuCl (0.004 g, 0.04 mmol) and tetrakis(triphenylphosphine)palladium (0.017 g, 0.015 mmol) were added and the mixture was heated at 110° C. for 2 h. The mixture was diluted with EtOAc (30 mL), washed with water (20 mL) and brine (20 ml), dried on Na$_2$SO$_4$ and concentrated under reduced pressure. Purification by FC (EtOAc/heptane 0:1→1:0) afforded methyl 4-fluoro-5-(pyrimidin-5-yl)thiophene-2-carboxylate (0.049 g, 0.21 mmol, 70%) as a white solid. LCMS: calc. for [M+H]$^+$=239.02, found 239.0.

Synthesis of 4-fluoro-5-(pyrimidin-5-yl)thiophene-2-carboxylic acid (A23)

LiOH.H$_2$O (0.018 g, 0.43 mmol) was added to a solution of methyl 4-fluoro-5-(pyrimidin-5-yl)thiophene-2-carboxylate (0.048 g, 0.20 mmol) in THF (2 mL) and water (1 mL). The reaction was stirred at RT for 1 h. The mixture was concentrated under reduced pressure. The residue was acidified to pH 3-4 using aqueous 1 M HCl. i-PrOH (5 mL) was added and the solids were filtered off and washed with Et$_2$O to obtain 4-fluoro-5-(pyrimidin-5-yl)thiophene-2-carboxylic acid (A23, 0.045 g, 0.20 mmol, 100%) as a solid. LCMS: calc. for [M+H]$^+$=225.01, found 225.0.

The following biaryls were synthesized as described for A23

| Biaryl acid A | | Starting materials | analytical data |
|---|---|---|---|
| 4-fluoro-5-(pyridazin-4-yl)thiophene-2-carboxylic acid hydrochloride | A24 | methyl 5-bromo-4-fluorothiophene-2-carboxylate, 4-(tributylstannyl)pyridazine | LCMS [M + H$^+$] = 225.0 |

Synthesis of 3-fluoro-5-(pyrimidin-5-yl)thiophene-2-carboxylic acid (A25)

Synthesis of 2-(methoxycarbonyl)thiophene-3-diazonium hexafluorophosphate

Methyl 3-aminothiophene-2-carboxylate (4.13 g, 26.2 mmol) was dissolved in HCl (6 M solution in water, 20 mL) and stirred at RT for 5 min. The reaction was cooled to 0° C. and NaNO$_2$ (2.17 g, 31.5 mmol) was added. The mixture was stirred for 1 h at 0° C. and hexafluoro phosphoric acid (60% in water, 20 mL) was added. The solid diazonium salt precipitated out of the solution. Stirring was continued for 10 min and the RM was allowed to warm up to 15° C. The solid was filtered off washed with MeOH (5 mL) and Et$_2$O (5 mL) and dried at the air to give 2-(methoxycarbonyl)thiophene-3-diazonium hexafluorophosphate (7.00 g, 22.3 mmol, 85%).

Synthesis of methyl 3-fluorothiophene-2-carboxylate

A mixture of 2-(methoxycarbonyl)thiophene-3-diazonium hexafluorophosphate (7.00 g, 22.3 mmol) and sand (50 g) was heated at 250° C. under vacuum (0.01 torr) in a Kugelrohr apparatus equipped with a trap at −78° C. and two traps in liquid N$_2$. A brown liquid started to distill and condensed in the traps and it was carefully collected using Et$_2$O (50 mL). The ether was decanted, washed with aqueous saturated NaHCO$_3$ (50 mL) and dried over Na$_2$SO$_4$. The solvent was evaporated to give methyl 3-fluorothiophene-2-carboxylate (1.90 g, 11.9 mmol, 53%). GCMS: calc. for [M]$^+$=160.00, found 160.1.

Synthesis of methyl 5-bromo-3-fluorothiophene-2-carboxylate

Bromine (0.998 g, 6.24 mmol, 0.322 mL) was added to a mixture of methyl 3-fluorothiophene-2-carboxylate (0.100 g, 0.624 mmol) in CHCl$_3$ (5 mL) and the mixture was heated at 70° C. and stirred for 1 h. The solution was cooled to RT and poured in an aqueous solution of Na$_2$S$_2$O$_3$ (10%, 10 mL) and stirred for 30 min. The phases were separated and the aqueous layer extracted with DCM (3×10 mL). The collected organic layer was washed with brine (20 mL), dried over Na$_2$SO$_4$ and evaporated in vacuo to leave a yellow solid (0.200 g). The solid was sublimated in the kugelrohr at 150° C. under vacuum (50 torr) to yield methyl 5-bromo-3-fluorothiophene-2-carboxylate (0.070 g, 0.16 mmol, 26%, purity 55%; contains dibromide). GCMS: calc. for [M]$^+$=238.91, found 238.9.

Synthesis of methyl 3-fluoro-5-(pyrimidin-5-yl)thiophene-2-carboxylate

A solution of 5-(tributylstannyl)pyrimidine (0.130 g, 0.351 mmol) and methyl 5-bromo-3-fluorothiophene-2-carboxylate (0.070 g, 0.29 mmol) in 1,4-dioxane (5 mL) was degassed with Ar. Tri(furan-2-yl)phosphine (0.014 g, 0.059 mmol), and Pd$_2$(dba)$_3$ (0.027 g, 0.029 mmol) were added and the mixture was heated at 90° C. for 16 h. The mixture was cooled to RT and concentrated under reduced pressure. Purification by FC (EtOAc/heptane 1:9→2:3) afforded methyl 3-fluoro-5-(pyrimidin-5-yl)thiophene-2-carboxylate (0.032 g, 0.13 mmol, 46%) as a white solid. LCMS: calc. for [M+H]$^+$=239.02, found 239.1.

Synthesis of 3-fluoro-5-(pyrimidin-5-yl)thiophene-2-carboxylic acid

LiOH.H$_2$O (0.017 g, 0.40 mmol) was added to a solution of methyl 3-fluoro-5-(pyrimidin-5-yl)thiophene-2-carboxylate (0.030 g, 0.13 mmol) in THF (2 mL) and water (1 mL). The reaction was stirred at RT for 1 h. The mixture was concentrated under reduced pressure. The residue was acidified to pH 3-4 using aqueous 1 M HCl. i-PrOH (5 mL) was added and the solids were filtered off and washed with Et$_2$O to obtain 3-fluoro-5-(pyrimidin-5-yl)thiophene-2-carboxylic acid (A25, 0.023 g, 0.10 mmol, 81%) as a solid. LCMS: calc. for [M+H]$^+$=225.01, found 225.0.

The following biaryls were synthesized as described for A25

Synthesis of 5-(2-(trifluoromethyl)pyrimidin-5-yl)thiazole-2-carboxylic acid trifluoroacetate (A28)

Synthesis of tert-butyl 5-(tributylstannyl)thiazole-2-carboxylate

At −78° C. n-butyllithium (2.5 M in hexanes, 4.75 mmol, 1.90 mL) was added to a solution of N,N-diisopropylamine (0.481 g, 4.75 mmol, 0.668 mL) in dry Et$_2$O (40 mL). The mixture was stirred at 0° C. for 1 h. The mixture was cooled to −100° C. (Et$_2$O/liquid N$_2$). A solution of tert-butyl thiazole-2-carboxylate (0.800 g, 4.32 mmol, synthesis see above) in dry Et$_2$O (40 mL) was added dropwise at −100° C. and the mixture was stirred for 15 min. Tributylchlorostannane (1.55 g, 4.75 mmol, 1.29 mL) was added and the RM was stirred for 10 min at −100° C., 1 h at −78° C. and then allowed to reach to RT. The reaction was quenched by adding aqueous NH$_4$Cl(50 mL). The aqueous layer extracted three times with Et$_2$O (3×25 ml). The combined organic layers was dried over Na$_2$SO$_4$ and concentrated in vacuo. FC (EtOAc/heptane 0:1→1:1) gave tert-butyl 5-(tributylstannyl)thiazole-2-carboxylate (1.03 g, 2.17 mmol, 50%) as a clear oil.

Synthesis of tert-butyl 5-(2-(trifluoromethyl)pyrimidin-5-yl)thiazole-2-carboxylate tert-butyl 5-(tributylstannyl)thiazole-2-carboxylate (1.03 g, 2.17 mmol), 5-bromo-2-(trifluoromethyl)pyrimidine (0.493 g, 2.17 mmol), tri(furan-2-yl)phosphine (0.101 g, 0.434 mmol) and Pd$_2$(dba)$_3$ (0.199 g, 0.217 mmol) were dissolved in dry 1,4-dioxane (30 mL) and the resulting solution was heated at 90° C. and stirred for 4 h. The mixture was filtered over Celite and flushed with EtOAc (100 mL). Solvents were evaporated in vacuo. FC (EtOAc/heptane 0:1→1:1) afforded tert-butyl 5-(2-(trifluoromethyl)pyrimidin-5-yl)thiazole-2-carboxylate (0.597 g, 1.80 mmol, 83%) as a yellow solid. LCMS: calc. for [M+H]$^+$=332.06, found 276.0 (-tBu).

Synthesis of 5-(2-(trifluoromethyl)pyrimidin-5-yl)thiazole-2-carboxylic acid trifluoroacetate (A28)

TFA (10 mL) was added to a solution of tert-butyl 5-(2-(trifluoromethyl)pyrimidin-5-yl)thiazole-2-carboxylate (0.597 g, 1.80 mmol) in DCM (10 mL) at 10° C. The RM was allowed to warm to RT and stirred for 3 h. The solvent was evaporated in vacuo and the residue was stripped with DCM (2×5 mL) to give 5-(2-(trifluoromethyl)pyrimidin-5-yl)thiazole-2-carboxylic acid trifluoroacetate (A28). LCMS: calc. for [M+H]$^+$=276.00, found 276.0.

The following biaryls were synthesized as described for A28

| Biaryl acid A | | Starting materials | analytical data |
| --- | --- | --- | --- |
| 3-fluoro-5-(pyridazin-4-yl)thiophene-2-carboxylic acid | A26 | methyl 5-bromo-3-fluorothiophene-2-carboxylate, 4-(tributylstannyl)pyridazine | LCMS [M + H$^+$] = 225.0 |

| Biaryl acid A | | Starting materials | analytical data |
|---|---|---|---|
| 5-(2-cyclopropylpyrimidin-5-yl)-thiazole-2-carboxylic acid trifluoroacetate | A27 | tert-butyl thiazole-2-carboxylate, 5-bromo-2-cyclopropylpyrimidine | LCMS [M + H$^+$] = 248.0 |
| 5-(2-cyclopropylpyridin-4-yl)-thiazole-2-carboxylic acid trifluoroacetate | A30 | tert-butyl thiazole-2-carboxylate, 4-bromo-2-cyclopropylpyridine | LCMS [M + H$^+$] = 247.0 |

Synthesis of
5-(2-ethylpyridin-4-yl)thiazole-2-carboxylic acid
trifluoroacetate (A31)

Synthesis of 2-ethylpyridine 1-oxide $H_2O_2$ (35.0 mL, 343 mmol, 30% w/w) was added to a solution of 2-ethylpyridine (10.0 g, 93.0 mmol) in acetic acid (40 mL). The mixture was heated at 80° C. for 6 h. The mixture was allowed to cool to RT. Water (250 mL) was added and the mixture was extracted with DCM (8×100 mL). The combined organic layer was washed with brine (400 mL), dried on $Na_2SO_4$ and concentrated under reduced pressure. The residue was dissolved in DCM (100 mL) and washed with saturated aqueous $NaHCO_3$ (100 mL). The aqueous layer was extracted with DCM (10×50 mL). The combined organic layer was dried over $Na_2SO_4$ and concentrated under reduced pressure to obtain 2-ethylpyridine 1-oxide (9.50 g, 77.0 mmol, 83%) as an oil.

Synthesis of 2-ethyl-4-nitropyridine 1-oxide

A solution of 2-ethylpyridine 1-oxide (9.50 g, 77.0 mmol) in sulfuric acid (20 mL) was cooled to 0° C. Nitric acid (20 mL, 70%) was added dropwise. After addition, the mixture was heated at 95° C. for 18 h. The mixture was allowed to cool to RT and slowly poured into 300 mL ice water. Aqueous 1 M NaOH (175 mL) was added to obtain pH 9-10. The mixture was extracted with DCM (4×100 mL). The combined organic layer was dried over $Na_2SO_4$ and concentrated under reduced pressure. $Et_2O$ (30 mL) was added and the solids were filtered off to obtain 2-ethyl-4-nitropyridine 1-oxide (5.02 g, 29.8 mmol, 39%). The filtrate was dissolved in sulfuric acid (10 mL) and cooled to 0° C. Nitric acid (10 mL, 70%) was added dropwise. After addition, the mixture was heated at 110° C. for 18 h. The mixture was allowed to cool to RT and slowly poured into 200 mL ice water. Aqueous 1 M NaOH (110 mL) was added to obtain pH 9-10. The mixture was extracted with DCM (3×100 mL). The combined organic layer was dried over $Na_2SO_4$ and concentrated under reduced pressure. $Et_2O$ (20 mL) was added and the solids were filtered off to obtain 2-ethyl-4-nitropyridine 1-oxide (3.31 g, 19.7 mmol, 26%/total: 8.33 g, 49.5 mmol, 64% of a pale yellow solid. LCMS: calc. for [M+H]$^+$=169.05, found 169.2.

Synthesis of 4-bromo-2-ethylpyridine 1-oxide

A solution of 2-ethyl-4-nitropyridine 1-oxide (8.33 g, 49.5 mmol) in hydrobromic acid in acetic acid (80 mL, 457 mmol, 33% w/w) was heated at 100° C. for 5 days. The mixture was allowed to cool to RT and slowly poured into 200 mL ice water. Aqueous 1 M NaOH was added to obtain pH 9-10. The mixture was extracted with DCM (3×150 mL). The combined organic layer was dried over $Na_2SO_4$ and concentrated under reduced pressure. FC (EtOAc/heptane 1:4→1:0) afforded 4-bromo-2-ethylpyridine 1-oxide (5.49 g, 27.2 mmol, 55%) as a crystalline solid.

Synthesis of 4-(2-(tert-butoxycarbonyl)thiazol-5-yl)-2-ethylpyridine 1-oxide

A solution of 4-bromo-2-ethylpyridine 1-oxide (0.503 g, 2.49 mmol), tert-butyl 5-(tributylstannyl)thiazole-2-carboxylate (1.18 g, 2.49 mmol, synthesis see above) and CsF (1.13 g, 7.46 mmol) in 1,4-dioxane (40 mL) was degassed with Ar. $PdCl_2$(dppf) (0.091 g, 0.12 mmol) and CuCl (0.032 g, 0.32 mmol) were added and the mixture was heated at 80° C. for 3 h. KF (0.50 g, 8.6 mmol) in 20 mL water was added and the mixture was stirred at RT for 18 h. The mixture was filtered over Celite and rinsed with EtOAc (60 mL). The filtrate was washed with water (25 mL) and brine (25 mL), dried over $Na_2SO_4$ and concentrated under reduced pressure. FC (EtOAc/heptane 1:9→1:0) afforded 4-(2-(tert-butoxycarbonyl)thiazol-5-yl)-2-ethylpyridine 1-oxide (0.560 g (89% w/w), 1.63 mmol, 65%) as a solid. LCMS: calc. for [M+H]$^+$=307.10, found 307.1.

Synthesis of tert-butyl
5-(2-ethylpyridin-4-yl)thiazole-2-carboxylate

Under $N_2$, palladium (10% on activated carbon, 0.173 g, 0.163 mmol) was added to a solution of 4-(2-(tert-butoxycarbonyl)thiazol-5-yl)-2-ethylpyridine 1-oxide (0.560 g (89% w/w), 1.63 mmol) in EtOH (35 mL). $H_2$ was applied (balloon) and the mixture was stirred at RT overnight. The mixture was filtered over Celite and the filtrate was concentrated under reduced pressure to obtain tert-butyl 5-(2-ethylpyridin-4-yl)thiazole-2-carboxylate (0.375 g, 1.29 mmol, 79%). LCMS: calc. for [M+H]$^+$=291.11, found 291.1.

Synthesis of
5-(2-ethylpyridin-4-yl)thiazole-2-carboxylic acid
trifluoroacetate (A31)

TFA (10 mL) was added to a solution of tert-butyl 5-(2-ethylpyridin-4-yl)thiazole-2-carboxylate (0.375 g, 1.29 mmol) in DCM (10 mL) at 010° C. The RM was allowed to warm to RT and stirred for 4 h. The solvent was evaporated in vacuo and the residue was co-evaporated with DCM (2×5 mL) to give 5-(2-ethylpyridin-4-yl)thiazole-2-carboxylic acid trifluoroacetate (A31). LCMS: calc. for [M+H]$^+$= 235.05, found 235.2.

Synthesis of
5-(6-methylpyridazin-4-yl)thiazole-2-carboxylic
acid trifluoroacetate (A29)

Synthesis of 6-methylpyridazine 1-oxide

To a solution of 3-methylpyridazine (4.60 g, 48.9 mmol) in acetic acid (30.0 mL) was added $H_2O_2$ (29.4 g, 259 mmol, 29.4 mL, 30% (w/w) in water). The mixture was heated at 120° C. for 6 h. The mixture was allowed to cool to RT and poured in aqueous saturated NaHCO$_3$ (500 mL) and extracted with DCM (5×50 mL). The combined organic layer was dried over Na$_2$SO$_4$ and concentrated in vacuo to afford 6-methylpyridazine 1-oxide (2.22 g, 20.2 mmol, 41%). LCMS: calc. for [M+H]$^+$=111.05, found 111.2. $^1$H-NMR shows a 1:1 mixture of both possible N-oxides.

Synthesis of 6-methyl-4-nitropyridazine 1-oxide

To a solution of 6-methylpyridazine 1-oxide (2.10 g, 19.1 mmol) in sulphuric acid (37.5 g, 383 mmol, 20.4 mL) at 0° C. under N$_2$ was added fuming nitric acid (10.8 g, 172 mmol, 7.31 mL) dropwise. The mixture was heated at 110° C. for 4 h and stirred at RT for 16 h. The mixture was slowly poured in ice-water (200 mL). This mixture was poured in 1 M NaOH (100 mL) and aqueous saturated NaHCO$_3$ (80 mL) was added to give pH 7□8. The water layer was extracted with EtOAc (3×100 mL). The combined organic layer was dried over Na$_2$SO$_4$ and concentrated in vacuo to afford an orange solid. The water layer was extracted with DCM (5×50 mL). The combined organic layer was dried over Na$_2$SO$_4$, combined with the earlier obtained orange solid and concentrated in vacuo to afford crude product. The crude product was purified by FC (acetone/DCM 2:98 isocratic) and FC (acetone/DCM 2:98 isocratic) to obtain 6-methyl-4-nitropyridazine 1-oxide (0.940 g, 6.06 mmol, 32%), the pure N-oxide, as a yellow solid. LCMS: calc. for [M+H]$^+$=156.03, found 156.2.

Synthesis of 4-bromo-6-methylpyridazine 1-oxide

HBr in acetic acid (21.3 g, 86.9 mmol, 15.0 mL, 33%) was added to 6-methyl-4-nitropyridazine 1-oxide (0.759 g, 4.89 mmol). The mixture was heated at 100° C. for 2 h. This mixture was poured in ice-water (50 mL) and basified by addition of 6 M NaOH (45 mL). The water layer was extracted with DCM (3×50 mL). The combined organic layer was dried over Na$_2$SO$_4$ and concentrated in vacuo to afford crude product. The crude product was purified by FC (acetone/DCM 3:97) and FC (acetone/DCM 2:98) to obtain 4-bromo-6-methylpyridazine 1-oxide (0.689 g, 3.66 mmol, 75%) as a yellow solid. LCMS: calc. for [M+H]$^+$=188.96, found 189.0.

Synthesis of 4-(2-(tert-butoxycarbonyl)thiazol-5-yl)-6-methylpyridazine 1-oxide

A solution of 4-bromo-6-methylpyridazine 1-oxide (0.386 g, 2.04 mmol) and tert-butyl 5-(tributylstannyl)thiazole-2-carboxylate (0.970 g, 2.04 mmol, synthesis see above) in dry 1,4-dioxane (25 mL) was degassed with N$_2$. Tri(furan-2-yl)phosphine (0.095 g, 0.409 mmol) and Pd$_2$(dba)$_3$ (0.187 g, 0.205 mmol) were added and the resulting solution was heated at 90° C. and stirred for 4 h. The mixture was filtered over Celite and flushed with EtOAc (50 mL). Solvents were evaporated in vacuo. FC (EtOAc/heptane 0:1→3:7) and FC (acetone/DCM 5:95) afforded 4-(2-(tert-butoxycarbonyl)thiazol-5-yl)-6-methylpyridazine 1-oxide (0.288 g, 0.982 mmol, 48%) as a yellow solid. LCMS: calc. for [M+H]$^+$=294.08, found 294.2.

Synthesis of tert-butyl 5-(6-methyl pyridazin-4-yl)thiazole-2-carboxylate

A solution of 4-(2-(tert-butoxycarbonyl)thiazol-5-yl)-6-methylpyridazine 1-oxide (0.286 g, 0.975 mmol) in ammonium hydroxide (8 mL, 32% in water), MeOH (5 mL) and DCM (5 mL) was degassed with N$_2$. Palladium (0.300 g, 2.82 mmol, 10% on activated carbon) was added. The mixture was saturated with H$_2$ by alternating vacuum/H$_2$ purges. H$_2$ was then bubbled through the mixture for 1.5 h. The RM was purged with N$_2$ and filtered over Celite. The filter layer was rinsed with warm MeOH (2×10 mL) and DCM (2×10 mL). The filtrate was concentrated and redissolved in MeOH (5 mL) and DCM (5 mL). To the mixture NEt$_3$ (2.00 mL, 14.4 mmol) and palladium (10% on activated carbon, catalytic spatula tip) were added. The mixture was saturated with H$_2$ by alternating vacuum/H$_2$ purges. H$_2$ was then bubbled through the mixture for 20 h. Additional palladium (10% on activated carbon, catalytic spatula tip) was added and stirring was continued for 6 h. The RM was purged with N$_2$ and filtered over Celite. The filter layer was rinsed with warm MeOH (3×20 mL). The filtrate was concentrated. The residue was diluted with DCM (20 mL) and poured in saturated NH$_4$Cl (30 mL). The water layer was extracted with DCM (2×10 mL). The combined organic layer was washed with brine (30 mL), dried over Na$_2$SO$_4$ and concentrated in vacuo. FC (MeOH/DCM 2:98→4:96) and FC (MeOH/DCM 2:98) afforded tert-butyl 5-(6-methyl pyridazin-4-yl)thiazole-2-carboxylate (0.110 g, 0.397 mmol, 41%). LCMS: calc. for [M+H]$^+$=278.09, found 278.2.

Synthesis of 5-(6-methylpyridazin-4-yl)thiazole-2-carboxylic acid trifluoroacetate (A29)

A solution of tert-butyl 5-(6-methylpyridazin-4-yl)thiazole-2-carboxylate (0.109 g, 0.393 mmol) in DCM (4 mL) was cooled to −15° C. TFA (1.5 mL, 20.3 mmol) was added dropwise. After addition, the mixture was stirred at −15° C. for 15 min and then allowed to warm up to RT and stirred for 4 h. The RM was cooled to −15° C. TFA (0.5 mL, 6.75 mmol) was added drop wise. After addition, the mixture was stirred at −15° C. for 15 min and then allowed to warm up to RT and stirred for 2.5 h. The mixture was concentrated under reduced pressure and co-evaporated with DCM (2×10 mL) and Et$_2$O (3×10 mL) to obtain 5-(6-methylpyridazin-4-yl)thiazole-2-carboxylic acid trifluoroacetate (A29). LCMS: calc. for [M+H]$^+$=222.03, found 222.0.

Synthesis of 4-(2-carboxythiazol-5-yl)-6-methylpyridazine 1-oxide trifluoroacetate (A32)

A solution of 4-(2-(tert-butoxycarbonyl)thiazol-5-yl)-6-methylpyridazine 1-oxide (0.150 g, 0.511 mmol, synthesis see above) in DCM (4 mL) was cooled to −15° C. under N$_2$. TFA (1.50 mL, 20.3 mmol) was added drop wise. After addition, the mixture was stirred at −15° C. for 15 min and then allowed to warm up to RT and stirred for 4 h. The RM was cooled to −15° C. TFA (2.00 mL, 27.0 mmol) was added drop wise. After addition, the mixture was stirred at −15° C. for 30 min and then allowed to warm up to RT and stirred for 5 h. The mixture was concentrated under reduced pressure and co-evaporated with DCM (2×10 mL) and Et$_2$O (3×10 mL) to obtain 4-(2-carboxythiazol-5-yl)-6-methylpyridazine 1-oxide trifluoroacetate (A32). LCMS: calc. for [M+H]$^+$=238.02, found 238.0.

Synthesis of
5-(6-methoxypyridazin-3-yl)thiophene-2-carboxylic
acid (A35)

Synthesis of ethyl
5-(tributylstannyl)thiophene-2-carboxylate

Diisopropylamine (3.89 g, 38.4 mmol, 5.43 mL) was dissolved in dry THF (20 mL) and cooled to −78° C. under a $N_2$. A solution of n-butyllithium (1.6 M in hexanes, 38.4 mmol, 24.0 mL) was added drop wise. The mixture was allowed to warm to 0° C. and stirred for 30 min. The solution was cooled to −78° C. and a solution of ethyl thiophene-2-carboxylate (5.00 g, 32.1 mmol, 4.30 mL) in dry THF (10 mL) was added drop wise. The mixture was stirred at −78° C. for 1 h. A solution of tributyltinchloride (10.9 g, 33.6 mmol, 9.12 mL) in dry THF (10 mL) was added drop wise and the solution was stirred at −78° C. for 1 h, then allowed to warm up to RT and stirred for 1 h. The mixture was poured into 200 mL aqueous saturated $NH_4Cl$ and extracted with EtOAc (3×100 mL). The combined organic layer was dried over $Na_2SO_4$ and concentrated in vacuo to obtain a brown oil. FC (EtOAc/heptane (+1% $NEt_3$) 0:1→1:20, 40 g silica) afforded ethyl 5-(tributylstannyl)thiophene-2-carboxylate (13.2 g, 29.7 mmol, 93%) as a clear orange-brown liquid.

Synthesis of ethyl
5-(6-methoxypyridazin-3-yl)thiophene-2-carboxylate

A solution of ethyl 5-(tributylstannyl)thiophene-2-carboxylate (1.69 g, 3.80 mmol) and 3-chloro-6-methoxypyridazine (0.500 g, 3.46 mmol) in DMF (10 mL) was degassed with Ar. CsF (1.58 g, 10.38 mmol), CuCl (0.045 g, 0.45 mmol) and $PdCl_2(dppf)$ (0.314 g, 0.346 mmol) were added and the mixture was heated at 100° C. for 16 h. The mixture was diluted with EtOAc (100 mL) and water (100 mL). The layers were separated, the aqueous layer was extracted with EtOAc (2×100 mL). The combined organic layer was washed with brine (25 mL), dried over $Na_2SO_4$, filtered over Celite and concentrated in vacuo. FC (EtOAc/heptane 0:1→1:0) afforded ethyl 5-(6-methoxypyridazin-3-yl)thiophene-2-carboxylate (0.630 g, 2.03 mmol, 59%) as a pale yellow solid. LCMS: calc. for [M+H]+=265.06, found 265.2.

Synthesis of
5-(6-methoxypyridazin-3-yl)thiophene-2-carboxylic
acid (A35)

$LiOH.H_2O$ (0.238 g, 5.68 mmol) was added to a suspension of ethyl 5-(6-methoxypyridazin-3-yl)thiophene-2-carboxylate (0.500 g, 1.89 mmol) in THF (20 mL) and water (8 mL). The mixture stirred at RT for 16 h. The mixture was concentrated in vacuo. The residue was acidified to pH 3-4 using aqueous 2M HCl (2.84 mL). To this i-PrOH (15 mL) was added. The solids were filtered off and washed with $Et_2O$, dried in vacuo to obtain 5-(6-methoxypyridazin-3-yl)thiophene-2-carboxylic acid (A35, 0.363 g, 1.38 mmol, 73%) as a yellow solid. LCMS: calc. for [M+H]+=237.03, found 237.2.

The following biaryls were synthesized as described for A35

| Biaryl acid A | | Starting materials | analytical data |
| --- | --- | --- | --- |
| 5-(6-methylpyridazin-3-yl)thiophene-2-carboxylic acid | A36 | ethyl thiophene-2-carboxylate, 3-chloro-6-methylpyridazine | LCMS [M + H+] = 221.2 |
| 5-(5-fluoropyrimidin-4-yl)thiophene-2-carboxylic acid | A37 | ethyl thiophene-2-carboxylate, 4-bromo-5-fluoropyrimidine | LCMS [M + H+] = 225.2 |
| 5-(5-methylpyridazin-3-yl)thiophene-2-carboxylic acid | A39 | ethyl thiophene-2-carboxylate, 3-chloro-5-methylpyridazine | |
| 4-fluoro-5-(pyridazin-3-yl)thiophene-2-carboxylic acid | A40 | methyl 4-fluorothiophene-2-carboxylate, 3-hydroxypyridazine | LCMS [M + H+] = 225.0 |
| 3-fluoro-5-(pyridazin-3-yl)thiophene-2-carboxylic acid | A42 | methyl 3-fluorothiophene-2-carboxylate, 3-hydroxypyridazine | LCMS [M + H+] = 225.0 |
| 5-(2-(trifluoromethyl)pyrimidin-5-yl)thiophene-2-carboxylic acid | A43 | ethyl thiophene-2-carboxylate, 5-bromo-2-(trifluoromethyl)pyrimidine | LCMS [M + H+] = 275.0 |
| 3-fluoro-5-(pyridin-3-yl)thiophene-2-carboxylic acid | A44 | methyl 3-fluorothiophene-2-carboxylate, 3-iodopyridine | LCMS [M + H+] = 224.0 |
| 5-(2,4-dimethylpyrimidin-5-yl)thiophene-2-carboxylic acid | A48 | methyl thiophene-2-carboxylate, 5-bromo-2,4-dimethylpyrimidine | LCMS [M + H+] = 235.2 |
| 5-(2-methylpyridin-3-yl)thiophene-2-carboxylic acid | A49 | methyl thiophene-2-carboxylate, 3-bromo-2-methylpyridine | LCMS [M + H+] = 220.0 |
| 5-(4-methylpyridazin-3-yl)thiophene-2-carboxylic acid | A50 | methyl thiophene-2-carboxylate, 3-chloro-4-methylpyridazine | LCMS [M + H+] = 221.2 |
| 5-(2,5-dimethylpyridin-4-yl)thiophene-2-carboxylic acid | A52 | methyl thiophene-2-carboxylate, 4-chloro-2,5-dimethylpyridine | LCMS [M + H+] = 234.2 |

Synthesis of 5-(6-fluoropyridazin-3-yl)thiophene-2-carboxylic acid trifluoroacetate (A38)

Synthesis of 3-fluoro-6-iodopyridazine

To a solution of 3,6-diiodopyridazine (1.00 g, 3.01 mmol) in dimethylsulfoxide (5 mL) was added CsF (0.53 g, 3.5 mmol). This was heated at 120° C. for 16 h. The mixture was diluted with EtOAc (20 mL) and poured in water (50 mL). The water layer was extracted with EtOAc (4×20 mL). The combined organic layer was washed with water (2×50 mL) and brine (50 mL), dried over $Na_2SO_4$ and concentrated in vacuo to afford 3-fluoro-6-iodopyridazine (0.53 g 2.2 mmol, 72%) as a brown solid. LCMS: calc. for $[M+H]^+=224.92$, found 225.0.

Synthesis of tert-butyl 5-(tributylstannyl)thiophene-2-carboxylate

Diisopropylamine (0.659 g, 6.51 mmol, 0.920 mL) was dissolved in dry THF (6 mL) and cooled to −78° C. under $N_2$. A solution of n-butyllithium (1.6 M in hexanes, 6.51 mmol, 4.07 mL) was added drop wise. The mixture was allowed to warm to 0° C. and stirred for 30 min. The solution was cooled to −78° C. and a solution of tert-butyl thiophene-2-carboxylate (1.00 g, 5.43 mmol) in dry THF (6 mL) was added drop wise. The mixture was stirred at −78° C. for 1 h. A solution of tributyltinchloride (1.86 g, 5.70 mmol, 1.55 mL) in dry THF (5 mL) was added drop wise and the solution was stirred at −78° C. for 1 h, then allowed to warm up to RT and stirred for 1 h. The mixture was poured into aqueous saturated $NH_4Cl$ (40 mL) and extracted with EtOAc (2×20 mL). The combined organic layer was washed with brine (20 mL), dried over $Na_2SO_4$ and concentrated in vacuo. Crude product was purified by silica column chromatography ($NEt_3$/EtOAc/heptane 1:40:500) to afford tert-butyl 5-(tributylstannyl)thiophene-2-carboxylate (2.20 g, 4.65 mmol, 86%) as a colorless oil.

Synthesis of tert-butyl 5-(6-fluoropyridazin-3-yl)thiophene-2-carboxylate

A solution of 3-fluoro-6-iodopyridazine (0.470 g, 1.93 mmol) and tert-butyl 5-(tributylstannyl)thiophene-2-carboxylate (1.00 g, 2.12 mmol) in DMF (1.5 mL) was degassed with $N_2$. CsF (1.17 g, 7.72 mmol), CuCl (0.019 g, 0.193 mmol) and tetrakis(triphenylphosphine) palladium (0.223 g, 0.193 mmol) were added and the mixture was heated at 110° C. under microwave conditions for 30 min. The mixture was diluted with EtOAc (30 mL) and poured in water (100 mL). The water layer was extracted with EtOAc (2×30 mL). The combined organic layer was washed with brine (3×40 mL), dried over $Na_2SO_4$ and filtered over Celite. The filter cake was washed with EtOAc (2×30 mL). The filtrate was concentrated in vacuo. The crude product was purified by FC (MeOH/DCM 0:1→6:94) to afford tert-butyl 5-(6-fluoropyridazin-3-yl)thiophene-2-carboxylate (0.311 g, 1.11 mmol, 58%) as an off-white solid. LCMS: calc. for $[M+H]^+=281.16$, found 281.2.

Synthesis of 5-(6-fluoropyridazin-3-yl)thiophene-2-carboxylic acid trifluoroacetate (A38)

A solution of tert-butyl 5-(6-fluoropyridazin-3-yl)thiophene-2-carboxylate (0.284 g, 1.01 mmol) in DCM (16 mL) was cooled to 0° C. TFA (4.16 g, 36.5 mmol, 2.70 mL) was added drop wise. After addition, the mixture was allowed to warm to RT and stirred for 2 h. The mixture was cooled to 0° C. and TFA (2.16 g, 18.9 mmol, 1.40 mL) was added drop wise. The mixture was allowed to warm to RT and stirred for 2 h. The mixture was concentrated under reduced pressure and co-evaporated with toluene/DCM 1:1, (4×30 mL) and $Et_2O$ (3×30 mL) to afford 5-(6-fluoropyridazin-3-yl)thiophene-2-carboxylic acid trifluoroacetate (A38). LCMS: calc. for $[M+H]^+=225.01$, found 225.0.

The following biaryls were synthesized as described for A38

| Biaryl acid A | | Starting materials | analytical data |
|---|---|---|---|
| 5-(2-cyclopropylpyrimidin-5-yl)thiophene-2-carboxylic acid trifluoroacetate | A41 | tert-butyl thiophene-2-carboxylate, 5-bromo-2-cyclopropylpyrimidine | LCMS $[M + H^+] = 247.0$ |
| 5-(5-methoxypyridazin-3-yl)thiophene-2-carboxylic acid trifluoroacetate | A45 | tert-butyl thiophene-2-carboxylate, 3-chloro-5-methoxypyridazine | LCMS $[M + H^+] = 237.0$ |
| 5-(6-hydroxypyridazin-4-yl)thiophene-2-carboxylic acid trifluoroacetate | A47 | tert-butyl thiophene-2-carboxylate, 5-chloropyridazin-3-ol | LCMS $[M + H^+] = 223.0$ |

Synthesis of 5-(5-ethylpyridazin-3-yl)thiophene-2-carboxylic acid (A46)

Synthesis of ethyl 5-(5-chloropyridazin-3-yl)thiophene-2-carboxylate

A solution of 3,5-dichloropyridazine (2.68 g, 18.0 mmol) and ethyl 5-(tributylstannyl)thiophene-2-carboxylate (8.0 g, 18 mmol, synthesis see above) in 1,4-dioxane (25 mL) was degassed with Ar. CsF (8.19 g, 53.9 mmol), CuCl (0.18 g, 1.8 mmol) and $PdCl_2(dppf)$ (0.66 g, 0.90 mmol) were added and the mixture was heated at 70° C. for 2 h. KF (4.0 g, 70 mmol) in 50 mL water was added and the mixture was stirred at RT for 2 h. The mixture was filtered over Celite and the filter rinsed with DCM (15 mL) and brine (15 mL). The organic layer was dried over $Na_2SO_4$, filtered and concentrated in vacuo. FC (EtOAc/heptane 0:1→1:1) afforded ethyl 5-(5-chloropyridazin-3-yl)thiophene-2-carboxylate (1.80 g, 6.70 mmol, 37%). LCMS: calc. for $[M+H]^+=269.01$, found 269.0.

Synthesis of ethyl 5-(5-ethylpyridazin-3-yl)thiophene-2-carboxylate

A suspension of ethyl 5-(5-chloropyridazin-3-yl)thiophene-2-carboxylate (0.500 g, 1.86 mmol) in THF (15 mL) was degassed with Ar. $PdCl_2(dppf)$ (0.136 g, 0.186 mmol) was added, followed by dropwise addition of diethylzinc (1

M in hexane) (1.82 g, 2.50 mmol, 2.5 mL). After complete addition, the mixture was heated at 70° C. for 4 h. The mixture was diluted with water (30 mL) and extracted with DCM (2×20 mL). The combined organic layer was washed with brine (10 mL), dried on $Na_2SO_4$ and concentrated in vacuo. FC (EtOAc/DCM 0:1→3:1) afforded ethyl 5-(5-ethylpyridazin-3-yl)thiophene-2-carboxylate (0.274 g, 1.04 mmol, 56%). LCMS: calc. for $[M+H]^+$=263.08, found 263.1.

Synthesis of
5-(5-ethylpyridazin-3-yl)thiophene-2-carboxylic acid (A46)

LiOH.$H_2O$ (0.110 g, 2.62 mmol) was added to a solution of ethyl 5-(5-ethylpyridazin-3-yl)thiophene-2-carboxylate (0.274 g, 1.04 mmol) in THF (10 mL) and water (2 mL). The reaction was stirred at RT for 6 h. The mixture was concentrated under reduced pressure. The residue was acidified to pH 3□4 using aqueous 2 M HCl. The solids were filtered off to obtain 5-(5-ethylpyridazin-3-yl)thiophene-2-carboxylic acid (A46, 0.202 g, 0.862 mmol, 83%). LCMS: calc. for $[M+H]^+$=235.05, found 235.0.

Synthesis of
5-(2-ethylpyridin-4-yl)thiophene-2-carboxylic acid (A51)

Synthesis of methyl
5-(tributylstannyl)thiophene-2-carboxylate

Diisopropylamine (4.27 g, 42.2 mmol, 5.96 mL) was dissolved in dry THF (50 mL) and cooled to −78° C. under $N_2$. A solution of n-butyllithium (1.6 M in hexanes, 42.2 mmol, 26.4 mL) was added dropwise. The mixture was allowed to warm to 0° C. and stirred for 30 min. The solution was cooled to −78° C. and a solution of methyl thiophene-2-carboxylate (5.00 g, 35.2 mmol) in dry THF (50 mL) was added drop wise. The mixture was stirred at −78° C. for 1 h. A solution of tributyltinchloride (12.0 g, 36.9 mmol, 10.0 mL) in dry THF (50 mL) was added drop wise and the solution was stirred at −78° C. for 1 h, then allowed to warm up to RT and stirred for 16 h. The mixture was poured into 250 mL aqueous saturated $NH_4Cl$ and extracted with EtOAc (3×150 mL). The combined organic layer was washed with brine (400 mL), dried over $Na_2SO_4$ and concentrated in vacuo. FC (EtOAc (+8% $NEt_3$)/heptane 0:1→1:40) afforded methyl 5-(tributylstannyl)thiophene-2-carboxylate (11.2 g, 25.9 mmol, 74%) as a brown oil.

Synthesis of 2-ethyl-4-(5-(methoxycarbonyl)thiophen-2-yl)pyridine 1-oxide

A solution of 4-bromo-2-ethylpyridine 1-oxide (0.937 g, 4.64 mmol, synthesis see above), methyl 5-(tributylstannyl)thiophene-2-carboxylate (2.00 g, 4.64 mmol) and CsF (2.11 g, 13.9 mmol) in 1,4-dioxane (40 mL) was degassed with Ar. $PdCl_2$(dppf) (0.170 g, 0.232 mmol) and CuCl (0.060 g, 0.60 mmol) were added and the mixture was heated at 80° C. for 4 h. KF (0.50 g, 8.6 mmol) in 20 mL water was added and the mixture was stirred at RT for 18 h. The mixture was filtered over Celite and rinsed with EtOAc (100 mL). The filtrate was washed with water (40 mL) and brine (40 mL), dried over $Na_2SO_4$ and concentrated under reduced pressure. FC (EtOAc/heptane 1:9→1:0) afforded 2-ethyl-4-(5-(methoxycarbonyl)thiophen-2-yl)pyridine 1-oxide (0.960 g, 3.65 mmol, 79%) as a solid. LCMS: calc. for $[M+H]^+$=264.06, found 264.1.

Synthesis of methyl
5-(2-ethylpyridin-4-yl)thiophene-2-carboxylate

Under $N_2$, palladium (10% on activated carbon, 0.190 g, 0.789 mmol) was added to a solution of 2-ethyl-4-(5-(methoxycarbonyl)thiophen-2-yl)pyridine 1-oxide (0.470 g, 1.79 mmol) in EtOH (35 mL). $H_2$ was applied (balloon) and the mixture was stirred at RT overnight. The mixture was filtered over Celite and the filtrate was concentrated under reduced pressure to obtain methyl 5-(2-ethylpyridin-4-yl)thiophene-2-carboxylate (0.439 g, 1.78 mmol, 99%). LCMS: calc. for $[M+H]^+$=248.07, found 248.1.

Synthesis of
5-(2-ethylpyridin-4-yl)thiophene-2-carboxylic acid (A51)

LiOH.$H_2O$ (0.163 g, 3.88 mmol) was added to a solution of methyl 5-(2-ethylpyridin-4-yl)thiophene-2-carboxylate (0.439 g, 1.78 mmol) in THF (15 mL) and water (10 mL). The reaction was stirred at RT for 2 h. The mixture was concentrated under reduced pressure. i-PrOH (5 mL) was added and the mixture was acidified to pH 3-4 using aqueous 1 M HCl. The solids were filtered off and washed with $Et_2O$ to obtain 5-(2-ethylpyridin-4-yl)thiophene-2-carboxylic acid (A51, 0.316 g, 1.36 mmol, 76%) as a solid. LCMS: calc. for $[M+H]^+$=234.05, found 234.2.

Synthesis of 5-(5-(methylsulfinyl)pyridazin-3-yl)thiophene-2-carboxylic acid trifluoroacetate (A53)

Synthesis of tert-butyl
5-(5-chloropyridazin-3-yl)thiophene-2-carboxylate

A solution of 3,5-dichloropyridazine (2.00 g, 13.4 mmol) and tert-butyl 5-(tributylstannyl)thiophene-2-carboxylate (6.35 g, 13.4 mmol, synthesis see above) in 1,4-dioxane (25 mL) was degassed with Ar. CsF (6.12 g, 40.3 mmol), CuCl (0.133 g, 1.34 mmol) and $PdCl_2$(dppf) (0.491 g, 0.671 mmol) were added and the mixture was heated at 70° C. for 2 h. KF (3.12 g, 53.7 mmol) in 50 mL water was added and the mixture was stirred at RT for 2 h. The mixture was filtered over Celite and rinsed with DCM (15 mL) and brine (15 mL). The organic layer was dried over $Na_2SO_4$, filtered and concentrated in vacuo. FC (EtOAc/DCM 0:1→1:1) afforded tert-butyl 5-(5-chloropyridazin-3-yl)thiophene-2-carboxylate (2.14 g, 6.65 mmol, 49%). LCMS: calc. for $[M+H]^+$=297.04, found 297.0.

Synthesis tert-butyl 5-(5-(methylthio)pyridazin-3-yl)thiophene-2-carboxylate

To a stirred solution of (methyldisulfanyl)methane (0.175 g, 1.85 mmol, 0.167 mL) in THF (10 mL) cooled at 0° C., under dry $N_2$, was added n-butyllithium (1.6 M in hexanes, 2.02 mmol, 1.26 mL). The solution was stirred at 0° C. for 10 min, then added to a suspension of tert-butyl 5-(5-chloropyridazin-3-yl)thiophene-2-carboxylate (0.500 g, 1.69 mmol) in THF (10 mL). The mixture was allowed to reach RT. Water (10 mL) was added and the mixture was extracted with DCM (3×20 mL). The combined organic layer was dried with $Na_2SO_4$, filtered and concentrated in vacuo. Purification by FC (EtOAc/heptane 0:1→1:0) gave tert-butyl 5-(5-(methylthio)pyridazin-3-yl)thiophene-2-carboxylate (0.481 g, 1.48 mmol, 88%). LCMS: calc. for [M+H]$^+$=309.07, found 309.1.

Synthesis of tert-butyl 5-(5-(methylsulfinyl)pyridazin-3-yl)thiophene-2-carboxylate $H_2O_2$ (30% in water, w/w, 0.088 g, 0.78 mmol, 0.079 mL) was added to a solution of tert-butyl 5-(5-(methylthio)pyridazin-3-yl)thiophene-2-carboxylate (0.200 g, 0.648 mmol) in hexafluoro-2-propanol (4 mL). The mixture was stirred at RT for 16 h. $H_2O_2$ (30% in water, w/w, 0.088 g, 0.78 mmol, 0.079 mL) was added again and the reaction stirred for 16 h. $H_2O_2$ (30% in water, w/w, 0.088 g, 0.78 mmol, 0.08 mL) was added and the reaction stirred for another 16 h. An aqueous 10% solution of $Na_2S_2O_4$ (2 mL) and DCM (10 mL) were added. The layers were separated over a phase separation filter. The organic layer was concentrated under reduced pressure to obtain a light brown oil. Purification by FC (EtOAc/heptane 0:1→1:0) gave tert-butyl 5-(5-(methylsulfinyl)pyridazin-3-yl)thiophene-2-carboxylate (0.180 g, 0.527 mmol, 81%). LCMS: calc. for [M+H]$^+$=325.06, found 325.0.

Synthesis of 5-(5-(methylsulfinyl)pyridazin-3-yl)thiophene-2-carboxylic acid trifluoroacetate (A53)

To a solution of tert-butyl 5-(5-(methylsulfinyl)pyridazin-3-yl)thiophene-2-carboxylate (0.18 g, 0.56 mmol) in DCM (1 mL) was added TFA (1.49 g, 13.1 mmol, 1 mL) and the mixture was stirred at RT for 1 h. The mixture was concentrated in vacuo and stripped twice with DCM to remove excess TFA yielding 5-(5-(methylsulfinyl)pyridazin-3-yl)thiophene-2-carboxylic acid trifluoroacetate (A53, 0.269 g, 0.591 mmol, 100%). LCMS: calc. for [M+H]$^+$=269.00, found 269.0.

Synthesis of 5-(5-cyclopropylpyridazin-3-yl)thiophene-2-carboxylic acid (A54)

Synthesis of ethyl 5-(5-cyclopropylpyridazin-3-yl)thiophene-2-carboxylate

A suspension of ethyl 5-(5-chloropyridazin-3-yl)thiophene-2-carboxylate (0.600 g, 2.23 mmol, synthesis see above), cyclopropylboronic acid (0.29 mg, 3.35 mmol) and potassiumphosphate, tribasic (1.42 g, 6.70 mmol) in toluene (75 mL) and water (7.5 mL) was degassed with Ar. Palladium acetate (0.025 g, 0.112 mmol) and tricyclohexylphosphine (0.063 g, 0.223 mmol) were added and the mixture was heated at 100° C. for 16 h. The mixture was filtered over Celite, washed with EtOAc. The filtrate was concentrated under reduced pressure. FC (EtOAc/DCM 0:1→3:1) afforded ethyl 5-(5-cyclopropylpyridazin-3-yl)thiophene-2-carboxylate (0.485 g, 1.68 mmol, 75%). LCMS: calc. for [M+H]$^+$=275.08, found 275.1.

Synthesis of 5-(5-cyclopropylpyridazin-3-yl)thiophene-2-carboxylic acid (A54)

LiOH.$H_2O$ (0.220 g, 5.30 mmol) was added to a solution of ethyl 5-(5-cyclopropylpyridazin-3-yl)thiophene-2-carboxylate (0.485 g, 1.68 mmol) in THF (10 mL) and water (4 mL). The reaction was stirred at RT for 16 h. The mixture was concentrated under reduced pressure. The residue was acidified to pH 3-4 using aqueous 2 M HCl. i-PrOH (5 mL) was added and the solids were filtered off and washed with $Et_2O$ to obtain 5-(5-cyclopropylpyridazin-3-yl)thiophene-2-carboxylic acid (A54, 0.325 g, 1.25 mmol, 71%) as a solid. LCMS: calc. for [M+H]$^+$=247.05, found 247.0.

Synthesis of 5-(5-(methylsulfonyl)pyridazin-3-yl)thiophene-2-carboxylic acid trifluoroacetate (A33)

Synthesis of tert-butyl 5-(5-(methylsulfonyl)pyridazin-3-yl)thiophene-2-carboxylate 3-Chloroperbenzoic acid (0.320 g, 3.30 mmol, 70%, w/w) was added to a solution of tert-butyl 5-(5-(methylthio)pyridazin-3-yl)thiophene-2-carboxylate (0.20 g, 0.648 mmol, synthesis see above) in DCM (4 mL). The mixture was stirred at RT for 16 h. The mixture was quenched with 10% solution of $Na_2S_2O_4$ (10 mL). Aqueous saturated $NaHCO_3$ (10 mL) was added and the mixture was extracted with DCM (2×20 mL). The combined organic layer was dried over $Na_2SO_4$ and concentrated in vacuo. FC (EtOAc/heptane 0:1→1:0) afforded 514-1 (0.118 g, 0.312 mmol, 48%). LCMS: calc. for [M+H]$^+$=341.06, found 341.0.

Synthesis of 5-(5-(methylsulfonyl)pyridazin-3-yl)thiophene-2-carboxylic acid trifluoroacetate (A33)

To a solution of tert-butyl 5-(5-(methylsulfonyl)pyridazin-3-yl)thiophene-2-carboxylate (0.118 g, 0.347 mmol) in DCM (1 mL) was added TFA (1.49 g, 13.1 mmol, 1.00 mL) and the mixture was stirred at RT for 1 h. The mixture was concentrated in vacuo and stripped twice with DCM to remove excess TFA yielding 5-(5-(methylsulfonyl)pyridazin-3-yl)thiophene-2-carboxylic acid trifluoroacetate (A33, 0.138 g, 0.347 mmol, 100%) its TFA salt. LCMS: calc. for [M+H]$^+$=284.99, found 285.0.

Synthesis of 3-(5-carboxythiophen-2-yl)pyridazine 1-oxide (A34)

Synthesis of 3-bromopyridazine

Phosphorous oxybromide (158 g, 552 mmol) was heated to 80° C. under mechanical stirring until molten. 3-Hydroxypyridazine (30.5 g, 317 mmol) was added in one portion to the orange liquid, which afforded immediately a yellow, then a black solid. This was heated to 120° C. and left at this temperature for 3 h. After cooling the black solid was cooled with an ice water bath, small portions of ice water (in total: 300 ml) were slowly added and an exotherm was observed (white smoke). During stirring, some solids didn't dissolve 2 M aqueous NaOH (180 mL) was added at RT and stirred for 45 min until all solids were dissolved. The dark red/brown solution was poured into a mechanically stirred ice/water bath, which contained 2 M aqueous NaOH solution (910 mL). The internal temperature was kept below 25° C. during the addition. The pH was adjusted to ~9.5 by addition of 2 M aqueous NaOH (50 mL). The brown solution was extracted with DCM (5×250 mL). The combined yellow organic layer was dried over $Na_2SO_4$, filtered and concentrated in vacuo to obtain a grey/brown solid. The crude material was coated on silica (98 g) and filtered with heptane/EtOAc (1:1) over a plug of silica (200 g). Product containing fractions were combined and concentrated in vacuo to afford 3-bromopyridazine (34.7 g 216 mmol, 69%) as a green/grey solid. GCMS: >99% pure.

Synthesis of ethyl 5-(tributylstannyl)thiophene-2-carboxylate

Diisopropylamine (21.8 g, 215 mmol, 30.4 mL) was dissolved in dry THF (200 mL) and cooled to −78° C. under N$_2$. A solution of n-butyllithium (1.6 M in hexanes, 215 mmol, 134 mL) was added drop wise. The mixture was allowed to warm to 0° C. and stirred for 30 min. The solution was cooled to −78° C. and a solution of ethyl thiophene-2-carboxylate (33.6 g, 215 mmol, 29.0 mL) in dry THF (50 mL) was added drop wise. The mixture was stirred at −78° C. for 1 h. A solution of tributyltinchloride (70 g, 215 mmol, 58.3 mL) in dry THF (50 mL) was added drop wise and the solution was stirred at −78° C. for 1 h, then allowed to warm up to RT and stirred for 1 h. The mixture was poured into 1 L aqueous saturated NH$_4$Cl and extracted with EtOAc (2×750 mL). The combined organic layer was dried over Na$_2$SO$_4$ and concentrated in vacuo to obtain a brown oil. Filtration over silica (~500 g, eluted with EtOAc/heptane 1:19) afforded ethyl 5-(tributylstannyl)thiophene-2-carboxylate (86.8 g, 195 mmol, 91%) as a clear orange/brown solution.

Synthesis of ethyl 5-(pyridazin-3-yl)thiophene-2-carboxylate

A solution of 3-bromopyridazine (28.2 g, 177 mmol) and ethyl 5-(tributylstannyl)thiophene-2-carboxylate (86.8 g, 195 mmol) was degassed with Ar. CsF (81.0 g, 532 mmol), CuCl (2.28 g, 23.0 mmol) and PdCl$_2$(dppf) (6.96 g, 9.51 mmol) were added and the mixture was heated at 100° C. for 3 h. A solution of KF (25.0 g, 430 mmol) in 200 mL of water was added and the mixture was stirred vigorously for 3 h. The mixture was filtered over Celite, rinsed with EtOAc (3×400 mL). The filtrate was diluted with aqueous saturated NaHCO$_3$ (500 mL) and water (500 mL). The layers were separated; the aqueous layer was extracted with EtOAc (750 mL). The combined organic layer was washed with brine (2×1 L), dried over Na$_2$SO$_4$ and concentrated in vacuo. The aqueous layer was divided in three 1 L portions, which were extracted twice with EtOAc. The combined organic layer was dried over Na$_2$SO$_4$ and concentrated in vacuo and combined with the previous organic fraction. The product was purified by gravity column chromatography (~1 kg of silica, product loaded on Isolute, eluted with 5 L (EtOAc/heptane 1:4), 4 L (EtOAc/heptane 2:3), 4 L (EtOAc/heptane 3:2), 5 L (EtOAc/heptane 4:1), then pure EtOAc) to obtain ethyl 5-(pyridazin-3-yl)thiophene-2-carboxylate (15.6 g, 66.4 mmol, 38%) as a yellow solid. LCMS: calc. for [M+H]$^+$=235.05, found 235.1.

Synthesis of 5-(pyridazin-3-yl)thiophene-2-carboxylic acid

LiOH.H$_2$O (5.70 g, 136 mmol) was added to a suspension of ethyl 5-(pyridazin-3-yl)thiophene-2-carboxylate (15.6 g, 66.4 mmol) in THF (200 mL) and water (150 mL). The mixture was heated at 65° C. for 1 h. The mixture was concentrated in vacuo. The residue was acidified to pH ~4 using aqueous 2 M HCl (~70 mL). To this i-PrOH (100 mL) was added. The solids were filtered off and washed with Et$_2$O, dried in vacuo to obtain 5-(pyridazin-3-yl)thiophene-2-carboxylic acid (13.1 g, 63.5 mmol, 96%) as a yellow solid. LCMS: calc. for [M+H]$^+$=207.01, found 207.2.

Synthesis of methyl 5-(pyridazin-3-yl)thiophene-2-carboxylate

A suspension of 5-(pyridazin-3-yl)thiophene-2-carboxylic acid (0.500 g, 2.43 mmol, synthesis see above) in dry MeOH (20 mL) was cooled to 0° C. under N$_2$. Thionyl chloride (0.640 g, 5.38 mmol, 0.390 mL) was added dropwise. The mixture was allowed to warm to RT and then heated at 60° C. for 16 h. Additional thionyl chloride (0.288 g, 2.43 mmol, 0.100 mL) was added dropwise and the mixture was heated at 60° C. for 5 h. The mixture was concentrated in vacuo and to the residue was added ice-water (40 mL) and DCM (30 mL). The water layer was extracted with DCM (3×30 mL). The combined organic layer was washed with brine (50 mL), dried over Na$_2$SO$_4$ and concentrated in vacuo to obtain methyl 5-(pyridazin-3-yl)thiophene-2-carboxylate (0.475 g, 2.16 mmol, 89%) as a yellow solid. LCMS: calc. for [M+H]$^+$=221.03, found 221.0.

Synthesis of 3-(5-(methoxycarbonyl)thiophen-2-yl)pyridazine 1-oxide

To a solution of methyl 5-(pyridazin-3-yl)thiophene-2-carboxylate (0.371 g, 1.68 mmol) in acetic acid (10 mL) was added H$_2$O$_2$ (30% in water, w/w, 1.10 g, 9.71 mmol, 1.10 mL). The mixture was heated at 120° C. for 17 h. The mixture was allowed to cool to RT and poured in aqueous saturated NaHCO$_3$ (160 mL) and extracted with DCM (5×80 mL). The combined organic layer was dried over Na$_2$SO$_4$ and concentrated in vacuo. FC (acetone/toluene 1:9→1:1) afforded 3-(5-(methoxycarbonyl)thiophen-2-yl)pyridazine 1-oxide (0.222 g, 0.940 mmol, 56%) as a beige solid. LCMS: calc. for [M+H]$^+$=237.03, found 237.0.

Synthesis of 3-(5-carboxythiophen-2-yl)pyridazine 1-oxide (A34)

LiOH.H$_2$O (0.069 g, 1.6 mmol) was added to a solution of 3-(5-(methoxycarbonyl)thiophen-2-yl)pyridazine 1-oxide (0.18 g, 0.75 mmol) in THF (5 mL), water (1 mL) and MeOH (4 mL). The RM was stirred at RT for 2 h. The RM was concentrated in vacuo. The residue was acidified to pH 4☐5 by addition of aqueous 1 M HCl (1.9 mL) and triturated with i-PrOH (4 mL). The resulting solid was obtained by filtration, washed with cold i-PrOH (2 mL) and pentane (2×4 mL) and dried to afford 3-(5-carboxythiophen-2-yl)pyridazine 1-oxide (A34, 0.13 g, 0.56 mmol, 76%) as a beige solid. LCMS: calc. for [M+H]$^+$=223.01, found 223.0.

Synthesis of 5-(3-methylpyridazin-4-yl)thiophene-2-carboxylic acid (A55)

Synthesis of methyl 5-(6-chloro-3-methylpyridazin-4-yl)thiophene-2-carboxylate Reaction was performed in two equal batches. A solution of 4,6-dichloro-3-methylpyridazine (0.851 g, 5.22 mmol), methyl 5-(4,4,5,5-tetramethyl-1,3,2-dioxaborolan-2-yl)thiophene-2-carboxylate (1.40 g, 5.22 mmol) and KF (0.758 g, 13.1 mmol) in toluene (9.6 mL) and water (2.4 mL) was degassed with N$_2$. Palladium acetate (0.059 g, 0.26 mmol) and 1,2,3,4,5-pentaphenyl-1'-(di-tert-butylphosphino)ferrocene (0.184 g, 0.261 mmol) were added and the mixture was heated at 70° C. for 16 h. The mixture was diluted with EtOAc (40 mL) and filtered over Celite. The filter layer was rinsed with EtOAc (2×40 mL). The filtrate was concentrated and purified by FC (EtOAc/heptane 0:1→4:6), FC (EtOAc/heptane 0:1→3:7) and FC (EtOAc/heptane 0:1→3:7) to obtain methyl 5-(6-chloro-3-methylpyridazin-4-yl)thiophene-2-carboxylate (0.414 g, 1.45 mmol, 28%) as a pink solid. LCMS: calc. for [M+H]$^+$=269.01, found 269.0.

Synthesis of methyl 5-(3-methylpyridazin-4-yl)thiophene-2-carboxylate

A solution of methyl 5-(6-chloro-3-methylpyridazin-4-yl)thiophene-2-carboxylate (0.398 g, 1.40 mmol) in MeOH (50 mL) was degassed with $N_2$. Palladium (10% on activated carbon, 0.556 g, 5.23 mmol) was added. The mixture was saturated with $H_2$ by alternating vacuum/$H_2$ purges. $H_2$ was then bubbled through the mixture for 1.5 h. The mixture was filtered over Celite. The filter layer was rinsed with warm MeOH (3×30 mL). The filtrate was concentrated and purified by trituration with DCM. The mother liquor was concentrated and purified by FC (EtOAc/heptane 0:1→8:2). The triturated portion and the purified mother liquor were combined to obtain methyl 5-(3-methylpyridazin-4-yl)thiophene-2-carboxylate (0.196 g, 0.812 mmol, 58%) as a white solid. LCMS: calc. for $[M+H]^+$=235.05, found 235.1.

Synthesis of 5-(3-methylpyridazin-4-yl)thiophene-2-carboxylic acid (A55)

LiOH.$H_2$O (0.068 g, 1.6 mmol) was added to a solution of methyl 5-(3-methylpyridazin-4-yl)thiophene-2-carboxylate (0.182 g, 0.777 mmol) in THF (8 mL) and water (1.6 mL). The RM was stirred at RT for 1.5 h. The RM was concentrated in vacuo. The residue was acidified to pH ~4 by addition of aqueous 1 M HCl (~1.7 mL) and triturated with i-PrOH (5 mL). The resulting solid was obtained by filtration, washed with cold i-PrOH (2×1.5 mL) and pentane (2×1.5 mL) and dried to afford 5-(3-methylpyridazin-4-yl)thiophene-2-carboxylic acid (A55, 0.084 g, 0.38 mmol, 49%) as a green solid. LCMS: calc. for $[M+H]^+$=221.03, found 221.0.

Synthesis of 5-(6-methylpyridazin-4-yl)thiophene-2-carboxylic acid (A56)

Synthesis of 6-methylpyridazine 1-oxide

To a solution of 3-methylpyridazine (4.60 g, 48.9 mmol) in acetic acid (30.0 mL) was added $H_2O_2$ (30% in water, w/w, 29.4 g, 259 mmol, 29.4 mL,). The mixture was heated at 120° C. for 6 h. The mixture was allowed to cool to RT and poured in aqueous saturated NaHCO$_3$ (500 mL) and extracted with DCM (5×50 mL). The combined organic layer was dried over $Na_2SO_4$ and concentrated in vacuo to afford 6-methylpyridazine 1-oxide (2.22 g, 20.2 mmol, 41%). LCMS: calc. for $[M+H]^+$=111.05, found 111.2. $^1$H NMR shows a 1:1 mixture of both possible N-oxides.

Synthesis of 6-methyl-4-nitropyridazine 1-oxide

To a solution of 6-methylpyridazine 1-oxide (2.10 g, 19.1 mmol) in sulphuric acid (37.5 g, 383 mmol, 20.4 mL) at 0° C. under $N_2$ was added fuming nitric acid (10.8 g, 172 mmol, 7.31 mL) drop wise. The mixture was heated at 110° C. for 4 h and stirred at RT for 16 h. The mixture was slowly poured in ice-water (200 mL). This mixture was poured in 1 M NaOH (100 mL) and aqueous saturated NaHCO$_3$ (80 mL) was added to give pH 7☐8. The water layer was extracted with EtOAc (3×100 mL). The combined organic layer was dried over $Na_2SO_4$ and concentrated in vacuo to afford an orange solid. The water layer was extracted with DCM (5×50 mL). The combined organic layer was dried over $Na_2SO_4$, combined with the earlier obtained orange solid and concentrated in vacuo to afford crude product. The crude product was purified by FC (acetone/DCM 2:98 isocratic) and FC (acetone/DCM 2:98 isocratic) to obtain 6-methyl-4-nitropyridazine 1-oxide (0.940 g, 6.06 mmol, 32%), the pure N-oxide, as a yellow solid. LCMS: calc. for $[M+H]^+$=156.03, found 156.2.

Synthesis of 4-bromo-6-methylpyridazine 1-oxide

HBr in acetic acid (21.3 g, 86.9 mmol, 15.0 mL, 33%) was added to 6-methyl-4-nitropyridazine 1-oxide (0.759 g, 4.89 mmol). The mixture was heated at 100° C. for 2 h. This mixture was poured in ice-water (50 mL) and basified by addition of 6 M NaOH (45 mL). The water layer was extracted with DCM (3×50 mL). The combined organic layer was dried over $Na_2SO_4$ and concentrated in vacuo to afford crude product. The crude product was purified by FC (acetone/DCM 3:97) and FC (acetone/DCM 2:98) to obtain 4-bromo-6-methylpyridazine 1-oxide (0.689 g, 3.66 mmol, 75%) as a yellow solid. LCMS: calc. for $[M+H]^+$=188.96, found 189.0.

Synthesis of 4-(5-(methoxycarbonyl)thiophen-2-yl)-6-methylpyridazine 1-oxide A solution of 4-bromo-6-methylpyridazine 1-oxide (0.565 g, 2.99 mmol), methyl 5-(4,4,5,5-tetramethyl-1,3,2-dioxaborolan-2-yl)thiophene-2-carboxylate (0.802 g, 2.99 mmol) and $Cs_2CO_3$ (1.95 g, 5.98 mmol) in 1,4-dioxane (15 mL) and water (3 mL) was degassed with $N_2$. To this was added PdCl$_2$(dppf) (0.244 g, 0.299 mmol) and the mixture was heated at 110° C. for 1.5 h. The mixture was diluted with EtOAc (20 mL) and filtered over Celite. The filter layer was rinsed with EtOAc (3×10 mL). The filtrate was poured in saturated NaHCO$_3$ solution (50 mL). The water layer was extracted with EtOAc (3×20 mL). The combined organic layer was washed with water (50 mL) and brine (50 mL), dried over $Na_2SO_4$ and concentrated in vacuo. FC (acetone/DCM 5:95) afforded 4-(5-(methoxycarbonyl)thiophen-2-yl)-6-methylpyridazine 1-oxide (0.311 g, 1.24 mmol, 42%) as a yellow solid. LCMS: calc. for $[M+H]^+$=251.04, found 251.0.

Synthesis of methyl 5-(6-methylpyridazin-4-yl)thiophene-2-carboxylate

A solution of 4-(5-(methoxycarbonyl)thiophen-2-yl)-6-methylpyridazine 1-oxide (0.305 g, 1.22 mmol) in ammonium hydroxide (10 mL, 32% in water), MeOH (5 mL) and DCM (5 mL) was degassed with $N_2$. Palladium (10% on activated carbon, catalytic spatula tip) was added. The mixture was saturated with $H_2$ by alternating vacuum/$H_2$ purges. $H_2$ was then bubbled through the mixture for 1.5 h. The RM was purged with $N_2$ and filtered over Celite. The filter layer was rinsed with warm MeOH (2×10 mL) and DCM (2×10 mL). To the filtrate palladium (10% on activated carbon, catalytic spatula tip) was added. The mixture was saturated with $H_2$ by alternating vacuum/$H_2$ purges. $H_2$ was then bubbled through the mixture for 5.5 h. The RM was purged with $N_2$ and filtered over Celite. The filter layer was rinsed with warm MeOH (2×10 mL) and DCM (2×10 mL). The filtrate was concentrated. The residue was dissolved DCM (20 mL) and poured in saturated NH$_4$Cl (20 mL). The water layer was extracted with DCM (3×10 mL). The combined organic layer was washed with water (20 mL) and brine (20 mL), dried over $Na_2SO_4$ and concentrated in vacuo. FC (MeOH/DCM 1:99→5:95) and FC (MeOH/DCM 1:99) afforded methyl 5-(6-methylpyridazin-4-yl)thiophene-2-carboxylate (0.102 g, 0.435 mmol, 36%). LCMS: calc. for [M+H]⁺=235.05, found 235.0.

Synthesis of 5-(6-methylpyridazin-4-yl)thiophene-2-carboxylic acid (A56)

LiOH.H₂O (0.036 g, 0.86 mmol) was added to a solution of methyl 5-(6-methylpyridazin-4-yl)thiophene-2-carboxylate (0.099 g, 0.42 mmol) in THF (3 mL) and water (0.6 mL). The RM was stirred at RT for 2 h. The RM was concentrated in vacuo. The residue was acidified to pH 4☐5 by addition of aqueous 1 M HCl (~0.9 mL) and triturated with i-PrOH (2.5 mL). The resulting solid was obtained by filtration, washed with cold i-PrOH (2×1.5 mL) and pentane (3×1.5 mL) and dried to afford 5-(6-methylpyridazin-4-yl)thiophene-2-carboxylic acid (A56, 0.080 g, 0.36 mmol, 86%) as a beige solid. LCMS: calc. for [M+H]⁺=221.03, found 221.0.

Synthesis of 5-(3,6-dimethylpyridazin-4-yl)thiophene-2-carboxylic acid (A57)

Synthesis of methyl 5-(3,6-dimethylpyridazin-4-yl)thiophene-2-carboxylate

Reaction was performed in two equal batches. To a solution of methyl 5-(6-chloro-3-methylpyridazin-4-yl)thiophene-2-carboxylate (0.333 g, 1.24 mmol, synthesis see above) and Cs₂CO₃ (0.808 g, 2.48 mmol) in dioxane (8.0 mL) and water (0.2 mL) was added trimethylboroxine (3.5 M solution in THF, 0.933 g, 3.72 mmol, 1.04 mL). The mixture was degassed with N₂ for 5 min and PdCl₂(dppf) (0.051 g, 0.062 mmol) was added. The mixture was heated at 100° C. for 4 h and stirred at RT for 16 h. The mixture was filtered over Celite. The filter cake was washed with warm EtOAc (2×20 mL). The filtrate was poured in aqueous saturated NaHCO₃ (30 mL) and extracted with EtOAc (2×20 mL). The combined organic layer was washed with brine (30 mL), dried over Na₂SO₄ and concentrated in vacuo. The crude product was purified by FC (EtOAc/heptane 1:1→1:0) to obtain methyl 5-(3,6-dimethylpyridazin-4-yl)thiophene-2-carboxylate (0.303 g, 1.15 mmol, 93%) as a yellow solid. LCMS: calc. for [M+H]⁺=249.06, found 249.2.

Synthesis of 5-(3,6-dimethylpyridazin-4-yl)thiophene-2-carboxylic acid (A57)

LiOH.H₂O (0.130 g, 3.10 mmol) was added to a solution of methyl 5-(3,6-dimethylpyridazin-4-yl)thiophene-2-carboxylate (0.297 g, 1.13 mmol) in THF (10 mL) and water (2 mL). The RM was stirred at 30° C. for 2.5 h. The RM was concentrated in vacuo. The residue was acidified to pH 3-4 by addition of aqueous 2 M HCl (1.6 mL) and triturated with a mixture of i-PrOH (2 mL) and pentane (3 mL). The resulting solid was obtained by filtration, washed with cold i-PrOH (1 mL) and pentane (3×3 mL) and dried to afford 5-(3,6-dimethylpyridazin-4-yl)thiophene-2-carboxylic acid (A57, 0.202 g, 0.855 mmol, 76%) as a brown solid. LCMS: calc. for [M+H]⁺=235.05, found 235.2.

Synthesis of 5-(6-methoxypyridazin-4-yl)thiophene-2-carboxylic acid (A58)

Synthesis of methyl 5-(6-chloropyridazin-4-yl)thiophene-2-carboxylate

A suspension of 3,5-dichloropyridazine (0.400 g, 2.68 mmol), methyl 5-(4,4,5,5-tetramethyl-1,3,2-dioxaborolan-2-yl)thiophene-2-carboxylate (0.720 g, 2.68 mmol) and KF (0.390 g, 6.71 mmol) in toluene (15 mL) and water (3 mL) was degassed with Ar for 10 min. Palladium(II) acetate (0.030 g, 0.13 mmol) and 1,2,3,4,5-pentaphenyl-1'-(di-tert-butylphosphino)ferrocene (0.095 g, 0.13 mmol) were added and the mixture was degassed with Ar for 3 more min, then heated at 70° C. for 18 h. The mixture was filtered over Celite. The filtrate was concentrated under reduced pressure and purified by FC (EtOAc/heptane 1:19→2:3) to obtain methyl 5-(6-chloropyridazin-4-yl)thiophene-2-carboxylate (0.300 g, 85%, w/w, 1.00 mmol, 37%). LCMS: calc. for [M+H]⁺=254.99, found 255.0.

Synthesis of 5-(6-methoxypyridazin-4-yl)thiophene-2-carboxylic acid (A58)

A solution of sodium hydride (0.220 g, 60%, w/w, 5.50 mmol) in MeOH (10 mL) was added to a solution of methyl 5-(6-chloropyridazin-4-yl)thiophene-2-carboxylate (0.300 g, 85% (w/w), 1.00 mmol) in MeOH (10 mL). The mixture was heated at 50° C. for 3 h. The mixture was concentrated under reduced pressure. The residue was suspended in i-PrOH (5 mL) and acidified to pH ~3-4 with 1 M aqueous HCl The solids were filtered off to obtain 5-(6-methoxypyridazin-4-yl)thiophene-2-carboxylic acid (A58, 0.105 g, 0.444 mmol, 44%) as a brown solid. LCMS: calc. for [M+H]⁺=237.03, found 237.0.

Synthesis of 5-(6-ethylpyridazin-4-yl)thiophene-2-carboxylic acid hydrochloride (A59)

Synthesis of methyl 5-(6-ethylpyridazin-4-yl)thiophene-2-carboxylate

A solution of methyl 5-(6-chloropyridazin-4-yl)thiophene-2-carboxylate (0.380 g, 1.39 mmol, synthesis see above) in THF (2.4 mL) was degassed with N₂ for 5 min. Then PdCl₂(dppf) (0.072 g, 0.088 mmol) and diethylzinc (1 M in hexanes, 5.40 mmol, 5.40 mL) were added. The mixture was heated at 70° C. for 1.5 h. The mixture was poured in water (40 mL) and extracted with DCM (4×20 mL). The combined organic layer was washed with brine (50 mL), dried over Na₂SO₄ and concentrated in vacuo. The crude product was purified by FC (EtOAc/DCM 1:99→2:8) and by reversed phase chromatography (MeCN/H₂O (+0.1% HCOOH) 1:19→1:0) and co-evaporated with toluene (3×25 mL) to obtain methyl 5-(6-ethylpyridazin-4-yl)thiophene-2-carboxylate (0.177 g, 0.713 mmol, 51%) as a beige solid. LCMS: calc. for [M+H]⁺=249.06, found 249.2.

Synthesis of 5-(6-ethylpyridazin-4-yl)thiophene-2-carboxylic acid hydrochloride (A59)

LiOH.H₂O (0.068 g, 1.6 mmol) was added to a solution of methyl 5-(6-ethylpyridazin-4-yl)thiophene-2-carboxylate (0.175 g, 0.705 mmol) in THF (5 mL) and water (1 mL). The RM was stirred at RT for 1 h. LiOH.H₂O (0.020 g, 0.48 mmol) was added and the mixture was heated at 50° C. for 1 h. The RM was concentrated in vacuo. The residue was acidified to pH 4☐5 by addition of aqueous 1 M HCl (1.9 mL) and triturated with i-PrOH (3 mL). The resulting semi-solid could not be obtained by filtration. The mixture was concentrated in vacuo to afford 5-(6-ethylpyridazin-4- yl)thiophene-2-carboxylic acid hydrochloride (A59) as a yellow solid. LCMS: calc. for [M+H]$^+$=235.05, found 235.1.

Synthesis of 5-(2-methylpyrimidin-4-yl)thiazole-2-carboxylic acid trifluoroacetate (A60)

Synthesis of tert-butyl 5-acetyl)thiazole-2-carboxylate

Thiazole tert-butyl thiazole-2-carboxylate (1.15 g, 6.21 mmol, synthesis see above) was added to a solution of LDA (1 M in THF/heptane/ethylbenzene, 6.83 mmol, 6.83 mL) in dry THF (10 mL) at −78° C. and the mixture was stirred for 30 min. N-Methoxy-N-methylacetamide (0.96 g, 9.31 mmol) was added and the RM was stirred for 3 h. The RM was quenched by adding a saturated aqueous solution of NH$_4$Cl (10 mL). The mixture was allowed to reach to RT. The aqueous layer was extracted with EtOAC (2×10 ml). The combined organic layer was dried over Na$_2$SO$_4$ and concentrated in vacuo. FC (EtOAc/heptane 0:1→1:4) afforded tert-butyl 5-acetyl)thiazole-2-carboxylate (0.40 g, 1.76 mmol, 28%). LCMS: calc. for [M+H]$^+$=228.06, found 228.1.

Synthesis of tert-butyl 5-(3-(dimethylamino)acryloyl)thiazole-2-carboxylate tert-butyl 5-acetyl)thiazole-2-carboxylate (0.50 g, 2.20 mmol) was dissolved in 1,1-dimethoxy-N,N-dimethylmethanamine (5.24 g, 44.0 mmol, 6.55 mL) and the mixture was warmed up to 70° C. and stirred for 2 h. The reaction was allowed to reach RT and the solvent evaporated to leave tert-butyl 5-(3-(dimethylamino)acryloyl)thiazole-2-carboxylate (0.70 g). LCMS: calc. for [M+H]$^+$=283.10, found 283.2.

Synthesis of tert-butyl 5-(2-methylpyrimidin-4-yl)thiazole-2-carboxylate tert-butyl 5-(3-(dimethylamino)acryloyl)thiazole-2-carboxylate (0.26 g, 0.92 mmol), and K$_2$CO$_3$ (0.260 g, 2.76 mmol) were added to a solution of acetimidamide hydrochloride (0.640 g, 4.60 mmol) in dry DMF (10 mL) and the reaction was heated up to 90° C. and stirred for 2 h. The reaction was cooled to RT and diluted with aqueous saturated NaHCO$_3$ (10 mL) and extracted with EtOAc (3×20 mL). The combined organic layer was dried over Na$_2$SO$_4$ and concentrated in vacuo. FC (EtOAc/heptane 1:1→9:1) afforded tert-butyl 5-(2-methylpyrimidin-4-yl)thiazole-2-carboxylate (0.17 g, 0.65 mmol, 70%). LCMS: calc. for [M+H]$^+$=278.34, found 278.2.

Synthesis of 5-(2-methylpyrimidin-4-yl)thiazole-2-carboxylic acid trifluoroacetate (A60)

TFA (5 mL) was added to a solution of tert-butyl 5-(2-methylpyrimidin-4-yl)thiazole-2-carboxylate (0.18 g, 0.65 mmol) in DCM at −10° C. The RM was allowed to warm to RT and stirred for 3 h. The solvent was evaporated in vacuo to give 5-(2-methylpyrimidin-4-yl)thiazole-2-carboxylic acid trifluoroacetate (A60, 0.22 g, 0.57 mmol, 87%). LCMS: calc. for [M+H]$^+$=222.03, found 222.2.

Synthesis of 3-(5-carboxythiophen-2-yl)pyridine 1-oxide (A61)

To a slurry of 5-(pyridin-3-yl)thiophene-2-carboxylic acid (0.500 g, 2.44 mmol) in DCM (5 mL) at RT was added 3-chlorobenzenecarboperoxoic acid (0.841 g, 4.87 mmol) and the resulting slurry was stirred for 16 h. The mixture was concentrated in vacuo and rinsed with THF (10 mL). The residue was dried to the air yielding 3-(5-carboxythiophen-2-yl)pyridine 1-oxide (A61, 0.562 g, 2.41 mmol, 99%) as a yellow solid. LCMS: calc. for [M+H]$^+$=222.01, found 222.0.

Synthesis of 5-(5-methylpyridazin-4-yl)thiophene-2-carboxylic acid hydrochloride (A62)

Synthesis of 3-bromo-4-methylfuran-2,5-dione

3-Methylfuran-2,5-dione (6.24 g, 55.6 mmol, 5.00 mL) was placed in a closed pressure vial. Under N$_2$AlBr$_3$ (0.178 g, 0.668 mmol) was added, followed by Br$_2$ (8.89 g, 55.6 mmol, 2.87 mL). The mixture was stirred at 120° C. for 16 h. The vial was cooled to 0° C. Solids were removed from the vial and recrystallized from toluene/heptane, washed with heptane and dried in vacuo to obtain 3-bromo-4-methylfuran-2,5-dione (7.80 g, 40.8 mmol, 73%) as a brown crystalline solid. LCMS: calc. for [M+H]$^+$=190.93, fd 191.0.

Synthesis of 4-bromo-5-methylpyridazine-3,6-diol

Hydrazine sulfate (0.681 g, 5.24 mmol) was suspended in water (10 mL). The mixture was heated to 100° C. and at this temperature 3-bromo-4-methylfuran-2,5-dione (1.00 g, 5.24 mmol) was added. The mixture was heated for 16 h at 95° C. (a white precipitate forms). HBr (48% w/w in water, 0.033 g, 0.20 mmol, 0.022 mL) was added and the mixture was heated to 95° C. for 2 h. The mixture was cooled and the precipitate was filtered, washed with water (20 mL) and dried in vacuo to obtain 4-bromo-5-methylpyridazine-3,6-diol (0.960 g, 4.68 mmol, 89%) as a white solid. LCMS: calc. for [M+H]$^+$=204.95, fd 205.0.

Synthesis of tert-butyl 5-(3,6-dihydroxy-5-methylpyridazin-4-yl)thiophene-2-carboxylate (5-(tert-Butoxycarbonyl)thiophen-2-yl)boronic acid (0.763 g, 3.34 mmol) and 4-bromo-5-methylpyridazine-3,6-diol (0.754 g, 3.68 mmol) were dissolved in 1,4-dioxane (28 mL) and water (7 mL). Cs$_2$CO$_3$ (2.18 g, 6.69 mmol) was added. The mixture was degassed with Ar for 5 min. PdCl$_2$(dppf) (0.304 g, 0.334 mmol) was added. The mixture was heated at 110° C. (hot start) for 1.5 h. The mixture was cooled and acidified to pH 5-6 with aqueous 2 M HCl. Solvents were evaporated in vacuo. FC (CH$_2$Cl$_2$/MeOH 1:0→9:1) afforded tert-butyl 5-(3,6-dihydroxy-5-methylpyridazin-4-yl)thiophene-2-carboxylate (0.874 g, 1.98 mmol, 59%, 70% purity). LCMS: calc. for [M+H]$^+$=309.35, fd 309.2.

Synthesis of 5-(3,6-dichloro-5-methylpyridazin-4-yl)thiophene-2-carboxylic acid tert-butyl 5-(3,6-dihydroxy-5-methylpyridazin-4-yl)thiophene-2-carboxylate (0.724 g, 2.348 mmol) was suspended in dry MeCN (25 mL). Tetraethylammonium chloride (1.17 g, 7.04 mmol) was added, followed by phosphorus oxychloride (1.58 g, 10.3 mmol, 0.963 mL). The mixture was stirred at reflux for 2 h. Solvents were evaporated in vacuo. The residue was stripped with DCM. FC (EtOAc/heptane 1:9→1:0) afforded 5-(3,6-dichloro-5-methylpyridazin-4-yl)

thiophene-2-carboxylic acid (0.355 g, 1.23 mmol, 52%) as a white solid. LCMS: calc. for [M+H]⁺=288.95, fd 289.0.

Synthesis of methyl 5-(5-methylpyridazin-4-yl)thiophene-2-carboxylate 5-(3,6-dichloro-5-methylpyridazin-4-yl)thiophene-2-carboxylic acid (0.324 g, 1.12 mmol) was dissolved in MeOH (20 mL). Palladium/carbon (0.162 g, 0.152 mmol, 10% w/w) was added, followed by NEt₃ (0.340 g, 3.36 mmol, 0.469 mL). The mixture was brought under H₂ and was stirred at RT for 1 h. The mixture was filtered over Celite and flushed with MeOH (80 mL). Solvents were evaporated in vacuo. The residue was diluted with DCM (50 mL) and half saturated NaHCO₃ (50 mL). The water layer was extracted with DCM (2×50 mL). The organic layer was dried over Na₂SO₄ and concentrated in vacuo. FC (EtOAc/heptane 1:9→1:0) afforded methyl 5-(5-methylpyridazin-4-yl)thiophene-2-carboxylate (0.175 g, 0.747 mmol, 67%) as a yellowish solid. LCMS: calc. for [M+H]⁺=235.27, fd 235.2.

Synthesis of 5-(5-methylpyridazin-4-yl)thiophene-2-carboxylic acid hydrochloride (A62)

LiOH.H₂O (0.125 g, 2.99 mmol) was added to a suspension of methyl 5-(5-methylpyridazin-4-yl)thiophene-2-carboxylate (0.175 g, 0.747 mmol) in THF (5 mL) and water (5 mL). The mixture was stirred at RT for 2 h. The mixture was concentrated in vacuo. The residue was acidified to pH 2-3 using aqueous 2M HCl. To this i-PrOH (15 mL) was added. Solvents were evaporated in vacuo. The solid was stripped with toluene (2×) and DIPE (2×), and dried in vacuo to obtain 5-(5-methylpyridazin-4-yl)thiophene-2-carboxylic acid hydrochloride (A62) as a yellow solid as its HCl salt. LCMS: calc. for [M+H]⁺=221.03, fd 221.2

Synthesis of Final Compounds

Final compound can be obtained by coupling the biaryl acids A with amine INT-1, which can be obtained in analogy to its cyclopentyl derivative as described in WO2008007127, p. 104f. This yields the alcohols INT-A that are oxidized to give final compounds B (Scheme 2).

Scheme 2: Synthesis of final compounds

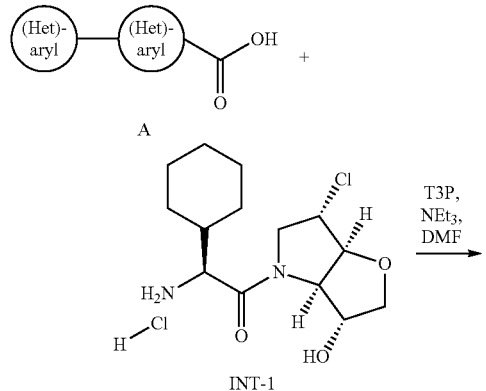

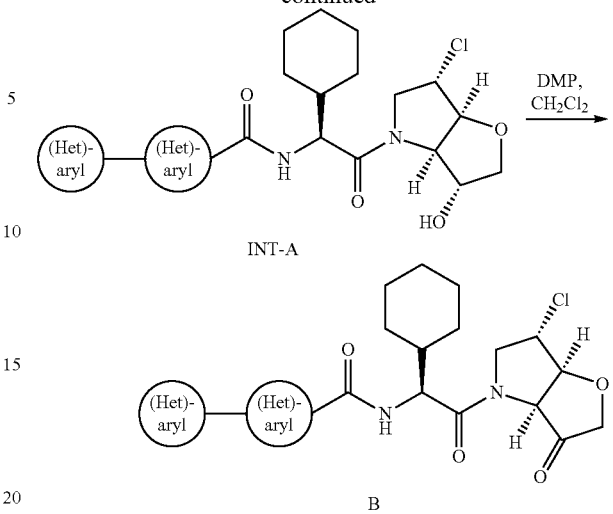

Synthesis of N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide

Example 41

Synthesis of N-((S)-2-((3R,3aR,6S,6aS)-6-chloro-3-hydroxytetrahydro-2H-furo[3,2-b]pyrrol-4(5H)-yl)-1-cyclohexyl-2-oxoethyl)-5-(2-methylpyrimidin-5-yl)thiazole-2-carboxamide A suspension of 5-(2-methylpyrimidin-5-yl)thiazole-2-carboxylic acid trifluoroacetate (A1), (S)-2-amino-1-((3R,3aR,6S,6aS)-6-chloro-3-hydroxytetrahydro-2H-furo[3,2-b]pyrrol-4(5H)-yl)-2-cyclohexylethanone hydrochloride (1, 0.130 g, 0.382 mmol), NEt₃ (0.532 mL, 3.82 mmol) and propylphosphonic anhydride (50% in DMF, 0.295 mL, 0.496 mmol) in DMF (5 mL) was stirred at RT for 2 days. The mixture was diluted with saturated aqueous NaHCO₃ (20 mL) and extracted with EtOAc (2×20 mL). The combined organic layer was washed with water (20 mL) and brine (20 mL), dried on Na₂SO₄ and concentrated under reduced pressure. FC (EtOAc/heptane 2:3→1:0) afforded N-((S)-2-((3R,3aR,6S,6aS)-6-chloro-3-hydroxytetrahydro-2H-furo[3,2-b]pyrrol-4(5H)-yl)-1-cyclohexyl-2-oxoethyl)-5-(2-methylpyrimidin-5-yl)thiazole-2-carboxamide (0.110 g, 0.217 mmol, 39% yield over 2 steps) as a white solid. LCMS: calc. for [M+H]⁺=506.16, found 506.2.

Synthesis of N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide

Example 41

DMP (0.184 g, 0.435 mmol) was added to a solution of N-((S)-2-((3R,3aR,6S,6aS)-6-chloro-3-hydroxytetrahydro-2H-furo[3,2-b]pyrrol-4(5H)-yl)-1-cyclohexyl-2-oxoethyl)-5-(2-methylpyrimidin-5-yl)thiazole-2-carboxamide (0.110 g, 0.217 mmol) in DCM (5 mL). The mixture was stirred at RT for 1 h. An aqueous solution of Na₂S₂O₄ (10%, 5 mL) was added and the mixture was stirred vigorously for 30 min. An aqueous saturated solution of NaHCO$_3$ (10 mL) and DCM (15 mL) were added. The layers were separated over a phase separation filter. The organic layer was concentrated in vacuo. Purification by basic preparative HPLC (C18, MeCN (1% 10 mM NH$_4$HCO$_3$), 10 mM NH$_4$HCO$_3$ in H$_2$O) and lyophilisation (MeCN/H2O) afforded N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide (Example 41, 0.070 g, 0.14 mmol, 64%) as a white solid. LCMS: calc. for [M+H]$^+$=504.14, found 504.2. $^1$H-NMR (400 MHz, DMSO-d$_6$) as a mixture of hydrates and rotamers δ=9.19-9.04 (m, 2H), 8.67 (d, 0.15H), 8.61-8.57 (m, 1H), 8.56 (d, 0.20H), 8.20 (d, 0.58H), 7.92 (d, 0.07H), 6.66 (s, 0.5H), 6.49 (s, 0.5H), 6.45 (s, 0.2H), 5.84 (s, 0.2H), 5.25-3.40 (m, 8H), 2.68 (s, 3H), 2.00-1.48 (m, 6H), 1.32-0.77 (m, 5H) ppm.

The following final compounds (table 1) were synthesized as described for Example 41.

TABLE 1

| Nr | Chemical Structure | Chemical name |
|---|---|---|
| 30 | 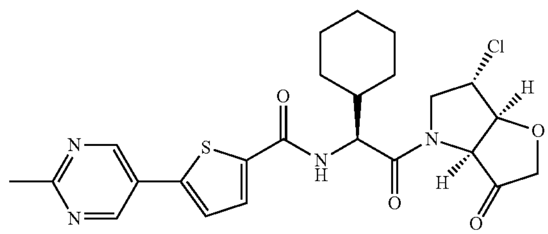 [SMILES: Cc1ncc(-c2ccc(C(=O)N[C@H](C(=O)N3C[C@H](Cl)[C@H]4OCC(=O)[C@H]43)C3CCCCC3)s2)cn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiophene-2-carboxamide |
| 31 | 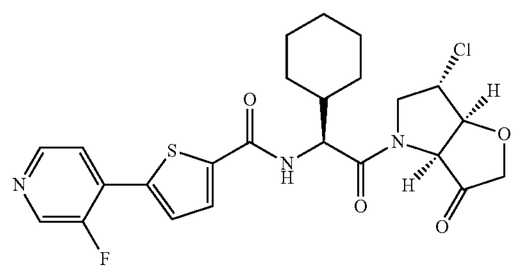 [SMILES: O=C(N[C@H](C(=O)N1C[C@H](Cl)[C@H]2OCC(=O)[C@H]21)C1CCCCC1)c1ccc(-c2ccncc2F)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiophene-2-carboxamide |
| 32 | 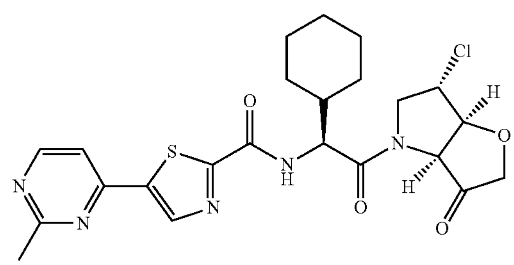 [SMILES: Cc1nccc(-c2cnc(C(=O)N[C@H](C(=O)N3C[C@H](Cl)[C@H]4OCC(=O)[C@H]43)C3CCCCC3)s2)n1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiazole-2-carboxamide |
| 33 | 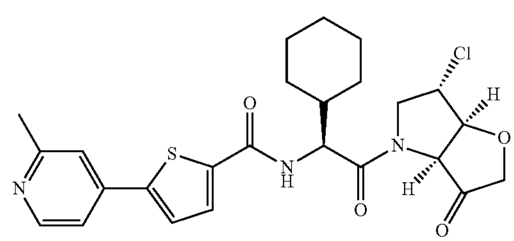 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-4-yl)thiophene-2-carboxamide |
| 34 | 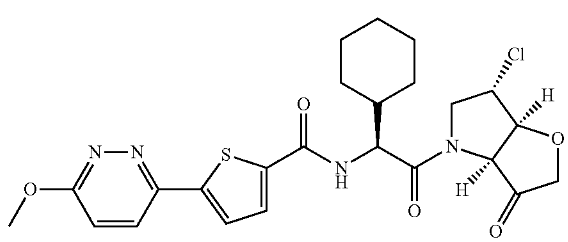 [SMILES: COc1ccc(-c2ccc(C(=O)N[C@H](C(=O)N3C[C@H](Cl)[C@H]4OCC(=O)[C@H]43)C3CCCCC3)s2)nn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-3-yl)thiophene-2-carboxamide |

TABLE 1-continued

| Nr | Chemical Structure | Chemical name |
|---|---|---|
| 35 | 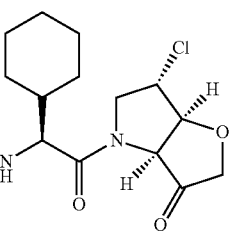 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-3-yl)thiophene-2-carboxamide |
| 36 | 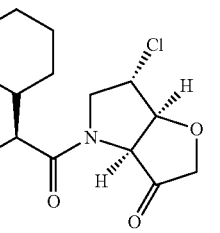 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyrimidin-4-yl)thiophene-2-carboxamide |
| 37 | 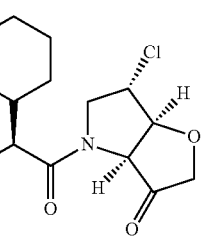 | N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-6-(pyrimidin-5-yl)thiophene-2-carboxamide |
| 38 | 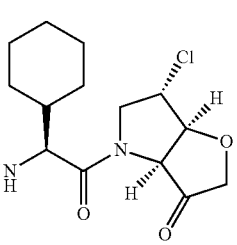 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-fluoropyridazin-3-yl)thiophene-2-carboxamide |
| 39 | 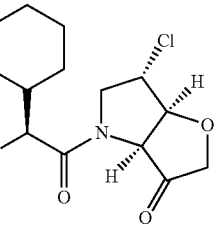 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiophene-2-carboxamide |
| 40 | 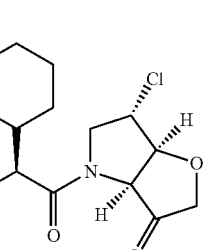 | N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-4-yl)thiophene-2-carboxamide |

TABLE 1-continued

| Nr | Chemical Structure | Chemical name |
|---|---|---|
| 41 | 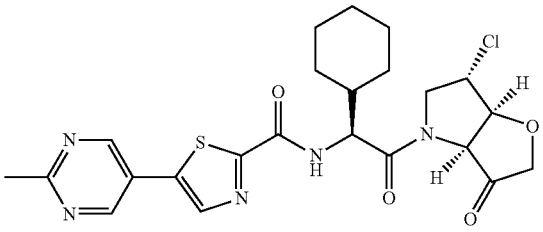 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide |
| 42 | 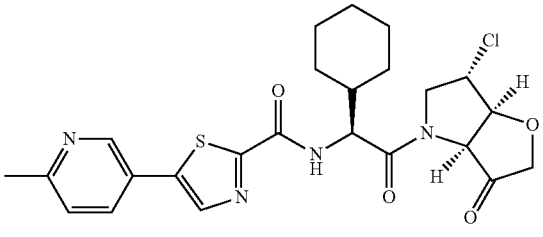 [SMILES: Cc1ccc(-c2cnc(C(=O)N[C@H](C(=O)N3C[C@H](Cl)[C@H]4OCC(=O)[C@H]43)C3CCCCC3)s2)cn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridin-3-yl)thiazole-2-carboxamide |
| 43 | 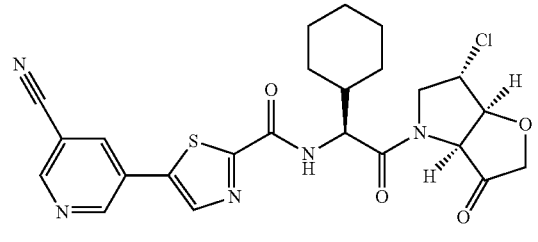 [SMILES: N#Cc1cncc(-c2cnc(C(=O)N[C@H](C(=O)N3C[C@H](Cl)[C@H]4OCC(=O)[C@H]43)C3CCCCC3)s2)c1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiazole-2-carboxamide |
| 44 | 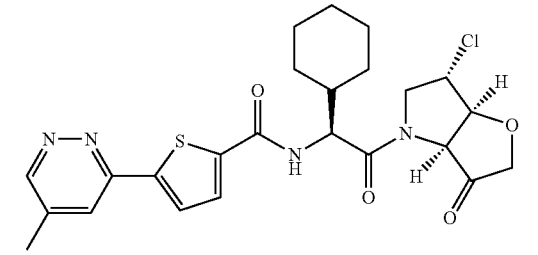 [SMILES: Cc1cnnc(-c2ccc(C(=O)N[C@H](C(=O)N3C[C@H](Cl)[C@H]4OCC(=O)[C@H]43)C3CCCCC3)s2)c1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-3-yl)thiophene-2-carboxamide |
| 45 | 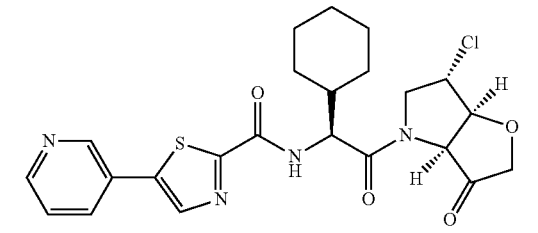 [SMILES: O=C(N[C@H](C(=O)N1C[C@H](Cl)[C@H]2OCC(=O)[C@H]21)C1CCCCC1)c1ncc(-c2cccnc2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)thiazole-2-carboxamide |
| 46 | 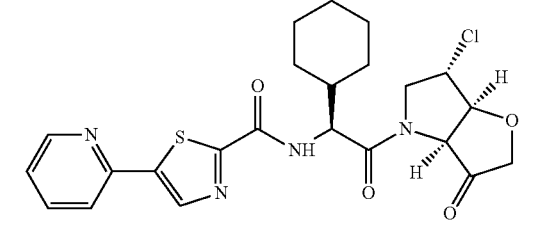 [SMILES: O=C(N[C@H](C(=O)N1C[C@H](Cl)[C@H]2OCC(=O)[C@H]21)C1CCCCC1)c1ncc(-c2ccccn2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiazole-2-carboxamide |

| Nr | Chemical Structure | Chemical name |
|----|-------------------|---------------|
| 47 | 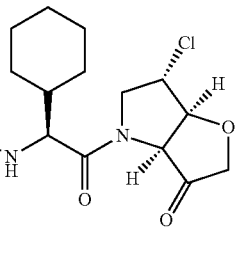 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyridin-3-yl)thiazole-2-carboxamide |
| 48 | 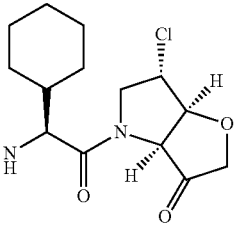 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)thiazole-2-carboxamide |
| 49 | 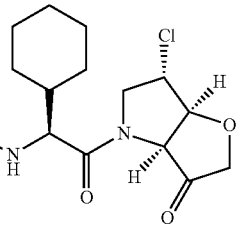 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)thiazole-2-carboxamide |
| 50 | 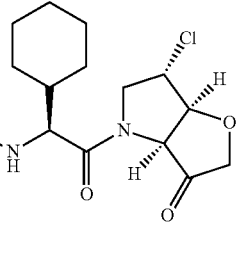 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiazole-2-carboxamide |
| 51 | 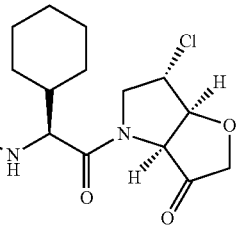 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-4-yl)thiazole-2-carboxamide |
| 52 | 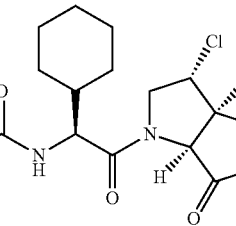 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-chloropyridin-3-yl)thiazole-2-carboxamide |

TABLE 1-continued

| Nr | Chemical Structure | Chemical name |
|---|---|---|
| 53 | 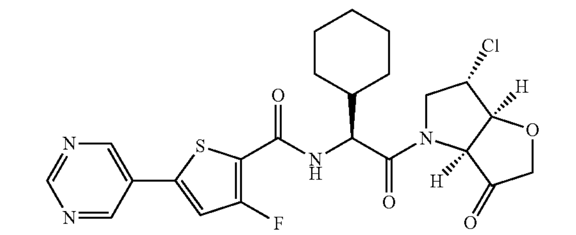 [SMILES: O=C(N[C@H](C(=O)N1C[C@H](Cl)[C@H]2OCC(=O)[C@H]21)C1CCCCC1)c1sc(-c2cncnc2)cc1F] | N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyrimidin-5-yl)thiophene-2-carboxamide |
| 54 | 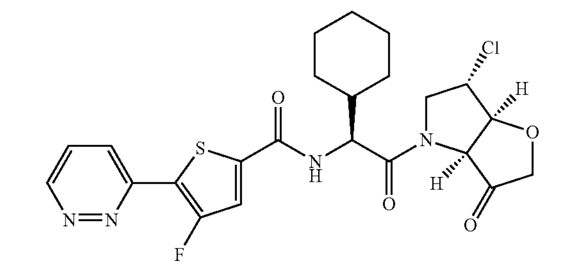 [SMILES: O=C(N[C@H](C(=O)N1C[C@H](Cl)[C@H]2OCC(=O)[C@H]21)C1CCCCC1)c1cc(F)c(-c2cccnn2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-3-yl)thiophene-2-carboxamide |
| 55 | 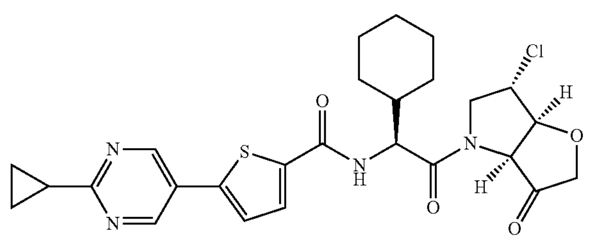 [SMILES: O=C(N[C@H](C(=O)N1C[C@H](Cl)[C@H]2OCC(=O)[C@H]21)C1CCCCC1)c1ccc(-c2cnc(C3CC3)nc2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiophene-2-carboxamide |
| 56 | 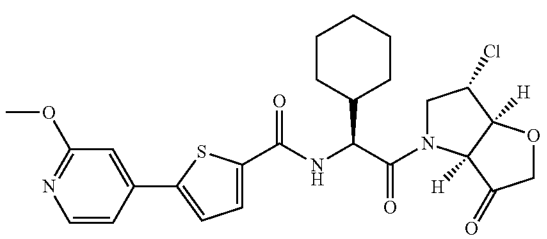 [SMILES: COc1cc(-c2ccc(C(=O)N[C@H](C(=O)N3C[C@H](Cl)[C@H]4OCC(=O)[C@H]43)C3CCCCC3)s2)ccn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methoxypyridin-4-yl)thiophene-2-carboxamide |
| 57 | 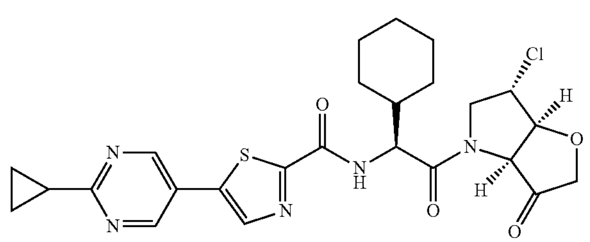 [SMILES: O=C(N[C@H](C(=O)N1C[C@H](Cl)[C@H]2OCC(=O)[C@H]21)C1CCCCC1)c1ncc(-c2cnc(C3CC3)nc2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiazole-2-carboxamide |
| 58 | 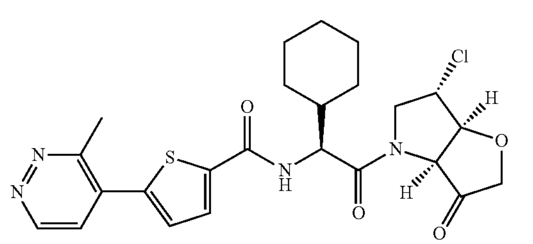 [SMILES: Cc1nnccc1-c1ccc(C(=O)N[C@H](C(=O)N2C[C@H](Cl)[C@H]3OCC(=O)[C@H]32)C2CCCCC2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-methylpyridazin-4-yl)thiophene-2-carboxamide |

TABLE 1-continued

| Nr | Chemical Structure | Chemical name |
|---|---|---|
| 59 | 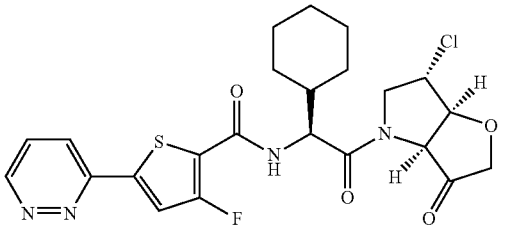 | N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-3-yl)thiophene-2-carboxamide |
| 60 | 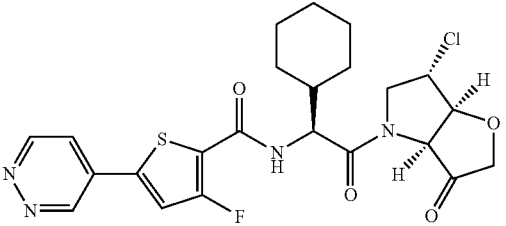 [SMILES: O=C(N[C@H](C(=O)N1C[C@H](Cl)[C@H]2OCC(=O)[C@H]21)C1CCCCC1)c1sc(-c2ccnnc2)cc1F] | N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-4-yl)thiophene-2-carboxamide |
| 61 | 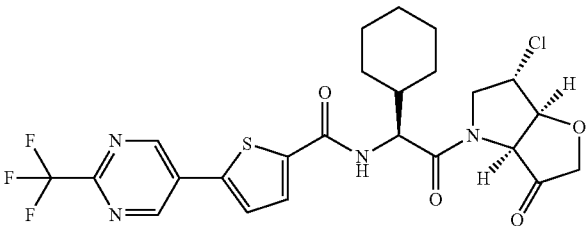 [SMILES: O=C(N[C@H](C(=O)N1C[C@H](Cl)[C@H]2OCC(=O)[C@H]21)C1CCCCC1)c1ccc(-c2cnc(C(F)(F)F)nc2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiophene-2-carboxamide |
| 62 | 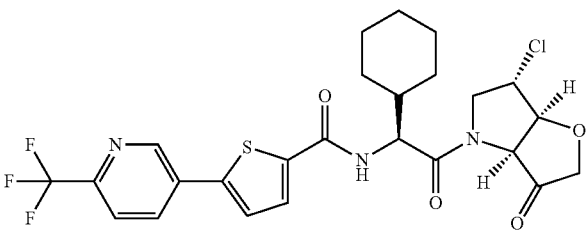 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiophene-2-carboxamide |
| 63 | 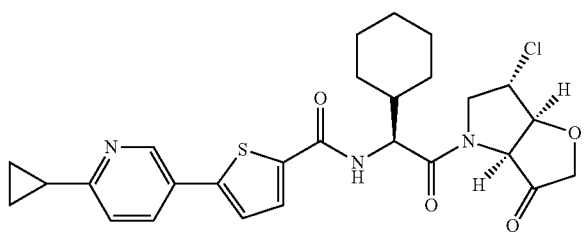 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiophene-2-carboxamide |
| 64 | 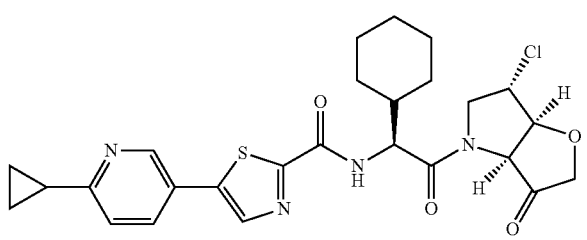 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiazole-2-carboxamide |

TABLE 1-continued

| Nr | Chemical Structure | Chemical name |
|----|---|---|
| 65 | 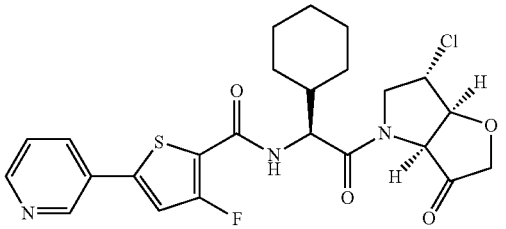 [SMILES: O=C(N[C@H](C(=O)N1C[C@H](Cl)[C@H]2OCC(=O)[C@H]21)C1CCCCC1)c1sc(-c2cccnc2)cc1F] | N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridin-3-yl)thiophene-2-carboxamide |
| 66 | 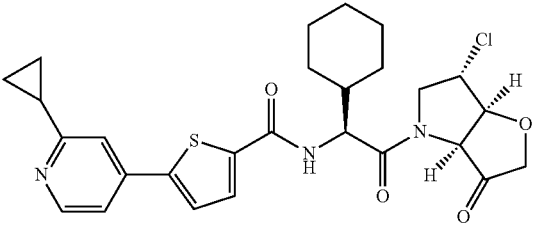 [SMILES: O=C(N[C@H](C(=O)N1C[C@H](Cl)[C@H]2OCC(=O)[C@H]21)C1CCCCC1)c1ccc(-c2ccnc(C3CC3)c2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiophene-2-carboxamide |
| 67 | 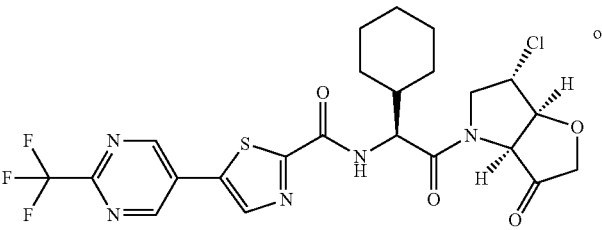 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiazole-2-carboxamide |
| 68 | 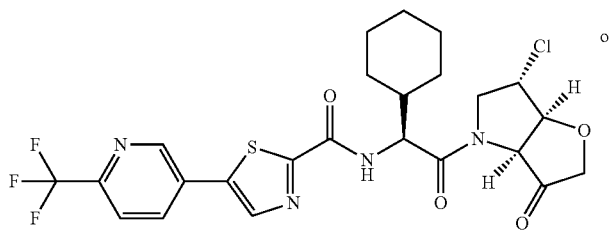 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiazole-2-carboxamide |
| 69 | 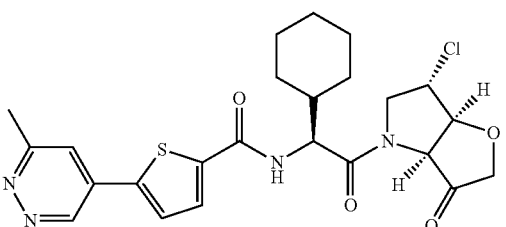 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiophene-2-carboxamide |
| 70 | 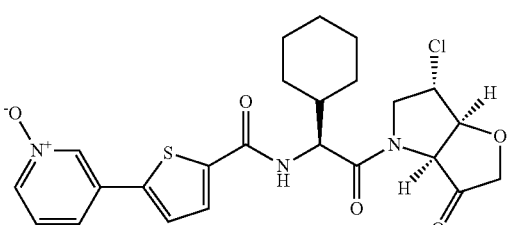 | 3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridine 1-oxide |

TABLE 1-continued

| Nr | Chemical Structure | Chemical name |
|---|---|---|
| 71 | 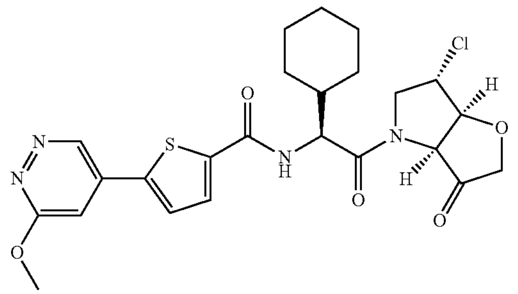 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-4-yl)thiophene-2-carboxamide |
| 72 | 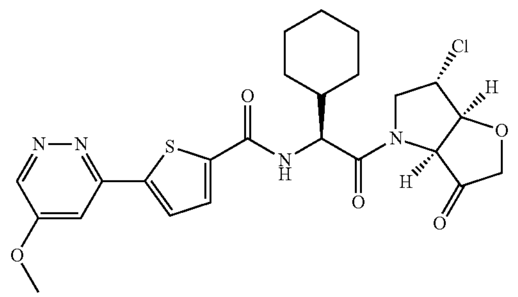 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methoxypyridazin-3-yl)thiophene-2-carboxamide |
| 73 | 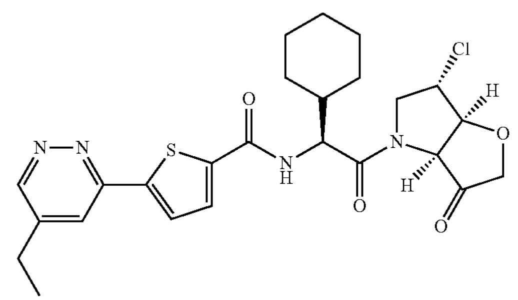 [SMILES: CCc1cnnc(-c2ccc(C(=O)N[C@H](C(=O)N3C[C@H](Cl)[C@H]4OCC(=O)[C@H]43)C3CCCCC3)s2)c1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-ethylpyridazin-3-yl)thiophene-2-carboxamide |
| 74 | 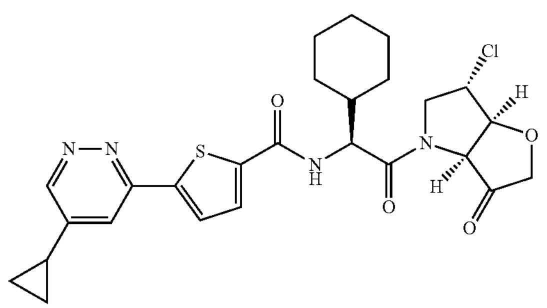 [SMILES: O=C(N[C@H](C(=O)N1C[C@H](Cl)[C@H]2OCC(=O)[C@H]21)C1CCCCC1)c1ccc(-c2cc(C3CC3)cnn2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyclopropylpyridazin-3-yl)thiophene-2-carboxamide |
| 75 | 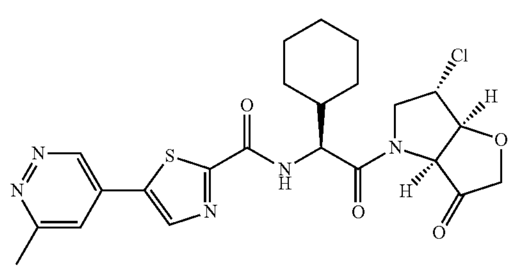 [SMILES: Cc1cc(-c2cnc(C(=O)N[C@H](C(=O)N3C[C@H](Cl)[C@H]4OCC(=O)[C@H]43)C3CCCCC3)s2)cnn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiazole-2-carboxamide |

TABLE 1-continued

| Nr | Chemical Structure | Chemical name |
|---|---|---|
| 76 | 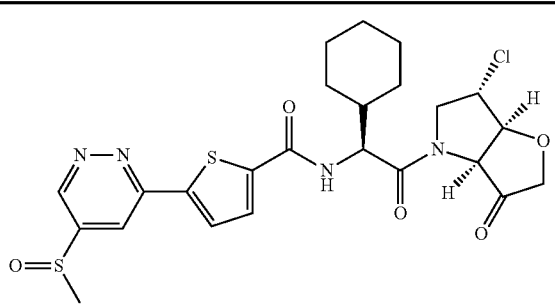 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfinyl)pyridazin-3-yl)thiophene-2-carboxamide |
| 77 | 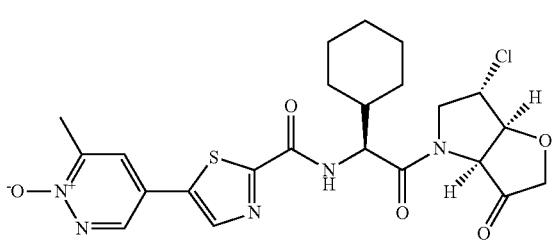 | 4-(2-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiazol-5-yl)-6-methylpyridazine 1-oxide |
| 78 | 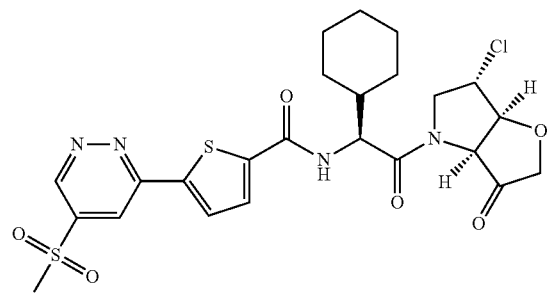 [SMILES: CS(=O)(=O)c1cnnc(-c2ccc(C(=O)N[C@H](C(=O)N3C[C@H](Cl)[C@H]4OCC(=O)[C@H]43)C3CCCCC3)s2)c1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfonyl)pyridazin-3-yl)thiophene-2-carboxamide |
| 79 | 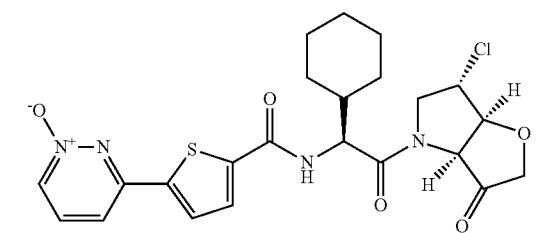 | 3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridazine 1-oxide |
| 80 | 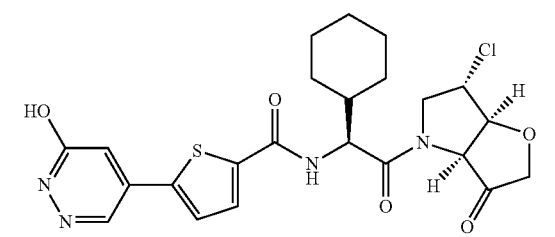 [SMILES: O=C(N[C@H](C(=O)N1C[C@H](Cl)[C@H]2OCC(=O)[C@H]21)C1CCCCC1)c1ccc(-c2cnnc(O)c2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-hydroxypyridazin-4-yl)thiophene-2-carboxamide |
| 81 | 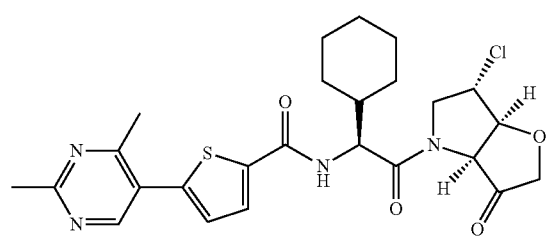 [SMILES: Cc1ncc(-c2ccc(C(=O)N[C@H](C(=O)N3C[C@H](Cl)[C@H]4OCC(=O)[C@H]43)C3CCCCC3)s2)c(C)n1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,4-dimethylpyrimidin-5-yl)thiophene-2-carboxamide |

| Nr | Chemical Structure | Chemical name |
|----|---|---|
| 82 | 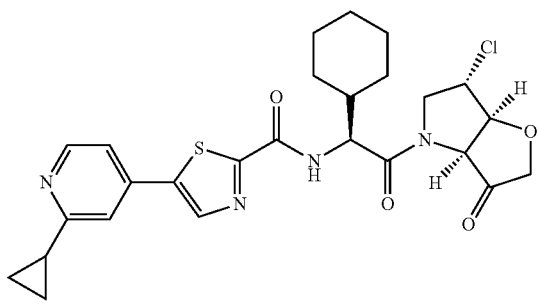 [SMILES: O=C(N[C@H](C(=O)N1C[C@H](Cl)[C@H]2OCC(=O)[C@H]21)C1CCCCC1)c1ncc(-c2ccnc(C3CC3)c2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiazole-2-carboxamide |
| 83 | 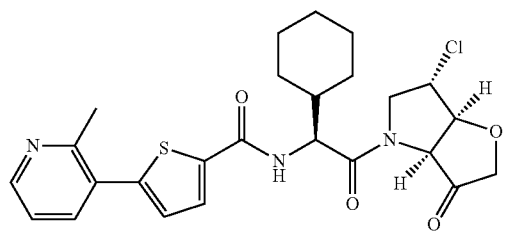 [SMILES: Cc1ncccc1-c1ccc(C(=O)N[C@H](C(=O)N2C[C@H](Cl)[C@H]3OCC(=O)[C@H]32)C2CCCCC2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-3-yl)thiophene-2-carboxamide |
| 84 | 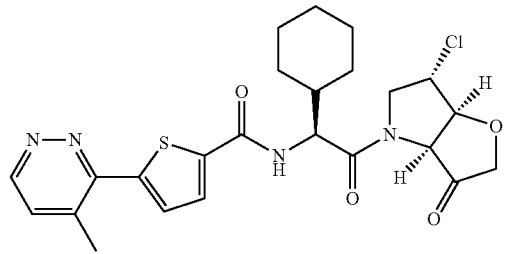 [SMILES: Cc1ccnnc1-c1ccc(C(=O)N[C@H](C(=O)N2C[C@H](Cl)[C@H]3OCC(=O)[C@H]32)C2CCCCC2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(4-methylpyridazin-3-yl)thiophene-2-carboxamide |
| 85 | 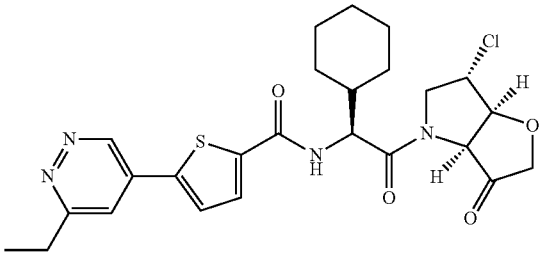 [SMILES: CCc1cc(-c2ccc(C(=O)N[C@H](C(=O)N3C[C@H](Cl)[C@H]4OCC(=O)[C@H]43)C3CCCCC3)s2)cnn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-ethylpyridazin-4-yl)thiophene-2-carboxamide |
| 86 | 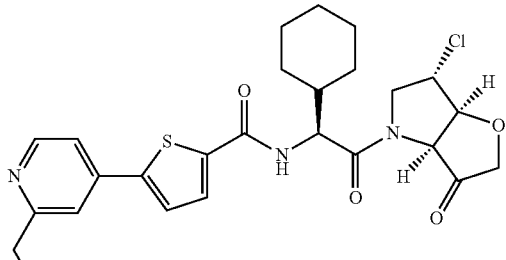 | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiophene-2-carboxamide |

TABLE 1-continued

| Nr | Chemical Structure | Chemical name |
|----|---|---|
| 87 | 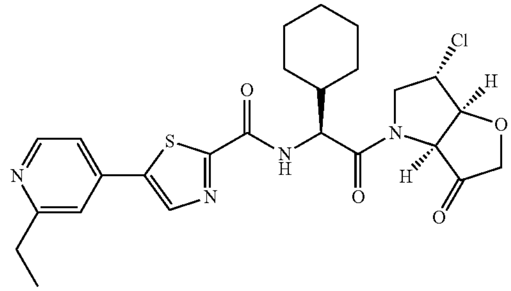 [SMILES: CCc1cc(-c2cnc(C(=O)N[C@H](C(=O)N3C[C@H](Cl)[C@H]4OCC(=O)[C@H]43)C3CCCCC3)s2)ccn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiazole-2-carboxamide |
| 88 | 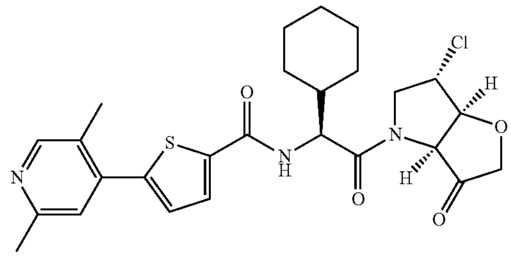 [SMILES: Cc1cc(-c2ccc(C(=O)N[C@H](C(=O)N3C[C@H](Cl)[C@H]4OCC(=O)[C@H]43)C3CCCCC3)s2)c(C)cn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,5-dimethylpyridin-4-yl)thiophene-2-carboxamide |
| 89 | 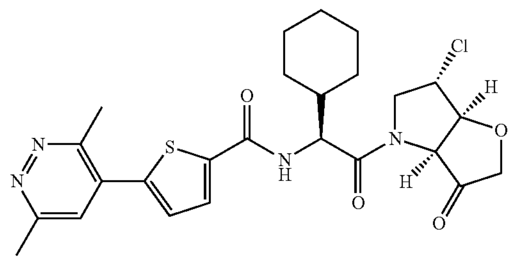 [SMILES: Cc1cc(-c2ccc(C(=O)N[C@H](C(=O)N3C[C@H](Cl)[C@H]4OCC(=O)[C@H]43)C3CCCCC3)s2)c(C)nn1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3,6-dimethylpyridazin-4-yl)thiophene-2-carboxamide |
| 90 | 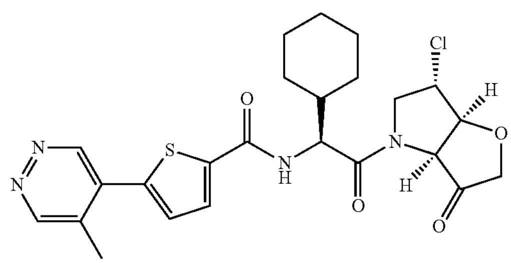 [SMILES: Cc1cnncc1-c1ccc(C(=O)N[C@H](C(=O)N2C[C@H](Cl)[C@H]3OCC(=O)[C@H]32)C2CCCCC2)s1] | N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-4-yl)thiophene-2-carboxamide |

The compounds were prepared according to the procedure for Example 13 using the appropriate biaryl acid A (Table 2).

| Nr | Purification | Yield [%] | Acid | $^1$H NMR (400 MHz, DMSO-$d_6$) as a mixture of hydrates and rotamers | LCMS [M + H]$^+$ cal/fd |
|----|---|---|---|---|---|
| 30 | FC, EtOAc(1%Et$_3$N)/ heptane 0:1 → 1:0 | 59 | A8 | 9.31-8.69 (m, 3H), 8.23-7.97 (m, 1H), 7.84-7.63 (m, 1H), 6.72 (s, 0.55H), 6.45 (s, 0.31H), 6.31 (s, 0.55H), 5.82 (s, 0.31H), 4.94-3.40 (m, 8H), 2.73-2.56 (m, 3H), 2.03-1.43 (m, 6H), 1.36-0.75 (m, 5H) | 503.1 503.2 |
| 31 | (EtOAc(1%Et$_3$N)/ heptane 0:1 → 1:0) | 66 | A9 | 9.18-8.84 (m, 1H), 8.79-8.63 (m, 1H), 8.57-8.41 (m, 1H), 8.25-8.02 (m, 1H), 8.02-7.78 (m, 2H), 6.72 (s, 0.46H), 6.46 (s, 0.27H), 6.30 (s, 0.46H), 5.82 (s, 0.27H), 5.12-3.41 (m, 8H), 2.02-1.46 (m, 6H), 1.36-0.79 (m, 5H) | 506.1 506.1 |

-continued

| Nr | Purification | Yield [%] | Acid | $^1$H NMR (400 MHz, DMSO-$d_6$) as a mixture of hydrates and rotamers | LCMS [M + H]$^+$ cal/fd |
|---|---|---|---|---|---|
| 32 | basic preparative HPLC (C18, MeCN (1% 10 mM NH$_4$HCO$_3$), 10 mM NH$_4$HCO$_3$ in H$_2$O) | 53 | A60 | 9.04-8.89 (m, 1H), 8.87-8.78 (m, 1H), 8.75-8.53 (m, 0.4H), 8.35-7.91 (m, 1.6H), 6.69 (s, 0.39H), 6.46 (s, 0.39H), 6.44 (s, 0.13H), 5.83 (s, 0.13H), 5.25-3.38 (m, 8H), 2.05-1.47 (m, 6H), 1.34-0.84 (m, 5H) | 504.1 504.2 |
| 33 | (EtOAc(1%Et$_3$N)/ heptane 0:1 → 1:0) | 69 | A10 | 9.08-8.77 (m, 1H), 8.60-8.42 (m, 1H), 8.28-7.92 (m, 1H), 7.89-7.73 (m, 1H), 7.68-7.44 (m, 2H), 6.73 (s, 0.28H), 6.46 (s, 0.16H), 6.32 (s, 0.28H), 5.83 (s, 0.16H), 5.15-3.39 (m, 8H), 2.58-2.44 (m, 3H), 2.05-1.46 (m, 6H), 1.37-0.75 (m, 5H) | 502.1 502.2 |
| 34 | Crystallization from EtOAc and heptane | 44 | A35 | 9.03-8.91 (m, 0.40H), 8.87-8.75 (m, 0.60H), 8.30-8.17 (m, 1H), 8.17-8.07 (m, 0.40H), 8.05-7.96 (m, 0.60H), 7.90-7.84 (m, 0.40H), 7.84-7.77 (m, 0.60H), 7.41-7.30 (m, 1H), 6.76 (s, 0.30H), 6.47 (s, 0.15H), 6.38 (s, 0.30H), 5.83 (s, 0.15H), 5.18-3.44 (m, 11H), 2.01-1.49 (m, 6H), 1.27-0.85 (m, 5H) | 503.14 503.1 |
| 35 | Crystallization from EtOAc | 56 | A36 | 9.03-8.93 (m, 0.5H), 8.90-8.79 (m, 0.5H), 8.23-8.12 (m, 1.5H), 8.05-7.98 (m, 0.5H), 7.95-7.85 (m, 1H), 7.71-7.63 (m, 1H), 6.76 (s, 0.40H), 6.47 (s, 0.21H), 6.37 (s, 0.40H), 5.83 (s, 0.21H), 5.13-3.42 (m, 8H), 2.72-2.58 (m, 3H), 2.03-1.50 (m, 6H), 1.26-0.91 (m, 5H) | 503.14 503.1 |
| 36 | Crystallization from EtOAc and heptane | 23 | A37 | 9.20-9.09 (m, 0.45H), 9.09-8.96 (m, 2.50H), 8.44-8.37 (m, 0.05H), 8.26-8.19 (m, 0.40H), 8.14-8.07 (m, 0.60H), 8.02-7.91 (m, 1H), 6.91-6.14 (m, 0.80H), 5.97-5.69 (m, 0.12H), 5.17-3.42 (m, 8H), 2.05-1.48 (m, 6H), 1.27-0.89 (m, 5H) | 507.12 507.2 |
| 37 | basic preparative HPLC (C18, MeCN (1% 10 mM NH$_4$HCO$_3$), | 39 | A23 | 9.24-9.15 (m, 1H), 9.15-9.05 (m, 2H), 9.05-8.95 (m, 0.9H), 8.50-8.44 (m, 0.1H), 8.25 (s, 0.2H), 8.20 (s, 0.1H), 8.11 (s, 0.7H), 6.69 (s, 0.15H), 6.47 (s, 0.09H), 6.22 (s, 0.15H), 5.83 (s, 0.09H), 5.11-3.39 (m, 8H), 2.03-1.38 (m, 6H), 1.35-0.74 (m, 5H) | 507.12 507.2 |
| 38 | acidic preparative HPLC (C18, MeCN (0.1% formic acid in water), 0.1% formic acid in water). | 49 | A38 | 9.04-8.82 (m, 1H), 8.61-8.46 (m, 1H), 8.28-8.23 (m, 0.07H), 8.20-8.13 (m, 0.38H), 8.10-7.90 (m, 1.55H), 7.90-7.78 (m, 1H), 6.77 (s, 0.36H), 6.50 (s, 0.20H), 6.36 (s, 0.36H), 5.86 (s, 0.20H), 5.12-3.44 (m, 8H), 2.03-1.47 (m, 6H), 1.30-0.82 (m, 5H) | 507.12 507.2 |
| 39 | basic preparative HPLC (C18, MeCN (1% 10 mM NH$_4$HCO$_3$), 10 mM NH$_4$HCO$_3$ in H$_2$O) | 34 | A11 | 9.36-9.06 (m, 1H), 9.01-8.94 (m, 1H), 8.92-8.16 (m, 1H), 8.08-7.99 (m, 1H), 7.83-7.74 (m, 1H), 6.36 (s, 0.01H), 6.21 (s, 0.06H), 5.66 (s, 0.01H), 5.45 (s, 0.06H), 5.25-3.39 (m, 8H), 2.11-1.45 (m, 6H), 1.06 (m,5H) | 513.14 513.2 |
| 40 | Recrystallization (DCM/heptane) | 75 | A24 | 9.60-9.45 (m, 1H), 9.39-9.25 (m, 1H), 9.21-8.51 (m, 1H), 8.31-8.05 (m, 1H), 8.00-7.81 (m, 1H), 6.68 (s, 0.11H), 6.47 (s, 0.07H), 6.21 (s, 0.11H), 5.84 (s, 0.07H), 5.20-3.43 (m, 8H), 2.03-1.40 (m, 6H), 1.34-0.71 (m, 5H) | 507.12 507.2 |
| 41 | basic preparative HPLC (C18, MeCN (1% 10 mM NH$_4$HCO$_3$) | 64 | A1 | 9.19-9.04 (m, 2H), 8.67 (d, J = 8.9 Hz, 0.15H), 8.61-8.57 (m, 1H), 8.56 (d, J = 8.9 Hz, 0.20H), 8.20 (d, J = 8.5 Hz, 0.58H), 7.92 (d, J = 8.9 Hz, 0.07H), 6.66 (s, 0.5H), 6.49 (s, 0.5H), 6.45 (s, 0.2H), 5.84 (s, 0.2H), 5.25-3.40 (m, 8H), 2.68 (s, 3H), 2.00-1.48 (m, 6H), 1.32-0.77 (m, 5H | 504.14 504.2 |
| 42 | basic preparative HPLC (C18, MeCN (1% 10 mM NH$_4$HCO$_3$), 10 mM NH$_4$HCO$_3$ in H$_2$O) | 49 | A2 | 8.92-8.82 (m, 1H), 8.65-8.42 (m, 1.5H), 8.23-7.85 (m, 1.5H), 7.45-7.33 (m, 1H), 6.67 (s, 0.23H), 6.50 (s, 0.23H), 6.46 (s, 0.09H), 5.85 (s, 0.09H), 5.43-3.39 (m, 8H), 2.51 (s, 3H), 2.01-1.53 (m, 6H), 1.34-0.88 (m, 5H) | 503.14 503.2 |
| 43 | basic preparative HPLC (C18, MeCN (1% 10 mM | 31 | A3 | 9.34-9.16 (m, 1H), 9.13-8.99 (m, 1H), 8.96-8.46 (m, 2.4H), 8.04-7.89 (m, 0.3H), 7.89-7.71 (m, 0.3H), 6.56 (s, 0.13H), 6.41 | 514.1 514.2 |

-continued

| Nr | Purification | Yield [%] | Acid | $^1$H NMR (400 MHz, DMSO-$d_6$) as a mixture of hydrates and rotamers | LCMS [M + H]$^+$ cal/fd |
|---|---|---|---|---|---|
| | NH$_4$HCO$_3$), 10 mM NH$_4$HCO$_3$ in H$_2$O) | | | (s, 0.07H), 6.18 (s, 0.03H), 5.91-3.46 (m, 8H), 2.07-1.50 (m, 6H), 1.50-0.75 (m, 5H) | |
| 44 | FC, EtOAc(1%Et$_3$N)/ heptane(1%Et$_3$N) 1:1 → 1:0 | 59 | A39 | 9.05 (m, 1H), 9.01-8.14 (m, 1H), 8.19-8.00 (m, 2H), 7.97-7.87 (m, 1H), 6.76 (s, 0.22H), 6.46 (s, 0.12H), 6.37 (s, 0.22H), 5.83 (s, 0.12H), 5.17-3.43 (m, 8H), 2.38 (s, 3H), 2.05-1.48 (m, 6H), 1.29-0.74 (m, 5H) | 503.1 503.1 |
| 45 | — | 83 | A17 | 9.13-8.91 (m, 1H), 8.71-8.44 (m, 2.36H), 8.31-7.85 (m, 1.64H), 7.64-7.44 (m, 1H), 6.66 (s, 0.49H), 6.49 (s, 0.49H), 6.45 (s, 0.20H), 5.84 (s, 0.20H), 5.24-3.42 (m, 8H), 2.05-1.47 (m, 6H), 1.34-0.78 (m, 5H | 489.1 489.2 |
| 46 | basic preparative HPLC (C18, MeCN (1% 10 mM NH$_4$HCO$_3$), 10 mM NH$_4$HCO$_3$ in H$_2$O) | 50 | A18 | 8.75-8.68 (m, 1H), 8.68-8.59 (m, 1H), 8.56 (d, J = 8.8 Hz, 0.24H), 8.46 (d, J = 8.8 Hz, 0.15H), 8.19 (d, J = 8.3 Hz, 0.45H), 8.16-8.09 (m, 1H), 8.00-7.83 (m, 1.16H), 7.48-7.33 (m, 1H), 6.67 (s, 0.38H), 6.50 (s, 0.38H), 6.45 (s, 0.12H), 5.84 (s, 0.12H), 5.25-3.41 (m, 8H), 2.00-1.54 (m, 6H), 1.39-0.87 (m, 5H) | 489.13, 489.2 |
| 47 | Recrystallization (EtOAc) | 33 | A4 | 9.01-8.83 (m, 1H), 8.73-8.52 (m, 2.5H), 8.33-8.24 (m, 1H), 8.24-7.88 (m, 0.5H), 6.66 (s, 0.25H), 6.48 (s, 0.25H), 6.45 (s, 0.08H), 5.84 (s, 0.08H), 5.28-3.39 (m, 8H), 2.13-1.47 (m, 6H) 1.35-0.77 (m, 5H) | 507.12 507.2 |
| 48 | — | 88 | A19 | 9.45-9.38 (m, 1H), 8.91-8.83 (m, 1H), 8.75-8.54 (m, 2.39H), 8.28-8.20 (m, 0.48H), 8.00-7.94 (m, 0.13H), 6.66 (s, 0.44H), 6.49 (s, 0.44H), 6.45 (s, 0.16H), 5.84 (s, 0.16H), 5.23-3.40 (m, 8H), 2.02-1.51 (m, 6H), 1.13 (m, 5H) | 490.12 490.2 |
| 49 | Crystallization from EtOAc and heptane | 67 | A20 | 8.75-8.62 (m, 3H), 8.62-8.52 (m, 0.3H), 8.26-8.16 (m, 0.5H), 7.99-7.91 (m, 0.2H), 7.86-7.74 (m, 2H), 6.66 (s, 0.41H), 6.50 (s, 0.41H), 6.46 (s, 0.15H), 5.85 (s, 0.15H), 5.27-3.35 (m, 8H), 2.02-1.51 (m, 6H), 1.34-0.82 (m, 5H) | 489.13 489.2 |
| 50 | Crystallization from EtOAc and heptane | 68 | A5 | 8.82-8.69 (m, 2.1H), 8.67-8.60 (m, 0.2H), 8.60-8.49 (m, 1H), 8.30-8.20 (m, 0.5H), 8.10-8.01 (m, 1H), 8.01-7.93 (m, 0.2H), 6.66 (s, 0.45H), 6.49 (s, 0.45H), 6.45 (s, 0.16H), 5.84 (s, 0.16H), 5.25-3.39 (m, 8H), 2.01-1.49 (m, 6H), 1.28-0.89 (m, 5H) | 507.12 507.2 |
| 51 | HPLC (C18, MeCN (1% 10 mM NH$_4$HCO$_3$), 10 mM NH$_4$HCO$_3$ in H$_2$O) | 43 | A21 | 8.72-8.61 (m, 1.34H), 8.60-8.49 (m, 1.16H), 8.21 (d, J = 8.4 Hz, 0.34H), 7.94 (d, J = 8.5 Hz, 0.16H), 7.74-7.64 (m, 1H), 7.64-7.52 (m, 1H), 6.68 (s, 0.34H), 6.52 (s, 0.13H), 6.46 (s, 0.34H), 5.85 (s, 0.13H), 5.23-3.41 (m, 8H), 2.04-1.53 (m, 6H), 1.38-0.77 (m, 5H) | 503.14 503.2 |
| 52 | basic preparative HPLC (C18, MeCN (1% 10 mM NH$_4$HCO$_3$), 10 mM NH$_4$HCO$_3$ in H$_2$O) | 44 | A22 | 8.97-8.80 (m, 1H), 8.65 (d, J = 8.3 Hz, 0.25H), 8.63-8.57 (m, 1H), 8.55 (d, J = 9.2 Hz, 0.25H), 8.37-8.24 (m, 1H), 8.19 (d, J = 8.6 Hz, 0.37H), 7.92 (d, J = 7.7 Hz, 0.13H), 7.77-7.60 (m, 1H), 6.66 (s, 0.3H), 6.49 (s, 0.3H), 6.45 (s, 0.1H), 5.84 (s, 0.1H), 5.23-3.41 (m, 8H), 2.01-1.51 (m, 6H), 1.37-0.83 (m, 5H) | 523.09 523.0 |
| 53 | basic preparative HPLC (C18, MeCN (1% 10 mM NH$_4$HCO$_3$), 10 mM NH$_4$HCO$_3$ in H$_2$O | 50 | A25 | 9.28-9.14 (m, 3H), 8.04-7.95 (m, 0.45H), 7.93-7.81 (m, 1H), 7.70-7.36 (m, 0.55H), 6.65 (s, 0.1H), 6.45 (s, 0.1H), 6.45 (s, 0.03H), 5.85 (s, 0.03H), 5.26-3.43 (m, 8H), 1.94-1.53 (m, 6H), 1.32-0.90 (m, 5H) | 507.12 507.2 |
| 54 | basic preparative HPLC (C18, MeCN (1% 10 mM NH$_4$HCO$_3$), 10 mM NH4HCO$_3$ in H$_2$O) | 74 | A40 | 9.33-9.16 (m, 1H), 9.15-8.93 (m, 1H), 8.48-8.16 (m, 0.6H), 8.16-7.99 (m, 1.4H), 7.93-7.75 (m, 1H), 6.72 (s, 0.3H), 6.46 (s, 0.19H), 6.25 (s, 0.3H), 5.83 (s, 0.19H), 5.15-3.47 (m, 8H), 2.01-1.49 (m, 6H), 1.35-0.93 (m, 5H) | 507.12 507.2 |

| Nr | Purification | Yield [%] | Acid | ¹H NMR (400 MHz, DMSO-d₆) as a mixture of hydrates and rotamers | LCMS [M + H]⁺ cal/fd |
|---|---|---|---|---|---|
| 55 | — | 82 | A41 | 9.14-8.70 (m, 2.78H), 8.26-7.90 (m, 1H), 7.73-7.52 (m, 1.22H), 6.72 (s, 0.43H), 6.46 (s, 0.25H), 6.32 (s, 0.43H), 5.83 (s, 0.25H), 5.09-3.40 (m, 8H), 2.31-2.19 (m, 1H), 2.05-1.48 (m, 6H), 1.30-0.82 (m, 9H) | 529.16 529.2 |
| 56 | Crystallization from EtOAc/heptane | 55 | A12 | 9.05-8.95 (m, 0.35H), 8.93-8.78 (m, 0.65H), 8.28-8.17 (m, 1H), 8.16-8.11 (m, 0.3H), 8.06-7.97 (m, 0.7H), 7.85-7.81 (m, 0.3H), 7.81-7.73 (m, 0.7H), 7.36-7.24 (m, 1H), 7.16-7.06 (m, 1H), 6.73 (s, 0.22H), 6.47 (s, 0.13H), 6.32 (s, 0.22H), 5.84 (s, 0.13H), 5.11-3.41 (m, 8H), 3.91-3.84 (m, 3H), 2.01-1.47 (m, 6H), 1.29-0.85 (m, 5H) | 518.1 4518.2 |
| 57 | Crystallization from EtOAc/pentane | 83 | A27 | 9.16-8.96 (m, 2H), 8.68-8.47 (m, 1.41H), 8.18 (d, J = 8.4 Hz, 0.53H), 7.91 (d, J = 8.7 Hz, 0.06H), 6.65 (s, 0.5H), 6.48 (s, 0.5H), 6.44 (s, 0.19H), 5.83 (s, 0.19H), 5.24-3.41 (m, 8H), 2.35-2.21 (m, 1H), 2.02-1.52 (m, 6H), 1.33-0.91 (m, 9H) | 530.16 530.2 |
| 58 | — | 88 | A55 | 9.20-8.84 (m, 2H), 8.24-8.03 (m, 1H), 7.82-7.62 (m, 2H), 6.73 (s, 0.42H), 6.47 (s, 0.25H), 6.30 (s, 0.42H), 5.84 (s, 0.25H), 5.14-3.42 (m, 8H), 2.93-2.73 (m, 3H), 2.05-1.48 (m, 6H), 1.35-0.75 (m, 5H) | 503.14 503.0 |
| 59 | basic preparative HPLC (C18, MeCN (1% 10 mM NH₄HCO₃), 10 mM NH₄HCO₃ in H₂O) | 60 | A42 | 9.36-9.11 (m, 1H), 8.44-8.25 (m, 1H), 8.16-8.00 (m, 1.20H), 7.98-7.91 (m, 0.25H), 7.91-7.81 (m, 1H), 7.80-7.66 (m, 0.45H), 7.46-7.38 (m, 0.10H), 6.67 (s, 0.40H), 6.46 (s, 0.40H), 6.44 (s, 0.10H), 5.84 (s, 0.10H), 5.26-3.45 (m, 8H), 2.04-1.55 (m, 6H), 1.41-0.90 (m, 5H) | 507.12 507.22 |
| 60 | basic preparative HPLC (C18, MeCN (1% 10 mM NH₄HCO₃), 10 mM NH₄HCO₃ in H₂O) | 50 | A26 | 9.74-9.62 (m, 1H), 9.39-9.26 (m, 1H), 8.21-8.05 (m, 1.5H), 8.05-7.95 (m, 1.1H), 7.80-7.71 (m, 0.3H), 7.51-7.40 (m, 0.1H), 6.66 (s, 0.3H), 6.45 (s, 0.4H), 5.85 (s, 0.1H), 5.26-3.45 (m, 8H), 2.01-1.53 (m, 6H), 1.34-0.90 (m, 5H) | 507.12 507.2 |
| 61 | — | 90 | A43 | 9.49-9.35 (m, 1.83H), 9.11-8.85 (m, 0.78H), 8.61-7.68 (m, 2.39H), 6.71 (s, 0.26H), 6.46 (s, 0.16H), 6.29 (s, 0.26H), 5.83 (s, 0.16H), 5.20-3.45 (m, 8H), 2.06-1.39 (m, 6H), 1.35-0.76 (m, 5H). | 557.12 557.0 |
| 62 | Crystallization from EtOAc/heptane | 74 | A13 | 9.21-9.11 (m, 1H), 9.05-8.99 (m, 0.3H), 8.94-8.84 (m, 0.5H), 8.42-8.34 (m, 1H), 8.32-7.77 (m, 3.2H), 6.73 (s, 0.34H), 6.47 (s, 0.2H), 6.31 (s, 0.34H), 5.83 (s, 0.2H), 5.12-3.43 (m, 8H), 2.01-1.49 (m, 6H), 1.26-0.90 (m, 5H) | 556.1 556.0 |
| 63 | Crystallization from EtOAc/heptane | 75 | A14 | 8.97-8.87 (m, 0.4H), 8.82-8.69 (m, 1.6H), 8.16-8.08 (m, 0.4H), 8.02-7.88 (m, 1.6H), 7.62-7.57 (m, 0.4H), 7.57-7.52 (m, 0.6H), 7.42-7.33 (m, 1H), 6.74 (s, 0.34H), 6.46 (s, 0.18H), 6.35 (s, 0.34H), 5.83 (s, 0.18H), 5.14-3.42 (m, 8H), 2.19-2.08 (m, 1H), 1.99-1.49 (m, 6H), 1.29-1.03 (m, 4H), 1.02-0.90 (m, 5H) | 528.16 528.2 |
| 64 | basic preparative HPLC (C18, MeCN (1% 10 mM NH₄HCO₃), 10 mM NH₄HCO₃ in H₂O) | 51 | A6 | 8.94-8.75 (m, 1H), 8.58 (d, J= 8.5 Hz, 0.18H), 8.54-8.40 (m, 1.25H), 8.16 (d, J = 8.6 Hz, 0.55H), 8.12-8.00 (m, 1H), 7.89 (d, J = 8.5 Hz, 0.12H), 7.51-7.36 (m, 1H), 6.67 (s, 0.45H), 6.49 (s, 0.45H), 6.46 (s, 0.15H), 5.85 (s, 0.15H), 5.24-3.40 (m, 8H), 2.25-2.08 (m, 1H), 2.02-1.48 (m, 6H), 1.37-0.76 (m, 9H) | 529.16 529.2 |
| 65 | basic preparative HPLC (C18, MeCN (1% 10 mM NH₄HCO₃), 10 mM NH₄HCO₃ in H₂O) | 38 | A44 | 8.99 (s, 1H), 8.61 (s, 1H), 8.21-8.04 (m, 1H), 7.97-7.88 (m, 0.2H), 7.88-7.73 (m, 1.2H), 7.73-7.59 (m, 0.4H), 7.59-7.47 (m, 1H), 7.44-7.25 (m, 0.2H), 6.68 (s, 0.3H), 6.56-6.41 (m, 0.4H), 5.86 (s, 0.1H), 5.27-3.45 (m, 8H), 1.98-1.51 (m, 6H), 1.43-0.90 (m, 5H) ppm. | 506.12 506.2 |
| 66 | Crystallization from EtOAc/heptane | 46 | A15 | 9.03-8.94 (m, 0.4H), 8.91-8.80 (m, 0.6H), 8.46-8.38 (m, 1H), 8.26-8.20 (m, 0.05H), 8.19-8.11 (m, 0.4H), 8.06-7.99 (m, 0.55H), 7.86-7.81 (m, 0.4H), 7.81-7.76 | 528.16 528.2 |

| Nr | Purification | Yield [%] | Acid | ¹H NMR (400 MHz, DMSO-d₆) as a mixture of hydrates and rotamers | LCMS [M + H]⁺ cal/fd |
|---|---|---|---|---|---|
| | | | | (m, 0.6H), 7.66-7.57 (m, 1H), 7.47-7.38 (m, 1H), 6.73 (s, 0.37H), 6.47 (s, 0.21H), 6.33 (s, 0.37H), 5.83 (s, 0.21H), 5.10-3.44 (m, 8H), 2.21-2.10 (m, 1H), 2.03-1.48 (m, 6H), 1.26-1.02 (m, 4H), 1.02-0.89 (m, 5H) | |
| 67 | acidic preparative HPLC (C18, MeCN (0.1% HCOOC), H₂O (0.1% HCOOC)) | 54 | A28 | 9.58-9.48 (m, 2H), 8.85-8.64 (m, 1.57H), 8.25 (d, J = 8.5 Hz, 0.25H), 7.98 (d, J = 8.6 Hz, 0.18H), 6.68 (s, 0.24H), 6.51 (s, 0.24H), 6.46 (s, 0.09H), 5.85 (s, 0.09H), 5.25-3.39 (m, 8H), 2.03-1.53 (m, 6H), 1.32-0.91 (m, 5H) | 558.11 558.0 |
| 68 | basic preparative HPLC (C18, MeCN (1% 10 mM NH₄HCO₃), 10 mM NH₄HCO₃ in H₂O) | 34 | A7 | 9.22 (s, 1H), 8.76-8.66 (m, 1.25H), 8.61 (d, 0.25H), 8.55-8.45 (m, 1H), 8.22 (d, J = 8.2 Hz, 0.35H), 8.09-8.00 (m, 1H), 7.96 (d, J = 8.5 Hz, 0.15H), 6.66 (s, 0.25H), 6.49 (s, 0.25H), 6.45 (s, 0.10H), 5.84 (s, 0.10H), 5.30-3.39 (m, 8H), 2.09-1.53 (m, 6H), 1.53-0.87 (m, 5H) | 557.12 557.2 |
| 69 | — | 78 | A56 | 9.62-9.29 (m, 1H), 9.11-8.85 (m, 1H), 8.34-7.73 (m, 3H), 6.72 (s, 0.42H), 6.46 (s, 0.26H), 6.29 (s, 0.42H), 5.83 (s, 0.26H), 5.19-3.44 (m, 8H), 2.77-2.60 (m, 3H), 2.10-1.44 (m, 6H), 1.39-0.76 (m, 5H) | 503.14 503.2 |
| 70 | Crystallization from EtOAc/heptane | 67 | A61 | 9.06-8.95 (m, 0.5H), 8.92-8.80 (m, 0.5H), 8.73-8.62 (m, 1H), 8.25-8.16 (m, 1H), 8.16-8.10 (m, 0.5H), 8.06-7.96 (m, 0.5H), 7.80-7.75 (m, 0.5H), 7.75-7.70 (m, 0.5H), 7.69-7.60 (m, 1H), 7.52-7.41 (m, 1H), 6.73 (s, 0.46H), 6.47 (s, 0.27H), 6.32 (s, 0.46H), 5.84 (s, 0.27H), 5.08-3.44 (m, 8H), 2.00-1.49 (m, 6H), 1.25-0.90 (m, 5H) | 504.13 504.1 |
| 71 | basic preparative HPLC (C18, MeCN (1% 10 mM NH₄HCO₃), 10 mM NH₄HCO₃ in H₂O) | 59 | A58 | 9.36-9.24 (m, 1H), 9.11-9.02 (m, 0.3H), 9.00-8.87 (m, 0.6H), 8.36-8.28 (m, 0.1H), 8.22-8.14 (m, 0.3H), 8.06 (m, 0.7H), 8.03-7.89 (m, 1H), 7.52-7.43 (m, 1H), 6.72 (s, 0.25H), 6.47 (s, 0.15H), 6.29 (s, 0.25H), 5.84 (s, 0.15H), 5.10-3.46 (m, 11H), 2.01-1.47 (m, 6H), 1.06 (dd, J = 78.4, 8.8 Hz, 5H) | 519.14 519.1 |
| 72 | acidic preparative HPLC (C18, MeCN (0.1% HCOOC), H₂O (0.1% HCOOC)) | 37 | A45 | 9.01-8.94 (m, 0.5H), 8.94-8.88 (m, 1H), 8.88-8.78 (m, 0.5H), 8.20-8.13 (m, 0.5H), 8.10-8.06 (m, 0.5H), 8.06-8.00 (m, 1H), 7.90-7.79 (m, 1H), 6.77 (s, 0.5H), 6.47 (s, 0.25H), 6.37 (s, 0.5H), 5.84 (s, 0.25H), 5.21-3.43 (m, 11H), 2.04-1.45 (m, 6H), 1.38-0.83 (m, 5H) | 519.14 519.1 |
| 73 | Crystallization from EtOAc/heptane | 41 | A46 | 9.14-9.03 (m, 1H), 9.01-8.91 (m, 0.4H), 8.87-8.77 (m, 0.6H), 8.54-8.43 (m, 0.01H), 8.22-8.10 (m, 1.4H), 8.08-8.02 (m, 0.6H), 8.02-7.98 (m, 0.4H), 7.98-7.91 (m, 0.6H), 6.76 (s, 0.33H), 6.46 (s, 0.18H), 6.37 (s, 0.33H), 5.83 (s, 0.18H), 5.15-3.43 (m, 8H), 2.77-2.63 (m, 2H), 2.02-1.49 (m, 6H), 1.32-1.23 (m, 3H), 1.23-0.89 (m, 5H) | 517.16 517.2 |
| 74 | Crystallization from EtOAc/heptane | 50 | A54 | 9.05-8.99 (m, 1H), 8.98-8.92 (m, 0.4H), 8.86-8.76 (m, 0.6H), 8.19-8.11 (m, 0.4H), 8.06-8.00 (m, 1H), 7.99-7.94 (m, 0.6H), 7.91-7.84 (m, 1H), 6.76 (s, 0.35H), 6.46 (s, 0.19H), 6.37 (s, 0.35H), 5.83 (s, 0.19H), 5.18-3.44 (m, 8H), 2.07-1.97 (m, 1H), 1.97-1.49 (m, 6H), 1.26-0.89 (m, 9H) | 529.16 529.2 |
| 75 | — | 80 | A29 | 9.69-9.42 (m, 1H), 8.95-8.57 (m, 1.51H), 8.30-8.17 (m, 0.26H), 8.07-7.88 (m, 1.23H), 6.65 (s, 0.18H), 6.49 (s, 0.18H), 6.45 (s, 0.07H), 5.84 (s, 0.07H), 5.25-3.43 (m, 8H), 2.77-2.61 (m, 3H), 2.03-1.41 (m, 6H), 1.34-0.82 (m, 5H) | 504.14 504.0 |
| 76 | Crystallization from EtOAc and heptane | 56 | A53 | 9.48-9.37 (m, 1H), 9.07-8.98 (m, 0.4H), 8.95-8.85 (m, 0.6H), 8.52-8.42 (m, 1H), 8.31-8.26 (m, 0.05H), 8.22-8.16 (m, 0.35H), 8.14-8.10 (m, 0.40H), 8.10-8.02 (m, 1.2H), 6.77 (s, 0.31H), 6.48 (s, 0.17H), 6.36 (s, 0.31H), 5.84 (s, 0.17H), | 551.11 551.1 |

-continued

| Nr | Purification | Yield [%] | Acid | $^1$H NMR (400 MHz, DMSO-d$_6$) as a mixture of hydrates and rotamers | LCMS [M + H]$^+$ cal/fd |
|---|---|---|---|---|---|
| 77 | — | 79 | A32 | 5.19-3.41 (m, 8H), 3.05-2.95 (m, 3H), 2.01-1.49 (m, 6H), 1.26-0.90 (m, 5H) 9.07-8.97 (m, 1H), 8.73-7.89 (m, 3H), 6.65 (s, 0.47H), 6.48 (s, 0.47H), 6.44 (s, 0.19H), 5.83 (s, 0.19H), 5.22-3.39 (m, 8H), 2.45-2.33 (m, 3H), 2.01-1.48 (m, 6H), 1.30-0.87 (m, 5H | 520.13 520.2 |
| 78 | basic preparative HPLC (C18, MeCN (1% 10 mM NH$_4$HCO$_3$), 10 mM NH$_4$HCO$_3$ in H$_2$O) | 23 | A33 | 9.65-9.54 (m, 1H), 9.08-9.00 (m, 0.3H), 8.98-8.89 (m, 0.7H), 8.76-8.68 (m, 1H), 8.36-8.27 (m, 0.2H), 8.26-8.16 (m, 1H), 8.14-8.06 (m, 0.8H), 6.77 (s, 0.12H), 6.48 (s, 0.06H), 6.35 (s, 0.12H), 5.84 (s, 0.06H), 5.16-3.42 (m, 11H), 2.02-1.50 (m, 6H), 1.27-0.92 (m, 5H) | 567.11 567.2 |
| 79 | — | 90 | A34 | 9.08-8.82 (m, 1H), 8.42-7.66 (m, 5H), 6.74 (s, 0.44H), 6.46 (s, 0.26H), 6.32 (s, 0.44H), 5.82 (s, 0.26H), 5.12-3.42 (m, 8H), 2.03-1.47 (m, 6H), 1.30-0.86 (m, 5H) | 505.12 505.2 |
| 80 | basic preparative HPLC (C18, MeCN (1% 10 mM NH$_4$HCO$_3$), 10 mM NH$_4$HCO$_3$ in H$_2$O) | 17 | A47 | 12.94 (s, 1H), 9.12-9.01 (m, 0.4H), 8.99-8.88 (m, 0.6H), 8.55-8.51 (m, 0.01H), 8.37-8.28 (m, 1H), 8.19-8.13 (m, 0.3H), 8.09-8.01 (m, 0.7H), 7.94-7.84 (m, 1H), 7.15-7.07 (m, 1H), 6.73 (s, 0.23H), 6.49 (s, 0.14H), 6.30 (s, 0.23H), 5.86 (s, 0.14H), 5.16-3.42 (m, 8H), 2.00-1.48 (m, 6H), 1.27-0.89 (m, 5H) | 505.12 505.0 |
| 81 | — | 92 | A48 | 9.04-8.93 (m, 0.45H), 8.91-8.78 (m, 0.55H), 8.72-8.62 (m, 1H), 8.20-8.12 (m, 0.45H), 8.08-7.99 (m, 0.55H), 7.47-7.41 (m, 0.45H), 7.41-7.34 (m, 0.55H), 6.73 (s, 0.4H), 6.47 (s, 0.2H), 6.32 (s, 0.4H), 5.83 (s, 0.2H), 5.10-3.44 (m, 8H), 2.65-2.59 (m, 3H), 2.59-2.55 (m, 3H), 2.03-1.45 (m, 6H), 1.35-0.80 (m, 5H) | 517.16 517.2 |
| 82 | — | 84 | A30 | 8.70-8.65 (m, 1.19H), 8.60-8.54 (m, 0.17H), 8.50-8.44 (m, 1H), 8.24-8.17 (m, 0.52H), 7.97-7.91 (m, 0.12H), 7.75-7.67 (m, 1H), 7.55-7.47 (m, 1H), 6.65 (s, 0.44H), 6.49 (s, 0.44H), 6.45 (s, 0.17H), 5.84 (s, 0.17H), 5.22-3.40 (m, 8H), 2.23-2.12 (m, 1H), 1.99-1.53 (m, 6H), 1.28-0.80 (m, 9H) | 529.16 529.2 |
| 83 | — | 77 | A49 | 9.02-8.76 (m, 1H), 8.53-8.45 (m, 1H), 8.22-7.96 (m, 1H), 7.87-7.78 (m, 1H), 7.41-7.28 (m, 2H), 6.74 (s, 0.31H), 6.47 (s, 0.16H), 6.34 (s, 0.31H), 5.84 (s, 0.16H), 5.12-3.48 (m, 8H), 2.66-2.57 (m, 3H), 2.00-1.51 (m, 6H), 1.28-0.89 (m, 5H) | 502.15 502.2 |
| 84 | basic preparative HPLC (C18, MeCN (1% 10 mM NH$_4$HCO$_3$), 10 mM NH$_4$HCO$_3$ in H$_2$O) | 53 | A50 | 9.08-8.97 (m, 1.5H), 8.92-8.82 (m, 0.5H), 8.23 (d, J = 7.9 Hz, 0.03H), 8.17 (d, J = 4.1 Hz, 0.37H), 8.08-8.01 (m, 0.6H), 7.78-7.63 (m, 2H), 6.78 (s, 0.34H), 6.49 (s, 0.19H), 6.38 (s, 0.34H), 5.85 (s, 0.19H), 5.19-3.47 (m, 8H), 2.66-2.55 (m, 3H), 2.03-1.52 (m, 6H), 1.29-0.90 (m, 5H) | 503.14 503.2 |
| 85 | — | 96 | A59 | 9.54-9.42 (m, 1H), 9.27-9.22 (m, 0.02H), 9.12-9.00 (m, 0.42H), 9.00-8.87 (m, 0.50H), 8.62-8.56 (m, 0.01H), 8.36-8.28 (m, 0.03H), 8.26-8.15 (m, 0.42H), 8.13-8.04 (m, 0.59H), 8.04-7.99 (m, 0.42H), 7.99-7.93 (m, 0.59H), 7.92-7.80 (m, 1H), 6.73 (s, 0.42H), 6.48 (s, 0.25H), 6.30 (s, 0.42H), 5.85 (s, 0.25H), 5.11-3.44 (m, 8H), 3.04-2.89 (m, 2H), 2.03-1.46 (m, 6H), 1.41-1.26 (m, 3H), 1.25-0.82 (m, 5H) | 517.16 517.2 |
| 86 | — | 55 | A51 | .03-8.94 (m, 0.4H), 8.91-8.80 (m, 0.6H), 8.55-8.47 (m, 1H), 8.17-8.12 (m, 0.4H), 8.05-8.00 (m, 0.6H), 7.85-7.82 (m, 0.4H), 7.82-7.77 (m, 0.6H), 7.62-7.55 (m, 1H), 7.55-7.44 (m, 1H), 6.73 (s, 0.34H), 6.47 (s, 0.19H), 6.32 (s, 0.34H), 5.83 (s, 0.19H), 5.07-3.44 (m, 8H), 2.86-2.71 (m, 2H), 2.01-1.44 (m, 6H), 1.30-1.22 (m, 3H), 1.22-0.90 (m, 5H) | 516.16 516.2 |

-continued

| Nr | Purification | Yield [%] | Acid | $^1$H NMR (400 MHz, DMSO-$d_6$) as a mixture of hydrates and rotamers | LCMS [M + H]$^+$ cal/fd |
|---|---|---|---|---|---|
| 87 | acidic preparative HPLC (C18, MeCN (0.1% HCOOC), H$_2$O (0.1% HCOOC)) and lyophilisation (MeCN/H$_2$O) | 15 | A31 | 9.03-8.94 (m, 0.4H), 8.91-8.80 (m, 0.6H), 8.74-8.63 (m, 1.3H), 8.63-8.51 (m, 1.2H), 8.29-8.13 (m, 0.4H), 7.98-7.90 (m, 0.1H), 7.74-7.64 (m, 1H), 7.64-7.51 (m, 1H), 6.66 (s, 0.4H), 6.49 (s, 0.4H), 6.45 (s, 0.1H), 5.84 (s, 0.1H), 5.20-3.43 (m, 8H), 2.92-2.73 (m, 2H), 2.00-1.53 (m, 6H), 1.31-1.23 (m, 3H), 1.23-0.83 (m, 5H) | 517.16 517.2 |
| 88 | basic preparative HPLC (C18, MeCN (1% 10 mM NH$_4$HCO$_3$), 10 mM NH$_4$HCO$_3$ in H$_2$O) | 24 | A52 | 9.05-8.92 (m, 0.15H), 8.91-8.79 (m, 0.7H), 8.47-8.34 (m, 1H), 8.25-8.19 (m, 0.15H), 8.19-8.14 (m, 0.15H), 8.09-7.97 (m, 0.85H), 7.51-7.48 (m, 0.15H), 7.48-7.43 (m, 0.85H), 7.39-7.33 (m, 1H), 6.75 (s, 0.06H), 6.46 (s, 0.03H), 6.34 (s, 0.06H), 5.85 (s, 0.03H), 5.14-3.46 (m, 8H), 2.47-2.43 (m, 3H), 2.41-2.37 (m, 3H), 2.03-1.46 (m, 6H), 1.32-0.86 (m, 5H) | 516.16 515.2 |
| 89 | — | 90 | A57 | 9.10-9.01 (m, 0.46H), 8.96-8.86 (m, 0.46H), 8.59-8.53 (m, 0.04H), 8.33-8.28 (m, 0.03H), 8.24-8.14 (m, 0.49H), 8.12-8.04 (m, 0.52H), 7.72-7.56 (m, 2H), 6.73 (s, 0.44H), 6.47 (s, 0.26H), 6.30 (s, 0.44H), 5.84 (s, 0.26H), 5.10-3.42 (m, 8H), 2.84-2.71 (m, 3H), 2.67-2.57 (m, 3H), 2.10-1.47 (m, 6H), 1.27-0.88 (m, 5H) | 517.16 517.2 |
| 90 | acidic preparative HPLC (C18, MeCN (0.1% HCOOH), H$_2$O (0.1% HCOOH)) | 40 | A62 | 9.34-9.25 (m, 1H), 9.21-9.12 (m, 1H), 9.04-8.83 (m, 0.75H), 8.30-8.23 (m, 0.08H), 8.23-8.17 (m, 0.17H), 8.13-8.03 (m, 1H), 7.75-7.63 (m, 1H), 6.68 (s, 0.13H), 6.42 (s, 0.07H), 6.26 (s, 0.13H), 5.78 (s, 0.07H), 5.21-3.34 (m, 8H), 2.50 (m, 3H), 2.01-1.45 (m, 6H), 1.28-0.81 (m, 5H) | 503.1, 503.2 |

2. Biological and Pharmacokinetic Characterization 2.1 Cat S/K/L Functional Enzyme Assays Reference and test compounds were assayed for inhibitory potency (IC50) against human cathepsins using the following assay setups:

Recombinant human cathepsins (CatS, CatK, CatL) were purchased from a Enzo Life Sciences. All assays were carried out in 96-well format using a buffer of 50 mM KH$_2$PO$_4$, 50 mM NaCl, 2 mM EDTA, 0.5 mM DTT and 1% Triton-X-100, pH 6.5 for Cathepsin S and a buffer of 50 mM NaOAc, 10 mM EDTA, 1 mM DTT and 0.01% Triton-X-100, pH 5.5 for CatK/L/B. For CatS, the enzyme (0.0007 mU/well) was incubated with fluorogeninc substrate (Z-VVR-AMC, 5 μM) at RT for 10 min. For CatK the enzyme (0.00175 mU/well) was incubated with fluorogeninc substrate (Z-FR-AMC, 40 μM) at RT for 10 min. For CatL, the enzyme (0.000874 mU/well) was incubated with fluorogeninc substrate (Z-VVR-AMC, 40 μM) at RT for 10 min. Flourogenic substrate turnover was detected using a microplate reader (Synergy™ H4, BioTek). Ki values were calculated using the Cheng Prusoff equation (Cheng & Prosoff 1973).

| Ex-Cmpd | hCatS, Ki [μM] | hCatS, inhibition [%] at 10 μM | hCatK, Ki [μM] | hCatK, inhibition [%] at 10 μM | hCatL, inhibition [%] at 31.6 μM | Selectivity Ki(hCatS)/Ki(hCatK) |
|---|---|---|---|---|---|---|
| 1 | 0.402 | nd | 0.014 | nd | 3 | 28.7 |
| 2 | 0.115 | nd | 0.005 | nd | 10 | 23.0 |
| 3 | 0.103 | nd | 0.003 | nd | 5 | 34.3 |
| 4 | 0.184 | nd | 0.014 | nd | 17 | 13.1 |
| 5 | 0.048 | nd | 0.031 | nd | 27 | 1.5 |
| 6 | 0.06 | nd | 0.011 | nd | 36 | 5.5 |
| 7 | 0.056 | nd | 0.012 | nd | 28 | 4.7 |
| 8 | 0.021 | nd | 0.017 | nd | 32 | 1.2 |
| 9 | 1.470 | nd | 0.018 | nd | 4 | 81.7 |
| 10 | 0.612 | nd | 0.054 | nd | 16 | 11.3 |
| 11 | 0.099 | nd | 0.087 | nd | 14 | 1.1 |
| 12 | 0.521 | nd | 0.05 | nd | 18 | 10.4 |
| 13 | nd | 73 | 0.029 | nd | 16 | nd |
| 14 | nd | 70 | nd | 88 | 21 | nd |
| 15 | 0.193 | nd | 0.025 | nd | 12 | 7.7 |
| 16 | 0.259 | nd | 0.013 | nd | 15 | 19.9 |
| 17 | 0.347 | nd | 0.016 | nd | 9 | 21.7 |
| 18 | 0.037 | nd | 0.031 | nd | 15 | 1.2 |
| 19 | 0.074 | nd | 0.093 | nd | 12 | 0.8 |

-continued

| Ex-Cmpd | hCatS, Ki [μM] | hCatS, inhibition [%] at 10 μM | hCatK, Ki [μM] | hCatK, inhibition [%] at 10 μM | hCatL, inhibition [%] at 31.6 μM | Selectivity Ki(hCatS)/Ki(hCatK) |
|---|---|---|---|---|---|---|
| 20 | 0.727 | nd | 0.225 | nd | 16 | 3.2 |
| 21 | 0.527 | nd | 0.278 | nd | 15 | 1.9 |
| 22 | nd | 73 | 0.037 | nd | 17 | nd |
| 23 | nd | 60 | nd | 52 | 0 | nd |
| 24 | 0.061 | nd | 0.022 | nd | 10 | 2.8 |
| 25 | 0.833 | nd | 0.153 | nd | 20 | 5.4 |
| 26 | 0.22 | nd | 0.048 | nd | 32 | 4.6 |
| 27 | 0.699 | nd | 0.262 | nd | 18 | 2.7 |
| 28 | nd | 83 | 0.014 | nd | 14 | nd |
| 29 | 0.238 | nd | 0.009 | nd | 6 | 26.4 |
| 30 | 0.072 | nd | 0.010 | nd | 28 | 7.2 |
| 31 | 0.440 | nd | 0.005 | nd | 14 | 88.0 |
| 32 | 0.317 | nd | 0.020 | nd | 22 | 15.9 |
| 33 | 0.086 | nd | 0.004 | nd | 12 | 21.5 |
| 34 | 0.344 | nd | 0.016 | nd | 15 | 21.5 |
| 35 | 0.172 | nd | 0.016 | nd | 23 | 10.7 |
| 36 | 0.469 | nd | 0.022 | nd | 9 | 21.3 |
| 37 | 0.401 | nd | 0.015 | nd | 29 | 26.7 |
| 38 | 0.213 | nd | 0.020 | nd | 30 | 10.7 |
| 39 | 0.225 | nd | 0.019 | nd | 19 | 11.8 |
| 40 | 0.453 | nd | 0.012 | nd | 39 | 37.8 |
| 41 | 0.144 | nd | 0.026 | nd | 25 | 5.5 |
| 42 | 0.356 | nd | 0.014 | nd | 18 | 25.4 |
| 43 | 0.769 | nd | 0.243 | nd | 16 | 3.2 |
| 44 | 0.070 | nd | 0.015 | nd | 33 | 4.7 |
| 45 | 0.262 | nd | 0.008 | nd | 26 | 32.8 |
| 46 | 0.413 | nd | 0.009 | nd | 6 | 45.9 |
| 47 | 0.221 | nd | 0.020 | nd | 28 | 11.1 |
| 48 | 0.242 | nd | 0.014 | nd | 7 | 17.3 |
| 49 | 0.376 | nd | 0.009 | nd | 4 | 41.8 |
| 50 | 0.733 | nd | 0.011 | nd | 15 | 66.6 |
| 51 | 0.173 | nd | 0.007 | nd | 6 | 24.7 |
| 52 | 0.203 | nd | 0.014 | nd | 7 | 14.5 |
| 53 | 0.302 | nd | 0.034 | nd | 40 | 8.9 |
| 54 | 0.528 | nd | 0.021 | nd | 27 | 25.1 |
| 55 | 0.070 | nd | 0.029 | nd | 13 | 2.4 |
| 56 | 0.092 | nd | 0.006 | nd | 20 | 16.6 |
| 57 | 0.150 | nd | 0.042 | nd | 23 | 3.6 |
| 58 | 0.051 | nd | 0.034 | nd | 21 | 1.5 |
| 59 | 0.726 | nd | 0.118 | nd | 0 | 6.2 |
| 60 | 0.238 | nd | 0.104 | nd | 11 | 2.3 |
| 61 | 0.302 | nd | 0.076 | nd | 0 | 4.0 |
| 62 | 0.580 | nd | 0.058 | nd | 25 | 10.0 |
| 63 | 0.525 | nd | 0.019 | nd | 1 | 27.6 |
| 64 | 0.616 | nd | 0.029 | nd | 5 | 21.3 |
| 65 | 0.646 | nd | 0.551 | nd | 5 | 1.2 |
| 66 | 0.034 | nd | 0.007 | nd | 3 | 5.0 |
| 67 | 0.198 | nd | 0.042 | nd | 8 | 4.7 |
| 68 | 0.383 | nd | 0.065 | nd | 5 | 5.9 |
| 69 | 0.009 | nd | 0.008 | nd | 24 | 1.1 |
| 70 | 0.027 | nd | 0.019 | nd | 41 | 1.5 |
| 71 | 0.023 | nd | 0.008 | nd | 32 | 3.0 |
| 72 | 0.055 | nd | 0.039 | nd | 30 | 1.4 |
| 73 | 0.013 | nd | 0.015 | nd | 26 | 0.9 |
| 74 | 0.007 | nd | 0.022 | nd | 19 | 0.3 |
| 75 | 0.021 | nd | 0.018 | nd | 28 | 1.2 |
| 76 | 0.029 | nd | 0.030 | nd | 19 | 1.0 |
| 77 | 0.025 | nd | 0.020 | nd | 12 | 1.3 |
| 78 | 0.016 | nd | 0.020 | nd | 21 | 0.8 |
| 79 | 0.056 | nd | 0.021 | nd | 25 | 2.7 |
| 80 | 0.042 | nd | 0.016 | nd | 30 | 2.6 |
| 81 | 0.133 | nd | 0.011 | nd | 18 | 12.1 |
| 82 | 0.129 | nd | 0.009 | nd | 24 | 14.3 |
| 83 | 0.296 | nd | 0.007 | nd | 1 | 44.0 |
| 84 | 0.358 | nd | 0.016 | nd | 6 | 21.8 |
| 85 | 0.006 | nd | 0.005 | nd | 14 | 1.1 |
| 86 | 0.024 | nd | 0.001 | nd | 25 | 16.7 |
| 87 | 0.059 | nd | 0.004 | nd | 14 | 16.2 |
| 88 | 0.335 | nd | 0.018 | nd | 0 | 18.6 |

-continued

| Ex-Cmpd | hCatS, Ki [µM] | hCatS, inhibition [%] at 10 µM | hCatK, Ki [µM] | hCatK, inhibition [%] at 10 µM | hCatL, inhibition [%] at 31.6 µM | Selectivity Ki(hCatS)/ Ki(hCatK) |
|---|---|---|---|---|---|---|
| 89 | 0.013 | nd | 0.018 | nd | 12 | 0.7 |
| 90 | 0.073 | nd | 0.010 | nd | 20 | 7.3 |
| C1 (Ex 7 of WO 2009112839) | 0.146 | nd | 0.038 | nd | 71 | 3.8 | nd = not determined

The compounds according to the invention exhibit good to very good inhibition of both hCatS and hCatK. Additionally, the compounds according to the invention exhibit lower inhibition of the hCatL compared to the compounds from the prior art resulting in an improved selectivity over hCatL.

2.2 Caco 2 Permeability Assay

The intestinal permeability of a potential drug is assessed by in vitro cell culture from a human colon adenomacarcinoma derived cell line. This cell line expresses some of the systems considered relevant to active drug transport e.g. Poly-glycoprotein (P-gp). In vitro cellular permeability assays can reflect both, permeation by passive diffusion and active transport (uptake and efflux). The rate of permeation across monolayers of Caco 2 cells were correlated to the extents of absorption (Hidalgo et al., Gastroenterology 1989; 96(3):736 49). Original methodology was developed by Artursson and Taveli (Drug Bioavailability. Series: Methods and Principles in Medicinal Chemistry. Weinheim: Wiley-VCH Verlag; 2003; p. 72-89).

The assay is performed as a trans-flux experiment. Caco-2 cells (cells from ATCC) are seeded and grown to confluence to form a monolayer (ca. 3 weeks, between passage numbers 40-60) on a readily permeable support in a plastic well supported within a chamber (Millipore Multiscreen Caco-2 plates, at a cell density of ca. $1 \times 10^5$ cells/cm$^2$). Cells are cultured for 20 days in DMEM and media is changed every two or three days. The cells form tight junctions, so paracellular diffusion is not possible, and grow in a polarised manner, efflux transporters (P-gp) are expressed on their apical surfaces facing the culture medium, rather than at their basolateral surfaces through which they are attached to the support membrane. A low concentration of a test compound is added to the upper (apical: A) or lower (basolateral: B) chambers, and the rate of loss from the donor compartment, and the rate of transfer to the acceptor chamber, is determined by LC-MS/MS. Consequently the influence of efflux transporters expressed in the apical membrane can be determined by comparing permeability rates from A to B and B to A. Assays are generally performed in gently shaken protein-free buffer.

On ca. day 20 the permeability study is performed. The monolayers are prepared by rinsing both basolateral and apical surfaces twice with Hanks Balanced Salt Solution (HBSS) pH 7.4 buffer with HEPES (25 mM) and 4.45 mM glucose at 37° C. Cells are then incubated with HBSS in both apical and basolateral compartments for 40 min to stabilise physiological parameters. Incubations are carried out in an atmosphere of 5% $CO_2$ with a rel. humidity of 95% at 37° C.

HBSS is next removed from the apical compartment and replaced with test compound dosing solution. Test compound dosing solutions are made by diluting 10 mM test compound in DMSO with HBSS to give a final test compound concentration of 10 µM (final DMSO concentration 1%).

The fluorescent integrity marker lucifer yellow is also included in the dosing solution. Analytical standards are made from dosing solutions. The apical compartment inserts are then placed into 'companion' plates containing fresh HBSS. For basolateral to apical (B-A) permeability determination the experiment is initiated by replacing buffer in the inserts then placing them in companion plates containing dosing solutions. At 120 min the companion plate is removed and apical and basolateral samples diluted for analysis by LC-MS/MS. Test compound permeability is assessed in duplicate. On each plate reference compounds of known permeability characteristics are also run as controls, these are atenolol and propranolol and talinolol (human absorption of approximately 50 and 90% respectively). Talinolol (a known P-gp substrate 2) is also included as a control compound to assess whether functional P-gp is present in the Caco-2 cell monolayer.

Test and control compounds are quantified by LC-MS/MS cassette analysis using a 5-point calibration with appropriate dilution of the samples. The starting concentration (C0) and experimental recovery are calculated from both apical and basolateral compartment concentrations.

Data Analysis

Apparent permeability (Papp), used interchangeably with effective permeability (Peff) and efflux ratio (ER) are generated for each compound and reference compound. The permeability coefficient for each compound (Papp) is calculated from the following equation:

$$Peff = dQ/dt/C0 \times A$$

Where dQ/dt is the rate of permeation of the drug across the cells, C0 is the donor compartment concentration at time zero and A is the area of the cell monolayer. C0 is obtained from analysis of donor and receiver compartments at the end of the incubation period. It is assumed that all of the test compound measured after 120 min incubation was initially present in the donor compartment at 0 min. An efflux ratio is derived thus:

$$ER = Peff(B-A)/Peff(A-B)$$

It is assumed that Peff values greater than $1*10^{-6}$ cm/sec indicate that there will be no serious problem with absorption (intermediate permeability ($10^{-6}$ to $10^{-5}$ cm/sec) to high permeability ($>10^{-5}$ cm/sec), and that Peff values lower than $1*10^{-6}$ cm/sec might indicate an absorption problem (low permeability ($<10^{-6}$ cm/sec)).

An efflux ratio greater than three shows efflux from the Caco-2 cells (ER=$P_{eff(B-A)}/P_{eff(A-B)}$>3: active efflux), which indicates that the compound may have potential absorption problems in vivo, and an efflux ratio less than three shows no efflux from the Caco-2 cells (ER=$P_{eff\ (B-A)}/P_{eff\ (A-B)}$<3: no active efflux observed).

The following data were obtained

| Compound | Peff [$10^{-6}$ cm/s] a – b | Peff [$10^{-6}$ cm/s] b – a | ER |
|---|---|---|---|
| C1 (Ex 7 of WO 2009112839) | 0.53 | 24.65 | 46.1 |
| Example 5 | 4.13 | 14.25 | 3.5 |
| Example 7 | 5.37 | 7.03 | 1.3 |
| Example 8 | 1.67 | 12.5 | 7.5 |

Example C1 shows poor A to B permeability with good B to A permeability and an extremely high efflux ratio (ER), suggesting this will exhibit poor intestinal absorption. Example 5, 7 and 8 show moderate A to B permeability with good B to A permeability and an intermediate/low efflux ratio (ER).

The invention claimed is:
1. A compound of the general formula (I),

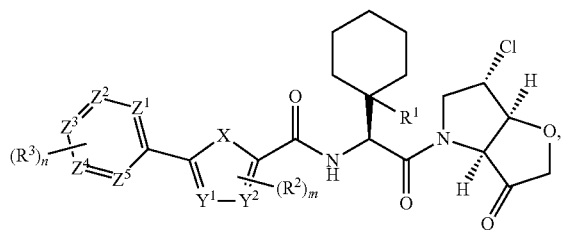

(I)

wherein
$R^1$ represents H or F;
X represents S or O;
$Y^1$ and $Y^2$ independently represents CH or N;
$Z^1$, $Z^2$, $Z^3$, $Z^4$ and $Z^5$ independently represent CH or N, with the proviso that 1, 2 or 3 of $Z^1$, $Z^2$, $Z^3$, $Z^4$ and $Z^5$ represent N;
m denotes 0, 1 or 2;
n denotes 0, 1, 2 or 3;
each $R^2$ and each $R^3$ is independently selected from the group consisting of F; Cl; Br; CN; $CF_3$; $CF_2H$; $CFH_2$; $CF_2Cl$; $CFCl_2$; $C_{1-4}$-alkyl; C(=O)—($C_{1-4}$-alkyl); C(=O)—$NH_2$; C(=O)—N(H)($C_{1-4}$-alkyl); C(=O)—N($C_{1-4}$-alkyl)$_2$; OH; O—$C_{1-4}$-alkyl; $OCF_3$; $OCF_2H$; $OCFH_2$; $OCF_2Cl$; $OCFCl_2$; $NH_2$; N(H)($C_{1-4}$-alkyl); N($C_{1-4}$-alkyl)$_2$; N(H)—C(=O)—($C_{1-4}$-alkyl); N($C_{1-4}$-alkyl)-C(=O)—($C_{1-4}$-alkyl); N(H)—S(=O)$_2$—($C_{1-4}$-alkyl); N(H)—C(=O)—$NH_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl)and S(=O)$_2$-(cyclopropyl);
wherein the above-mentioned substituents $C_{1-4}$-alkyl and cyclopropyl, may in each case be unsubstituted or substituted one or more times by identical or different substituents; and the above-mentioned substituent $C_{1-4}$-alkyl may in each case be branched or unbranched;
in the form of an individual stereoisomer or a mixture thereof; in the form of a tautomer; of a free compound; of an N-oxide; or in the form of a solvate and/or of a physiologically acceptable salt.

2. A compound according to claim 1, wherein $R^1$ is H.
3. A compound according to claim 1, wherein $Y^1$ represents CH or N and $Y^2$ represents CH; or $Y^1$ represents CH and $Y^2$ represents CH or N.
4. A compound according to claim 1, wherein X represents S.
5. A compound according to claim 1, wherein X represents S, $Y^1$ represents CH and $Y^2$ represents CH.
6. A compound according to claim 1, wherein X represents S, $Y^1$ represents CH and $Y^2$ represents N.
7. A compound according to claim 1, wherein the compound of the general formula (I) is a compound according to general formula (Ia),

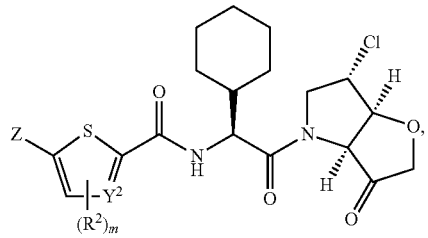

(Ia)

wherein Z represents

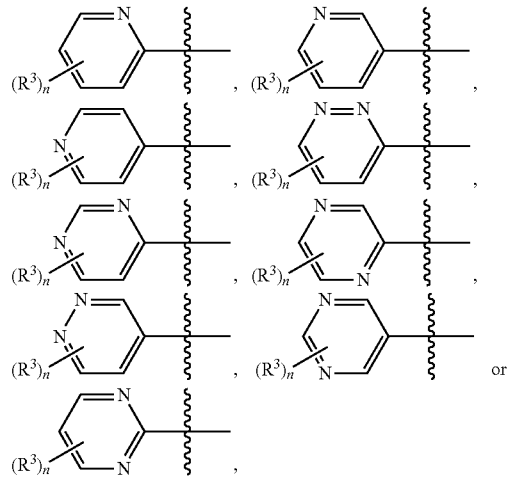

m denotes 0 or 1;
$Y^2$ represents N or CH;
$R^2$ is selected from the group consisting of F; Cl; Br; CN; $CF_3$; $CF_2H$; $CFH_2$; $CF_2Cl$; $CFCl_2$; $C_{1-4}$-alkyl; C(=O)—($C_{1-4}$-alkyl); C(=O)—$NH_2$; C(=O)—N(H)($C_{1-4}$-alkyl); C(=O)—N($C_{1-4}$-alkyl)$_2$; OH; O—$C_{1-4}$-alkyl; $OCF_3$; $OCF_2H$; $OCFH_2$; $OCF_2Cl$; $OCFCl_2$; $NH_2$; N(H)($C_{1-4}$-alkyl); N($C_{1-4}$-alkyl)$_2$; N(H)—C(=O)—($C_{1-4}$-alkyl); N($C_{1-4}$-alkyl)-C(=O)—($C_{1-4}$-alkyl); N(H)—S(=O)$_2$—($C_{1-4}$-alkyl); N(H)—C(=O)—$NH_2$; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)$_2$—($C_{1-4}$-alkyl); S(=O)$_2$—N(H)($C_{1-4}$-alkyl); cyclopropyl; O-cyclopropyl; NH-cyclopropyl; N(H)—C(=O)-cyclopropyl; S(=O)-(cyclopropyl) and S(=O)$_2$-(cyclopropyl);

n denotes 0, 1 or 2; and

R³ is independently selected from the group consisting of F; Cl; Br; CN; CF₃; CF₂H; CFH₂; CF₂Cl; CFCl₂; $C_{1-4}$-alkyl; C(=O)—($C_{1-4}$-alkyl); C(=O)—NH₂; C(=O)—N(H)($C_{1-4}$-alkyl); C(=O)—N($C_{1-4}$-alkyl)₂; OH; O—$C_{1-4}$-alkyl; OCF₃; OCF₂H; OCFH₂; OCF₂Cl; OCFCl₂; NH₂; N(H)($C_{1-4}$-alkyl); N($C_{1-4}$-alkyl)₂; N(H)—C(=O)—($C_{1-4}$-alkyl); N($C_{1-4}$-alkyl)-C(=O)—($C_{1-4}$-alkyl); N(H)—S(=O)₂—($C_{1-4}$-alkyl); N(H)—C(=O)—NH₂; N(H)—C(=O)—N(H)($C_{1-4}$-alkyl); N(H)—C(=O)—N($C_{1-4}$-alkyl)($C_{1-4}$-alkyl); S—($C_{1-4}$-alkyl); S(=O)—($C_{1-4}$-alkyl); S(=O)₂—($C_{1-4}$-alkyl); S(=O)₂—N(H)($C_{1-4}$-alkyl); cyclopropyl; O-cyclopropyl; NH-cyclopropyl; N(H)—C(=O)-cyclopropyl; S(=O)-(cyclopropyl) and S(=O)₂-(cyclopropyl).

8. A compound according to claim 7, wherein m denotes 0 or 1;

R² is F;

n denotes 0, 1 or 2; and

R³ is independently selected from the group consisting of F; Cl; CN; CF₃; CF₂H; CFH₂; CH₃; CH₂CH₃; CH(CH₃)₂; C(=O)CH₃; C(=O)NH₂; C(=O)N(H)(CH₃); C(=O)N(CH₃)₂; OH; OCH₃; OCF₃; OCF₂H; OCFH₂; NH₂; N(H)(CH₃); N(CH₃)₂; N(H)—C(=O)CH₃; N(H)—S(=O)₂CH₃; S(=O)CH₃; S(=O)₂CH₃; S(=O)₂—N(H)(CH₃); cyclopropyl and O-cyclopropyl.

9. A compound according to claim 7, wherein Z represents

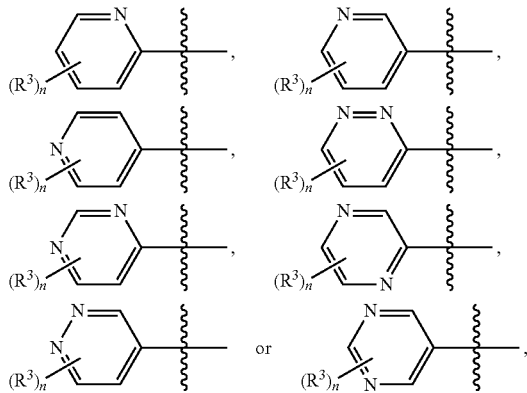

m denotes 0 or 1;

R² is F;

n denotes 0 or 1 or 2; and

R³ is independently selected from the group consisting of F; Cl; CN; CF₃; CF₂H; CFH₂; CH₃; CH₂CH₃; CH(CH₃)₂; C(=O)CH₃; C(=O)NH₂; C(=O)N(H)(CH₃); C(=O)N(CH₃)₂; OH; OCH₃; OCF₃; OCF₂H; OCFH₂; NH₂; N(H)(CH₃); N(CH₃)₂; N(H)—C(=O)CH₃; N(H)—S(=O)₂CH₃; S(=O)CH₃; S(=O)₂CH₃; S(=O)₂—N(H)(CH₃); cyclopropyl and O-cyclopropyl.

10. A compound according to claim 1, wherein the compound of the general formula (I) is a compound according to general formula (Ib),

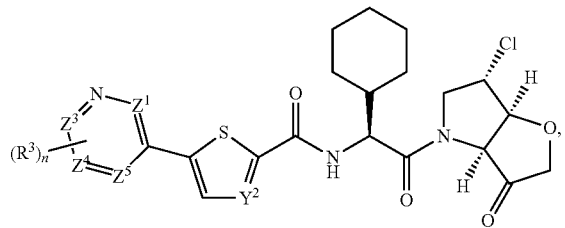

wherein Y² represents CH or N;

Z³, Z⁴ and Z⁵ each represent CH and Z¹ represents N;
or
Z¹, Z⁴ and Z⁵ each represent CH and Z³ represents N;
or
Z¹, Z³ and Z⁵ each represent CH and Z⁴ represents N;
or
Z¹, Z³ and Z⁴ each represent CH and Z⁵ represents N;

n denotes 0 or 1 or 2; and

R³ is selected from the group consisting of F; Cl; CN; CF₃; CF₂H; CFH₂; CH₃; CH₂CH₃; S(=O)CH₃; S(=O)₂CH₃; OCH₃; OCF₃ and cyclopropyl.

11. A compound according to claim 1, wherein the compound of the general formula (I) is a compound according to general formula (Ic),

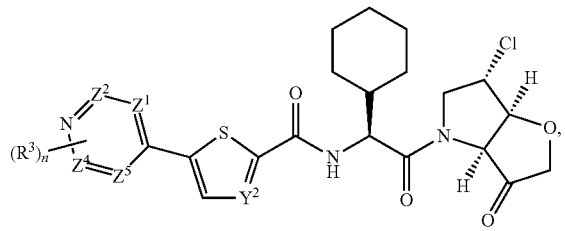

wherein Y² represents CH or N;

Z², Z⁴ and Z⁵ each represent CH and Z¹ represents N;
or
Z¹, Z⁴ and Z⁵ each represent CH and Z² represents N;

n denotes 0 or 1 or 2; and

R³ is selected from the group consisting of F; Cl; CN; CF₃; CF₂H; CFH₂; CH₃; CH₂CH₃; S(=O)CH₃; S(=O)₂CH₃; OCH₃; OCF₃ and cyclopropyl.

12. A compound according to claim 10, wherein

Y² represents CH.

13. A compound according to claim 1, which is selected from the group consisting of:

1 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiophene-2-carboxamide 2 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)thiophene-2-carboxamide 3 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)thiophene-2-carboxamide 4 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)thiophene-2-carboxamide 5. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)thiophene-2-carboxamide
6. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)thiophene-2-carboxamide
7. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)thiophene-2-carboxamide
8. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)thiophene-2-carboxamide
9. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-2-yl)thiophene-2-carboxamide
10. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)furan-2-carboxamide
11. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)furan-2-carboxamide
12. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)furan-2-carboxamide
13. N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridin-3-yl)thiazole-5-carboxamide
14. N-((S)-2-((3aS,6S,6aS)-6-chloro-3-oxotetrahydro-2H-furo[3,2-b]pyrrol-4(5H)-yl)-1-cyclohexyl-2-oxoethyl)-4-methyl-2-(pyridin-3-yl)thiazole-5-carboxamide
15. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)thiazole-2-carboxamide
16. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyridin-3-yl)thiophene-2-carboxamide
17. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-chloropyridin-3-yl)thiophene-2-carboxamide
18. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)thiazole-2-carboxamide
19. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-4-yl)furan-2-carboxamide
20. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridazin-3-yl)furan-2-carboxamide
21. N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridazin-4-yl)oxazole-5-carboxamide
22. N-((S)-2-((3aS,6S,6aS)-6-chloro-3-oxotetrahydro-2H-furo[3,2-b]pyrrol-4(5H)-yl)-1-cyclohexyl-2-oxoethyl)-4-methyl-2-(pyrazin-2-yl)thiazole-5-carboxamide
23. N-((S)-2-((3aS,6S,6aS)-6-chloro-3-oxotetrahydro-2H-furo[3,2-b]pyrrol-4(5H)-yl)-1-cyclohexyl-2-oxoethyl)-2-(pyridin-3-yl)-4-(trifluoromethyl)thiazole-5-carboxamide
24. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-5-yl)thiazole-2-carboxamide
25. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)furan-2-carboxamide
26. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)thiazole-2-carboxamide
27. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrimidin-4-yl)furan-2-carboxamide
28. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)-1,3,4-thiadiazole-2-carboxamide
29. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiophene-2-carboxamide
30. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiophene-2-carboxamide
31. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiophene-2-carboxamide
32. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-4-yl)thiazole-2-carboxamide
33. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-4-yl)thiophene-2-carboxamide
34. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-3-yl)thiophene-2-carboxamide
35. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-3-yl)thiophene-2-carboxamide
36. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyrimidin-4-yl)thiophene-2-carboxamide
37. N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyrimidin-5-yl)thiophene-2-carboxamide
38. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-fluoropyridazin-3-yl)thiophene-2-carboxamide
39. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiophene-2-carboxamide
40. N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-4-yl)thiophene-2-carboxamide
41. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyrimidin-5-yl)thiazole-2-carboxamide
42. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridin-3-yl)thiazole-2-carboxamide
43. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyanopyridin-3-yl)thiazole-2-carboxamide
44. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-3-yl)thiophene-2-carboxamide
45. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-3-yl)thiazole-2-carboxamide
46. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-2-yl)thiazole-2-carboxamide
47. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-fluoropyridin-3-yl)thiazole-2-carboxamide
48. N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyrazin-2-yl)thiazole-2-carboxamide 49 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(pyridin-4-yl)thiazole-2-carboxamide 50 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-fluoropyridin-4-yl)thiazole-2-carboxamide 51 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-4-yl)thiazole-2-carboxamide 52 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-chloropyridin-3-yl)thiazole-2-carboxamide 53 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyrimidin-5-yl)thiophene-2-carboxamide 54 N-((S)-2-((3aS,6S,6aS)-6-chloro-3-oxotetrahydro-2H-furo[3,2-b]pyrrol-4(5H)-yl)-1-cyclohexyl-2-oxoethyl)-4-fluoro-5-(pyridazin-3-yl)thiophene-2-carboxamide 55 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiophene-2-carboxamide 56 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methoxypyridin-4-yl)thiophene-2-carboxamide 57 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyrimidin-5-yl)thiazole-2-carboxamide 58 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3-methylpyridazin-4-yl)thiophene-2-carboxamide 59 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-3-yl)thiophene-2-carboxamide 60 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridazin-4-yl)thiophene-2-carboxamide 61 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiophene-2-carboxamide 62 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiophene-2-carboxamide 63 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiophene-2-carboxamide 64 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-cyclopropylpyridin-3-yl)thiazole-2-carboxamide 65 N-((S)-2-((3aS,6S,6aS)-6-chloro-3-oxotetrahydro-2H-furo[3,2-b]pyrrol-4(5H)-yl)-1-cyclohexyl-2-oxoethyl)-3-fluoro-5-(pyridin-3-yl)thiophene-2-carboxamide 66 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiophene-2-carboxamide 67 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-(trifluoromethyl)pyrimidin-5-yl)thiazole-2-carboxamide 68 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-(trifluoromethyl)pyridin-3-yl)thiazole-2-carboxamide 69 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiophene-2-carboxamide 70 3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridine 1-oxide 71 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methoxypyridazin-4-yl)thiophene-2-carboxamide 72 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methoxypyridazin-3-yl)thiophene-2-carboxamide 73 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-ethylpyridazin-3-yl)thiophene-2-carboxamide 74 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-cyclopropylpyridazin-3-yl)thiophene-2-carboxamide 75 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-methylpyridazin-4-yl)thiazole-2-carboxamide 76 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfinyl)pyridazin-3-yl)thiophene-2-carboxamide 77 4-(2-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiazol-5-yl)-6-methylpyridazine 1-oxide 78 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-(methylsulfonyl)pyridazin-3-yl)thiophene-2-carboxamide 79 3-(5-(((S)-2-((3aS,6S,6aS)-6-chloro-3-oxotetrahydro-2H-furo[3,2-b]pyrrol-4(5H)-yl)-1-cyclohexyl-2-oxoethyl)carbamoyl)thiophen-2-yl)pyridazine 1-oxide 80 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-hydroxypyridazin-4-yl)thiophene-2-carboxamide 81 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,4-dimethylpyrimidin-5-yl)thiophene-2-carboxamide 82 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-cyclopropylpyridin-4-yl)thiazole-2-carboxamide 83 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-methylpyridin-3-yl)thiophene-2-carboxamide 84 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(4-methylpyridazin-3-yl)thiophene-2-carboxamide 85 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(6-ethylpyridazin-4-yl)thiophene-2-carboxamide 86 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiophene-2-carboxamide 87 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2-ethylpyridin-4-yl)thiazole-2-carboxamide 88 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(2,5-dimethylpyridin-4-yl)thiophene-2-carboxamide 89 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(3,6-dimethylpyridazin-4-yl)thiophene-2-carboxamide 90 N-((S)-2-((3aS,6S,6aS)-6-chloro-3-oxotetrahydro-2H-furo[3,2-b]pyrrol-4(5H)-yl)-1-cyclohexyl-2-oxoethyl)-5-(5-methylpyridazin-4-yl)thiophene-2-carboxamide in the form of an individual stereoisomer or a mixture thereof; in the form of a tautomer; of a free compound; of an N-oxide; or in the form of a solvate and/or of a physiologically acceptable salt.

14. A pharmaceutical composition comprising at least one compound according to claim 1.

15. A method for the treatment of a disorder selected from the group consisting of nociceptive pain; neuropathic pain; erosive osteoarthritis (EO), erosive osteoarthritis of the hand; Sjögren's Syndrome; rheumatoid arthritis (RA); psoriatic arthritis (PsA); Psoriasis; Spondylarthritis, ankylosing spondylitis; osteoporosis; Complex Regional Pain Syndrome; CRPS I; Lupus erythematodes (SLE); Lupus nephritis; multiple sclerosis (MS); diabetes; chronic obstructive pulmonary disease (COPD); COPD subpopoulation with osteoporosis; asthma; and severe asthma subpopoulation with osteoporosis; said method comprising administering to a patient in need thereof an effective amount therefor of at least one compound according to claim 1.

* * * * *